US012012443B2

(12) United States Patent
Oda et al.

(10) Patent No.: US 12,012,443 B2
(45) Date of Patent: Jun. 18, 2024

(54) IMMUNOMODULATORY FUSION PROTEINS AND USES THEREOF

(71) Applicant: Fred Hutchinson Cancer Center, Seattle, WA (US)

(72) Inventors: Shannon K. Oda, Lake Forest Park, WA (US); Philip D. Greenberg, Mercer Island, WA (US); Thomas M. Schmitt, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 164 days.

(21) Appl. No.: 17/166,903

(22) Filed: Feb. 3, 2021

(65) Prior Publication Data

US 2021/0403532 A1 Dec. 30, 2021

Related U.S. Application Data

(63) Continuation of application No. 15/555,951, filed as application No. PCT/US2016/021064 on Mar. 4, 2016, now abandoned.

(60) Provisional application No. 62/128,979, filed on Mar. 5, 2015.

(51) Int. Cl.

| | |
|---|---|
| ***C07K 14/705*** | (2006.01) |
| ***A61K 35/17*** | (2015.01) |
| ***C07K 14/725*** | (2006.01) |
| ***C12N 5/0783*** | (2010.01) |
| *A61K 38/00* | (2006.01) |
| *A61K 48/00* | (2006.01) |

(52) U.S. Cl.

CPC ........ *C07K 14/70596* (2013.01); *A61K 35/17* (2013.01); *C07K 14/70503* (2013.01); *C07K 14/70507* (2013.01); *C07K 14/7051* (2013.01); *C07K 14/70517* (2013.01); *C07K 14/70521* (2013.01); *C07K 14/70578* (2013.01); *C12N 5/0636* (2013.01); *C12N 5/0637* (2013.01); *C12N 5/0638* (2013.01); *A61K 38/00* (2013.01); *A61K 48/00* (2013.01); *C07K 2319/03* (2013.01); *C07K 2319/74* (2013.01); *C12N 2510/00* (2013.01)

(58) Field of Classification Search

CPC ........................ C07K 2319/75; C07K 2319/74
USPC ........................................... 424/133.1, 136.1
See application file for complete search history.

(56) References Cited

U.S. PATENT DOCUMENTS

| | | | |
|---|---|---|---|
| 5,712,149 A | 1/1998 | Roberts | |
| 6,083,751 A | 7/2000 | Feldhaus et al. | |
| 9,163,258 B2 | 10/2015 | Riddell et al. | |
| 9,987,308 B2 | 6/2018 | Riddell et al. | |
| 10,188,749 B2 | 1/2019 | Stephan et al. | |
| 10,350,245 B2 | 7/2019 | Adair et al. | |
| 11,725,210 B2 * | 8/2023 | Oda | C07K 14/70521 424/93.21 |
| 2013/0202622 A1 | 8/2013 | Riddell et al. | |
| 2014/0219975 A1 | 8/2014 | June et al. | |
| 2014/0242049 A1 | 8/2014 | Choi et al. | |
| 2014/0314795 A1 | 10/2014 | Riddell et al. | |
| 2016/0008399 A1 | 1/2016 | Stephan | |
| 2016/0083449 A1 | 3/2016 | Schmitt et al. | |
| 2018/0044404 A1 | 2/2018 | Oda et al. | |
| 2018/0353588 A1 | 12/2018 | Boyd et al. | |
| 2018/0369280 A1 | 12/2018 | Schmitt et al. | |
| 2019/0046572 A1 | 2/2019 | Stephan | |
| 2019/0054121 A1 | 2/2019 | Stephan | |
| 2019/0111153 A1 | 4/2019 | Stephan et al. | |
| 2019/0127435 A1 | 5/2019 | Schmitt et al. | |
| 2019/0209671 A1 | 7/2019 | Dai et al. | |
| 2020/0009190 A1 * | 1/2020 | Oda | C07K 14/4705 |

FOREIGN PATENT DOCUMENTS

| | | |
|---|---|---|
| AU | 2016226022 B2 | 9/2017 |
| CN | 103492406 A | 1/2014 |
| CN | 103965361 A | 8/2014 |
| CN | 110330567 A | 10/2019 |
| EP | 3265481 A1 | 1/2018 |
| JP | 2014-524234 A | 9/2014 |
| JP | 2014-532642 A | 12/2014 |
| WO | 2012/042480 A1 | 4/2012 |

(Continued)

OTHER PUBLICATIONS

Oda et al (Cancer Research, (Nov. 2022) vol. 82, No. 22, Supp. Supplement. Abstract No. PR008. Meeting Info: AACR Special Conference: Pancreatic Cancer. Boston, MA, United States. Sep. 13, 2022-Sep. 16, 2022).*

(Continued)

*Primary Examiner* — Lynn A Bristol

(74) *Attorney, Agent, or Firm* — Seed IP Law Group LLP

(57) ABSTRACT

Described herein are immunomodulatory fusion proteins containing an extracellular binding domain and an intracellular signaling domain, wherein binding of a target can generate a modulatory signal in a host cell, such as a T cell. Some immunomodulatory fusion proteins as described comprise a SIRPα extracellular component and hydrophobic and intracellular components comprising transmembrane and/or signaling domains of a CD28, respectively. Such fusion proteins are capable of delivering a positive or costimulatory signal in response to a binding event that in a natural setting would result in an inhibitory signal. Uses of immune cells expressing such immunomodulatory fusion proteins to treat certain diseases, such as cancer or infectious disease, are also described.

16 Claims, 45 Drawing Sheets

Specification includes a Sequence Listing.

(56) References Cited

FOREIGN PATENT DOCUMENTS

| | | | |
|---|---|---|---|
| WO | 2012/079000 | A1 | 6/2012 |
| WO | 2012/138858 | A1 | 10/2012 |
| WO | 2013/019615 | A2 | 2/2013 |
| WO | 2013/123061 | A1 | 8/2013 |
| WO | 2014/106839 | A1 | 7/2014 |
| WO | 2014/172584 | A1 | 10/2014 |
| WO | 2016/014535 | A1 | 1/2016 |
| WO | 2016/014565 | A2 | 1/2016 |
| WO | 2016/014576 | A1 | 1/2016 |
| WO | WO 2016024021 | * | 2/2016 |
| WO | 2016/102965 | A1 | 6/2016 |
| WO | 2016/141357 | A1 | 9/2016 |
| WO | WO 2016203048 | A1 | 12/2016 |
| WO | 2018/170475 | A1 | 9/2018 |

OTHER PUBLICATIONS

Office Action of Oct. 30, 2019 from U.S. Appl. No. 15/555,951 (Applicant's remarks; pp. 1-10).*

Jena et al., "Redirecting T-cell specificity by introducing a tumor-specific chimeric antigen receptor," *Blood 116*(7): 1035-1044, 2010.

Jones et al., "Lentiviral Vector Design for Optimal T Cell Receptor Gene Expression in the Transduction of Peripheral Blood Lymphocytes and Tumor-Infiltrating Lymphocytes," *Human Gene Therapy 20*:630-640, 2009.

Kuhlmann, "Unleashing T cells for adoptive immunotherapy," https://www.fredhutch.org/en/news/spotlight/2017/12/crd_oda blood.html, 2017 (3 pages).

Leccia et al., "Cytometric and Biochemical Characterization of Human Breast Cancer Cells Reveals Heterogenous Myoepithelial Phenotypes," *Cytometry Part A 81A*:960-972, 2012.

Ma et al., "Isolation, Culture and Biological Characteristics of Tumor Stem Cells in Human Colorectal Carcinoma," *Cancer Res Prev Treat 41*(4):345-349, 2014 (5 pages) (with English abstract).

Anderson et al., "Engineering adoptive T cell therapy to co-opt Fas ligand-mediated death signaling in ovarian cancer enhances therapeutic efficacy," *Journal for ImmunoTherapy of Cancer 10*:e003959, 2022. (14 pages).

Oda et al., "A Fas-4-1BB fusion protein converts a death to a pro-survival signal and enhances T cell therapy," *J. Exp. Med. 217*(12):e20191166, 2020. (20 pages).

Alakoskela et al., "Mechanisms for Size-Dependent Protein Segregation at Immune Synapses Assessed with Molecular Rulers," *Biophys. J. 100*(12):2865-2874, 2011.

Ankri et al., "Human T Cells Engineered To Express a Programmed Death 1/28 Costimulatory Retargeting Molecule Display Enhanced Antitumor Activity," *J. Immunol. 191*(8):4121-4129, 2013. (10 pages).

Brenner, "Errors in genome annotation," *Trends in Genetics 15*(4):132-133, 1999.

Chen et al., "Fusion Protein Linkers: Property, Design and Functionality," *Adv Drug Deliv Rev.* 65(10): 1357-1369, 2013 (NIH Public Access Author Manuscript, available in PMC Oct. 15, 2014) (32 pages).

Cherkassky et al., "Human Car T cells with cell-intrinsic PD-1 checkpoint blockade resist tumor-mediated inhibition," *J. Clin Invest. 126*(8):3130-3144, 2016.

Cheuk et al., "Role of 4-1BB:4-1BB ligand in cancer immunotherapy," *Cancer Gene Therapy 11*(3):215-226, 2004.

Coles et al., "Expression of CD200 on AML blasts directly suppresses memory T-cell function," *Leukemia 26*(9):2148-2151, 2012.

Coles et al., "The immunosuppressive ligands PD-L1 and CD200 are linked in AML T-cell immunosuppression: identification of a new immunotherapeutic synapse," *Leukemia 29*(9): 1952-1954, 2015.

Contini et al., "In vivo apoptosis of CD8+ lymphocytes in acute myeloid leukemia patients: involvment of soluble HLA-1 and Fas ligand," *Leukemia 21*: 253-260, 2007.

Dustin et al., "Understanding the Structure and Function of the Immunological Synapse," *CSH Perspectives in Biology 2*(10):a002311, 2010. (14 Pages).

Feldhaus et al., "A CD2/CD28 chimeric receptor triggers the CD28 signaling pathway in CTLL.2 cells," *Gene Therapy 4*(8):833-838, 1997.

Fourcade et al., "CD8(+) T cells specific for tumor antigens can be rendered dysfunctional by the tumor microenvironment through upregulation of the inhibitory receptors BTLA and PD-1," *Cancer Res. 72*(4):887-896, 2012. (15 pages).

Frankel et al., "Characterization of diphtheria fusion proteins targeted to the human interleukin-3 receptor," *Protein Engineering 13*(8):575-581, 2000.

Genbank, "*Homo sapiens* CD2 molecule (CD2), mRNA," Accession No. NM_001767.3, Mar. 15, 2015, 4 pages.

Genbank, "*Homo sapiens* Fas cell surface death receptor (FAS), transcript variant 1, mRNA," Accession No. NM_000043.4, Mar. 15, 2015, 6 pages.

Genbank, "*Homo sapiens* hepatitis A virus cellular receptor 2 (HAVCR2), mRNA," Accession No. NM_032782.4, Sep. 23, 2018, 5 pages.

Genbank, "*Homo sapiens* lymphocyte activating 3 (LAG3), mRNA," Accession No. NM_002286.5, Jun. 17, 2018, 5 pages.

Grassmann et al., "S81. Proffered paper: A new PD1-CD28 chimeric receptor overcomes PD-1-mediated immunosuppression in adoptive T cell therapy," *J. Immunother. Cancer 2*(Suppl. 2):119, 2014. (1 Page).

Hanada et al., "Augmenting adoptive T cell therapy through universal chimeric costimulators," *J. Immunother. Cancer 1*(Suppl. 1):P14, 2013. (1 Page).

Hatherley et al., "Paired Receptor Specificity Explained by Structures of Signal Regulatory Proteins Alone and Complexed with CD47," *Molecular Cell 31*:266-277, 2008.

Hatherley et al., "Structures of CD200/CD200 Receptor Family and Implications for Topology, Regulation, and Evolution," *Structure 21*(5):820-832, 2013.

Ho et al., "CD200 Is a Marker of LSC Activity in Acute Myeloid Leukemia," *Blood 128*:1705, 2016 (Abstract only) (6 pages).

James et al., "Biophysical Mechanism of T Cell Receptor Triggering in a Reconstituted System," *Nature 487*(7405):64-69, 2012. (16 Pages).

Kawalekar et al., "Distinct Signaling of Coreceptors Regulates Specific Metabolism Pathways and Impacts Memory Development in Car T Cells," *Immunity 44*:380-390, 2016.

Kawasaki et al., "Cancer stem cells, CD200 and immunoevasion," *Trends in Immunology 29*(10):464-468, 2008.

Kawasaki et al., "Co-expression of the toleragenic glycoprotein, CD200, with markers for cancer stem cells," Biochem Biophys Res Commun.364(4):778-782, 2007 (NIH Public Access Author Manuscript, available in PMC Dec. 28, 2007)(11 pages).

Keir et al., "PD-1 and its ligands in tolerance and immunity," *Annu. Rev. Immunol. 26*:677-704, 2008. (Abstract Only).

Kharfan-Dabaja et al., "Immunotherapy for chronic lymphocytic leukemia in the era of BTK inhibitors," *Leukemia 28*(3):507-517, 2014.

Kono, "Current status of cancer immunotherapy," *Journal of Stem Cells & Regenerative Medicine 10*(1): 8-13, 2014.

Kornmann et al., Fas and Fas-Ligand Expression in Human Pancreatic Cancer, *Annals of Surgery 231*(3):368-379, 2000.

Krause et al., "Antigen-dependent CD28 Signaling Selectively Enhances Survival and Proliferation in Genetically Modified Activated Human Primary T Lymphocytes," *J. Exp. Med. 188*(4):619-626, 1998.

Lavrik, "Regulation of Death Receptor-Induced Apoptosis Induced via CD95/Fas and Other Death Receptors," *Molecular Biology 45*(1):173-179, 2011.

Lazar-Molnar et al., "The interchain disulfide linkage is not a prerequisite but enhances CD28 costimulatory function," *Cell Immunol. 244*(2):125-129, 2006. (9 Pages).

Ledbetter et al., "CD28 Ligation in T-Cell Activation: Evidence for Two Signal Transduction Pathways," *Blood 75*(7):1531-1539, 1990. (10 Pages).

(56) References Cited

OTHER PUBLICATIONS

Liu et al., "Synthesis of full length recombinant chimeric receptor anti-erbB2 scFv-CD28-ζ and construction of its eukaryotic expression vector," *J Chinese PLA Postgrad Med Sch 31*(4):360-362, 2010 (with English Abstract).
Liu et al., "The role of N-glycosylation of CD200-CD200R1 interaction of classical microglial activation," *Journal of Inflammation 15*(28):1-10, 2018.
Ma et al., "CD28 T cell costimulatory receptor function is negatively regulated by N-linked carbohydrates," *Biochemical and Biophysical Research Communications* 317(1):60-67, 2004.
Maeda et al., "Engineering of functional chimeric protein G-Vargula Luciferase," *Analytical Biochemistry* 249(2):147-152, 1997.
Maus et al., "Antibody-modified T cells: CARs take the front seat for hematologic malignancies," *Blood 123*(17):2625-2635, 2014. (12 Pages).
Milstein et al., "Nanoscale Increases in CD2-CD48-mediated Intermembrane Spacing Decrease Adhesion and Reorganize the Immunological Synapse," *J. Biol. Chem. 283*(49):34414-34422, 2008.
Moreaux et al., "CD200: A putative therapeutic target in cancer," *Biochemical and Biophysical Research Communications* 366(1):117-122, 2008.
Motz et al., "Tumor Endothelium FasL Establishes a Selective Immune Barrier Promoting Tolerance in Tumors," Nature Medicine 20: 607-615, 2014 (HHS Public Access Author Manuscript, available in PMC Dec. 1, 2014)(26 pages).
Oda et al., "A CD200R-CD28 fusion protein appropriates an inhibitory signal to enhance T-cell function and therapy of murine leukemia," *Blood 130*(22): 2410-2419, 2017.
Oda et al., "Cheating Death: A Fas-41BB Immunomodulatory Fusion Protein Obviates a Death Signal to Enhance T Cell Function and Adoptive Therapy Targeting Leukemia and Solid Tumors," Conference Program, Retrieved from https://www.keystonesymposia.org/index.cfm?e=Web.Meeting.Program&meetingid=1518&subTab=program [Retrieved Jun. 19, 2018}, 22 pages, 2018.
Oda et al., "Cheating Death: A Fas-41BB Immunomodulatory Fusion Protein Obviates a Death Signal to Enhance T Cell Function and Adoptive Therapy Targeting Leukemia and Solid Tumors," *J. Immunol 200* (1 Supplement) 179.11, 2018 (4 pages).
Pakula et al. "Genetic analysis of protein stability and function," *Annual Review of Genetics* 23(1):289-310, 1989.
Pardoll, "The blockade of immune checkpoints in cancer immunotherapy," *Nat. Rev. Cancer 12*(4):252-264, 2012. (31 Pages).
Prosser et al., "Primary Human CD8+ T Cells Engineered to Express a PD1-CD28 Chimeric Receptor are Co-Stimulated through the Exploitation of Tumor Expressed PD-L1," *Molecular Therapy 19* (Supplement 1):S192, 2011.
Prosser et al., "Tumor PD-L1 co-stimulates primary human CD8+ cytotoxic T cells modified to express a PD1: CD28 chimeric receptor," *Mol. Immunol. 51*(3-4):263-272, 2012.
Rossy et al., "The integration of signaling and the spatial organization of the T cell synapse," *Front. Immunol. 3*:352, 2012. (12 Pages).
Rudd et al., "CD28 and CTLA-4 coreceptor expression and signal transduction," *Immunol. Rev. 229*(1):12-26, 2009. (26 Pages).
Shirakabe et al., "Mechanistic insights into ectodomain shedding: susceptibility of CADM1 adhesion molecule is determined by alternative splicing and O-glycosylation," *Scientific Reports 7*:46174, 1-12, 2017.
Siva et al., "Immune modulation by melanoma and ovarian tumor cells through expression of the immunosuppressive molecule CD200," *Cancer Immunol Immunother. 57*:987-996, 2008.
Smith et al., The challenges of genome sequence annotation or "The devil is in the details," *Nature Biotechnology 15*:1222-1223, 1997.
Snauwaert et al., "Can immunotherapy specifically target acute myeloid leukemic stem cells?" *OncoImmunology 2*(2): e22943, 10 pages, 2013.
Soto et al., "MHC-class I-restricted CD4 T cells: a nanomolar affinity TCR has improved anti- tumor efficacy in vivo compared to the micromolar wild type TCR," *Cancer Immunol. Immunother. 62*(2):359-369, 2013. (20 pages).
Stromnes et al., "Abrogating Cbl-b in effector CD8+ T cells improves the efficacy of adoptive therapy of leukemia in mice," *The Journal of Clinical Investigation* 120(10): 3722-3734, 2010.
Stromnes et al., "Re-adapting T cells for cancer therapy: from mouse models to clinical trials," Immunol Rev.257(1): 145-164, 2014 (NIH Public Access Author Manuscript, available in PMC Jan. 1, 2015)(34 pages).
Stromnes et al., "T cells engineered against a native antigen can surmount immunologic and physical barriers to treat pancreatic ductal adenocarcinoma," Cancer Cell 28(5): 638-652, 2015 (HHS Public Access Author Manuscript, available in PMC Nov. 9, 2016)(30 pages).
Stumpfova et al., "The immunosuppressive surface ligand CD200 augments the metastatic capacity of squamous cell carcinoma," *Cancer Res. 70*(7):2962-2972, 2010.
Subramanian et al., "Species- and cell type-specific interactions between CD47 and human SIRPa," *Blood* 107(6): 2548-2556, Mar. 15, 2006 (26 pages).
Tang et al., "The advantages of PD1 activating chimeric receptor (PD1-ACR) engineered lymphocytes for PDL1+ cancer therapy," *Am. J. Transl. Res. 7*(3):460-473, 2015.
Tonks et al., "CD200 as a prognostic factor in acute myeloid leukaemia," *Leukemia 21*(3):566-568, 2007.
Van den Borne et al., "The CD200-CD200 Receptor Inhibitory Axis Controls Arteriogenesis and Local T Lymphocyte Influx," *PLOS One 9*(6):e98820, 2014 (10 pages).
Willingham et al., "The CD47-signal regulatory protein alpha (SIRPa) interaction is a therapeutic target for human solid tumors," *Proc. Natl. Acad. Sci. USA 109*(17):6662-6667, 2012.
Yamao et al., "Mouse and Human SHPS-1: Molecular Cloning of cDNAs and Chromosomal Localization of Genes," *Biochemical and Biophysical Research Communications 231*: 61-67, 1997.
Anderson et al., "Obstacles Posed by the Tumor Microenvironment to T cell Activity: A Case for Synergistic Therapies," *Cancer Cell 31*:311-325, Mar. 13, 2017 (15 pages).
Arch et al., "4-1BB and Ox40 Are Members of a Tumor Necrosis Factor (TNF)-Nerve Growth Factor Receptor Subfamily That Bind TNF Receptor-Associated Factors and Activate Nuclear Factor κB," *Molecular and Cellular Biology 18*(1)558-565, Jan. 1998 (8 pages).
Bajorath et al., "Analysis of Fas-ligand interactions using a molecular model of the receptor-ligand interface," *Journal of Computer-Aided Molecular Design 13*:409-418, Jul. 1999 (10 pages).
Barao, "The TNF receptor-ligands 4-1BB-4-1BBL and GITR-GITRL in NK cell responses," *Frontiers in Immunology 3*(402), Jan. 2013 (8 pages).
Dolan et al., "PD-1 Pathway Inhibitors: Changing the Landscape of Cancer Immunotherapy," *Cancer Control 21*(3):231-237, Jul. 2014 (7 pages).
Hatherley et al., "The Structure of the Macrophage Signal Regulatory Protein α (SIRPα) Inhibitory Receptor Reveals a Binding Face Reminiscent of That Used by T Cell Receptors," *The Journal of Biological Chemistry 282*(19):14567-14575, May 2007 (9 pages).
Jang et al., "Human 4-1BB (CD137) Signals Are Mediated by TRAF2 and Activate Nuclear Factor-κB," *Biochemical and Biophysical Research Communications 242*(3):613-620, Jan. 1998 (8 pages).
Oda et al., "A Fas-4-1BB Immunomodulatory Fusion Protein Converts a Pro-Death to a Pro-Survival Signal, Enhancing T Cell Function and Efficacy of Adoptive Cell Therapy in Murine Models of AML and Pancreatic Cancer," *J Immunother Cancer 8*(Suppl 3):A1-A559, 2020 (Abstract Only) (2 pages).
Orlinick et al., "Requirement of Cysteine-rich Repeats of the Fas Receptor for Binding by the Fas Ligand," *The Journal of Biological Chemistry 272*(46):28889-28894, Nov. 1997 (6 pages).
Ramaswamy et al., "Many Checkpoints on the Road to Cell Death: Regulation of Fas-FasL Interactions and Fas Signaling in Peripheral Immune Responses," Results and Problems in Cell Differentiation; Springer-Verlag Berlin Heidelberg, pp. 17-47, 2009 [Published Online Jan. 1, 2009] (31 pages).

(56) References Cited

OTHER PUBLICATIONS

Ramsay et al., "Multiple inhibitory ligands induce impaired T cell immunological synapse function in chronic lymphocytic leukemia that can be blocked with lenalidomide: establishing a reversible immune evasion mechanism in human cancer," *Blood First Edition Paper*, prepublished online Apr. 30, 2012 (36 pages).
Starling et al., "Analysis of the Ligand Binding Site in Fas (CD95) by Site-Directed Mutagenesis and Comparison with TNFR and CD40," *Biochemistry 37*(11):3723-3726, Mar. 1998 (4 pages).
Starling et al., "Identification of Amino Acid Residues Important for Ligand Binding to Fas," *J. Exp. Med. 185*(8):1487-1492, Apr. 21, 1997 (6 pages).
Takata-Tomokuni et al., "Detection, epitope-mapping and function of anti-Fas autoantibody in patients with silicosis," *Immunology 116*:21-29, Sep. 2005 (10 pages).
Teague et al., "Interleukin-15 rescues tolerant $CD8^+$ T cells for use in adoptive immunotherapy of established tumors," *Nature Medicine 12*(3):335-341, Mar. 2006 [published online Feb. 12, 2006] (7 pages).
U.S. Appl. No. 18/339,197 (Unpublished). Cited unpublished U.S. patent applications are not provided based upon the good faith belief that such applications are available in the USPTO's Image File Wrapper system.
Walton et al., "CRISPR/Cas9-Mediated Trp53 and Brca2 Knockout to Generate Improved Murine Models of Ovarian High-Grade Serous Carcinoma," *Cancer Res 76*(20):6118- 6129, Oct. 2016 (13 pages).

* cited by examiner

C4
C4 + CD200R

Stimulator cells = WT1-pulsed T2

SEQUENCE LISTING

```
<160> NUMBER OF SEQ ID NOS: 179

<210> SEQ ID NO 1
<211> LENGTH: 915
<212> TYPE: DNA
<213> ORGANISM: Artificial Sequence
<220> FEATURE:
<223> OTHER INFORMATION: huCD200Rtm-CD28 construct

<400> SEQUENCE: 1

atgctgtgcc cttggagaac cgccaacctg ggcctgctgc tgatcctgac catcttcctg      60

gtggccgcca gcagcagcct gtgcatggac gagaagcaga tcacccagaa ctacagcaag     120

gtgctggccg aagtgaacac cagctggccc gtgaagatgg ccaccaacgc cgtgctgtgc     180

tgccctccta tcgccctgcg gaacctgatc atcatcacct gggagatcat cctgcggggc     240

cagcccagct gtaccaaggc ctaccggaaa gagacaaacg agacaaaaga aacaaactgc     300

accgacgagc ggatcacatg ggtgtccaga cccgaccaga acagcgacct gcagatcaga     360

cccgtggcca tcacccacga cggctactac cggtgcatca tggtcacccc cgatggcaac     420

ttccaccggg gataccatct gcaggtgctc gtgacccccg aagtgaccct gttccagaac     480

cggaacagaa ccgccgtgtg caaggccgtg gccggaaaac ctgccgccca gatctcttgg     540

atccccgagg gcgattgcgc caccaagcag gaatactggt ccaacggcac cgtgaccgtg     600

aagtccacct gtcactggga ggtgcacaac gtgtccaccg tgacatgcca cgtgtcccac     660

ctgaccggca acaagagcct gtacatcgag ctgctgcctg tgcctggcgc caagaagtcc     720

gccaagctgt acatccccta catcatcctg acaatcatca ttctgaccat cgtgggcttc     780

atctggctgc tgcgcagcaa gcggagcaga ggcggccaca gcgactacat gaacatgacc     840

cctagacggc ctggccccac cagaaagcac taccagccct acgcccctcc ccgggacttt     900

gccgcctaca gaagc                                                      915


<210> SEQ ID NO 2
<211> LENGTH: 728
<212> TYPE: DNA
<213> ORGANISM: Artificial Sequence
<220> FEATURE:
<223> OTHER INFORMATION: huCD200R entire extracellular domain

<400> SEQUENCE: 2

tgctgtgccc ttggagaacc gccaacctgg gcctgctgct gatcctgacc atcttcctgg      60

tggccgccag cagcagcctg tgcatggacg agaagcagat cacccagaac tacagcaagg     120

tgctggccga agtgaacacc agctggcccg tgaagatggc caccaacgcc gtgctgtgct     180
```

```
gccctcctat cgccctgcgg aacctgatca tcatcacctg ggagatcatc ctgcggggcc    240

agcccagctg taccaaggcc taccggaaag agacaaacga gacaaaagaa acaaactgca    300

ccgacgagcg gatcacatgg gtgtccagac ccgaccagaa cagcgacctg cagatcagac    360

ccgtggccat cacccacgac ggctactacc ggtgcatcat ggtcaccccc gatggcaact    420

tccaccgggg ataccatctg caggtgctcg tgacccccga agtgaccctg ttccagaacc    480

ggaacagaac cgccgtgtgc aaggccgtgg ccggaaaacc tgccgcccag atctcttgga    540

tccccgaggg cgattgcgcc accaagcagg aatactggtc caacggcacc gtgaccgtga    600

agtccacctg tcactgggag gtgcacaacg tgtccaccgt gacatgccac gtgtcccacc    660

tgaccggcaa caagagcctg tacatcgagc tgctgcctgt gcctggcgcc aagaagtccg    720

ccaagctg                                                              728
```

<210> SEQ ID NO 3
<211> LENGTH: 63
<212> TYPE: DNA
<213> ORGANISM: Artificial Sequence
<220> FEATURE:
<223> OTHER INFORMATION: huCD200R transmembrane domain

<400> SEQUENCE: 3

```
tacatcccct acatcatcct gacaatcatc attctgacca tcgtgggctt catctggctg     60

ctg                                                                    63
```

<210> SEQ ID NO 4
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 4

```
ttctgggtgc tggtggtggt cggaggcgtg ctggcctgct acagcctgct ggtcaccgtg     60

gccttcatca tcttttgggt c                                                81
```

<210> SEQ ID NO 5
<211> LENGTH: 123
<212> TYPE: DNA
<213> ORGANISM: Artificial Sequence
<220> FEATURE:
<223> OTHER INFORMATION: CD28 intracellular domain

<400> SEQUENCE: 5

```
cgcagcaagc ggagcagagg cggccacagc gactacatga acatgacccc tagacggcct     60

ggccccacca gaaagcacta ccagccctac gcccctcccc gggactttgc cgcctacaga    120

agc                                                                   123
```

<210> SEQ ID NO 6
<211> LENGTH: 933
<212> TYPE: DNA
<213> ORGANISM: Artificial Sequence
<220> FEATURE:
<223> OTHER INFORMATION: huCD200R-CD28tm construct

<400> SEQUENCE: 6

```
atgctgtgcc cttggagaac cgccaacctg ggcctgctgc tgatcctgac catcttcctg     60

gtggccgcca gcagcagcct gtgcatggac gagaagcaga tcacccagaa ctacagcaag    120
```

```
gtgctggccg aagtgaacac cagctggccc gtgaagatgg ccaccaacgc cgtgctgtgc    180

tgccctccta tcgccctgcg gaacctgatc atcatcacct gggagatcat cctgcggggc    240

cagcccagct gtaccaaggc ctaccggaaa gagacaaacg agacaaaaga aacaaactgc    300

accgacgagc ggatcacatg ggtgtccaga cccgaccaga acagcgacct gcagatcaga    360

cccgtggcca tcacccacga cggctactac cggtgcatca tggtcacccc cgatggcaac    420

ttccaccggg gataccatct gcaggtgctc gtgacccccg aagtgaccct gttccagaac    480

cggaacagaa ccgccgtgtg caaggccgtg gccggaaaac ctgccgccca gatctcttgg    540

atccccgagg gcgattgcgc caccaagcag gaatactggt ccaacggcac cgtgaccgtg    600

aagtccacct gtcactggga ggtgcacaac gtgtccaccg tgacatgcca cgtgtcccac    660

ctgaccggca acaagagcct gtacatcgag ctgctgcctg tgcctggcgc caagaagtcc    720

gccaagctgt tctgggtgct ggtggtggtc ggaggcgtgc tggcctgcta cagcctgctg    780

gtcaccgtgg ccttcatcat cttttgggtc cgcagcaagc ggagcagagg cggccacagc    840

gactacatga acatgacccc tagacggcct ggccccacca gaaagcacta ccagccctac    900

gcccctcccc gggactttgc cgcctacaga agc                                 933
```

<210> SEQ ID NO 7
<211> LENGTH: 942
<212> TYPE: DNA
<213> ORGANISM: Artificial Sequence
<220> FEATURE:
<223> OTHER INFORMATION: huCD200R-9aas-CD28Cys construct

<400> SEQUENCE: 7

```
atgctgtgcc cttggagaac cgccaacctg ggcctgctgc tgatcctgac catcttcctg     60

gtggccgcca gcagcagcct gtgcatggac gagaagcaga tcacccagaa ctacagcaag    120

gtgctggccg aagtgaacac cagctggccc gtgaagatgg ccaccaacgc cgtgctgtgc    180

tgccctccta tcgccctgcg gaacctgatc atcatcacct gggagatcat cctgcggggc    240

cagcccagct gtaccaaggc ctaccggaaa gagacaaacg agacaaaaga aacaaactgc    300

accgacgagc ggatcacatg ggtgtccaga cccgaccaga acagcgacct gcagatcaga    360

cccgtggcca tcacccacga cggctactac cggtgcatca tggtcacccc cgatggcaac    420

ttccaccggg gataccatct gcaggtgctc gtgacccccg aagtgaccct gttccagaac    480

cggaacagaa ccgccgtgtg caaggccgtg gccggaaaac ctgccgccca gatctcttgg    540

atccccgagg gcgattgcgc caccaagcag gaatactggt ccaacggcac cgtgaccgtg    600

aagtccacct gtcactggga ggtgcacaac gtgtccaccg tgacatgcca cgtgtcccac    660

ctgaccggca acaagagcct gtacatcgag ctgctgcctg tgtgtcccag ccctctgttt    720

cccggcccta gcaagccttt ctgggtgctg gtggtggtcg gaggcgtgct ggcctgctac    780

agcctgctgg tcaccgtggc cttcatcatc ttttgggtcc gcagcaagcg gagcagaggc    840

ggccacagcg actacatgaa catgacccct agacggcctg gccccaccag aaagcactac    900

cagccctacg cccctccccg ggactttgcc gcctacagaa gc                       942
```

<210> SEQ ID NO 8
<211> LENGTH: 702
<212> TYPE: DNA
<213> ORGANISM: Artificial Sequence
<220> FEATURE:
<223> OTHER INFORMATION: huCD200R-9aas portion of extracellular domain

<400> SEQUENCE: 8

```
atgctgtgcc cttggagaac cgccaacctg ggcctgctgc tgatcctgac catcttcctg     60

gtggccgcca gcagcagcct gtgcatggac gagaagcaga tcacccagaa ctacagcaag    120

gtgctggccg aagtgaacac cagctggccc gtgaagatgg ccaccaacgc cgtgctgtgc    180

tgccctccta tcgccctgcg gaacctgatc atcatcacct gggagatcat cctgcggggc    240

cagcccagct gtaccaaggc ctaccggaaa gagacaaacg agacaaaaga aacaaactgc    300

accgacgagc ggatcacatg ggtgtccaga cccgaccaga acagcgacct gcagatcaga    360

cccgtggcca tcacccacga cggctactac cggtgcatca tggtcacccc cgatggcaac    420

ttccaccggg gataccatct gcaggtgctc gtgacccccg aagtgaccct gttccagaac    480

cggaacagaa ccgccgtgtg caaggccgtg gccggaaaac ctgccgccca gatctcttgg    540

atccccgagg gcgattgcgc caccaagcag gaatactggt ccaacggcac cgtgaccgtg    600

aagtccacct gtcactggga ggtgcacaac gtgtccaccg tgacatgcca cgtgtcccac    660

ctgaccggca acaagagcct gtacatcgag ctgctgcctg tg                       702
```

<210> SEQ ID NO 9
<211> LENGTH: 36
<212> TYPE: DNA
<213> ORGANISM: Artificial Sequence
<220> FEATURE:
<223> OTHER INFORMATION: CD28Cys multimerization domain

<400> SEQUENCE: 9

```
tgtcccagcc ctctgtttcc cggccctagc aagcct                               36
```

<210> SEQ ID NO 10
<211> LENGTH: 933
<212> TYPE: DNA
<213> ORGANISM: Artificial Sequence
<220> FEATURE:
<223> OTHER INFORMATION: huCD200R-12aas-CD28Cys construct

<400> SEQUENCE: 10

```
atgctgtgcc cttggagaac cgccaacctg ggcctgctgc tgatcctgac catcttcctg     60

gtggccgcca gcagcagcct gtgcatggac gagaagcaga tcacccagaa ctacagcaag    120

gtgctggccg aagtgaacac cagctggccc gtgaagatgg ccaccaacgc cgtgctgtgc    180

tgccctccta tcgccctgcg gaacctgatc atcatcacct gggagatcat cctgcggggc    240

cagcccagct gtaccaaggc ctaccggaaa gagacaaacg agacaaaaga aacaaactgc    300

accgacgagc ggatcacatg ggtgtccaga cccgaccaga acagcgacct gcagatcaga    360

cccgtggcca tcacccacga cggctactac cggtgcatca tggtcacccc cgatggcaac    420

ttccaccggg gataccatct gcaggtgctc gtgacccccg aagtgaccct gttccagaac    480

cggaacagaa ccgccgtgtg caaggccgtg gccggaaaac ctgccgccca gatctcttgg    540

atccccgagg gcgattgcgc caccaagcag gaatactggt ccaacggcac cgtgaccgtg    600

aagtccacct gtcactggga ggtgcacaac gtgtccaccg tgacatgcca cgtgtcccac    660

ctgaccggca acaagagcct gtacatcgag ctgtgtccca gccctctgtt tcccggccct    720

agcaagcctt tctgggtgct ggtggtggtc ggaggcgtgc tggcctgcta cagcctgctg    780

gtcaccgtgg ccttcatcat cttttgggtc cgcagcaagc ggagcagagg cggccacagc    840

gactacatga acatgacccc tagacggcct ggccccacca gaaagcacta ccagccctac    900

gcccctcccc gggactttgc cgcctacaga agc                                 933
```

<210> SEQ ID NO 11
<211> LENGTH: 693
<212> TYPE: DNA
<213> ORGANISM: Artificial Sequence
<220> FEATURE:
<223> OTHER INFORMATION: huCD200R-12aas portion of extracellular domain

<400> SEQUENCE: 11
atgctgtgcc cttggagaac cgccaacctg ggcctgctgc tgatcctgac catcttcctg 60
gtggccgcca gcagcagcct gtgcatggac gagaagcaga tcacccagaa ctacagcaag 120
gtgctggccg aagtgaacac cagctggccc gtgaagatgg ccaccaacgc cgtgctgtgc 180
tgccctccta tcgccctgcg gaacctgatc atcatcacct gggagatcat cctgcggggc 240
cagcccagct gtaccaaggc ctaccggaaa gagacaaacg agacaaaaga aacaaactgc 300
accgacgagc ggatcacatg ggtgtccaga cccgaccaga acagcgacct gcagatcaga 360
cccgtggcca tcacccacga cggctactac cggtgcatca tggtcacccc cgatggcaac 420
ttccaccggg gataccatct gcaggtgctc gtgacccccg aagtgaccct gttccagaac 480
cggaacagaa ccgccgtgtg caaggccgtg gccggaaaac ctgccgccca gatctcttgg 540
atccccgagg gcgattgcgc caccaagcag gaatactggt ccaacggcac cgtgaccgtg 600
aagtccacct gtcactggga ggtgcacaac gtgtccaccg tgacatgcca cgtgtcccac 660
ctgaccggca acaagagcct gtacatcgag ctg 693

<210> SEQ ID NO 12
<211> LENGTH: 945
<212> TYPE: DNA
<213> ORGANISM: Artificial Sequence
<220> FEATURE:
<223> OTHER INFORMATION: huCD200R-9aas-CD28Cys tm-41BBic construct

<400> SEQUENCE: 12
atgctgtgcc cttggagaac cgccaacctg ggcctgctgc tgatcctgac catcttcctg 60
gtggccgcca gcagcagcct gtgcatggac gagaagcaga tcacccagaa ctacagcaag 120
gtgctggccg aagtgaacac cagctggccc gtgaagatgg ccaccaacgc cgtgctgtgc 180
tgccctccta tcgccctgcg gaacctgatc atcatcacct gggagatcat cctgcggggc 240
cagcccagct gtaccaaggc ctaccggaaa gagacaaacg agacaaaaga aacaaactgc 300
accgacgagc ggatcacatg ggtgtccaga cccgaccaga acagcgacct gcagatcaga 360
cccgtggcca tcacccacga cggctactac cggtgcatca tggtcacccc cgatggcaac 420
ttccaccggg gataccatct gcaggtgctc gtgacccccg aagtgaccct gttccagaac 480
cggaacagaa ccgccgtgtg caaggccgtg gccggaaaac ctgccgccca gatctcttgg 540
atccccgagg gcgattgcgc caccaagcag gaatactggt ccaacggcac cgtgaccgtg 600
aagtccacct gtcactggga ggtgcacaac gtgtccaccg tgacatgcca cgtgtcccac 660
ctgaccggca acaagagcct gtacatcgag ctgctgcctg tgtgtcccag ccctctgttt 720
cccggcccta gcaagccttt ctgggtgctg gtggtggtcg gaggcgtgct ggcctgctac 780
agcctgctgg tcaccgtggc cttcatcatc ttttgggtca agcggggcag aaagaagctg 840
ctgtacatct tcaagcagcc tttcatgcgg cccgtgcaga ccacccagga agaggacggc 900
tgctcctgca gattccccga ggaagaagaa ggcggctgcg agctg 945

<210> SEQ ID NO 13
<211> LENGTH: 126

<212> TYPE: DNA
<213> ORGANISM: Artificial Sequence
<220> FEATURE:
<223> OTHER INFORMATION: 4-1BB intracellular component

<400> SEQUENCE: 13
aagcggggca gaaagaagct gctgtacatc ttcaagcagc ctttcatgcg gcccgtgcag 60
accacccagg aagaggacgg ctgctcctgc agattccccg aggaagaaga aggcggctgc 120
gagctg 126

<210> SEQ ID NO 14
<211> LENGTH: 936
<212> TYPE: DNA
<213> ORGANISM: Artificial Sequence
<220> FEATURE:
<223> OTHER INFORMATION: huCD200R-12aas-CD28Cys tm-41BBic construct

<400> SEQUENCE: 14
atgctgtgcc cttggagaac cgccaacctg ggcctgctgc tgatcctgac catcttcctg 60
gtggccgcca gcagcagcct gtgcatggac gagaagcaga tcacccagaa ctacagcaag 120
gtgctggccg aagtgaacac cagctggccc gtgaagatgg ccaccaacgc cgtgctgtgc 180
tgccctccta tcgccctgcg gaacctgatc atcatcacct gggagatcat cctgcggggc 240
cagcccagct gtaccaaggc ctaccggaaa gagacaaacg agacaaaaga aacaaactgc 300
accgacgagc ggatcacatg ggtgtccaga cccgaccaga acagcgacct gcagatcaga 360
cccgtggcca tcacccacga cggctactac cggtgcatca tggtcacccc cgatggcaac 420
ttccaccggg gataccatct gcaggtgctc gtgacccccg aagtgaccct gttccagaac 480
cggaacagaa ccgccgtgtg caaggccgtg gccggaaaac ctgccgccca gatctcttgg 540
atccccgagg gcgattgcgc caccaagcag gaatactggt ccaacggcac cgtgaccgtg 600
aagtccacct gtcactggga ggtgcacaac gtgtccaccg tgacatgcca cgtgtcccac 660
ctgaccggca acaagagcct gtacatcgag ctgtgtccca gccctctgtt tcccggccct 720
agcaagcctt tctgggtgct ggtggtggtc ggaggcgtgc tggcctgcta cagcctgctg 780
gtcaccgtgg ccttcatcat cttttgggtc aagcggggca gaaagaagct gctgtacatc 840
ttcaagcagc ctttcatgcg gcccgtgcag accacccagg aagaggacgg ctgctcctgc 900
agattccccg aggaagaaga aggcggctgc gagctg 936

<210> SEQ ID NO 15
<211> LENGTH: 1059
<212> TYPE: DNA
<213> ORGANISM: Artificial Sequence
<220> FEATURE:
<223> OTHER INFORMATION: huCD200R-12aas-CD28Cys tm ic-41BBic construct

<400> SEQUENCE: 15
atgctgtgcc cttggagaac cgccaacctg ggcctgctgc tgatcctgac catcttcctg 60
gtggccgcca gcagcagcct gtgcatggac gagaagcaga tcacccagaa ctacagcaag 120
gtgctggccg aagtgaacac cagctggccc gtgaagatgg ccaccaacgc cgtgctgtgc 180
tgccctccta tcgccctgcg gaacctgatc atcatcacct gggagatcat cctgcggggc 240
cagcccagct gtaccaaggc ctaccggaaa gagacaaacg agacaaaaga aacaaactgc 300
accgacgagc ggatcacatg ggtgtccaga cccgaccaga acagcgacct gcagatcaga 360
cccgtggcca tcacccacga cggctactac cggtgcatca tggtcacccc cgatggcaac 420

```
ttccaccggg gataccatct gcaggtgctc gtgacccccg aagtgaccct gttccagaac    480
cggaacagaa ccgccgtgtg caaggccgtg gccggaaaac ctgccgccca gatctcttgg    540
atccccgagg gcgattgcgc caccaagcag gaatactggt ccaacggcac cgtgaccgtg    600
aagtccacct gtcactggga ggtgcacaac gtgtccaccg tgacatgcca cgtgtcccac    660
ctgaccggca acaagagcct gtacatcgag ctgtgtccca gccctctgtt tcccggccct    720
agcaagcctt tctgggtgct ggtggtggtc ggaggcgtgc tggcctgcta cagcctgctg    780
gtcaccgtgg ccttcatcat cttttgggtc cgcagcaagc ggagcagagg cggccacagc    840
gactacatga acatgacccc tagacggcct ggccccacca gaaagcacta ccagccctac    900
gcccctcccc gggactttgc cgcctacaga agcaagcggg gcagaaagaa gctgctgtac    960
atcttcaagc agcctttcat gcggcccgtg cagaccaccc aggaagagga cggctgctcc   1020
tgcagattcc ccgaggaaga agaaggcggc tgcgagctg                          1059
```

<210> SEQ ID NO 16
<211> LENGTH: 1305
<212> TYPE: DNA
<213> ORGANISM: Artificial Sequence
<220> FEATURE:
<223> OTHER INFORMATION: huSIRPalphatm-CD28 construct

<400> SEQUENCE: 16

```
atggaacctg ccggacctgc tcctggcaga ctgggacctc tgctgtgtct gctgctggcc     60
gcctcttgtg cttggagcgg agtggctggc gaagaggaac tgcaagtgat ccagcccgac    120
aagagcgtgc tggtggccgc tggcgaaacc gccaccctga gatgtacagc caccagcctg    180
atccccgtgg gccccatcca gtggtttaga ggcgctggcc ctggcagaga gctgatctac    240
aaccagaaag agggccactt ccccagagtg accaccgtgt ccgacctgac caagcggaac    300
aacatggact tcagcatccg gatcggcaac atcacccctg ccgatgccgg cacctactac    360
tgcgtgaagt tccggaaggg cagccccgac gacgtggaat tcaaaagcgg agccggcacc    420
gagctgagcg tgcgggctaa accttctgcc cctgtggtgt ctggacctgc cgccagagct    480
acacctcagc acaccgtgtc ttttacctgc gagagccacg gcttcagccc cagagacatc    540
accctgaagt ggttcaagaa cggcaacgag ctgtccgact tccagaccaa cgtggaccct    600
gtgggcgaga gcgtgtccta cagcatccac agcaccgcca aggtggtgct gacccgcgaa    660
gatgtgcaca gccaagtgat ctgcgaggtg gcccacgtga cactgcaggg cgatcctctg    720
agaggaaccg ccaacctgtc cgagacaatc agagtgcccc ccaccctgga agtgacccag    780
cagcctgtgc gggccgagaa ccaagtgaac gtgacctgcc aagtgcggaa gttctacccc    840
cagcggctgc agctgacctg gctggaaaac ggcaatgtgt cccggaccga gacagccagc    900
accgtgaccg agaacaagga tggcacctac aattggatga gctggctgct cgtgaacgtg    960
tccgcccacc gggacgatgt gaagctgaca tgccaggtgg aacacgacgg ccagcctgcc   1020
gtgtccaaga gccacgatct gaaggtgtca gcccatccca aagagcaggg ctccaacaca   1080
gccgccgaga acaccggcag caacgagcgg aacatctaca tcgtcgtggg cgtcgtgtgc   1140
accctgctgg tggcactgct gatggccgct ctgtacctcg tgcgcagcaa gcggagcaga   1200
ggcggccaca gcgactacat gaacatgacc cctagacggc ctggccccac cagaaagcac   1260
taccagccct acgcccctcc ccgggacttt gccgcctaca gaagc                   1305
```

<210> SEQ ID NO 17
<211> LENGTH: 1119

<212> TYPE: DNA
<213> ORGANISM: Artificial Sequence
<220> FEATURE:
<223> OTHER INFORMATION: huSIRP alpha entire extracellular domain

<400> SEQUENCE: 17

```
atggaacctg ccggacctgc tcctggcaga ctgggacctc tgctgtgtct gctgctggcc      60

gcctcttgtg cttggagcgg agtggctggc gaagaggaac tgcaagtgat ccagcccgac     120

aagagcgtgc tggtggccgc tggcgaaacc gccaccctga gatgtacagc caccagcctg     180

atccccgtgg gccccatcca gtggtttaga ggcgctggcc ctggcagaga gctgatctac     240

aaccagaaag agggccactt ccccagagtg accaccgtgt ccgacctgac caagcggaac     300

aacatggact tcagcatccg gatcggcaac atcacccctg ccgatgccgg cacctactac     360

tgcgtgaagt tccggaaggg cagccccgac gacgtggaat tcaaaagcgg agccggcacc     420

gagctgagcg tgcgggctaa accttctgcc cctgtggtgt ctggacctgc cgccagagct     480

acacctcagc acaccgtgtc ttttacctgc gagagccacg gcttcagccc cagagacatc     540

accctgaagt ggttcaagaa cggcaacgag ctgtccgact tccagaccaa cgtggaccct     600

gtgggcgaga gcgtgtccta cagcatccac agcaccgcca aggtggtgct gacccgcgaa     660

gatgtgcaca gccaagtgat ctgcgaggtg gcccacgtga cactgcaggg cgatcctctg     720

agaggaaccg ccaacctgtc cgagacaatc agagtgcccc ccaccctgga agtgacccag     780

cagcctgtgc gggccgagaa ccaagtgaac gtgacctgcc aagtgcggaa gttctacccc     840

cagcggctgc agctgacctg gctggaaaac ggcaatgtgt cccggaccga gacagccagc     900

accgtgaccg agaacaagga tggcacctac aattggatga gctggctgct cgtgaacgtg     960

tccgcccacc gggacgatgt gaagctgaca tgccaggtgg aacacgacgg ccagcctgcc    1020

gtgtccaaga gccacgatct gaaggtgtca gcccatccca aagagcaggg ctccaacaca    1080

gccgccgaga acaccggcag caacgagcgg aacatctac                           1119
```

<210> SEQ ID NO 18
<211> LENGTH: 63
<212> TYPE: DNA
<213> ORGANISM: Artificial Sequence
<220> FEATURE:
<223> OTHER INFORMATION: huSIRP alpha  transmembrane domain

<400> SEQUENCE: 18

```
atcgtcgtgg gcgtcgtgtg caccctgctg gtggcactgc tgatggccgc tctgtacctc      60

gtg                                                                    63
```

<210> SEQ ID NO 19
<211> LENGTH: 1323
<212> TYPE: DNA
<213> ORGANISM: Artificial Sequence
<220> FEATURE:
<223> OTHER INFORMATION: huSIRP alpha-CD28tm construct

<400> SEQUENCE: 19

```
atggaacctg ccggacctgc tcctggcaga ctgggacctc tgctgtgtct gctgctggcc      60

gcctcttgtg cttggagcgg agtggctggc gaagaggaac tgcaagtgat ccagcccgac     120

aagagcgtgc tggtggccgc tggcgaaacc gccaccctga gatgtacagc caccagcctg     180

atccccgtgg gccccatcca gtggtttaga ggcgctggcc ctggcagaga gctgatctac     240

aaccagaaag agggccactt ccccagagtg accaccgtgt ccgacctgac caagcggaac     300
```

```
aacatggact tcagcatccg gatcggcaac atcacccctg ccgatgccgg cacctactac    360

tgcgtgaagt tccggaaggg cagccccgac gacgtggaat tcaaaagcgg agccggcacc    420

gagctgagcg tgcgggctaa accttctgcc cctgtggtgt ctggacctgc cgccagagct    480

acacctcagc acaccgtgtc ttttacctgc gagagccacg gcttcagccc cagagacatc    540

accctgaagt ggttcaagaa cggcaacgag ctgtccgact tccagaccaa cgtggaccct    600

gtgggcgaga gcgtgtccta cagcatccac agcaccgcca aggtggtgct gacccgcgaa    660

gatgtgcaca gccaagtgat ctgcgaggtg gcccacgtga cactgcaggg cgatcctctg    720

agaggaaccg ccaacctgtc cgagacaatc agagtgcccc ccaccctgga agtgacccag    780

cagcctgtgc gggccgagaa ccaagtgaac gtgacctgcc aagtgcggaa gttctacccc    840

cagcggctgc agctgacctg gctggaaaac ggcaatgtgt cccggaccga gacagccagc    900

accgtgaccg agaacaagga tggcacctac aattggatga gctggctgct cgtgaacgtg    960

tccgcccacc gggacgatgt gaagctgaca tgccaggtgg aacacgacgg ccagcctgcc   1020

gtgtccaaga gccacgatct gaaggtgtca gcccatccca aagagcaggg ctccaacaca   1080

gccgccgaga acaccggcag caacgagcgg aacatctact tctgggtgct ggtggtggtc   1140

ggaggcgtgc tggcctgcta cagcctgctg gtcaccgtgg ccttcatcat cttttgggtc   1200

cgcagcaagc ggagcagagg cggccacagc gactacatga acatgacccc tagacggcct   1260

ggccccacca gaaagcacta ccagccctac gcccctcccc gggactttgc cgcctacaga   1320

agc                                                                 1323
```

<210> SEQ ID NO 20
<211> LENGTH: 1323
<212> TYPE: DNA
<213> ORGANISM: Artificial Sequence
<220> FEATURE:
<223> OTHER INFORMATION: huSIRP alpha 12aas-CD28Cys construct

<400> SEQUENCE: 20

```
atggaacctg ccggacctgc tcctggcaga ctgggacctc tgctgtgtct gctgctggcc     60

gcctcttgtg cttggagcgg agtggctggc gaagaggaac tgcaagtgat ccagcccgac    120

aagagcgtgc tggtggccgc tggcgaaacc gccaccctga gatgtacagc caccagcctg    180

atccccgtgg gccccatcca gtggtttaga ggcgctggcc ctggcagaga gctgatctac    240

aaccagaaag agggccactt ccccagagtg accaccgtgt ccgacctgac caagcggaac    300

aacatggact tcagcatccg gatcggcaac atcacccctg ccgatgccgg cacctactac    360

tgcgtgaagt tccggaaggg cagccccgac gacgtggaat tcaaaagcgg agccggcacc    420

gagctgagcg tgcgggctaa accttctgcc cctgtggtgt ctggacctgc cgccagagct    480

acacctcagc acaccgtgtc ttttacctgc gagagccacg gcttcagccc cagagacatc    540

accctgaagt ggttcaagaa cggcaacgag ctgtccgact tccagaccaa cgtggaccct    600

gtgggcgaga gcgtgtccta cagcatccac agcaccgcca aggtggtgct gacccgcgaa    660

gatgtgcaca gccaagtgat ctgcgaggtg gcccacgtga cactgcaggg cgatcctctg    720

agaggaaccg ccaacctgtc cgagacaatc agagtgcccc ccaccctgga agtgacccag    780

cagcctgtgc gggccgagaa ccaagtgaac gtgacctgcc aagtgcggaa gttctacccc    840

cagcggctgc agctgacctg gctggaaaac ggcaatgtgt cccggaccga gacagccagc    900

accgtgaccg agaacaagga tggcacctac aattggatga gctggctgct cgtgaacgtg    960

tccgcccacc gggacgatgt gaagctgaca tgccaggtgg aacacgacgg ccagcctgcc   1020
```

```
gtgtccaaga gccacgatct gaaggtgtca gcccatccca aagagcaggg ctccaacaca   1080

gcctgtccca gccctctgtt tcccggccct agcaagcctt tctgggtgct ggtggtggtc   1140

ggaggcgtgc tggcctgcta cagcctgctg gtcaccgtgg ccttcatcat cttttgggtc   1200

cgcagcaagc ggagcagagg cggccacagc gactacatga acatgacccc tagacggcct   1260

ggccccacca gaaagcacta ccagccctac gcccctcccc gggactttgc cgcctacaga   1320

agc                                                                 1323
```

<210> SEQ ID NO 21
<211> LENGTH: 1083
<212> TYPE: DNA
<213> ORGANISM: Artificial Sequence
<220> FEATURE:
<223> OTHER INFORMATION: huSIRP alpha 12aas portion of extracellular domain

<400> SEQUENCE: 21

```
atggaacctg ccggacctgc tcctggcaga ctgggacctc tgctgtgtct gctgctggcc     60

gcctcttgtg cttggagcgg agtggctggc gaagaggaac tgcaagtgat ccagcccgac    120

aagagcgtgc tggtggccgc tggcgaaacc gccaccctga gatgtacagc caccagcctg    180

atccccgtgg gccccatcca gtggtttaga ggcgctggcc ctggcagaga gctgatctac    240

aaccagaaag agggccactt ccccagagtg accaccgtgt ccgacctgac caagcggaac    300

aacatggact tcagcatccg gatcggcaac atcacccctg ccgatgccgg cacctactac    360

tgcgtgaagt tccggaaggg cagccccgac gacgtggaat tcaaaagcgg agccggcacc    420

gagctgagcg tgcgggctaa accttctgcc cctgtggtgt ctggacctgc cgccagagct    480

acacctcagc acaccgtgtc ttttacctgc gagagccacg gcttcagccc cagagacatc    540

accctgaagt ggttcaagaa cggcaacgag ctgtccgact tccagaccaa cgtggaccct    600

gtgggcgaga gcgtgtccta cagcatccac agcaccgcca aggtggtgct gacccgcgaa    660

gatgtgcaca gccaagtgat ctgcgaggtg gcccacgtga cactgcaggg cgatcctctg    720

agaggaaccg ccaacctgtc cgagacaatc agagtgcccc ccaccctgga agtgacccag    780

cagcctgtgc gggccgagaa ccaagtgaac gtgacctgcc aagtgcggaa gttctacccc    840

cagcggctgc agctgacctg gctggaaaac ggcaatgtgt cccggaccga gacagccagc    900

accgtgaccg agaacaagga tggcacctac aattggatga gctggctgct cgtgaacgtg    960

tccgcccacc gggacgatgt gaagctgaca tgccaggtgg aacacgacgg ccagcctgcc   1020

gtgtccaaga gccacgatct gaaggtgtca gcccatccca aagagcaggg ctccaacaca   1080

gcc                                                                 1083
```

<210> SEQ ID NO 22
<211> LENGTH: 1326
<212> TYPE: DNA
<213> ORGANISM: Artificial Sequence
<220> FEATURE:
<223> OTHER INFORMATION: huSIRP alpha-12aas-CD28Cys tm-41BBic construct

<400> SEQUENCE: 22

```
atggaacctg ccggacctgc tcctggcaga ctgggacctc tgctgtgtct gctgctggcc     60

gcctcttgtg cttggagcgg agtggctggc gaagaggaac tgcaagtgat ccagcccgac    120

aagagcgtgc tggtggccgc tggcgaaacc gccaccctga gatgtacagc caccagcctg    180

atccccgtgg gccccatcca gtggtttaga ggcgctggcc ctggcagaga gctgatctac    240
```

```
aaccagaaag agggccactt ccccagagtg accaccgtgt ccgacctgac caagcggaac    300

aacatggact tcagcatccg gatcggcaac atcacccctg ccgatgccgg cacctactac    360

tgcgtgaagt tccggaaggg cagccccgac gacgtggaat tcaaaagcgg agccggcacc    420

gagctgagcg tgcgggctaa accttctgcc cctgtggtgt ctggacctgc cgccagagct    480

acacctcagc acaccgtgtc ttttacctgc gagagccacg gcttcagccc cagagacatc    540

accctgaagt ggttcaagaa cggcaacgag ctgtccgact tccagaccaa cgtggaccct    600

gtgggcgaga gcgtgtccta cagcatccac agcaccgcca aggtggtgct gacccgcgaa    660

gatgtgcaca gccaagtgat ctgcgaggtg gcccacgtga cactgcaggg cgatcctctg    720

agaggaaccg ccaacctgtc cgagacaatc agagtgcccc ccaccctgga agtgacccag    780

cagcctgtgc gggccgagaa ccaagtgaac gtgacctgcc aagtgcggaa gttctacccc    840

cagcggctgc agctgacctg gctggaaaac ggcaatgtgt cccggaccga gacagccagc    900

accgtgaccg agaacaagga tggcacctac aattggatga gctggctgct cgtgaacgtg    960

tccgcccacc gggacgatgt gaagctgaca tgccaggtgg aacacgacgg ccagcctgcc   1020

gtgtccaaga gccacgatct gaaggtgtca gcccatccca aagagcaggg ctccaacaca   1080

gcctgtccca gccctctgtt tcccggccct agcaagcctt tctgggtgct ggtggtggtc   1140

ggaggcgtgc tggcctgcta cagcctgctg gtcaccgtgg ccttcatcat cttttgggtc   1200

aagcggggca gaaagaagct gctgtacatc ttcaagcagc ctttcatgcg gcccgtgcag   1260

accacccagg aagaggacgg ctgctcctgc agattccccg aggaagaaga aggcggctgc   1320

gagctg                                                              1326
```

```
<210> SEQ ID NO 23
<211> LENGTH: 1449
<212> TYPE: DNA
<213> ORGANISM: Artificial Sequence
<220> FEATURE:
<223> OTHER INFORMATION: huSIRP alpha-12aas-CD28Cys tm ic-41BBic
      construct

<400> SEQUENCE: 23

atggaacctg ccggacctgc tcctggcaga ctgggacctc tgctgtgtct gctgctggcc     60

gcctcttgtg cttggagcgg agtggctggc gaagaggaac tgcaagtgat ccagcccgac    120

aagagcgtgc tggtggccgc tggcgaaacc gccaccctga gatgtacagc caccagcctg    180

atccccgtgg gccccatcca gtggtttaga ggcgctggcc ctggcagaga gctgatctac    240

aaccagaaag agggccactt ccccagagtg accaccgtgt ccgacctgac caagcggaac    300

aacatggact tcagcatccg gatcggcaac atcacccctg ccgatgccgg cacctactac    360

tgcgtgaagt tccggaaggg cagccccgac gacgtggaat tcaaaagcgg agccggcacc    420

gagctgagcg tgcgggctaa accttctgcc cctgtggtgt ctggacctgc cgccagagct    480

acacctcagc acaccgtgtc ttttacctgc gagagccacg gcttcagccc cagagacatc    540

accctgaagt ggttcaagaa cggcaacgag ctgtccgact tccagaccaa cgtggaccct    600

gtgggcgaga gcgtgtccta cagcatccac agcaccgcca aggtggtgct gacccgcgaa    660

gatgtgcaca gccaagtgat ctgcgaggtg gcccacgtga cactgcaggg cgatcctctg    720

agaggaaccg ccaacctgtc cgagacaatc agagtgcccc ccaccctgga agtgacccag    780

cagcctgtgc gggccgagaa ccaagtgaac gtgacctgcc aagtgcggaa gttctacccc    840

cagcggctgc agctgacctg gctggaaaac ggcaatgtgt cccggaccga gacagccagc    900
```

```
accgtgaccg agaacaagga tggcacctac aattggatga gctggctgct cgtgaacgtg    960

tccgcccacc gggacgatgt gaagctgaca tgccaggtgg aacacgacgg ccagcctgcc   1020

gtgtccaaga gccacgatct gaaggtgtca gcccatccca aagagcaggg ctccaacaca   1080

gcctgtccca gccctctgtt tcccggccct agcaagcctt tctgggtgct ggtggtggtc   1140

ggaggcgtgc tggcctgcta cagcctgctg gtcaccgtgg ccttcatcat cttttgggtc   1200

cgcagcaagc ggagcagagg cggccacagc gactacatga acatgacccc tagacggcct   1260

ggccccacca gaaagcacta ccagccctac gcccctcccc gggactttgc cgcctacaga   1320

agcaagcggg gcagaaagaa gctgctgtac atcttcaagc agcctttcat gcggcccgtg   1380

cagaccaccc aggaagagga cggctgctcc tgcagattcc ccgaggaaga agaaggcggc   1440

tgcgagctg                                                           1449
```

<210> SEQ ID NO 24
<211> LENGTH: 305
<212> TYPE: PRT
<213> ORGANISM: Artificial Sequence
<220> FEATURE:
<223> OTHER INFORMATION: huCD200Rtm-CD28 protein

<400> SEQUENCE: 24

```
Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu Tyr Ile Pro Tyr Ile Ile Leu Thr Ile Ile Ile Leu Thr
                245                 250                 255
```

```
Ile Val Gly Phe Ile Trp Leu Leu Arg Ser Lys Arg Ser Arg Gly Gly
            260                 265                 270

His Ser Asp Tyr Met Asn Met Thr Pro Arg Arg Pro Gly Pro Thr Arg
        275                 280                 285

Lys His Tyr Gln Pro Tyr Ala Pro Pro Arg Asp Phe Ala Ala Tyr Arg
    290                 295                 300

Ser
305


<210> SEQ ID NO 25
<211> LENGTH: 243
<212> TYPE: PRT
<213> ORGANISM: Artificial Sequence
<220> FEATURE:
<223> OTHER INFORMATION: huCD200R entire extracellular domain

<400> SEQUENCE: 25

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu


<210> SEQ ID NO 26
<211> LENGTH: 21
<212> TYPE: PRT
<213> ORGANISM: Artificial Sequence
<220> FEATURE:
<223> OTHER INFORMATION: huCD200R transmembrane domain

<400> SEQUENCE: 26
```

```
Tyr Ile Pro Tyr Ile Ile Leu Thr Ile Ile Ile Leu Thr Ile Val Gly
1               5                   10                  15

Phe Ile Trp Leu Leu
            20


<210> SEQ ID NO 27
<211> LENGTH: 27
<212> TYPE: PRT
<213> ORGANISM: Artificial Sequence
<220> FEATURE:
<223> OTHER INFORMATION: CD28 transmembrane domain protein

<400> SEQUENCE: 27

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 28
<211> LENGTH: 41
<212> TYPE: PRT
<213> ORGANISM: Artificial Sequence
<220> FEATURE:
<223> OTHER INFORMATION: CD28 intracellular domain protein

<400> SEQUENCE: 28

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 29
<211> LENGTH: 311
<212> TYPE: PRT
<213> ORGANISM: Artificial Sequence
<220> FEATURE:
<223> OTHER INFORMATION: huCD200R-CD28tm protein

<400> SEQUENCE: 29

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
```

```
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu Phe Trp Val Leu Val Val Val Gly Gly Val Leu Ala Cys
                245                 250                 255

Tyr Ser Leu Leu Val Thr Val Ala Phe Ile Ile Phe Trp Val Arg Ser
            260                 265                 270

Lys Arg Ser Arg Gly Gly His Ser Asp Tyr Met Asn Met Thr Pro Arg
        275                 280                 285

Arg Pro Gly Pro Thr Arg Lys His Tyr Gln Pro Tyr Ala Pro Pro Arg
    290                 295                 300

Asp Phe Ala Ala Tyr Arg Ser
305                 310


<210> SEQ ID NO 30
<211> LENGTH: 314
<212> TYPE: PRT
<213> ORGANISM: Artificial Sequence
<220> FEATURE:
<223> OTHER INFORMATION: huCD200R-9aas-CD28Cys protein

<400> SEQUENCE: 30

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
```

```
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Cys Pro Ser Pro Leu Phe
225                 230                 235                 240

Pro Gly Pro Ser Lys Pro Phe Trp Val Leu Val Val Val Gly Gly Val
                245                 250                 255

Leu Ala Cys Tyr Ser Leu Leu Val Thr Val Ala Phe Ile Ile Phe Trp
            260                 265                 270

Val Arg Ser Lys Arg Ser Arg Gly Gly His Ser Asp Tyr Met Asn Met
        275                 280                 285

Thr Pro Arg Arg Pro Gly Pro Thr Arg Lys His Tyr Gln Pro Tyr Ala
    290                 295                 300

Pro Pro Arg Asp Phe Ala Ala Tyr Arg Ser
305                 310


<210> SEQ ID NO 31
<211> LENGTH: 234
<212> TYPE: PRT
<213> ORGANISM: Artificial Sequence
<220> FEATURE:
<223> OTHER INFORMATION: huCD200R-9aas protein

<400> SEQUENCE: 31

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val
225                 230
```

```
<210> SEQ ID NO 32
<211> LENGTH: 12
<212> TYPE: PRT
<213> ORGANISM: Artificial Sequence
<220> FEATURE:
<223> OTHER INFORMATION: CD28Cys (extracellular portion) protein

<400> SEQUENCE: 32

Cys Pro Ser Pro Leu Phe Pro Gly Pro Ser Lys Pro
1               5                   10


<210> SEQ ID NO 33
<211> LENGTH: 311
<212> TYPE: PRT
<213> ORGANISM: Artificial Sequence
<220> FEATURE:
<223> OTHER INFORMATION: huCD200R-12aas-CD28Cys protein

<400> SEQUENCE: 33

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Cys Pro Ser Pro Leu Phe Pro Gly Pro
225                 230                 235                 240

Ser Lys Pro Phe Trp Val Leu Val Val Val Gly Gly Val Leu Ala Cys
                245                 250                 255

Tyr Ser Leu Leu Val Thr Val Ala Phe Ile Ile Phe Trp Val Arg Ser
            260                 265                 270

Lys Arg Ser Arg Gly Gly His Ser Asp Tyr Met Asn Met Thr Pro Arg
        275                 280                 285

Arg Pro Gly Pro Thr Arg Lys His Tyr Gln Pro Tyr Ala Pro Pro Arg
    290                 295                 300
```

```
Asp Phe Ala Ala Tyr Arg Ser
305                 310


<210> SEQ ID NO 34
<211> LENGTH: 231
<212> TYPE: PRT
<213> ORGANISM: Artificial Sequence
<220> FEATURE:
<223> OTHER INFORMATION: huCD200R-12aas protein

<400> SEQUENCE: 34

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu
225                 230


<210> SEQ ID NO 35
<211> LENGTH: 315
<212> TYPE: PRT
<213> ORGANISM: Artificial Sequence
<220> FEATURE:
<223> OTHER INFORMATION: huCD200R-9aas-CD28Cys tm-41BBic protein

<400> SEQUENCE: 35

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60
```

```
Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Cys Pro Ser Pro Leu Phe
225                 230                 235                 240

Pro Gly Pro Ser Lys Pro Phe Trp Val Leu Val Val Val Gly Gly Val
                245                 250                 255

Leu Ala Cys Tyr Ser Leu Leu Val Thr Val Ala Phe Ile Ile Phe Trp
            260                 265                 270

Val Lys Arg Gly Arg Lys Lys Leu Leu Tyr Ile Phe Lys Gln Pro Phe
        275                 280                 285

Met Arg Pro Val Gln Thr Thr Gln Glu Glu Asp Gly Cys Ser Cys Arg
    290                 295                 300

Phe Pro Glu Glu Glu Glu Gly Gly Cys Glu Leu
305                 310                 315


<210> SEQ ID NO 36
<211> LENGTH: 42
<212> TYPE: PRT
<213> ORGANISM: Artificial Sequence
<220> FEATURE:
<223> OTHER INFORMATION: 4-1BB intracellular component protein

<400> SEQUENCE: 36

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 37
<211> LENGTH: 312
<212> TYPE: PRT
<213> ORGANISM: Artificial Sequence
<220> FEATURE:
<223> OTHER INFORMATION: huCD200R-12aas-CD28Cys tm-41BBic protein

<400> SEQUENCE: 37

Met Leu Cys Pro Trp Arg Thr Ala Asn Leu Gly Leu Leu Leu Ile Leu
```

```
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Cys Pro Ser Pro Leu Phe Pro Gly Pro
225                 230                 235                 240

Ser Lys Pro Phe Trp Val Leu Val Val Val Gly Gly Val Leu Ala Cys
                245                 250                 255

Tyr Ser Leu Leu Val Thr Val Ala Phe Ile Ile Phe Trp Val Lys Arg
            260                 265                 270

Gly Arg Lys Lys Leu Leu Tyr Ile Phe Lys Gln Pro Phe Met Arg Pro
        275                 280                 285

Val Gln Thr Thr Gln Glu Glu Asp Gly Cys Ser Cys Arg Phe Pro Glu
    290                 295                 300

Glu Glu Glu Gly Gly Cys Glu Leu
305                 310


<210> SEQ ID NO 38
<211> LENGTH: 353
<212> TYPE: PRT
<213> ORGANISM: Artificial Sequence
<220> FEATURE:
<223> OTHER INFORMATION: huCD200R-12aas-CD28Cys tm ic-41BBic protein

<400> SEQUENCE: 38

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
```

```
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Cys Pro Ser Pro Leu Phe Pro Gly Pro
225                 230                 235                 240

Ser Lys Pro Phe Trp Val Leu Val Val Val Gly Gly Val Leu Ala Cys
                245                 250                 255

Tyr Ser Leu Leu Val Thr Val Ala Phe Ile Ile Phe Trp Val Arg Ser
            260                 265                 270

Lys Arg Ser Arg Gly Gly His Ser Asp Tyr Met Asn Met Thr Pro Arg
        275                 280                 285

Arg Pro Gly Pro Thr Arg Lys His Tyr Gln Pro Tyr Ala Pro Pro Arg
    290                 295                 300

Asp Phe Ala Ala Tyr Arg Ser Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu


<210> SEQ ID NO 39
<211> LENGTH: 435
<212> TYPE: PRT
<213> ORGANISM: Artificial Sequence
<220> FEATURE:
<223> OTHER INFORMATION: huSIRP alpha tm-CD28 protein

<400> SEQUENCE: 39

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60
```

```
Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ser Lys Arg Ser Arg
385                 390                 395                 400

Gly Gly His Ser Asp Tyr Met Asn Met Thr Pro Arg Arg Pro Gly Pro
                405                 410                 415

Thr Arg Lys His Tyr Gln Pro Tyr Ala Pro Pro Arg Asp Phe Ala Ala
            420                 425                 430

Tyr Arg Ser
        435
```

<210> SEQ ID NO 40
<211> LENGTH: 373
<212> TYPE: PRT
<213> ORGANISM: Artificial Sequence
<220> FEATURE:

```
<223> OTHER INFORMATION: huSIRP alpha entire extracellular domain
      protein

<400> SEQUENCE: 40

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
    370

<210> SEQ ID NO 41
```

```
<211> LENGTH: 21
<212> TYPE: PRT
<213> ORGANISM: Artificial Sequence
<220> FEATURE:
<223> OTHER INFORMATION: huSIRP alpha transmembrane domain protein

<400> SEQUENCE: 41

Ile Val Val Gly Val Val Cys Thr Leu Leu Val Ala Leu Leu Met Ala
1               5                   10                  15

Ala Leu Tyr Leu Val
            20


<210> SEQ ID NO 42
<211> LENGTH: 441
<212> TYPE: PRT
<213> ORGANISM: Artificial Sequence
<220> FEATURE:
<223> OTHER INFORMATION: huSIRP alpha -CD28tm protein

<400> SEQUENCE: 42

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
```

```
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Phe Trp Val Leu Val Val Val Gly Gly Val Leu
    370                 375                 380

Ala Cys Tyr Ser Leu Leu Val Thr Val Ala Phe Ile Ile Phe Trp Val
385                 390                 395                 400

Arg Ser Lys Arg Ser Arg Gly Gly His Ser Asp Tyr Met Asn Met Thr
                405                 410                 415

Pro Arg Arg Pro Gly Pro Thr Arg Lys His Tyr Gln Pro Tyr Ala Pro
            420                 425                 430

Pro Arg Asp Phe Ala Ala Tyr Arg Ser
        435                 440


<210> SEQ ID NO 43
<211> LENGTH: 441
<212> TYPE: PRT
<213> ORGANISM: Artificial Sequence
<220> FEATURE:
<223> OTHER INFORMATION: huSIRP alpha-12aas-CD28Cys protein

<400> SEQUENCE: 43

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
```

```
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Cys Pro Ser Pro Leu Phe Pro
        355                 360                 365

Gly Pro Ser Lys Pro Phe Trp Val Leu Val Val Val Gly Gly Val Leu
    370                 375                 380

Ala Cys Tyr Ser Leu Leu Val Thr Val Ala Phe Ile Ile Phe Trp Val
385                 390                 395                 400

Arg Ser Lys Arg Ser Arg Gly Gly His Ser Asp Tyr Met Asn Met Thr
                405                 410                 415

Pro Arg Arg Pro Gly Pro Thr Arg Lys His Tyr Gln Pro Tyr Ala Pro
            420                 425                 430

Pro Arg Asp Phe Ala Ala Tyr Arg Ser
        435                 440


<210> SEQ ID NO 44
<211> LENGTH: 361
<212> TYPE: PRT
<213> ORGANISM: Artificial Sequence
<220> FEATURE:
<223> OTHER INFORMATION: huSIRP alpha-12aas protein

<400> SEQUENCE: 44

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
```

```
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala
        355                 360


<210> SEQ ID NO 45
<211> LENGTH: 442
<212> TYPE: PRT
<213> ORGANISM: Artificial Sequence
<220> FEATURE:
<223> OTHER INFORMATION: huSIRP alpha-12aas-CD28Cys tm-41BBic protein

<400> SEQUENCE: 45

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
```

```
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Cys Pro Ser Pro Leu Phe Pro
        355                 360                 365

Gly Pro Ser Lys Pro Phe Trp Val Leu Val Val Val Gly Gly Val Leu
    370                 375                 380

Ala Cys Tyr Ser Leu Leu Val Thr Val Ala Phe Ile Ile Phe Trp Val
385                 390                 395                 400

Lys Arg Gly Arg Lys Lys Leu Leu Tyr Ile Phe Lys Gln Pro Phe Met
                405                 410                 415

Arg Pro Val Gln Thr Thr Gln Glu Glu Asp Gly Cys Ser Cys Arg Phe
            420                 425                 430

Pro Glu Glu Glu Glu Gly Gly Cys Glu Leu
        435                 440


<210> SEQ ID NO 46
<211> LENGTH: 483
<212> TYPE: PRT
<213> ORGANISM: Artificial Sequence
<220> FEATURE:
<223> OTHER INFORMATION: huSIRP alpha-12aas-CD28Cys tm ic-41BBic protein

<400> SEQUENCE: 46

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
```

```
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Cys Pro Ser Pro Leu Phe Pro
        355                 360                 365

Gly Pro Ser Lys Pro Phe Trp Val Leu Val Val Val Gly Gly Val Leu
    370                 375                 380

Ala Cys Tyr Ser Leu Leu Val Thr Val Ala Phe Ile Ile Phe Trp Val
385                 390                 395                 400

Arg Ser Lys Arg Ser Arg Gly Gly His Ser Asp Tyr Met Asn Met Thr
                405                 410                 415

Pro Arg Arg Pro Gly Pro Thr Arg Lys His Tyr Gln Pro Tyr Ala Pro
            420                 425                 430

Pro Arg Asp Phe Ala Ala Tyr Arg Ser Lys Arg Gly Arg Lys Lys Leu
        435                 440                 445

Leu Tyr Ile Phe Lys Gln Pro Phe Met Arg Pro Val Gln Thr Thr Gln
    450                 455                 460

Glu Glu Asp Gly Cys Ser Cys Arg Phe Pro Glu Glu Glu Glu Gly Gly
465                 470                 475                 480
```

Cys Glu Leu

<210> SEQ ID NO 47
<211> LENGTH: 900
<212> TYPE: DNA
<213> ORGANISM: Artificial Sequence
<220> FEATURE:
<223> OTHER INFORMATION: muCD200Rtm-CD28

<400> SEQUENCE: 47

```
atgttctgct tctggcggac aagcgccctg gccgtgctgc tgatctgggg agtgtttgtg     60

gccggcagca gctgcaccga caagaaccag accacccaga acaacagcag cagccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480

agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660

aaccagagcc tgagcatcga gctgagcaga ggcggaaacc agtccctgag gccctacatc    720

ccttacatca tccccagcat catcatcctg atcatcatcg gctgcatctg cctgctgaac    780

agcagaagaa acagaggcgg ccagagcgac tacatgaaca tgacccccag aaggcctggc    840

ctgaccagaa agccctacca gccttacgcc cctgccagag acttcgccgc ctacagacct    900
```

<210> SEQ ID NO 48
<211> LENGTH: 918
<212> TYPE: DNA
<213> ORGANISM: Artificial Sequence
<220> FEATURE:
<223> OTHER INFORMATION: muCD200R-CD28tm

<400> SEQUENCE: 48

```
atgttctgct tctggcggac aagcgccctg gccgtgctgc tgatctgggg agtgtttgtg     60

gccggcagca gctgcaccga caagaaccag accacccaga acaacagcag cagccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480

agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660

aaccagagcc tgagcatcga gctgagcaga ggcggaaacc agtccctgag gcccttctgg    720

gccctggtgg tggtggccgg cgtgctgttt tgttacggcc tgctcgtgac cgtggccctg    780
```

```
tgcgtgatct ggaccaacag cagaagaaac agaggcggcc agagcgacta catgaacatg    840

acccccagaa ggcctggcct gaccagaaag ccctaccagc cttacgcccc tgccagagac    900

ttcgccgcct acagacct                                                  918
```

<210> SEQ ID NO 49
<211> LENGTH: 945
<212> TYPE: DNA
<213> ORGANISM: Artificial Sequence
<220> FEATURE:
<223> OTHER INFORMATION: muCD200R-CD28Cys

<400> SEQUENCE: 49

```
atgttctgct tctggcggac aagcgccctg gccgtgctgc tgatctgggg agtgtttgtg     60

gccggcagca gctgcaccga caagaaccag accacccaga acaacagcag cagccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480

agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660

aaccagagcc tgagcatcga gctgagcaga ggcggaaacc agtccctgag gccctgccac    720

acccagagca gccccaagct gttctgggcc ctggtggtgg tggccggcgt gctgttttgt    780

tacggcctgc tcgtgaccgt ggccctgtgc gtgatctgga ccaacagcag aagaaacaga    840

ggcggccaga gcgactacat gaacatgacc cccagaaggc ctggcctgac cagaaagccc    900

taccagcctt acgcccctgc cagagacttc gccgcctaca gacct                    945
```

<210> SEQ ID NO 50
<211> LENGTH: 936
<212> TYPE: DNA
<213> ORGANISM: Artificial Sequence
<220> FEATURE:
<223> OTHER INFORMATION: muCD200R-3aas-CD28Cys

<400> SEQUENCE: 50

```
atgttctgct tctggcggac aagcgccctg gccgtgctgc tgatctgggg agtgtttgtg     60

gccggcagca gctgcaccga caagaaccag accacccaga acaacagcag cagccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480

agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660
```

```
aaccagagcc tgagcatcga gctgagcaga ggcggaaacc agtcctgcca cacccagagc    720

agccccaagc tgttctgggc cctggtggtg gtggccggcg tgctgttttg ttacggcctg    780

ctcgtgaccg tggccctgtg cgtgatctgg accaacagca gaagaaacag aggcggccag    840

agcgactaca tgaacatgac ccccagaagg cctggcctga ccagaaagcc ctaccagcct    900

tacgcccctg ccagagactt cgccgcctac agacct                              936
```

<210> SEQ ID NO 51
<211> LENGTH: 918
<212> TYPE: DNA
<213> ORGANISM: Artificial Sequence
<220> FEATURE:
<223> OTHER INFORMATION: muCD200R-9aas-CD28Cys

<400> SEQUENCE: 51

```
atgttctgct tctggcggac aagcgccctg gccgtgctgc tgatctgggg agtgtttgtg     60

gccggcagca gctgcaccga caagaaccag accacccaga acaacagcag cagcccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480

agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660

aaccagagcc tgagcatcga gctgagctgc cacacccaga gcagccccaa gctgttctgg    720

gccctggtgg tggtggccgg cgtgctgttt tgttacggcc tgctcgtgac cgtggccctg    780

tgcgtgatct ggaccaacag cagaagaaac agaggcggcc agagcgacta catgaacatg    840

acccccagaa ggcctggcct gaccagaaag ccctaccagc cttacgcccc tgccagagac    900

ttcgccgcct acagacct                                                  918
```

<210> SEQ ID NO 52
<211> LENGTH: 939
<212> TYPE: DNA
<213> ORGANISM: Artificial Sequence
<220> FEATURE:
<223> OTHER INFORMATION: muCD200R-9aas-CD28Cys tm-41BBic

<400> SEQUENCE: 52

```
atgttctgct tctggcggac aagcgccctg gccgtgctgc tgatctgggg agtgtttgtg     60

gccggcagca gctgcaccga caagaaccag accacccaga acaacagcag cagcccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480
```

```
agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660

aaccagagcc tgagcatcga gctgagctgc cacacccaga gcagccccaa gctgttctgg    720

gccctggtgg tggtggccgg cgtgctgttt tgttacggcc tgctcgtgac cgtggccctg    780

tgcgtgatct ggaccagcgt gctgaagtgg atcagaaaga agttccccca catcttcaag    840

cagcccttca agaaaaccac cggcgctgcc caggaagagg acgcctgcag ctgtagatgc    900

cctcaggaag aagaaggcgg cggaggcggc tacgagctg                           939
```

<210> SEQ ID NO 53
<211> LENGTH: 1062
<212> TYPE: DNA
<213> ORGANISM: Artificial Sequence
<220> FEATURE:
<223> OTHER INFORMATION: muCD200R-9aas-CD28Cys tm ic-41BBic

<400> SEQUENCE: 53

```
atgttctgct tctggcggac aagcgccctg gccgtgctgc tgatctgggg agtgtttgtg     60

gccggcagca gctgcaccga caagaaccag accacccaga acaacagcag cagccccctg    120

acccaagtga acaccaccgt gtccgtgcag atcggcacca aggccctgct gtgctgtttc    180

agcatccctc tgaccaaggc tgtgctgatc acctggatca tcaagctgag aggcctgccc    240

agctgcacaa tcgcctacaa ggtggacacc aagaccaacg agacaagctg cctgggcaga    300

aacatcacct gggccagcac cccagaccac agccctgagc tgcagatcag cgccgtgaca    360

ctgcagcacg agggcaccta cacatgcgag acagtgaccc ccgagggcaa cttcgagaag    420

aactacgatc tgcaggtgct ggtgcccccc gaagtgacct acttccccga gaagaataga    480

agcgccgtgt gcgaggccat ggctggcaaa cctgccgccc agatctcttg gagccctgac    540

ggcgactgtg tgaccaccag cgagagccac agcaacggca cagtgaccgt gcggagcacc    600

tgtcactggg agcagaacaa cgtgtccgac gtgtcctgca tcgtgtccca cctgaccggc    660

aaccagagcc tgagcatcga gctgagctgc cacacccaga gcagccccaa gctgttctgg    720

gccctggtgg tggtggccgg cgtgctgttt tgttacggcc tgctcgtgac cgtggccctg    780

tgcgtgatct ggaccaacag cagaagaaac agaggcggcc agagcgacta catgaacatg    840

acccccagaa ggcctggcct gaccagaaag ccctaccagc cttacgcccc tgccagagac    900

ttcgccgcct acagacctag cgtgctgaag tggatcagaa agaagttccc ccacatcttc    960

aagcagccct tcaagaaaac caccggcgct gcccaggaag aggacgcctg cagctgtaga   1020

tgccctcagg aagaagaagg cggcggaggc ggctacgagc tg                      1062
```

<210> SEQ ID NO 54
<211> LENGTH: 1305
<212> TYPE: DNA
<213> ORGANISM: Artificial Sequence
<220> FEATURE:
<223> OTHER INFORMATION: muSIRP alpha  tm-CD28

<400> SEQUENCE: 54

```
atggaacctg ctggacctgc ccctggcaga ctgggacctc tgctgctgtg cctgctgctg     60

agcgccagct gtttctgtac cggcgccacc ggcaaagaac tgaaagtgac ccagcccgag    120

aagtccgtgt ctgtggccgc tggcgacagc accgtgctga actgtaccct gaccagcctg    180

ctgcccgtgg gccccatcag atggtataga ggcgtgggcc ctagcagact gctgatctac    240
```

```
agcttcgctg gcgagtacgt gcccagaatc agaaacgtgt ccgacaccac caagcggaac    300

aacatggact tcagcatcag gatcagcaac gtgacccctg ccgacgccgg catctactac    360

tgcgtgaagt tccagaaggg cagcagcgag cccgacaccg agattcagtc tggcggcgga    420

accgaggtgt acgtgctggc taagcccagc cctcctgagg tgtccggccc tgctgataga    480

ggcatccccg accagaaagt gaacttcaca tgcaagagcc acggcttcag ccccagaaac    540

atcaccctga agtggttcaa ggacggccag gaactgcacc ccctggaaac caccgtgaac    600

cccagcggca agaacgtgtc ctacaacatc agctccaccg tgcgggtggt gctgaacagc    660

atggacgtga acagcaaagt gatctgcgag gtggcccaca tcacactgga cagaagcccc    720

ctgagaggaa tcgccaacct gagcaacttc atcagagtgt ccccaaccgt gaaagtgaca    780

cagcagagcc ccaccagcat gaaccaagtg aacctgacct gcagagccga gagattctac    840

cccgaggacc tgcagctgat ctggctggaa aacggcaacg tgtccagaaa cgacaccccc    900

aagaacctga caaagaacac cgacggcacc tacaactaca cctccctgtt tctcgtgaac    960

tcctccgccc accgcgagga cgtggtgttc acgtgccaag tgaagcacga ccagcagccc   1020

gccatcacca gaaaccacac agtgctgggc ttcgcccaca gcagcgacca gggcagcatg   1080

cagaccttcc ccgacaacaa cgccacccac aactggaacg tgttcatcgg cgtgggcgtg   1140

gcctgtgctc tgctggtggt gctgctgatg gccgccctgt ataacagcag aagaaacaga   1200

ggcggccaga gcgactacat gaacatgacc cccagaaggc ctggcctgac cagaaagccc   1260

taccagcctt acgcccctgc cagagacttc gccgcctaca gacct                   1305
```

<210> SEQ ID NO 55
<211> LENGTH: 1323
<212> TYPE: DNA
<213> ORGANISM: Artificial Sequence
<220> FEATURE:
<223> OTHER INFORMATION: muSIRP alpha-CD28tm

<400> SEQUENCE: 55

```
atggaacctg ctggacctgc ccctggcaga ctgggacctc tgctgctgtg cctgctgctg     60

agcgccagct gtttctgtac cggcgccacc ggcaaagaac tgaaagtgac ccagcccgag    120

aagtccgtgt ctgtggccgc tggcgacagc accgtgctga actgtaccct gaccagcctg    180

ctgcccgtgg gccccatcag atggtataga ggcgtgggcc ctagcagact gctgatctac    240

agcttcgctg gcgagtacgt gcccagaatc agaaacgtgt ccgacaccac caagcggaac    300

aacatggact tcagcatcag gatcagcaac gtgacccctg ccgacgccgg catctactac    360

tgcgtgaagt tccagaaggg cagcagcgag cccgacaccg agattcagtc tggcggcgga    420

accgaggtgt acgtgctggc taagcccagc cctcctgagg tgtccggccc tgctgataga    480

ggcatccccg accagaaagt gaacttcaca tgcaagagcc acggcttcag ccccagaaac    540

atcaccctga agtggttcaa ggacggccag gaactgcacc ccctggaaac caccgtgaac    600

cccagcggca agaacgtgtc ctacaacatc agctccaccg tgcgggtggt gctgaacagc    660

atggacgtga acagcaaagt gatctgcgag gtggcccaca tcacactgga cagaagcccc    720

ctgagaggaa tcgccaacct gagcaacttc atcagagtgt ccccaaccgt gaaagtgaca    780

cagcagagcc ccaccagcat gaaccaagtg aacctgacct gcagagccga gagattctac    840

cccgaggacc tgcagctgat ctggctggaa aacggcaacg tgtccagaaa cgacaccccc    900

aagaacctga caaagaacac cgacggcacc tacaactaca cctccctgtt tctcgtgaac    960
```

```
tcctccgccc accgcgagga cgtggtgttc acgtgccaag tgaagcacga ccagcagccc   1020
gccatcacca gaaaccacac agtgctgggc ttcgcccaca gcagcgacca gggcagcatg   1080
cagaccttcc ccgacaacaa cgccacccac aactggaact tctgggccct ggtggtggtg   1140
gccggcgtgc tgttttgtta cggcctgctc gtgaccgtgg ccctgtgcgt gatctggacc   1200
aacagcagaa gaaacagagg cggccagagc gactacatga acatgacccc cagaaggcct   1260
ggcctgacca gaaagcccta ccagccttac gcccctgcca gagacttcgc cgcctacaga   1320
cct                                                                 1323
```

<210> SEQ ID NO 56
<211> LENGTH: 1350
<212> TYPE: DNA
<213> ORGANISM: Artificial Sequence
<220> FEATURE:
<223> OTHER INFORMATION: muSIRP alpha-CD28cys

<400> SEQUENCE: 56

```
atggaacctg ctggacctgc ccctggcaga ctgggacctc tgctgctgtg cctgctgctg     60
agcgccagct gtttctgtac cggcgccacc ggcaaagaac tgaaagtgac ccagcccgag    120
aagtccgtgt ctgtggccgc tggcgacagc accgtgctga actgtaccct gaccagcctg    180
ctgcccgtgg gccccatcag atggtataga ggcgtgggcc ctagcagact gctgatctac    240
agcttcgctg gcgagtacgt gcccagaatc agaaacgtgt ccgacaccac caagcggaac    300
aacatggact tcagcatcag gatcagcaac gtgacccctg ccgacgccgg catctactac    360
tgcgtgaagt tccagaaggg cagcagcgag cccgacaccg agattcagtc tggcggcgga    420
accgaggtgt acgtgctggc taagcccagc cctcctgagg tgtccggccc tgctgataga    480
ggcatccccg accagaaagt gaacttcaca tgcaagagcc acggcttcag ccccagaaac    540
atcaccctga agtggttcaa ggacggccag gaactgcacc ccctggaaac caccgtgaac    600
cccagcggca agaacgtgtc ctacaacatc agctccaccg tgcgggtggt gctgaacagc    660
atggacgtga acagcaaagt gatctgcgag gtggcccaca tcacactgga cagaagcccc    720
ctgagaggaa tcgccaacct gagcaacttc atcagagtgt ccccaaccgt gaaagtgaca    780
cagcagagcc ccaccagcat gaaccaagtg aacctgacct gcagagccga gagattctac    840
cccgaggacc tgcagctgat ctggctggaa aacggcaacg tgtccagaaa cgacaccccc    900
aagaacctga caaagaacac cgacggcacc tacaactaca cctccctgtt tctcgtgaac    960
tcctccgccc accgcgagga cgtggtgttc acgtgccaag tgaagcacga ccagcagccc   1020
gccatcacca gaaaccacac agtgctgggc ttcgcccaca gcagcgacca gggcagcatg   1080
cagaccttcc ccgacaacaa cgccacccac aactggaact gccacaccca gagcagcccc   1140
aagctgttct gggctctggt ggtggtggcc ggcgtgctgt tttgttacgg cctgctcgtg   1200
accgtggccc tgtgcgtgat ctggaccaac agcagaagaa acagaggcgg ccagagcgac   1260
tacatgaaca tgacccccag aaggcctggc ctgacccgga agccttacca gccttacgcc   1320
cctgccagag acttcgccgc ctacagacct                                    1350
```

<210> SEQ ID NO 57
<211> LENGTH: 1332
<212> TYPE: DNA
<213> ORGANISM: Artificial Sequence
<220> FEATURE:
<223> OTHER INFORMATION: muSIRP alpha -6aas-CD28cys

<400> SEQUENCE: 57

```
atggaacctg ctggacctgc ccctggcaga ctgggacctc tgctgctgtg cctgctgctg     60
agcgccagct gtttctgtac cggcgccacc ggcaaagaac tgaaagtgac ccagcccgag    120
aagtccgtgt ctgtggccgc tggcgacagc accgtgctga actgtaccct gaccagcctg    180
ctgcccgtgg gccccatcag atggtataga ggcgtgggcc ctagcagact gctgatctac    240
agcttcgctg gcgagtacgt gcccagaatc agaaacgtgt ccgacaccac caagcggaac    300
aacatggact tcagcatcag gatcagcaac gtgacccctg ccgacgccgg catctactac    360
tgcgtgaagt tccagaaggg cagcagcgag cccgacaccg agattcagtc tggcggcgga    420
accgaggtgt acgtgctggc taagcccagc cctcctgagg tgtccggccc tgctgataga    480
ggcatccccg accagaaagt gaacttcaca tgcaagagcc acggcttcag ccccagaaac    540
atcaccctga agtggttcaa ggacggccag gaactgcacc ccctggaaac caccgtgaac    600
cccagcggca agaacgtgtc ctacaacatc agctccaccg tgcgggtggt gctgaacagc    660
atggacgtga acagcaaagt gatctgcgag gtggcccaca tcacactgga cagaagcccc    720
ctgagaggaa tcgccaacct gagcaacttc atcagagtgt ccccaaccgt gaaagtgaca    780
cagcagagcc ccaccagcat gaaccaagtg aacctgacct gcagagccga gagattctac    840
cccgaggacc tgcagctgat ctggctggaa aacggcaacg tgtccagaaa cgacaccccc    900
aagaacctga caaagaacac cgacggcacc tacaactaca cctccctgtt tctcgtgaac    960
tcctccgccc accgcgagga cgtggtgttc acgtgccaag tgaagcacga ccagcagccc   1020
gccatcacca gaaaccacac agtgctgggc ttcgcccaca gcagcgacca gggcagcatg   1080
cagaccttcc ccgacaacaa ctgccacacc cagagcagcc ccaagctgtt ctgggctctg   1140
gtggtggtgg ccggcgtgct gttttgttac ggcctgctcg tgaccgtggc cctgtgcgtg   1200
atctggacca acagcagaag aaacagaggc ggccagagcg actacatgaa catgaccccc   1260
agaaggcctg gcctgacccg gaagccttac cagccttacg cccctgccag agacttcgcc   1320
gcctacagac ct                                                       1332
```

```
<210> SEQ ID NO 58
<211> LENGTH: 1323
<212> TYPE: DNA
<213> ORGANISM: Artificial Sequence
<220> FEATURE:
<223> OTHER INFORMATION: muSIRP alpha -9aas-CD28cys

<400> SEQUENCE: 58

atggaacctg ctggacctgc ccctggcaga ctgggacctc tgctgctgtg cctgctgctg     60
agcgccagct gtttctgtac cggcgccacc ggcaaagaac tgaaagtgac ccagcccgag    120
aagtccgtgt ctgtggccgc tggcgacagc accgtgctga actgtaccct gaccagcctg    180
ctgcccgtgg gccccatcag atggtataga ggcgtgggcc ctagcagact gctgatctac    240
agcttcgctg gcgagtacgt gcccagaatc agaaacgtgt ccgacaccac caagcggaac    300
aacatggact tcagcatcag gatcagcaac gtgacccctg ccgacgccgg catctactac    360
tgcgtgaagt tccagaaggg cagcagcgag cccgacaccg agattcagtc tggcggcgga    420
accgaggtgt acgtgctggc taagcccagc cctcctgagg tgtccggccc tgctgataga    480
ggcatccccg accagaaagt gaacttcaca tgcaagagcc acggcttcag ccccagaaac    540
atcaccctga agtggttcaa ggacggccag gaactgcacc ccctggaaac caccgtgaac    600
cccagcggca agaacgtgtc ctacaacatc agctccaccg tgcgggtggt gctgaacagc    660
```

```
atggacgtga acagcaaagt gatctgcgag gtggcccaca tcacactgga cagaagcccc    720

ctgagaggaa tcgccaacct gagcaacttc atcagagtgt ccccaaccgt gaaagtgaca    780

cagcagagcc ccaccagcat gaaccaagtg aacctgacct gcagagccga gagattctac    840

cccgaggacc tgcagctgat ctggctggaa aacggcaacg tgtccagaaa cgacaccccc    900

aagaacctga caaagaacac cgacggcacc tacaactaca cctccctgtt tctcgtgaac    960

tcctccgccc accgcgagga cgtggtgttc acgtgccaag tgaagcacga ccagcagccc   1020

gccatcacca gaaaccacac agtgctgggc ttcgcccaca gcagcgacca gggcagcatg   1080

cagaccttcc cctgccacac ccagagcagc cccaagctgt tctgggctct ggtggtggtg   1140

gccggcgtgc tgttttgtta cggcctgctc gtgaccgtgg ccctgtgcgt gatctggacc   1200

aacagcagaa gaaacagagg cggccagagc gactacatga acatgacccc cagaaggcct   1260

ggcctgaccc ggaagcctta ccagccttac gcccctgcca gagacttcgc cgcctacaga   1320

cct                                                                 1323
```

<210> SEQ ID NO 59
<211> LENGTH: 1281
<212> TYPE: DNA
<213> ORGANISM: Artificial Sequence
<220> FEATURE:
<223> OTHER INFORMATION: muSIRP alpha-23aas-CD28cys

<400> SEQUENCE: 59

```
atggaacctg ctggacctgc ccctggcaga ctgggacctc tgctgctgtg cctgctgctg     60

agcgccagct gtttctgtac cggcgccacc ggcaaagaac tgaaagtgac ccagcccgag    120

aagtccgtgt ctgtggccgc tggcgacagc accgtgctga actgtaccct gaccagcctg    180

ctgcccgtgg gccccatcag atggtataga ggcgtgggcc ctagcagact gctgatctac    240

agcttcgctg gcgagtacgt gcccagaatc agaaacgtgt ccgacaccac caagcggaac    300

aacatggact tcagcatcag gatcagcaac gtgacccctg ccgacgccgg catctactac    360

tgcgtgaagt tccagaaggg cagcagcgag cccgacaccg agattcagtc tggcggcgga    420

accgaggtgt acgtgctggc taagcccagc cctcctgagg tgtccggccc tgctgataga    480

ggcatccccg accagaaagt gaacttcaca tgcaagagcc acggcttcag ccccagaaac    540

atcaccctga agtggttcaa ggacggccag gaactgcacc ccctggaaac caccgtgaac    600

cccagcggca agaacgtgtc ctacaacatc agctccaccg tgcgggtggt gctgaacagc    660

atggacgtga acagcaaagt gatctgcgag gtggcccaca tcacactgga cagaagcccc    720

ctgagaggaa tcgccaacct gagcaacttc atcagagtgt ccccaaccgt gaaagtgaca    780

cagcagagcc ccaccagcat gaaccaagtg aacctgacct gcagagccga gagattctac    840

cccgaggacc tgcagctgat ctggctggaa aacggcaacg tgtccagaaa cgacaccccc    900

aagaacctga caaagaacac cgacggcacc tacaactaca cctccctgtt tctcgtgaac    960

tcctccgccc accgcgagga cgtggtgttc acgtgccaag tgaagcacga ccagcagccc   1020

gccatcacca gaaaccacac agtgctgggc tgccacaccc agagcagccc caagctgttc   1080

tgggctctgg tggtggtggc cggcgtgctg ttttgttacg gcctgctcgt gaccgtggcc   1140

ctgtgcgtga tctggaccaa cagcagaaga aacagaggcg gccagagcga ctacatgaac   1200

atgaccccca gaaggcctgg cctgacccgg aagccttacc agccttacgc ccctgccaga   1260

gacttcgccg cctacagacc t                                             1281
```

<210> SEQ ID NO 60
<211> LENGTH: 137
<212> TYPE: PRT
<213> ORGANISM: Artificial Sequence
<220> FEATURE:
<223> OTHER INFORMATION: huPD-1 ectodomain

<400> SEQUENCE: 60

```
Pro Pro Thr Phe Ser Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
            20                  25                  30

Asn Trp Tyr Arg Met Ser Pro Ser Asn Gln Thr Asp Lys Leu Ala Ala
        35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg Val Thr
            100                 105                 110

Glu Arg Arg Ala Glu Val Pro Thr Ala His Pro Ser Pro Ser Pro Arg
        115                 120                 125

Ser Ala Gly Gln Phe Gln Thr Leu Val
    130                 135
```

<210> SEQ ID NO 61
<211> LENGTH: 627
<212> TYPE: DNA
<213> ORGANISM: Artificial Sequence
<220> FEATURE:
<223> OTHER INFORMATION: huCD2 entire extracellular domain

<400> SEQUENCE: 61

```
atgagctttc catgtaaatt tgtagccagc ttccttctga ttttcaatgt ttcttccaaa     60

ggtgcagtct ccaaagagat tacgaatgcc ttggaaacct ggggtgcctt gggtcaggac    120

atcaacttgg acattcctag ttttcaaatg agtgatgata ttgacgatat aaaatgggaa    180

aaaacttcag acaagaaaaa gattgcacaa ttcagaaaag agaaagagac tttcaaggaa    240

aaagatacat ataagctatt taaaaatgga actctgaaaa ttaagcatct gaagaccgat    300

gatcaggata tctacaaggt atcaatatat gatacaaaag gaaaaaatgt gttggaaaaa    360

atatttgatt tgaagattca agagagggtc tcaaaaccaa agatctcctg gacttgtatc    420

aacacaaccc tgacctgtga ggtaatgaat ggaactgacc ccgaattaaa cctgtatcaa    480

gatgggaaac atctaaaact ttctcagagg gtcatcacac acaagtggac caccagcctg    540

agtgcaaaat tcaagtgcac agcagggaac aaagtcagca aggaatccag tgtcgagcct    600

gtcagctgtc cagagaaagg tctggac                                        627
```

<210> SEQ ID NO 62
<211> LENGTH: 209
<212> TYPE: PRT
<213> ORGANISM: Artificial Sequence
<220> FEATURE:
<223> OTHER INFORMATION: huCD2 entire extracellular domain

<400> SEQUENCE: 62

```
Met Ser Phe Pro Cys Lys Phe Val Ala Ser Phe Leu Leu Ile Phe Asn
```

```
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp
```

<210> SEQ ID NO 63
<211> LENGTH: 78
<212> TYPE: DNA
<213> ORGANISM: Artificial Sequence
<220> FEATURE:
<223> OTHER INFORMATION: huCD2 transmembrane domain

<400> SEQUENCE: 63

```
atctatctca tcattggcat atgtggagga ggcagcctct tgatggtctt tgtggcactg     60

ctcgttttct atatcacc                                                   78
```

<210> SEQ ID NO 64
<211> LENGTH: 26
<212> TYPE: PRT
<213> ORGANISM: Artificial Sequence
<220> FEATURE:
<223> OTHER INFORMATION: huCD2 transmembrane domain

<400> SEQUENCE: 64

```
Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25
```

<210> SEQ ID NO 65
<211> LENGTH: 828
<212> TYPE: DNA
<213> ORGANISM: Artificial Sequence
<220> FEATURE:
<223> OTHER INFORMATION: huCD2tm-CD28 DNA

<400> SEQUENCE: 65

```
atgagctttc catgtaaatt tgtagccagc ttccttctga ttttcaatgt ttcttccaaa     60

ggtgcagtct ccaaagagat tacgaatgcc ttggaaacct ggggtgcctt gggtcaggac    120

atcaacttgg acattcctag ttttcaaatg agtgatgata ttgacgatat aaaatgggaa    180

aaaacttcag acaagaaaaa gattgcacaa ttcagaaaag agaaagagac tttcaaggaa    240

aaagatacat ataagctatt taaaaatgga actctgaaaa ttaagcatct gaagaccgat    300

gatcaggata tctacaaggt atcaatatat gatacaaaag gaaaaaatgt gttggaaaaa    360

atatttgatt tgaagattca agagagggtc tcaaaaccaa agatctcctg gacttgtatc    420

aacacaaccc tgacctgtga ggtaatgaat ggaactgacc ccgaattaaa cctgtatcaa    480

gatgggaaac atctaaaact ttctcagagg gtcatcacac acaagtggac caccagcctg    540

agtgcaaaat tcaagtgcac agcagggaac aaagtcagca aggaatccag tgtcgagcct    600

gtcagctgtc cagagaaagg tctggacatc tatctcatca ttggcatatg tggaggaggc    660

agcctcttga tggtctttgt ggcactgctc gttttctata tcacccgcag caagcggagc    720

agaggcggcc acagcgacta catgaacatg acccctagac ggcctggccc caccagaaag    780

cactaccagc cctacgcccc tccccgggac tttgccgcct acagaagc                 828
```

```
<210> SEQ ID NO 66
<211> LENGTH: 276
<212> TYPE: PRT
<213> ORGANISM: Artificial Sequence
<220> FEATURE:
<223> OTHER INFORMATION: huCD2tm-CD28

<400> SEQUENCE: 66

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
```

```
    210                 215                 220

Val Phe Val Ala Leu Leu Val Phe Tyr Ile Thr Arg Ser Lys Arg Ser
225                 230                 235                 240

Arg Gly Gly His Ser Asp Tyr Met Asn Met Thr Pro Arg Arg Pro Gly
                245                 250                 255

Pro Thr Arg Lys His Tyr Gln Pro Tyr Ala Pro Pro Arg Asp Phe Ala
            260                 265                 270

Ala Tyr Arg Ser
        275


<210> SEQ ID NO 67
<211> LENGTH: 831
<212> TYPE: DNA
<213> ORGANISM: Artificial Sequence
<220> FEATURE:
<223> OTHER INFORMATION: huCD2-CD28tm

<400> SEQUENCE: 67

atgagctttc catgtaaatt tgtagccagc ttccttctga ttttcaatgt ttcttccaaa      60

ggtgcagtct ccaaagagat tacgaatgcc ttggaaacct ggggtgcctt gggtcaggac     120

atcaacttgg acattcctag ttttcaaatg agtgatgata ttgacgatat aaaatgggaa     180

aaaacttcag acaagaaaaa gattgcacaa ttcagaaaag agaaagagac tttcaaggaa     240

aaagatacat ataagctatt taaaaatgga actctgaaaa ttaagcatct gaagaccgat     300

gatcaggata tctacaaggt atcaatatat gatacaaaag gaaaaaatgt gttggaaaaa     360

atatttgatt tgaagattca agagagggtc tcaaaaccaa agatctcctg gacttgtatc     420

aacacaaccc tgacctgtga ggtaatgaat ggaactgacc ccgaattaaa cctgtatcaa     480

gatgggaaac atctaaaact ttctcagagg gtcatcacac acaagtggac caccagcctg     540

agtgcaaaat tcaagtgcac agcagggaac aaagtcagca aggaatccag tgtcgagcct     600

gtcagctgtc cagagaaagg tctggacttc tgggtgctgg tggtggtcgg aggcgtgctg     660

gcctgctaca gcctgctggt caccgtggcc ttcatcatct tttgggtccg cagcaagcgg     720

agcagaggcg gccacagcga ctacatgaac atgaccccta gacggcctgg ccccaccaga     780

aagcactacc agccctacgc ccctccccgg gactttgccg cctacagaag c              831


<210> SEQ ID NO 68
<211> LENGTH: 277
<212> TYPE: PRT
<213> ORGANISM: Artificial Sequence
<220> FEATURE:
<223> OTHER INFORMATION: huCD2-CD28tm

<400> SEQUENCE: 68

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95
```

```
Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Phe Trp Val Leu Val Val Val Gly Gly Val Leu Ala Cys Tyr Ser
    210                 215                 220

Leu Leu Val Thr Val Ala Phe Ile Ile Phe Trp Val Arg Ser Lys Arg
225                 230                 235                 240

Ser Arg Gly Gly His Ser Asp Tyr Met Asn Met Thr Pro Arg Arg Pro
                245                 250                 255

Gly Pro Thr Arg Lys His Tyr Gln Pro Tyr Ala Pro Pro Arg Asp Phe
            260                 265                 270

Ala Ala Tyr Arg Ser
        275
```

<210> SEQ ID NO 69
<211> LENGTH: 969
<212> TYPE: DNA
<213> ORGANISM: Artificial Sequence
<220> FEATURE:
<223> OTHER INFORMATION: huCD200R-CD28Cys

<400> SEQUENCE: 69

```
atgctgtgcc cttggagaac cgccaacctg ggcctgctgc tgatcctgac catcttcctg      60

gtggccgcca gcagcagcct gtgcatggac gagaagcaga tcacccagaa ctacagcaag     120

gtgctggccg aagtgaacac cagctggccc gtgaagatgg ccaccaacgc cgtgctgtgc     180

tgccctccta tcgccctgcg gaacctgatc atcatcacct gggagatcat cctgcggggc     240

cagcccagct gtaccaaggc ctaccggaaa gagacaaacg agacaaaaga aacaaactgc     300

accgacgagc ggatcacatg ggtgtccaga cccgaccaga acagcgacct gcagatcaga     360

cccgtggcca tcacccacga cggctactac cggtgcatca tggtcacccc cgatggcaac     420

ttccaccggg gataccatct gcaggtgctc gtgacccccg aagtgaccct gttccagaac     480

cggaacagaa ccgccgtgtg caaggccgtg gccggaaaac ctgccgccca gatctcttgg     540

atccccgagg gcgattgcgc caccaagcag gaatactggt ccaacggcac cgtgaccgtg     600

aagtccacct gtcactggga ggtgcacaac gtgtccaccg tgacatgcca cgtgtcccac     660

ctgaccggca acaagagcct gtacatcgag ctgctgcctg tgcctggcgc caagaagtcc     720

gccaagctgt gtcccagccc tctgtttccc ggccctagca agcctttctg ggtgctggtg     780

gtggtcggag gcgtgctggc ctgctacagc ctgctggtca ccgtggcctt catcatcttt     840

tgggtccgca gcaagcggag cagaggcggc cacagcgact acatgaacat gacccctaga     900

cggcctggcc ccaccagaaa gcactaccag ccctacgccc ctccccggga ctttgccgcc     960
```

```
tacagaagc                                                          969


<210> SEQ ID NO 70
<211> LENGTH: 323
<212> TYPE: PRT
<213> ORGANISM: Artificial Sequence
<220> FEATURE:
<223> OTHER INFORMATION: huCD200R-CD28Cys

<400> SEQUENCE: 70

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu Cys Pro Ser Pro Leu Phe Pro Gly Pro Ser Lys Pro Phe
                245                 250                 255

Trp Val Leu Val Val Val Gly Gly Val Leu Ala Cys Tyr Ser Leu Leu
            260                 265                 270

Val Thr Val Ala Phe Ile Ile Phe Trp Val Arg Ser Lys Arg Ser Arg
        275                 280                 285

Gly Gly His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320

Tyr Arg Ser


<210> SEQ ID NO 71
<211> LENGTH: 519
<212> TYPE: DNA
<213> ORGANISM: Artificial Sequence
```

<220> FEATURE:
<223> OTHER INFORMATION: huFas entire extracellular domain

<400> SEQUENCE: 71

```
atgctgggca tctggaccct gctgcctctg gtgctgacaa gcgtggccag actgagcagc     60

aagagcgtga acgcccaagt gaccgacatc aacagcaagg gcctggaact gagaaagacc    120

gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360

cggacccaga acaccaagtg cagatgcaag cccaacttct tctgcaacag caccgtgtgc    420

gagcactgcg acccctgtac caagtgcgaa cacggcatca tcaaagagtg caccctgacc    480

tccaacacaa agtgcaaaga ggaaggcagc agaagcaac                           519
```

<210> SEQ ID NO 72
<211> LENGTH: 173
<212> TYPE: PRT
<213> ORGANISM: Artificial Sequence
<220> FEATURE:
<223> OTHER INFORMATION: huFas entire extracellular domain

<400> SEQUENCE: 72

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn
                165                 170
```

<210> SEQ ID NO 73
<211> LENGTH: 498
<212> TYPE: DNA
<213> ORGANISM: Artificial Sequence
<220> FEATURE:
<223> OTHER INFORMATION: huFas extracellular domain -7aas

<400> SEQUENCE: 73

```
atgctgggca tctggaccct gctgcctctg gtgctgacaa gcgtggccag actgagcagc     60

aagagcgtga acgcccaagt gaccgacatc aacagcaagg gcctggaact gagaaagacc    120
```

```
gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360

cggacccaga acaccaagtg cagatgcaag cccaacttct tctgcaacag caccgtgtgc    420

gagcactgcg acccctgtac caagtgcgaa cacggcatca tcaaagagtg caccctgacc    480

tccaacacaa agtgcaaa                                                  498
```

```
<210> SEQ ID NO 74
<211> LENGTH: 166
<212> TYPE: PRT
<213> ORGANISM: Artificial Sequence
<220> FEATURE:
<223> OTHER INFORMATION: huFas extracellular domain -7aas

<400> SEQUENCE: 74

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys
                165
```

```
<210> SEQ ID NO 75
<211> LENGTH: 483
<212> TYPE: DNA
<213> ORGANISM: Artificial Sequence
<220> FEATURE:
<223> OTHER INFORMATION: huFas extracellular domain -12aas

<400> SEQUENCE: 75

atgctgggca tctggaccct gctgcctctg gtgctgacaa gcgtggccag actgagcagc     60

aagagcgtga acgcccaagt gaccgacatc aacagcaagg gcctggaact gagaaagacc    120

gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360
```

cggacccaga acaccaagtg cagatgcaag cccaacttct tctgcaacag caccgtgtgc 420
gagcactgcg acccctgtac caagtgcgaa cacggcatca tcaaagagtg caccctgacc 480
tcc 483

<210> SEQ ID NO 76
<211> LENGTH: 161
<212> TYPE: PRT
<213> ORGANISM: Artificial Sequence
<220> FEATURE:
<223> OTHER INFORMATION: huFas extracellular domain -12aas

<400> SEQUENCE: 76

Met Leu Gly Ile Trp Thr Leu Leu Pro Leu Val Leu Thr Ser Val Ala
1 5 10 15

Arg Leu Ser Ser Lys Ser Val Asn Ala Gln Val Thr Asp Ile Asn Ser
20 25 30

Lys Gly Leu Glu Leu Arg Lys Thr Val Thr Thr Val Glu Thr Gln Asn
35 40 45

Leu Glu Gly Leu His His Asp Gly Gln Phe Cys His Lys Pro Cys Pro
50 55 60

Pro Gly Glu Arg Lys Ala Arg Asp Cys Thr Val Asn Gly Asp Glu Pro
65 70 75 80

Asp Cys Val Pro Cys Gln Glu Gly Lys Glu Tyr Thr Asp Lys Ala His
85 90 95

Phe Ser Ser Lys Cys Arg Arg Cys Arg Leu Cys Asp Glu Gly His Gly
100 105 110

Leu Glu Val Glu Ile Asn Cys Thr Arg Thr Gln Asn Thr Lys Cys Arg
115 120 125

Cys Lys Pro Asn Phe Phe Cys Asn Ser Thr Val Cys Glu His Cys Asp
130 135 140

Pro Cys Thr Lys Cys Glu His Gly Ile Ile Lys Glu Cys Thr Leu Thr
145 150 155 160

Ser

<210> SEQ ID NO 77
<211> LENGTH: 51
<212> TYPE: DNA
<213> ORGANISM: Artificial Sequence
<220> FEATURE:
<223> OTHER INFORMATION: huFas transmembrane domain

<400> SEQUENCE: 77
ctgggctggc tgtgcctcct gctgctgccc atccctctga tcgtgtgggt c 51

<210> SEQ ID NO 78
<211> LENGTH: 17
<212> TYPE: PRT
<213> ORGANISM: Artificial Sequence
<220> FEATURE:
<223> OTHER INFORMATION: huFas transmembrane domain

<400> SEQUENCE: 78

Leu Gly Trp Leu Cys Leu Leu Leu Leu Pro Ile Pro Leu Ile Val Trp
1 5 10 15

Val

<210> SEQ ID NO 79
<211> LENGTH: 693

```
<212> TYPE: DNA
<213> ORGANISM: Artificial Sequence
<220> FEATURE:
<223> OTHER INFORMATION: huFAStm-CD28

<400> SEQUENCE: 79

atgctgggca tctggaccct gctgcctctg gtgctgacaa gcgtggccag actgagcagc     60

aagagcgtga acgcccaagt gaccgacatc aacagcaagg gcctggaact gagaaagacc    120

gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360

cggacccaga acaccaagtg cagatgcaag cccaacttct tctgcaacag caccgtgtgc    420

gagcactgcg acccctgtac caagtgcgaa cacggcatca tcaaagagtg caccctgacc    480

tccaacacaa agtgcaaaga ggaaggcagc agaagcaacc tgggctggct gtgcctcctg    540

ctgctgccca tccctctgat cgtgtgggtc cgcagcaagc ggagcagagg cggccacagc    600

gactacatga acatgacccc tagacggcct ggccccacca gaaagcacta ccagccctac    660

gcccctcccc gggactttgc cgcctacaga agc                                 693


<210> SEQ ID NO 80
<211> LENGTH: 231
<212> TYPE: PRT
<213> ORGANISM: Artificial Sequence
<220> FEATURE:
<223> OTHER INFORMATION: huFAStm-CD28

<400> SEQUENCE: 80

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Arg Ser
            180                 185                 190

Lys Arg Ser Arg Gly Gly His Ser Asp Tyr Met Asn Met Thr Pro Arg
        195                 200                 205
```

```
Arg Pro Gly Pro Thr Arg Lys His Tyr Gln Pro Tyr Ala Pro Pro Arg
    210                 215                 220

Asp Phe Ala Ala Tyr Arg Ser
225                 230


<210> SEQ ID NO 81
<211> LENGTH: 723
<212> TYPE: DNA
<213> ORGANISM: Artificial Sequence
<220> FEATURE:
<223> OTHER INFORMATION: huFAS-CD28tm

<400> SEQUENCE: 81

atgctgggca tctggaccct gctgcctctg gtgctgacaa gcgtggccag actgagcagc      60

aagagcgtga acgcccaagt gaccgacatc aacagcaagg gcctggaact gagaaagacc     120

gtgaccaccg tggaaaccca gaacctggaa ggcctgcacc acgacggcca gttctgccac     180

aagccttgtc cccctggcga gcggaaggcc agagactgta ctgtgaacgg cgacgagccc     240

gactgcgtgc cctgtcagga aggcaaagag tacaccgaca aggcccactt cagcagcaag     300

tgccggcggt gcagactgtg tgatgagggc cacggcctgg aagtggaaat caactgcacc     360

cggacccaga acaccaagtg cagatgcaag cccaacttct tctgcaacag caccgtgtgc     420

gagcactgcg acccctgtac caagtgcgaa cacggcatca tcaaagagtg caccctgacc     480

tccaacacaa agtgcaaaga ggaaggcagc agaagcaact tctgggtgct ggtggtggtc     540

ggaggcgtgc tggcctgcta cagcctgctg gtcaccgtgg ccttcatcat cttttgggtc     600

cgcagcaagc ggagcagagg cggccacagc gactacatga acatgacccc tagacggcct     660

ggccccacca gaaagcacta ccagccctac gcccctcccc gggactttgc cgcctacaga     720

agc                                                                   723


<210> SEQ ID NO 82
<211> LENGTH: 241
<212> TYPE: PRT
<213> ORGANISM: Artificial Sequence
<220> FEATURE:
<223> OTHER INFORMATION: huFAS-CD28tm

<400> SEQUENCE: 82

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140
```

```
Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Phe Trp Val
                165                 170                 175

Leu Val Val Val Gly Gly Val Leu Ala Cys Tyr Ser Leu Leu Val Thr
            180                 185                 190

Val Ala Phe Ile Ile Phe Trp Val Arg Ser Lys Arg Ser Arg Gly Gly
        195                 200                 205

His Ser Asp Tyr Met Asn Met Thr Pro Arg Arg Pro Gly Pro Thr Arg
    210                 215                 220

Lys His Tyr Gln Pro Tyr Ala Pro Pro Arg Asp Phe Ala Ala Tyr Arg
225                 230                 235                 240

Ser
```

<210> SEQ ID NO 83
<211> LENGTH: 759
<212> TYPE: DNA
<213> ORGANISM: Artificial Sequence
<220> FEATURE:
<223> OTHER INFORMATION: huFAS-CD28Cys

<400> SEQUENCE: 83

```
atgctgggca tctggaccct gctgcctctg gtgctgacaa gcgtggccag actgagcagc     60

aagagcgtga acgcccaagt gaccgacatc aacagcaagg gcctggaact gagaaagacc    120

gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360

cggacccaga acaccaagtg cagatgcaag cccaacttct tctgcaacag caccgtgtgc    420

gagcactgcg acccctgtac caagtgcgaa cacggcatca tcaaagagtg caccctgacc    480

tccaacacaa agtgcaaaga ggaaggcagc agaagcaact gtcccagccc tctgtttccc    540

ggccctagca agcctttctg ggtgctggtg gtggtcggag gcgtgctggc ctgctacagc    600

ctgctggtca ccgtggcctt catcatcttt tgggtccgca gcaagcggag cagaggcggc    660

cacagcgact acatgaacat gacccctaga cggcctggcc ccaccagaaa gcactaccag    720

ccctacgccc ctccccggga ctttgccgcc tacagaagc                           759
```

<210> SEQ ID NO 84
<211> LENGTH: 253
<212> TYPE: PRT
<213> ORGANISM: Artificial Sequence
<220> FEATURE:
<223> OTHER INFORMATION: huFAS-CD28Cys

<400> SEQUENCE: 84

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60
```

```
Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Cys Pro Ser
                165                 170                 175

Pro Leu Phe Pro Gly Pro Ser Lys Pro Phe Trp Val Leu Val Val Val
            180                 185                 190

Gly Gly Val Leu Ala Cys Tyr Ser Leu Leu Val Thr Val Ala Phe Ile
        195                 200                 205

Ile Phe Trp Val Arg Ser Lys Arg Ser Arg Gly Gly His Ser Asp Tyr
    210                 215                 220

Met Asn Met Thr Pro Arg Arg Pro Gly Pro Thr Arg Lys His Tyr Gln
225                 230                 235                 240

Pro Tyr Ala Pro Pro Arg Asp Phe Ala Ala Tyr Arg Ser
                245                 250
```

<210> SEQ ID NO 85
<211> LENGTH: 738
<212> TYPE: DNA
<213> ORGANISM: Artificial Sequence
<220> FEATURE:
<223> OTHER INFORMATION: huFAS-7aas-CD28Cys

<400> SEQUENCE: 85

```
atgctgggca tctggaccct gctgcctctg gtgctgacaa gcgtggccag actgagcagc     60

aagagcgtga acgcccaagt gaccgacatc aacagcaagg gcctggaact gagaaagacc    120

gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360

cggacccaga acaccaagtg cagatgcaag cccaacttct tctgcaacag caccgtgtgc    420

gagcactgcg acccctgtac caagtgcgaa cacggcatca tcaaagagtg caccctgacc    480

tccaacacaa agtgcaaatg tcccagccct ctgtttcccg gccctagcaa gcctttctgg    540

gtgctggtgg tggtcggagg cgtgctggcc tgctacagcc tgctggtcac cgtggccttc    600

atcatctttt gggtccgcag caagcggagc agaggcggcc acagcgacta catgaacatg    660

acccctagac ggcctggccc caccagaaag cactaccagc cctacgcccc tccccgggac    720

tttgccgcct acagaagc                                                  738
```

<210> SEQ ID NO 86
<211> LENGTH: 246
<212> TYPE: PRT
<213> ORGANISM: Artificial Sequence
<220> FEATURE:
<223> OTHER INFORMATION: huFAS-7aas-CD28Cys

<400> SEQUENCE: 86

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Cys Pro Ser Pro Leu Phe Pro Gly Pro Ser
                165                 170                 175

Lys Pro Phe Trp Val Leu Val Val Val Gly Gly Val Leu Ala Cys Tyr
            180                 185                 190

Ser Leu Leu Val Thr Val Ala Phe Ile Ile Phe Trp Val Arg Ser Lys
        195                 200                 205

Arg Ser Arg Gly Gly His Ser Asp Tyr Met Asn Met Thr Pro Arg Arg
    210                 215                 220

Pro Gly Pro Thr Arg Lys His Tyr Gln Pro Tyr Ala Pro Pro Arg Asp
225                 230                 235                 240

Phe Ala Ala Tyr Arg Ser
                245
```

<210> SEQ ID NO 87
<211> LENGTH: 723
<212> TYPE: DNA
<213> ORGANISM: Artificial Sequence
<220> FEATURE:
<223> OTHER INFORMATION: FAS-12aas-CD28Cys

<400> SEQUENCE: 87

```
atgctgggca tctggaccct gctgcctctg gtgctgacaa gcgtggccag actgagcagc     60

aagagcgtga acgcccaagt gaccgacatc aacagcaagg gcctggaact gagaaagacc    120

gtgaccaccg tggaaaccca gaacctggaa ggcctgcacc acgacggcca gttctgccac    180

aagccttgtc cccctggcga gcggaaggcc agagactgta ctgtgaacgg cgacgagccc    240

gactgcgtgc cctgtcagga aggcaaagag tacaccgaca aggcccactt cagcagcaag    300

tgccggcggt gcagactgtg tgatgagggc cacggcctgg aagtggaaat caactgcacc    360

cggacccaga acaccaagtg cagatgcaag cccaacttct tctgcaacag caccgtgtgc    420

gagcactgcg acccctgtac caagtgcgaa cacggcatca tcaaagagtg caccctgacc    480

tcctgtccca gccctctgtt tcccggccct agcaagcctt tctgggtgct ggtggtggtc    540
```

ggaggcgtgc tggcctgcta cagcctgctg gtcaccgtgg ccttcatcat cttttgggtc 600
cgcagcaagc ggagcagagg cggccacagc gactacatga acatgacccc tagacggcct 660
ggccccacca gaaagcacta ccagccctac gcccctcccc gggactttgc cgcctacaga 720
agc 723

<210> SEQ ID NO 88
<211> LENGTH: 241
<212> TYPE: PRT
<213> ORGANISM: Artificial Sequence
<220> FEATURE:
<223> OTHER INFORMATION: FAS-12aas-CD28Cys

<400> SEQUENCE: 88

Met Leu Gly Ile Trp Thr Leu Leu Pro Leu Val Leu Thr Ser Val Ala
1 5 10 15

Arg Leu Ser Ser Lys Ser Val Asn Ala Gln Val Thr Asp Ile Asn Ser
20 25 30

Lys Gly Leu Glu Leu Arg Lys Thr Val Thr Thr Val Glu Thr Gln Asn
35 40 45

Leu Glu Gly Leu His His Asp Gly Gln Phe Cys His Lys Pro Cys Pro
50 55 60

Pro Gly Glu Arg Lys Ala Arg Asp Cys Thr Val Asn Gly Asp Glu Pro
65 70 75 80

Asp Cys Val Pro Cys Gln Glu Gly Lys Glu Tyr Thr Asp Lys Ala His
85 90 95

Phe Ser Ser Lys Cys Arg Arg Cys Arg Leu Cys Asp Glu Gly His Gly
100 105 110

Leu Glu Val Glu Ile Asn Cys Thr Arg Thr Gln Asn Thr Lys Cys Arg
115 120 125

Cys Lys Pro Asn Phe Phe Cys Asn Ser Thr Val Cys Glu His Cys Asp
130 135 140

Pro Cys Thr Lys Cys Glu His Gly Ile Ile Lys Glu Cys Thr Leu Thr
145 150 155 160

Ser Cys Pro Ser Pro Leu Phe Pro Gly Pro Ser Lys Pro Phe Trp Val
165 170 175

Leu Val Val Val Gly Gly Val Leu Ala Cys Tyr Ser Leu Leu Val Thr
180 185 190

Val Ala Phe Ile Ile Phe Trp Val Arg Ser Lys Arg Ser Arg Gly Gly
195 200 205

His Ser Asp Tyr Met Asn Met Thr Pro Arg Arg Pro Gly Pro Thr Arg
210 215 220

Lys His Tyr Gln Pro Tyr Ala Pro Pro Arg Asp Phe Ala Ala Tyr Arg
225 230 235 240

Ser

<210> SEQ ID NO 89
<211> LENGTH: 510
<212> TYPE: DNA
<213> ORGANISM: Artificial Sequence
<220> FEATURE:
<223> OTHER INFORMATION: huPD1 entire extracellular domain 2

<400> SEQUENCE: 89
atgcagatcc ctcaggcccc ttggcctgtc gtgtgggctg tgctgcagct gggatggcgg 60
cctggctggt ttctggacag ccccgacaga ccctggaacc cccctacatt ttcccctgcc 120

```
ctgctggtcg tgaccgaggg cgacaatgcc accttcacct gtagcttcag caacaccagc    180

gagagcttcg tgctgaactg gtacagaatg agccccagca accagaccga caagctggcc    240

gccttccccg aggatagatc tcagcccggc caggactgcc ggttcagagt gacccagctg    300

cccaacggcc gggacttcca catgtctgtc gtgcgggcca gacggaacga cagcggcaca    360

tatctgtgcg gcgccatcag cctggccccc aaggcccaga tcaaagagag cctgagagcc    420

gagctgagag tgaccgagag aagggccgaa gtgcctaccg cccaccctag cccatctcca    480

agacctgccg gccagttcca gacactggtc                                     510


<210> SEQ ID NO 90
<211> LENGTH: 170
<212> TYPE: PRT
<213> ORGANISM: Artificial Sequence
<220> FEATURE:
<223> OTHER INFORMATION: huPD1 entire extracellular domain 2

<400> SEQUENCE: 90

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170


<210> SEQ ID NO 91
<211> LENGTH: 474
<212> TYPE: DNA
<213> ORGANISM: Artificial Sequence
<220> FEATURE:
<223> OTHER INFORMATION: huPD1 2 -12aas

<400> SEQUENCE: 91

atgcagatcc ctcaggcccc ttggcctgtc gtgtgggctg tgctgcagct gggatggcgg     60

cctggctggt ttctggacag ccccgacaga ccctggaacc cccctacatt ttcccctgcc    120

ctgctggtcg tgaccgaggg cgacaatgcc accttcacct gtagcttcag caacaccagc    180

gagagcttcg tgctgaactg gtacagaatg agccccagca accagaccga caagctggcc    240

gccttccccg aggatagatc tcagcccggc caggactgcc ggttcagagt gacccagctg    300

cccaacggcc gggacttcca catgtctgtc gtgcgggcca gacggaacga cagcggcaca    360
```

```
tatctgtgcg gcgccatcag cctggccccc aaggcccaga tcaaagagag cctgagagcc    420

gagctgagag tgaccgagag aagggccgaa gtgcctaccg cccaccctag ccca          474


<210> SEQ ID NO 92
<211> LENGTH: 158
<212> TYPE: PRT
<213> ORGANISM: Artificial Sequence
<220> FEATURE:
<223> OTHER INFORMATION: huPD1 2 -12aas

<400> SEQUENCE: 92

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro
145                 150                 155


<210> SEQ ID NO 93
<211> LENGTH: 465
<212> TYPE: DNA
<213> ORGANISM: Artificial Sequence
<220> FEATURE:
<223> OTHER INFORMATION: huPD1 2 -15aas

<400> SEQUENCE: 93

atgcagatcc ctcaggcccc ttggcctgtc gtgtgggctg tgctgcagct gggatggcgg     60

cctggctggt ttctggacag ccccgacaga ccctggaacc cccctacatt ttcccctgcc    120

ctgctggtcg tgaccgaggg cgacaatgcc accttcacct gtagcttcag caacaccagc    180

gagagcttcg tgctgaactg gtacagaatg agccccagca accagaccga caagctggcc    240

gccttccccg aggatagatc tcagcccggc caggactgcc ggttcagagt gacccagctg    300

cccaacggcc gggacttcca catgtctgtc gtgcgggcca gacggaacga cagcggcaca    360

tatctgtgcg gcgccatcag cctggccccc aaggcccaga tcaaagagag cctgagagcc    420

gagctgagag tgaccgagag aagggccgaa gtgcctaccg cccac                    465


<210> SEQ ID NO 94
<211> LENGTH: 155
<212> TYPE: PRT
<213> ORGANISM: Artificial Sequence
<220> FEATURE:
<223> OTHER INFORMATION: huPD1 2 -15aas

<400> SEQUENCE: 94
```

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His
145                 150                 155
```

<210> SEQ ID NO 95
<211> LENGTH: 447
<212> TYPE: DNA
<213> ORGANISM: Artificial Sequence
<220> FEATURE:
<223> OTHER INFORMATION: huPD1 2 -21aas

<400> SEQUENCE: 95

```
atgcagatcc ctcaggcccc ttggcctgtc gtgtgggctg tgctgcagct gggatggcgg     60

cctggctggt ttctggacag ccccgacaga ccctggaacc cccctacatt ttcccctgcc    120

ctgctggtcg tgaccgaggg cgacaatgcc accttcacct gtagcttcag caacaccagc    180

gagagcttcg tgctgaactg gtacagaatg agccccagca accagaccga caagctggcc    240

gccttccccg aggatagatc tcagcccggc caggactgcc ggttcagagt gacccagctg    300

cccaacggcc gggacttcca catgtctgtc gtgcgggcca gacggaacga cagcggcaca    360

tatctgtgcg gcgccatcag cctggccccc aaggcccaga tcaaagagag cctgagagcc    420

gagctgagag tgaccgagag aagggcc                                        447
```

<210> SEQ ID NO 96
<211> LENGTH: 149
<212> TYPE: PRT
<213> ORGANISM: Artificial Sequence
<220> FEATURE:
<223> OTHER INFORMATION: huPD1 2 -21aas

<400> SEQUENCE: 96

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60
```

```
Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala
145


<210> SEQ ID NO 97
<211> LENGTH: 750
<212> TYPE: DNA
<213> ORGANISM: Artificial Sequence
<220> FEATURE:
<223> OTHER INFORMATION: huPD1-CD28Cys

<400> SEQUENCE: 97

atgcagatcc ctcaggcccc ttggcctgtc gtgtgggctg tgctgcagct gggatggcgg      60

cctggctggt ttctggacag ccccgacaga ccctggaacc cccctacatt ttcccctgcc     120

ctgctggtcg tgaccgaggg cgacaatgcc accttcacct gtagcttcag caacaccagc     180

gagagcttcg tgctgaactg gtacagaatg agccccagca accagaccga caagctggcc     240

gccttccccg aggatagatc tcagcccggc caggactgcc ggttcagagt gacccagctg     300

cccaacggcc gggacttcca catgtctgtc gtgcgggcca gacggaacga cagcggcaca     360

tatctgtgcg gcgccatcag cctggccccc aaggcccaga tcaaagagag cctgagagcc     420

gagctgagag tgaccgagag aagggccgaa gtgcctaccg cccaccctag cccatctcca     480

agacctgccg gccagttcca gacactggtc tgtcccagcc ctctgtttcc cggccctagc     540

aagcctttct gggtgctggt ggtggtcgga ggcgtgctgg cctgctacag cctgctggtc     600

accgtggcct tcatcatctt ttgggtccgc agcaagcgga gcagaggcgg ccacagcgac     660

tacatgaaca tgacccctag acggcctggc cccaccagaa agcactacca gccctacgcc     720

cctccccggg actttgccgc ctacagaagc                                     750


<210> SEQ ID NO 98
<211> LENGTH: 250
<212> TYPE: PRT
<213> ORGANISM: Artificial Sequence
<220> FEATURE:
<223> OTHER INFORMATION: huPD1-CD28Cys

<400> SEQUENCE: 98

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80
```

```
Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Cys Pro Ser Pro Leu Phe
                165                 170                 175

Pro Gly Pro Ser Lys Pro Phe Trp Val Leu Val Val Val Gly Gly Val
            180                 185                 190

Leu Ala Cys Tyr Ser Leu Leu Val Thr Val Ala Phe Ile Ile Phe Trp
        195                 200                 205

Val Arg Ser Lys Arg Ser Arg Gly Gly His Ser Asp Tyr Met Asn Met
    210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser
                245                 250
```

<210> SEQ ID NO 99
<211> LENGTH: 714
<212> TYPE: DNA
<213> ORGANISM: Artificial Sequence
<220> FEATURE:
<223> OTHER INFORMATION: huPD1-12aas-CD28Cys

<400> SEQUENCE: 99

```
atgcagatcc ctcaggcccc ttggcctgtc gtgtgggctg tgctgcagct gggatggcgg      60

cctggctggt ttctggacag ccccgacaga ccctggaacc cccctacatt ttcccctgcc     120

ctgctggtcg tgaccgaggg cgacaatgcc accttcacct gtagcttcag caacaccagc     180

gagagcttcg tgctgaactg gtacagaatg agccccagca accagaccga caagctggcc     240

gccttccccg aggatagatc tcagcccggc caggactgcc ggttcagagt gacccagctg     300

cccaacggcc gggacttcca catgtctgtc gtgcgggcca gacggaacga cagcggcaca     360

tatctgtgcg gcgccatcag cctggccccc aaggcccaga tcaaagagag cctgagagcc     420

gagctgagag tgaccgagag aagggccgaa gtgcctaccg cccaccctag cccatgtccc     480

agccctctgt ttcccggccc tagcaagcct ttctgggtgc tggtggtggt cggaggcgtg     540

ctggcctgct acagcctgct ggtcaccgtg gccttcatca tcttttgggt ccgcagcaag     600

cggagcagag gcggccacag cgactacatg aacatgaccc ctagacggcc tggccccacc     660

agaaagcact accagcccta cgcccctccc cgggactttg ccgcctacag aagc           714
```

<210> SEQ ID NO 100
<211> LENGTH: 238
<212> TYPE: PRT
<213> ORGANISM: Artificial Sequence
<220> FEATURE:
<223> OTHER INFORMATION: huPD1-12aas-CD28Cys

<400> SEQUENCE: 100

```
Met Gln Ile Pro Gln Ala Pro Trp Pro Val Val Trp Ala Val Leu Gln
1               5                   10                  15
```

```
Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Cys Pro
145                 150                 155                 160

Ser Pro Leu Phe Pro Gly Pro Ser Lys Pro Phe Trp Val Leu Val Val
                165                 170                 175

Val Gly Gly Val Leu Ala Cys Tyr Ser Leu Leu Val Thr Val Ala Phe
            180                 185                 190

Ile Ile Phe Trp Val Arg Ser Lys Arg Ser Arg Gly Gly His Ser Asp
        195                 200                 205

Tyr Met Asn Met Thr Pro Arg Arg Pro Gly Pro Thr Arg Lys His Tyr
    210                 215                 220

Gln Pro Tyr Ala Pro Pro Arg Asp Phe Ala Ala Tyr Arg Ser
225                 230                 235
```

```
<210> SEQ ID NO 101
<211> LENGTH: 705
<212> TYPE: DNA
<213> ORGANISM: Artificial Sequence
<220> FEATURE:
<223> OTHER INFORMATION: huPD1-15aas-CD28Cys

<400> SEQUENCE: 101

atgcagatcc ctcaggcccc ttggcctgtc gtgtgggctg tgctgcagct gggatggcgg     60

cctggctggt ttctggacag ccccgacaga ccctggaacc cccctacatt ttcccctgcc    120

ctgctggtcg tgaccgaggg cgacaatgcc accttcacct gtagcttcag caacaccagc    180

gagagcttcg tgctgaactg gtacagaatg agccccagca accagaccga caagctggcc    240

gccttccccg aggatagatc tcagcccggc caggactgcc ggttcagagt gacccagctg    300

cccaacggcc gggacttcca catgtctgtc gtgcgggcca gacggaacga cagcggcaca    360

tatctgtgcg gcgccatcag cctggccccc aaggcccaga tcaaagagag cctgagagcc    420

gagctgagag tgaccgagag aagggccgaa gtgcctaccg cccactgtcc cagccctctg    480

tttcccggcc ctagcaagcc tttctgggtg ctggtggtgg tcggaggcgt gctggcctgc    540

tacagcctgc tggtcaccgt ggccttcatc atcttttggg tccgcagcaa gcggagcaga    600

ggcggccaca gcgactacat gaacatgacc cctagacggc ctggccccac cagaaagcac    660

taccagccct acgcccctcc ccgggacttt gccgcctaca gaagc                    705

<210> SEQ ID NO 102
```

<211> LENGTH: 235
<212> TYPE: PRT
<213> ORGANISM: Artificial Sequence
<220> FEATURE:
<223> OTHER INFORMATION: huPD1-15aas-CD28Cys

<400> SEQUENCE: 102

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Cys Pro Ser Pro Leu
145                 150                 155                 160

Phe Pro Gly Pro Ser Lys Pro Phe Trp Val Leu Val Val Val Gly Gly
                165                 170                 175

Val Leu Ala Cys Tyr Ser Leu Leu Val Thr Val Ala Phe Ile Ile Phe
            180                 185                 190

Trp Val Arg Ser Lys Arg Ser Arg Gly Gly His Ser Asp Tyr Met Asn
        195                 200                 205

Met Thr Pro Arg Arg Pro Gly Pro Thr Arg Lys His Tyr Gln Pro Tyr
    210                 215                 220

Ala Pro Pro Arg Asp Phe Ala Ala Tyr Arg Ser
225                 230                 235
```

<210> SEQ ID NO 103
<211> LENGTH: 687
<212> TYPE: DNA
<213> ORGANISM: Artificial Sequence
<220> FEATURE:
<223> OTHER INFORMATION: huPD1-21aas-CD28Cys

<400> SEQUENCE: 103

```
atgcagatcc ctcaggcccc ttggcctgtc gtgtgggctg tgctgcagct gggatggcgg     60

cctggctggt ttctggacag ccccgacaga ccctggaacc cccctacatt ttcccctgcc    120

ctgctggtcg tgaccgaggg cgacaatgcc accttcacct gtagcttcag caacaccagc    180

gagagcttcg tgctgaactg gtacagaatg agccccagca accagaccga caagctggcc    240

gccttccccg aggatagatc tcagcccggc caggactgcc ggttcagagt gacccagctg    300

cccaacggcc gggacttcca catgtctgtc gtgcgggcca gacggaacga cagcggcaca    360

tatctgtgcg gcgccatcag cctggccccc aaggcccaga tcaaagagag cctgagagcc    420

gagctgagag tgaccgagag aagggcctgt cccagccctc tgtttcccgg ccctagcaag    480
```

```
cctttctggg tgctggtggt ggtcggaggc gtgctggcct gctacagcct gctggtcacc    540

gtggccttca tcatcttttg ggtccgcagc aagcggagca gaggcggcca cagcgactac    600

atgaacatga cccctagacg gcctggcccc accagaaagc actaccagcc ctacgcccct    660

ccccgggact ttgccgccta cagaagc                                          687


<210> SEQ ID NO 104
<211> LENGTH: 229
<212> TYPE: PRT
<213> ORGANISM: Artificial Sequence
<220> FEATURE:
<223> OTHER INFORMATION: huPD1-21aas-CD28Cys

<400> SEQUENCE: 104

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Cys Pro Ser Pro Leu Phe Pro Gly Pro Ser Lys
145                 150                 155                 160

Pro Phe Trp Val Leu Val Val Val Gly Gly Val Leu Ala Cys Tyr Ser
                165                 170                 175

Leu Leu Val Thr Val Ala Phe Ile Ile Phe Trp Val Arg Ser Lys Arg
            180                 185                 190

Ser Arg Gly Gly His Ser Asp Tyr Met Asn Met Thr Pro Arg Arg Pro
        195                 200                 205

Gly Pro Thr Arg Lys His Tyr Gln Pro Tyr Ala Pro Pro Arg Asp Phe
    210                 215                 220

Ala Ala Tyr Arg Ser
225


<210> SEQ ID NO 105
<211> LENGTH: 810
<212> TYPE: DNA
<213> ORGANISM: Artificial Sequence
<220> FEATURE:
<223> OTHER INFORMATION: muCD2tm-CD28

<400> SEQUENCE: 105

atgaagtgca agttcctggg ctcattcttc ctgctgttca gcctgagcgg caagggcgcc     60

gactgcagag acaacgagac aatctggggc gtgctgggcc acggcatcac cctgaacatc    120

cccaacttcc agatgaccga cgacatcgac gaagtgcgct gggtgcgaag aggcacactg    180
```

```
gtggccgagt tcaagagaaa gaagccccca ttcctgatca gcgagacata cgaggtgctg    240

gccaacggca gcctgaagat caagaaaccc atgatgagaa acgacagcgg cacctacaac    300

gtgatggtgt acggcaccaa cggcatgacc agactggaaa aggacctgga cgtgcggatc    360

ctggaaaggg tgtccaagcc catgatccac tgggagtgcc ccaacaccac cctgacctgt    420

gctgtgctgc agggcaccga cttcgagctg aagctgtacc agggcgagac actgctgaac    480

tccctgcccc agaaaaacat gagctaccag tggaccaacc tgaacgcccc cttcaagtgc    540

gaggccatca accccgtgtc caaagaaagc aagatggaag tcgtgaactg ccccgagaag    600

ggcctgagct tctacgtgac agtgggcgtg ggagctggcg gactgctgct ggtgctgctg    660

gtggccctgt tcatcttctg catctgcaac agcagacgga acagaggcgg ccagagcgac    720

tacatgaaca tgacccccag aaggcctggc ctgaccagaa agccctacca gccttacgcc    780

cctgccagag acttcgccgc ctacagacct                                     810
```

<210> SEQ ID NO 106
<211> LENGTH: 270
<212> TYPE: PRT
<213> ORGANISM: Artificial Sequence
<220> FEATURE:
<223> OTHER INFORMATION: muCD2tm-CD28

<400> SEQUENCE: 106

```
Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
            20                  25                  30

Gly His Gly Ile Thr Leu Asn Ile Pro Asn Phe Gln Met Thr Asp Asp
        35                  40                  45

Ile Asp Glu Val Arg Trp Val Arg Arg Gly Thr Leu Val Ala Glu Phe
    50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser
                85                  90                  95

Gly Thr Tyr Asn Val Met Val Tyr Gly Thr Asn Gly Met Thr Arg Leu
            100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
    130                 135                 140

Gly Thr Asp Phe Glu Leu Lys Leu Tyr Gln Gly Glu Thr Leu Leu Asn
145                 150                 155                 160

Ser Leu Pro Gln Lys Asn Met Ser Tyr Gln Trp Thr Asn Leu Asn Ala
                165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Phe Tyr Val Thr Val
        195                 200                 205

Gly Val Gly Ala Gly Gly Leu Leu Leu Val Leu Leu Val Ala Leu Phe
    210                 215                 220

Ile Phe Cys Ile Cys Asn Ser Arg Arg Asn Arg Gly Gly Gln Ser Asp
225                 230                 235                 240

Tyr Met Asn Met Thr Pro Arg Arg Pro Gly Leu Thr Arg Lys Pro Tyr
                245                 250                 255
```

```
Gln Pro Tyr Ala Pro Ala Arg Asp Phe Ala Ala Tyr Arg Pro
            260                 265                 270


<210> SEQ ID NO 107
<211> LENGTH: 813
<212> TYPE: DNA
<213> ORGANISM: Artificial Sequence
<220> FEATURE:
<223> OTHER INFORMATION: muCD2-CD28tm

<400> SEQUENCE: 107

atgaagtgca agttcctggg ctcattcttc ctgctgttca gcctgagcgg caagggcgcc      60

gactgcagag acaacgagac aatctggggc gtgctgggcc acggcatcac cctgaacatc     120

cccaacttcc agatgaccga cgacatcgac gaagtgcgct gggtgcgaag aggcacactg     180

gtggccgagt tcaagagaaa gaagcccccca ttcctgatca gcgagacata cgaggtgctg    240

gccaacggca gcctgaagat caagaaaccc atgatgagaa acgacagcgg cacctacaac     300

gtgatggtgt acggcaccaa cggcatgacc agactggaaa aggacctgga cgtgcggatc     360

ctggaaaggg tgtccaagcc catgatccac tgggagtgcc ccaacaccac cctgacctgt     420

gctgtgctgc agggcaccga cttcgagctg aagctgtacc agggcgagac actgctgaac     480

tccctgcccc agaaaaacat gagctaccag tggaccaacc tgaacgcccc cttcaagtgc     540

gaggccatca accccgtgtc caaagaaagc aagatggaag tcgtgaactg ccccgagaag     600

ggcctgagct tctgggccct ggtggtggtg gccggcgtgc tgttttgtta cggcctgctc     660

gtgaccgtgg ccctgtgcgt gatctggacc aacagcagaa gaaacagagg cggccagagc     720

gactacatga acatgacccc cagaaggcct ggcctgacca gaaagcccta ccagccttac     780

gcccctgcca gagacttcgc cgcctacaga ccc                                  813


<210> SEQ ID NO 108
<211> LENGTH: 271
<212> TYPE: PRT
<213> ORGANISM: Artificial Sequence
<220> FEATURE:
<223> OTHER INFORMATION: muCD2-CD28tm

<400> SEQUENCE: 108

Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
            20                  25                  30

Gly His Gly Ile Thr Leu Asn Ile Pro Asn Phe Gln Met Thr Asp Asp
        35                  40                  45

Ile Asp Glu Val Arg Trp Val Arg Arg Gly Thr Leu Val Ala Glu Phe
    50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser
                85                  90                  95

Gly Thr Tyr Asn Val Met Val Tyr Gly Thr Asn Gly Met Thr Arg Leu
            100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
    130                 135                 140
```

```
Gly Thr Asp Phe Glu Leu Lys Leu Tyr Gln Gly Glu Thr Leu Leu Asn
145                 150                 155                 160

Ser Leu Pro Gln Lys Asn Met Ser Tyr Gln Trp Thr Asn Leu Asn Ala
                165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Phe Trp Ala Leu Val
        195                 200                 205

Val Val Ala Gly Val Leu Phe Cys Tyr Gly Leu Leu Val Thr Val Ala
    210                 215                 220

Leu Cys Val Ile Trp Thr Asn Ser Arg Arg Asn Arg Gly Gly Gln Ser
225                 230                 235                 240

Asp Tyr Met Asn Met Thr Pro Arg Arg Pro Gly Leu Thr Arg Lys Pro
                245                 250                 255

Tyr Gln Pro Tyr Ala Pro Ala Arg Asp Phe Ala Ala Tyr Arg Pro
            260                 265                 270


<210> SEQ ID NO 109
<211> LENGTH: 840
<212> TYPE: DNA
<213> ORGANISM: Artificial Sequence
<220> FEATURE:
<223> OTHER INFORMATION: muCD2-CD28Cys

<400> SEQUENCE: 109

atgaagtgca agttcctggg ctcattcttc ctgctgttca gcctgagcgg caagggcgcc      60

gactgcagag acaacgagac aatctggggc gtgctgggcc acggcatcac cctgaacatc     120

cccaacttcc agatgaccga cgacatcgac gaagtgcgct gggtgcgaag aggcacactg     180

gtggccgagt tcaagagaaa gaagccccca ttcctgatca gcgagacata cgaggtgctg     240

gccaacggca gcctgaagat caagaaaccc atgatgagaa acgacagcgg cacctacaac     300

gtgatggtgt acggcaccaa cggcatgacc agactggaaa aggacctgga cgtgcggatc     360

ctggaaaggg tgtccaagcc catgatccac tgggagtgcc ccaacaccac cctgacctgt     420

gctgtgctgc agggcaccga cttcgagctg aagctgtacc agggcgagac actgctgaac     480

tccctgcccc agaaaaacat gagctaccag tggaccaacc tgaacgcccc cttcaagtgc     540

gaggccatca accccgtgtc caaagaaagc aagatggaag tcgtgaactg ccccgagaag     600

ggcctgagct gccacaccca gagcagcccc aagctgttct gggccctggt ggtggtggcc     660

ggcgtgctgt tttgttacgg cctgctcgtg accgtggccc tgtgcgtgat ctggaccaac     720

agcagaagaa acagaggcgg ccagagcgac tacatgaaca tgacccccag aaggcctggc     780

ctgaccagaa agccctacca gccttacgcc cctgccagag acttcgccgc ctacagacct     840


<210> SEQ ID NO 110
<211> LENGTH: 280
<212> TYPE: PRT
<213> ORGANISM: Artificial Sequence
<220> FEATURE:
<223> OTHER INFORMATION: muCD2-CD28Cys

<400> SEQUENCE: 110

Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
            20                  25                  30

Gly His Gly Ile Thr Leu Asn Ile Pro Asn Phe Gln Met Thr Asp Asp
```

```
        35                  40                  45

Ile Asp Glu Val Arg Trp Val Arg Arg Gly Thr Leu Val Ala Glu Phe
    50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser
                85                  90                  95

Gly Thr Tyr Asn Val Met Val Tyr Gly Thr Asn Gly Met Thr Arg Leu
            100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
    130                 135                 140

Gly Thr Asp Phe Glu Leu Lys Leu Tyr Gln Gly Glu Thr Leu Leu Asn
145                 150                 155                 160

Ser Leu Pro Gln Lys Asn Met Ser Tyr Gln Trp Thr Asn Leu Asn Ala
                165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Cys His Thr Gln Ser
        195                 200                 205

Ser Pro Lys Leu Phe Trp Ala Leu Val Val Val Ala Gly Val Leu Phe
    210                 215                 220

Cys Tyr Gly Leu Leu Val Thr Val Ala Leu Cys Val Ile Trp Thr Asn
225                 230                 235                 240

Ser Arg Arg Asn Arg Gly Gly Gln Ser Asp Tyr Met Asn Met Thr Pro
                245                 250                 255

Arg Arg Pro Gly Leu Thr Arg Lys Pro Tyr Gln Pro Tyr Ala Pro Ala
            260                 265                 270

Arg Asp Phe Ala Ala Tyr Arg Pro
        275                 280
```

<210> SEQ ID NO 111
<211> LENGTH: 861
<212> TYPE: DNA
<213> ORGANISM: Artificial Sequence
<220> FEATURE:
<223> OTHER INFORMATION: muCD2-CD28Cys-41BBic

<400> SEQUENCE: 111

```
atgaagtgca agttcctggg ctcattcttc ctgctgttca gcctgagcgg caagggcgcc     60

gactgcagag acaacgagac aatctggggc gtgctgggcc acggcatcac cctgaacatc    120

cccaacttcc agatgaccga cgacatcgac gaagtgcgct gggtgcgaag aggcacactg    180

gtggccgagt tcaagagaaa gaagcccccca ttcctgatca gcgagacata cgaggtgctg    240

gccaacggca gcctgaagat caagaaaccc atgatgagaa acgacagcgg cacctacaac    300

gtgatggtgt acggcaccaa cggcatgacc agactggaaa aggacctgga cgtgcggatc    360

ctggaaaggg tgtccaagcc catgatccac tgggagtgcc ccaacaccac cctgacctgt    420

gctgtgctgc agggcaccga cttcgagctg aagctgtacc agggcgagac actgctgaac    480

tccctgcccc agaaaaacat gagctaccag tggaccaacc tgaacgcccc cttcaagtgc    540

gaggccatca accccgtgtc caaagaaagc aagatggaag tcgtgaactg ccccgagaag    600

ggcctgagct gccacaccca gagcagcccc aagctgttct gggccctggt ggtggtggcc    660
```

```
ggcgtgctgt tttgttacgg cctgctcgtg accgtggccc tgtgcgtgat ctggaccagc    720

gtgctgaagt ggatcagaaa gaagttcccc cacatcttca agcagccctt caagaaaacc    780

accggcgctg cccaggaaga ggacgcctgc agctgtagat gccctcagga agaagaaggc    840

ggcggaggcg gctacgagct g                                              861
```

<210> SEQ ID NO 112
<211> LENGTH: 287
<212> TYPE: PRT
<213> ORGANISM: Artificial Sequence
<220> FEATURE:
<223> OTHER INFORMATION: muCD2-CD28Cys-41BBic

<400> SEQUENCE: 112

```
Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
            20                  25                  30

Gly His Gly Ile Thr Leu Asn Ile Pro Asn Phe Gln Met Thr Asp Asp
        35                  40                  45

Ile Asp Glu Val Arg Trp Val Arg Arg Gly Thr Leu Val Ala Glu Phe
    50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser
                85                  90                  95

Gly Thr Tyr Asn Val Met Val Tyr Gly Thr Asn Gly Met Thr Arg Leu
            100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
    130                 135                 140

Gly Thr Asp Phe Glu Leu Lys Leu Tyr Gln Gly Glu Thr Leu Leu Asn
145                 150                 155                 160

Ser Leu Pro Gln Lys Asn Met Ser Tyr Gln Trp Thr Asn Leu Asn Ala
                165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Cys His Thr Gln Ser
        195                 200                 205

Ser Pro Lys Leu Phe Trp Ala Leu Val Val Val Ala Gly Val Leu Phe
    210                 215                 220

Cys Tyr Gly Leu Leu Val Thr Val Ala Leu Cys Val Ile Trp Thr Ser
225                 230                 235                 240

Val Leu Lys Trp Ile Arg Lys Lys Phe Pro His Ile Phe Lys Gln Pro
                245                 250                 255

Phe Lys Lys Thr Thr Gly Ala Ala Gln Glu Glu Asp Ala Cys Ser Cys
            260                 265                 270

Arg Cys Pro Gln Glu Glu Glu Gly Gly Gly Gly Gly Tyr Glu Leu
        275                 280                 285
```

<210> SEQ ID NO 113
<211> LENGTH: 1080
<212> TYPE: DNA
<213> ORGANISM: Artificial Sequence
<220> FEATURE:
<223> OTHER INFORMATION: muCD200R-3aas-CD28Cys tm ic-41BB

<400> SEQUENCE: 113

```
atgttctgct tctggcggac aagcgccctg gccgtgctgc tgatctgggg agtgtttgtg     60
gccggcagca gctgcaccga caagaaccag accacccaga acaacagcag cagccccctg    120
acccaagtga acaccaccgt gtccgtgcag atcggcacca aggccctgct gtgctgtttc    180
agcatccctc tgaccaaggc tgtgctgatc acctggatca tcaagctgag aggcctgccc    240
agctgcacaa tcgcctacaa ggtggacacc aagaccaacg agacaagctg cctgggcaga    300
aacatcacct gggccagcac cccagaccac agccctgagc tgcagatcag cgccgtgaca    360
ctgcagcacg agggcaccta cacatgcgag acagtgaccc ccgagggcaa cttcgagaag    420
aactacgatc tgcaggtgct ggtgcccccc gaagtgacct acttccccga gaagaataga    480
agcgccgtgt gcgaggccat ggctggcaaa cctgccgccc agatctcttg gagccctgac    540
ggcgactgtg tgaccaccag cgagagccac agcaacggca cagtgaccgt gcggagcacc    600
tgtcactggg agcagaacaa cgtgtccgac gtgtcctgca tcgtgtccca cctgaccggc    660
aaccagagcc tgagcatcga gctgagcaga ggcggaaacc agtcctgcca cacccagagc    720
agccccaagc tgttctgggc cctggtggtg gtggccggcg tgctgttttg ttacggcctg    780
ctcgtgaccg tggccctgtg cgtgatctgg accaacagca gaagaaacag aggcggccag    840
agcgactaca tgaacatgac ccccagaagg cctggcctga ccagaaagcc ctaccagcct    900
tacgcccctg ccagagactt cgccgcctac agacctagcg tgctgaagtg gatcagaaag    960
aagttccccc acatcttcaa gcagcccttc aagaaaacca ccggcgctgc ccaggaagag   1020
gacgcctgca gctgtagatg ccctcaggaa gaagaaggcg gcggaggcgg ctacgagctg   1080
```

<210> SEQ ID NO 114
<211> LENGTH: 360
<212> TYPE: PRT
<213> ORGANISM: Artificial Sequence
<220> FEATURE:
<223> OTHER INFORMATION: muCD200R-3aas-CD28Cys tm ic-41BB

<400> SEQUENCE: 114

```
Met Phe Cys Phe Trp Arg Thr Ser Ala Leu Ala Val Leu Leu Ile Trp
1               5                   10                  15

Gly Val Phe Val Ala Gly Ser Ser Cys Thr Asp Lys Asn Gln Thr Thr
            20                  25                  30

Gln Asn Asn Ser Ser Ser Pro Leu Thr Gln Val Asn Thr Thr Val Ser
        35                  40                  45

Val Gln Ile Gly Thr Lys Ala Leu Leu Cys Cys Phe Ser Ile Pro Leu
    50                  55                  60

Thr Lys Ala Val Leu Ile Thr Trp Ile Ile Lys Leu Arg Gly Leu Pro
65                  70                  75                  80

Ser Cys Thr Ile Ala Tyr Lys Val Asp Thr Lys Thr Asn Glu Thr Ser
                85                  90                  95

Cys Leu Gly Arg Asn Ile Thr Trp Ala Ser Thr Pro Asp His Ser Pro
            100                 105                 110

Glu Leu Gln Ile Ser Ala Val Thr Leu Gln His Glu Gly Thr Tyr Thr
        115                 120                 125

Cys Glu Thr Val Thr Pro Glu Gly Asn Phe Glu Lys Asn Tyr Asp Leu
    130                 135                 140

Gln Val Leu Val Pro Pro Glu Val Thr Tyr Phe Pro Glu Lys Asn Arg
145                 150                 155                 160
```

-continued

```
Ser Ala Val Cys Glu Ala Met Ala Gly Lys Pro Ala Ala Gln Ile Ser
                165                 170                 175

Trp Ser Pro Asp Gly Asp Cys Val Thr Thr Ser Glu Ser His Ser Asn
            180                 185                 190

Gly Thr Val Thr Val Arg Ser Thr Cys His Trp Glu Gln Asn Asn Val
        195                 200                 205

Ser Asp Val Ser Cys Ile Val Ser His Leu Thr Gly Asn Gln Ser Leu
    210                 215                 220

Ser Ile Glu Leu Ser Arg Gly Gly Asn Gln Ser Cys His Thr Gln Ser
225                 230                 235                 240

Ser Pro Lys Leu Phe Trp Ala Leu Val Val Val Ala Gly Val Leu Phe
                245                 250                 255

Cys Tyr Gly Leu Leu Val Thr Val Ala Leu Cys Val Ile Trp Thr Asn
            260                 265                 270

Ser Arg Arg Asn Arg Gly Gly Gln Ser Asp Tyr Met Asn Met Thr Pro
        275                 280                 285

Arg Arg Pro Gly Leu Thr Arg Lys Pro Tyr Gln Pro Tyr Ala Pro Ala
    290                 295                 300

Arg Asp Phe Ala Ala Tyr Arg Pro Ser Val Leu Lys Trp Ile Arg Lys
305                 310                 315                 320

Lys Phe Pro His Ile Phe Lys Gln Pro Phe Lys Lys Thr Thr Gly Ala
                325                 330                 335

Ala Gln Glu Glu Asp Ala Cys Ser Cys Arg Cys Pro Gln Glu Glu Glu
            340                 345                 350

Gly Gly Gly Gly Gly Tyr Glu Leu
        355                 360
```

<210> SEQ ID NO 115
<211> LENGTH: 966
<212> TYPE: DNA
<213> ORGANISM: Artificial Sequence
<220> FEATURE:
<223> OTHER INFORMATION: muCD200R-CD28Cys tm ic-41BB

<400> SEQUENCE: 115

```
atgttctgct tctggcggac aagcgccctg gccgtgctgc tgatctgggg agtgtttgtg      60

gccggcagca gctgcaccga caagaaccag accacccaga acaacagcag cagccccctg     120

acccaagtga acaccaccgt gtccgtgcag atcggcacca aggccctgct gtgctgtttc     180

agcatccctc tgaccaaggc tgtgctgatc acctggatca tcaagctgag aggcctgccc     240

agctgcacaa tcgcctacaa ggtggacacc aagaccaacg agacaagctg cctgggcaga     300

aacatcacct gggccagcac cccagaccac agccctgagc tgcagatcag cgccgtgaca     360

ctgcagcacg agggcaccta cacatgcgag acagtgaccc ccgagggcaa cttcgagaag     420

aactacgatc tgcaggtgct ggtgcccccc gaagtgacct acttccccga gaagaataga     480

agcgccgtgt gcgaggccat ggctggcaaa cctgccgccc agatctcttg gagccctgac     540

ggcgactgtg tgaccaccag cgagagccac agcaacggca cagtgaccgt gcggagcacc     600

tgtcactggg agcagaacaa cgtgtccgac gtgtcctgca tcgtgtccca cctgaccggc     660

aaccagagcc tgagcatcga gctgagcaga ggcggaaacc agtccctgag gccctgccac     720

acccagagca gccccaagct gttctgggcc ctggtggtgg tggccggcgt gctgttttgt     780

tacggcctgc tcgtgaccgt ggccctgtgc gtgatctgga ccagcgtgct gaagtggatc     840

agaaagaagt tcccccacat cttcaagcag cccttcaaga aaaccaccgg cgctgcccag     900
```

gaagaggacg cctgcagctg tagatgccct caggaagaag aaggcggcgg aggcggctac 960
gagctg 966

<210> SEQ ID NO 116
<211> LENGTH: 322
<212> TYPE: PRT
<213> ORGANISM: Artificial Sequence
<220> FEATURE:
<223> OTHER INFORMATION: muCD200R-CD28Cys tm ic-41BB

<400> SEQUENCE: 116

Met Phe Cys Phe Trp Arg Thr Ser Ala Leu Ala Val Leu Leu Ile Trp
1 5 10 15

Gly Val Phe Val Ala Gly Ser Ser Cys Thr Asp Lys Asn Gln Thr Thr
20 25 30

Gln Asn Asn Ser Ser Ser Pro Leu Thr Gln Val Asn Thr Thr Val Ser
35 40 45

Val Gln Ile Gly Thr Lys Ala Leu Leu Cys Cys Phe Ser Ile Pro Leu
50 55 60

Thr Lys Ala Val Leu Ile Thr Trp Ile Ile Lys Leu Arg Gly Leu Pro
65 70 75 80

Ser Cys Thr Ile Ala Tyr Lys Val Asp Thr Lys Thr Asn Glu Thr Ser
85 90 95

Cys Leu Gly Arg Asn Ile Thr Trp Ala Ser Thr Pro Asp His Ser Pro
100 105 110

Glu Leu Gln Ile Ser Ala Val Thr Leu Gln His Glu Gly Thr Tyr Thr
115 120 125

Cys Glu Thr Val Thr Pro Glu Gly Asn Phe Glu Lys Asn Tyr Asp Leu
130 135 140

Gln Val Leu Val Pro Pro Glu Val Thr Tyr Phe Pro Glu Lys Asn Arg
145 150 155 160

Ser Ala Val Cys Glu Ala Met Ala Gly Lys Pro Ala Ala Gln Ile Ser
165 170 175

Trp Ser Pro Asp Gly Asp Cys Val Thr Thr Ser Glu Ser His Ser Asn
180 185 190

Gly Thr Val Thr Val Arg Ser Thr Cys His Trp Glu Gln Asn Asn Val
195 200 205

Ser Asp Val Ser Cys Ile Val Ser His Leu Thr Gly Asn Gln Ser Leu
210 215 220

Ser Ile Glu Leu Ser Arg Gly Gly Asn Gln Ser Leu Arg Pro Cys His
225 230 235 240

Thr Gln Ser Ser Pro Lys Leu Phe Trp Ala Leu Val Val Val Ala Gly
245 250 255

Val Leu Phe Cys Tyr Gly Leu Leu Val Thr Val Ala Leu Cys Val Ile
260 265 270

Trp Thr Ser Val Leu Lys Trp Ile Arg Lys Lys Phe Pro His Ile Phe
275 280 285

Lys Gln Pro Phe Lys Lys Thr Thr Gly Ala Ala Gln Glu Glu Asp Ala
290 295 300

Cys Ser Cys Arg Cys Pro Gln Glu Glu Glu Gly Gly Gly Gly Gly Tyr
305 310 315 320

Glu Leu

<210> SEQ ID NO 117
<211> LENGTH: 681

<212> TYPE: DNA
<213> ORGANISM: Artificial Sequence
<220> FEATURE:
<223> OTHER INFORMATION: muFas tm-CD28

<400> SEQUENCE: 117

```
atgctgtgga tctgggccgt gctgcctctg gtgctggctg gatcacagct gagagtgcac     60

acccagggca ccaacagcat cagcgagagc ctgaagctga gaagaagagt gcgcgagaca    120

gacaagaact gcagcgaggg cctgtaccag ggcggaccct tctgctgtca gccttgccag    180

cccggcaaga aaaaggtgga agattgcaag atgaacggcg gcacccctac ctgcgcccct    240

tgtacagagg gcaaagagta catggacaag aaccactacg ccgacaagtg cagacggtgc    300

accctgtgcg acgaggaaca cggcctggaa gtggaaacaa actgcaccct gacccagaac    360

accaagtgca agtgcaaacc cgacttctac tgcgacagcc ccggctgcga gcactgcgtc    420

agatgtgcct cttgcgagca cggcaccctg gaaccttgta ccgccaccag caacaccaac    480

tgccggaagc agagccccag aaacagactg tggctgctga ccatcctggt gctgctgatc    540

cccctggtgt tcatctacaa cagcagaaga aacagaggcg gccagagcga ctacatgaac    600

atgaccccca gaaggcctgg cctgaccaga aagccctacc agccttacgc ccctgccaga    660

gacttcgccg cctacagacc t                                              681
```

<210> SEQ ID NO 118
<211> LENGTH: 227
<212> TYPE: PRT
<213> ORGANISM: Artificial Sequence
<220> FEATURE:
<223> OTHER INFORMATION: muFas tm-CD28

<400> SEQUENCE: 118

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Leu Trp Leu Leu Thr Ile Leu
                165                 170                 175

Val Leu Leu Ile Pro Leu Val Phe Ile Tyr Asn Ser Arg Arg Asn Arg
            180                 185                 190

Gly Gly Gln Ser Asp Tyr Met Asn Met Thr Pro Arg Arg Pro Gly Leu
        195                 200                 205
```

Thr Arg Lys Pro Tyr Gln Pro Tyr Ala Pro Ala Arg Asp Phe Ala Ala
    210                 215                 220

Tyr Arg Pro
225

<210> SEQ ID NO 119
<211> LENGTH: 711
<212> TYPE: DNA
<213> ORGANISM: Artificial Sequence
<220> FEATURE:
<223> OTHER INFORMATION: muFas-CD28tm

<400> SEQUENCE: 119
atgctgtgga tctgggccgt gctgcctctg gtgctggctg gatcacagct gagagtgcac 60
acccagggca ccaacagcat cagcgagagc ctgaagctga gaagaagagt gcgcgagaca 120
gacaagaact gcagcgaggg cctgtaccag ggcggaccct tctgctgtca gccttgccag 180
cccggcaaga aaaaggtgga agattgcaag atgaacggcg gcacccctac ctgcgcccct 240
tgtacagagg gcaaagagta catggacaag aaccactacg ccgacaagtg cagacggtgc 300
accctgtgcg acgaggaaca cggcctggaa gtggaaacaa actgcaccct gacccagaac 360
accaagtgca agtgcaaacc cgacttctac tgcgacagcc ccggctgcga gcactgcgtc 420
agatgtgcct cttgcgagca cggcaccctg gaaccttgta ccgccaccag caacaccaac 480
tgccggaagc agagccccag aaacagattc tgggccctgg tggtggtggc cggcgtgctg 540
ttttgttacg gcctgctcgt gaccgtggcc ctgtgcgtga tctggaccaa cagcagaaga 600
aacagaggcg gccagagcga ctacatgaac atgaccccca gaaggcctgg cctgaccaga 660
aagccctacc agccttacgc ccctgccaga gacttcgccg cctacagacc t 711

<210> SEQ ID NO 120
<211> LENGTH: 237
<212> TYPE: PRT
<213> ORGANISM: Artificial Sequence
<220> FEATURE:
<223> OTHER INFORMATION: muFas-CD28tm

<400> SEQUENCE: 120

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn

```
145                 150                 155                 160

Cys Arg Lys Gln Ser Pro Arg Asn Arg Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235


<210> SEQ ID NO 121
<211> LENGTH: 738
<212> TYPE: DNA
<213> ORGANISM: Artificial Sequence
<220> FEATURE:
<223> OTHER INFORMATION: muFas-CD28Cys

<400> SEQUENCE: 121

atgctgtgga tctgggccgt gctgcctctg gtgctggctg gatcacagct gagagtgcac      60

acccagggca ccaacagcat cagcgagagc ctgaagctga gaagaagagt gcgcgagaca     120

gacaagaact gcagcgaggg cctgtaccag ggcggaccct tctgctgtca gccttgccag     180

cccggcaaga aaaaggtgga agattgcaag atgaacggcg gcacccctac ctgcgcccct     240

tgtacagagg gcaaagagta catggacaag aaccactacg ccgacaagtg cagacggtgc     300

accctgtgcg acgaggaaca cggcctggaa gtggaaacaa actgcaccct gacccagaac     360

accaagtgca agtgcaaacc cgacttctac tgcgacagcc ccggctgcga gcactgcgtc     420

agatgtgcct cttgcgagca cggcaccctg gaaccttgta ccgccaccag caacaccaac     480

tgccggaagc agagccccag aaacagatgc cacacccaga gcagccccaa gctgttctgg     540

gccctggtgg tggtggccgg cgtgctgttt tgttacggcc tgctcgtgac cgtggccctg     600

tgcgtgatct ggaccaacag cagaagaaac agaggcggcc agagcgacta catgaacatg     660

acccccagaa ggcctggcct gaccagaaag ccctaccagc cttacgcccc tgccagagac     720

ttcgccgcct acagacct                                                   738


<210> SEQ ID NO 122
<211> LENGTH: 246
<212> TYPE: PRT
<213> ORGANISM: Artificial Sequence
<220> FEATURE:
<223> OTHER INFORMATION: muFas-CD28Cys

<400> SEQUENCE: 122

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
```

```
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Cys His Thr Gln Ser Ser Pro
                165                 170                 175

Lys Leu Phe Trp Ala Leu Val Val Val Ala Gly Val Leu Phe Cys Tyr
            180                 185                 190

Gly Leu Leu Val Thr Val Ala Leu Cys Val Ile Trp Thr Asn Ser Arg
        195                 200                 205

Arg Asn Arg Gly Gly Gln Ser Asp Tyr Met Asn Met Thr Pro Arg Arg
    210                 215                 220

Pro Gly Leu Thr Arg Lys Pro Tyr Gln Pro Tyr Ala Pro Ala Arg Asp
225                 230                 235                 240

Phe Ala Ala Tyr Arg Pro
                245


<210> SEQ ID NO 123
<211> LENGTH: 711
<212> TYPE: DNA
<213> ORGANISM: Artificial Sequence
<220> FEATURE:
<223> OTHER INFORMATION: muFas-9aas-CD28Cys

<400> SEQUENCE: 123

atgctgtgga tctgggccgt gctgcctctg gtgctggctg gatcacagct gagagtgcac      60

acccagggca ccaacagcat cagcgagagc ctgaagctga gaagaagagt gcgcgagaca     120

gacaagaact gcagcgaggg cctgtaccag ggcggaccct tctgctgtca gccttgccag     180

cccggcaaga aaaaggtgga agattgcaag atgaacggcg gcacccctac ctgcgcccct     240

tgtacagagg gcaaagagta catggacaag aaccactacg ccgacaagtg cagacggtgc     300

accctgtgcg acgaggaaca cggcctggaa gtggaaacaa actgcaccct gacccagaac     360

accaagtgca agtgcaaacc cgacttctac tgcgacagcc ccggctgcga gcactgcgtc     420

agatgtgcct cttgcgagca cggcaccctg gaaccttgta ccgccaccag caacaccaac     480

tgccacaccc agagcagccc caagctgttc tgggccctgg tggtggtggc cggcgtgctg     540

ttttgttacg gcctgctcgt gaccgtggcc ctgtgcgtga tctggaccaa cagcagaaga     600

aacagaggcg gccagagcga ctacatgaac atgacccccca gaaggcctgg cctgaccaga     660

aagccctacc agccttacgc ccctgccaga gacttcgccg cctacagacc t              711


<210> SEQ ID NO 124
<211> LENGTH: 237
<212> TYPE: PRT
<213> ORGANISM: Artificial Sequence
<220> FEATURE:
<223> OTHER INFORMATION: muFas-9aas-CD28Cys

<400> SEQUENCE: 124

Met Leu Trp Ile Trp Ala Val Leu Pro Leu Val Leu Ala Gly Ser Gln
1               5                   10                  15
```

```
Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys His Thr Gln Ser Ser Pro Lys Leu Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235
```

<210> SEQ ID NO 125
<211> LENGTH: 693
<212> TYPE: DNA
<213> ORGANISM: Artificial Sequence
<220> FEATURE:
<223> OTHER INFORMATION: muPD1tm-CD28

<400> SEQUENCE: 125

```
atgtgggtgc gacaggtgcc ctggtctttc acctgggctg tgctgcagct gagctggcag     60

tctggctggc tgctggaagt gcctaacggc ccttggagaa gcctgacctt ctaccccgct    120

tggctgaccg tgtctgaggg cgccaacgcc accttcacct gtagcctgag caattggagc    180

gaggacctga tgctgaactg gaacagactg agccccagca accagaccga gaagcaggcc    240

gccttctgca acggcctgtc tcagcctgtg caggacgcca gattccagat catccagctg    300

cccaacagac acgacttcca catgaacatc ctggacacca gaagaaacga cagcggcatc    360

tacctgtgcg gcgccatcag cctgcacccc aaggccaaga tcgaggaatc tcctggcgcc    420

gagctggtcg tgaccgagag aatcctggaa acctccacca gatacccag ccccagccct    480

aagcccgagg gcagatttca gggcatggtc atcggcatca tgagcgccct cgtgggcatc    540

ccagtgttgc tgctgctggc ctgggccctg aacagcagaa gaaacagagg cggccagagc    600

gactacatga acatgacccc cagaaggcct ggcctgacca gaaagcccta ccagccttac    660

gcccctgcca gagacttcgc cgcctacaga cct                                 693
```

<210> SEQ ID NO 126
<211> LENGTH: 231

<212> TYPE: PRT
<213> ORGANISM: Artificial Sequence
<220> FEATURE:
<223> OTHER INFORMATION: muPD1tm-CD28

<400> SEQUENCE: 126

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Asn Ser
            180                 185                 190

Arg Arg Asn Arg Gly Gly Gln Ser Asp Tyr Met Asn Met Thr Pro Arg
        195                 200                 205

Arg Pro Gly Leu Thr Arg Lys Pro Tyr Gln Pro Tyr Ala Pro Ala Arg
    210                 215                 220

Asp Phe Ala Ala Tyr Arg Pro
225                 230
```

<210> SEQ ID NO 127
<211> LENGTH: 711
<212> TYPE: DNA
<213> ORGANISM: Artificial Sequence
<220> FEATURE:
<223> OTHER INFORMATION: muPD1-CD28tm

<400> SEQUENCE: 127

```
atgtgggtgc gacaggtgcc ctggtctttc acctgggctg tgctgcagct gagctggcag     60

tctggctggc tgctggaagt gcctaacggc ccttggagaa gcctgacctt ctaccccgct    120

tggctgaccg tgtctgaggg cgccaacgcc accttcacct gtagcctgag caattggagc    180

gaggacctga tgctgaactg gaacagactg agccccagca accagaccga gaagcaggcc    240

gccttctgca acggcctgtc tcagcctgtg caggacgcca gattccagat catccagctg    300

cccaacagac acgacttcca catgaacatc ctggacacca gaagaaacga cagcggcatc    360

tacctgtgcg gcgccatcag cctgcacccc aaggccaaga tcgaggaatc tcctggcgcc    420

gagctggtcg tgaccgagag aatcctggaa acctccacca gataccccag ccccagccct    480

aagcccgagg gcagatttca gggcatgttc tgggccctgg tggtggtggc cggcgtgctg    540
```

```
ttttgttacg gcctgctcgt gaccgtggcc ctgtgcgtga tctggaccaa cagcagaaga    600

aacagaggcg gccagagcga ctacatgaac atgaccccca gaaggcctgg cctgaccaga    660

aagccctacc agccttacgc ccctgccaga gacttcgccg cctacagacc t             711


<210> SEQ ID NO 128
<211> LENGTH: 237
<212> TYPE: PRT
<213> ORGANISM: Artificial Sequence
<220> FEATURE:
<223> OTHER INFORMATION: muPD1-CD28tm

<400> SEQUENCE: 128

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235


<210> SEQ ID NO 129
<211> LENGTH: 738
<212> TYPE: DNA
<213> ORGANISM: Artificial Sequence
<220> FEATURE:
<223> OTHER INFORMATION: muPD1-CD28Cys

<400> SEQUENCE: 129

atgtgggtgc gacaggtgcc ctggtctttc acctgggctg tgctgcagct gagctggcag     60

tctggctggc tgctggaagt gcctaacggc ccttggagaa gcctgacctt ctaccccgct    120

tggctgaccg tgtctgaggg cgccaacgcc accttcacct gtagcctgag caattggagc    180

gaggacctga tgctgaactg gaacagactg agccccagca accagaccga gaagcaggcc    240
```

```
gccttctgca acggcctgtc tcagcctgtg caggacgcca gattccagat catccagctg    300

cccaacagac acgacttcca catgaacatc ctggacacca gaagaaacga cagcggcatc    360

tacctgtgcg gcgccatcag cctgcacccc aaggccaaga tcgaggaatc tcctggcgcc    420

gagctggtcg tgaccgagag aatcctggaa acctccacca gataccccag ccccagccct    480

aagcccgagg gcagatttca gggcatgtgc cacacccaga gcagccccaa gctgttctgg    540

gctctggtgg tggtggccgg cgtgctgttt tgttacggcc tgctcgtgac cgtggccctg    600

tgcgtgatct ggaccaacag cagacggaac agaggcggcc agagcgacta catgaatatg    660

acccccagaa ggcctggcct gaccagaaag ccctaccagc cttacgcccc tgccagagac    720

ttcgccgcct acagacct                                                  738
```

```
<210> SEQ ID NO 130
<211> LENGTH: 246
<212> TYPE: PRT
<213> ORGANISM: Artificial Sequence
<220> FEATURE:
<223> OTHER INFORMATION: muPD1-CD28Cys

<400> SEQUENCE: 130

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Cys His Thr Gln Ser Ser Pro
                165                 170                 175

Lys Leu Phe Trp Ala Leu Val Val Val Ala Gly Val Leu Phe Cys Tyr
            180                 185                 190

Gly Leu Leu Val Thr Val Ala Leu Cys Val Ile Trp Thr Asn Ser Arg
        195                 200                 205

Arg Asn Arg Gly Gly Gln Ser Asp Tyr Met Asn Met Thr Pro Arg Arg
    210                 215                 220

Pro Gly Leu Thr Arg Lys Pro Tyr Gln Pro Tyr Ala Pro Ala Arg Asp
225                 230                 235                 240

Phe Ala Ala Tyr Arg Pro
                245

<210> SEQ ID NO 131
```

<211> LENGTH: 711
<212> TYPE: DNA
<213> ORGANISM: Artificial Sequence
<220> FEATURE:
<223> OTHER INFORMATION: muPD1-9aas-CD28Cys

<400> SEQUENCE: 131

```
atgtgggtgc gacaggtgcc ctggtctttc acctgggctg tgctgcagct gagctggcag     60

tctggctggc tgctggaagt gcctaacggc ccttggagaa gcctgacctt ctaccccgct    120

tggctgaccg tgtctgaggg cgccaacgcc accttcacct gtagcctgag caattggagc    180

gaggacctga tgctgaactg gaacagactg agccccagca accagaccga gaagcaggcc    240

gccttctgca acggcctgtc tcagcctgtg caggacgcca gattccagat catccagctg    300

cccaacagac acgacttcca catgaacatc ctggacacca gaagaaacga cagcggcatc    360

tacctgtgcg gcgccatcag cctgcacccc aaggccaaga tcgaggaatc tcctggcgcc    420

gagctggtcg tgaccgagag aatcctggaa acctccacca gataccccag ccccagccct    480

tgccacaccc agagcagccc caagctgttc tgggctctgg tggtggtggc cggcgtgctg    540

ttttgttacg gcctgctcgt gaccgtggcc ctgtgcgtga tctggaccaa cagcagacgg    600

aacagaggcg gccagagcga ctacatgaat atgaccccca gaaggcctgg cctgaccaga    660

aagccctacc agccttacgc ccctgccaga gacttcgccg cctacagacc t              711
```

<210> SEQ ID NO 132
<211> LENGTH: 237
<212> TYPE: PRT
<213> ORGANISM: Artificial Sequence
<220> FEATURE:
<223> OTHER INFORMATION: muPD1-9aas-CD28Cys

<400> SEQUENCE: 132

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Cys His Thr Gln Ser Ser Pro Lys Leu Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr
```

```
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235


<210> SEQ ID NO 133
<211> LENGTH: 675
<212> TYPE: DNA
<213> ORGANISM: Artificial Sequence
<220> FEATURE:
<223> OTHER INFORMATION: muPD1-21aas-CD28Cys

<400> SEQUENCE: 133

atgtgggtgc gacaggtgcc ctggtctttc acctgggctg tgctgcagct gagctggcag      60

tctggctggc tgctggaagt gcctaacggc ccttggagaa gcctgacctt ctaccccgct     120

tggctgaccg tgtctgaggg cgccaacgcc accttcacct gtagcctgag caattggagc     180

gaggacctga tgctgaactg gaacagactg agccccagca accagaccga gaagcaggcc     240

gccttctgca acggcctgtc tcagcctgtg caggacgcca gattccagat catccagctg     300

cccaacagac acgacttcca catgaacatc ctggacacca gaagaaacga cagcggcatc     360

tacctgtgcg gcgccatcag cctgcacccc aaggccaaga tcgaggaatc tcctggcgcc     420

gagctggtcg tgaccgagag aatctgccac acccagagca gccccaagct gttctgggct     480

ctggtggtgg tggccggcgt gctgttttgt tacggcctgc tcgtgaccgt ggccctgtgc     540

gtgatctgga ccaacagcag acggaacaga ggcggccaga gcgactacat gaatatgacc     600

cccagaaggc ctggcctgac cagaaagccc taccagcctt acgcccctgc cagagacttc     660

gccgcctaca gacct                                                      675


<210> SEQ ID NO 134
<211> LENGTH: 225
<212> TYPE: PRT
<213> ORGANISM: Artificial Sequence
<220> FEATURE:
<223> OTHER INFORMATION: muPD1-21aas-CD28Cys

<400> SEQUENCE: 134

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140
```

```
Thr Glu Arg Ile Cys His Thr Gln Ser Ser Pro Lys Leu Phe Trp Ala
145                 150                 155                 160

Leu Val Val Val Ala Gly Val Leu Phe Cys Tyr Gly Leu Leu Val Thr
                165                 170                 175

Val Ala Leu Cys Val Ile Trp Thr Asn Ser Arg Arg Asn Arg Gly Gly
            180                 185                 190

Gln Ser Asp Tyr Met Asn Met Thr Pro Arg Arg Pro Gly Leu Thr Arg
        195                 200                 205

Lys Pro Tyr Gln Pro Tyr Ala Pro Ala Arg Asp Phe Ala Ala Tyr Arg
    210                 215                 220

Pro
225


<210> SEQ ID NO 135
<211> LENGTH: 1512
<212> TYPE: DNA
<213> ORGANISM: Artificial Sequence
<220> FEATURE:
<223> OTHER INFORMATION: muLag3tm-CD28

<400> SEQUENCE: 135

atgagagagg acctgctgct gggctttctg ctgctgggac tgctgtggga ggcccctgtg     60

gtgtcatctg gccctggcaa agaactgccc gtcgtgtggg ctcaggaagg cgctcctgtg    120

catctgccct gcagcctgaa gtcccccaac ctggacccca acttcctgag aagaggcggc    180

gtgatctggc agcaccagcc tgattctggc cagcccacac ctatccctgc cctggatctg    240

caccagggca tgcctagccc tagacagcct gcccctggca gatacaccgt gctgtctgtg    300

gctcctggcg gcctgagaag tggcagacag cctctgcacc ctcacgtgca gctggaagag    360

aggggactgc agaggggcga cttcagcctg tggctgaggc ctgccctgag aacagatgcc    420

ggcgagtacc acgctaccgt gcggctgcct aacagagccc tgagctgctc cctgagactg    480

agagtgggcc aggccagcat gatcgcctct ccatctggcg tgctgaagct gagcgactgg    540

gtgctgctga actgcagctt ctccagaccc gacagacccg tgtccgtgca ctggttccag    600

ggacagaaca gagtgcccgt gtacaacagc cccagacact tcctggccga gacattcctg    660

ctgctgcccc aggtgtcccc tctggactct ggcacatggg gctgcgtgct gacatacagg    720

gacggcttca acgtgtccat cacctacaac ctgaaggtgc tgggcctgga acccgtggct    780

cctctgacag tgtacgccgc cgagggcagc agagtggaac tgccttgtca tctgccaccc    840

ggcgtgggca caccttctct gctgatcgcc aagtggaccc ctccaggcgg aggacctgaa    900

ctgccagtgg ctggcaagag cggcaacttc accctgcacc tggaagcagt gggcctggct    960

caggccggca cctacacctg tagcatccat ctgcagggcc agcagctgaa cgccaccgtg   1020

acactggccg tgatcaccgt gacccccaag agctttggcc tgcctggctc cagaggcaag   1080

ctgctgtgtg aagtgacccc cgccagcggc aaagaaagat tcgtgtggcg gcctctgaac   1140

aacctgagca gatcctgccc aggccccgtg ctggaaatcc aggaagccag actgctggcc   1200

gagcggtggc agtgccagct gtatgaggga cagcgactgc tgggcgccac tgtgtacgct   1260

gctgagtcta gctctggcgc ccacagcgcc agaagaatca gcggcgatct gaagggcggc   1320

cacctggtgc tggtgctgat cctgggcgct ctgagcctgt tcctgctggt ggctggcgct   1380

ttcggcttta acagcagaag aaacagaggc ggccagagcg actacatgaa catgaccccc   1440

agaaggcctg gcctgaccag aaagccctac cagccttacg cccctgccag agacttcgcc   1500

gcctacagac ct                                                         1512
```

<210> SEQ ID NO 136
<211> LENGTH: 504
<212> TYPE: PRT
<213> ORGANISM: Artificial Sequence
<220> FEATURE:
<223> OTHER INFORMATION: muLag3tm-CD28

<400> SEQUENCE: 136

```
Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365
```

```
Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe Asn
    450                 455                 460

Ser Arg Arg Asn Arg Gly Gly Gln Ser Asp Tyr Met Asn Met Thr Pro
465                 470                 475                 480

Arg Arg Pro Gly Leu Thr Arg Lys Pro Tyr Gln Pro Tyr Ala Pro Ala
                485                 490                 495

Arg Asp Phe Ala Ala Tyr Arg Pro
            500
```

<210> SEQ ID NO 137
<211> LENGTH: 1530
<212> TYPE: DNA
<213> ORGANISM: Artificial Sequence
<220> FEATURE:
<223> OTHER INFORMATION: muLag3-CD28tm

<400> SEQUENCE: 137

```
atgagagagg acctgctgct gggctttctg ctgctgggac tgctgtggga ggcccctgtg      60

gtgtcatctg gccctggcaa agaactgccc gtcgtgtggg ctcaggaagg cgctcctgtg     120

catctgccct gcagcctgaa gtcccccaac ctggacccca acttcctgag aagaggcggc     180

gtgatctggc agcaccagcc tgattctggc cagcccacac ctatccctgc cctggatctg     240

caccagggca tgcctagccc tagacagcct gcccctggca gatacaccgt gctgtctgtg     300

gctcctggcg gcctgagaag tggcagacag cctctgcacc ctcacgtgca gctggaagag     360

aggggactgc agaggggcga cttcagcctg tggctgaggc ctgccctgag aacagatgcc     420

ggcgagtacc acgctaccgt gcggctgcct aacagagccc tgagctgctc cctgagactg     480

agagtgggcc aggccagcat gatcgcctct ccatctggcg tgctgaagct gagcgactgg     540

gtgctgctga actgcagctt ctccagaccc gacagacccg tgtccgtgca ctggttccag     600

ggacagaaca gagtgcccgt gtacaacagc cccagacact tcctggccga gacattcctg     660

ctgctgcccc aggtgtcccc tctggactct ggcacatggg gctgcgtgct gacatacagg     720

gacggcttca acgtgtccat cacctacaac ctgaaggtgc tgggcctgga acccgtggct     780

cctctgacag tgtacgccgc cgagggcagc agagtggaac tgccttgtca tctgccaccc     840

ggcgtgggca caccttctct gctgatcgcc aagtggaccc ctccaggcgg aggacctgaa     900

ctgccagtgg ctggcaagag cggcaacttc accctgcacc tggaagcagt gggcctggct     960

caggccggca cctacacctg tagcatccat ctgcagggcc agcagctgaa cgccaccgtg    1020

acactggccg tgatcaccgt gacccccaag agctttggcc tgcctggctc cagaggcaag    1080

ctgctgtgtg aagtgacccc cgccagcggc aaagaaagat tcgtgtggcg gcctctgaac    1140

aacctgagca gatcctgccc aggccccgtg ctggaaatcc aggaagccag actgctggcc    1200

gagcggtggc agtgccagct gtatgaggga cagcgactgc tgggcgccac tgtgtacgct    1260
```

```
gctgagtcta gctctggcgc ccacagcgcc agaagaatca gcggcgatct gaagggcggc   1320

cacctgttct gggccctggt ggtggtggcc ggcgtgctgt tttgttacgg cctgctcgtg   1380

accgtggccc tgtgcgtgat ctggaccaac agcagaagaa acagaggcgg ccagagcgac   1440

tacatgaaca tgacccccag aaggcctggc ctgaccagaa agccctacca gccttacgcc   1500

cctgccagag acttcgccgc ctacagacct                                    1530


<210> SEQ ID NO 138
<211> LENGTH: 510
<212> TYPE: PRT
<213> ORGANISM: Artificial Sequence
<220> FEATURE:
<223> OTHER INFORMATION: muLag3-CD28tm

<400> SEQUENCE: 138

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
```

```
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Phe Trp Ala Leu Val Val
        435                 440                 445

Val Ala Gly Val Leu Phe Cys Tyr Gly Leu Leu Val Thr Val Ala Leu
    450                 455                 460

Cys Val Ile Trp Thr Asn Ser Arg Arg Asn Arg Gly Gly Gln Ser Asp
465                 470                 475                 480

Tyr Met Asn Met Thr Pro Arg Arg Pro Gly Leu Thr Arg Lys Pro Tyr
                485                 490                 495

Gln Pro Tyr Ala Pro Ala Arg Asp Phe Ala Ala Tyr Arg Pro
            500                 505                 510


<210> SEQ ID NO 139
<211> LENGTH: 1557
<212> TYPE: DNA
<213> ORGANISM: Artificial Sequence
<220> FEATURE:
<223> OTHER INFORMATION: muLag3-CD28Cys

<400> SEQUENCE: 139

atgagagagg acctgctgct gggctttctg ctgctgggac tgctgtggga ggcccctgtg      60

gtgtcatctg gccctggcaa agaactgccc gtcgtgtggg ctcaggaagg cgctcctgtg     120

catctgccct gcagcctgaa gtcccccaac ctggacccca acttcctgag aagaggcggc     180

gtgatctggc agcaccagcc tgattctggc cagcccacac ctatccctgc cctggatctg     240

caccagggca tgcctagccc tagacagcct gcccctggca gatacaccgt gctgtctgtg     300

gctcctggcg gcctgagaag tggcagacag cctctgcacc ctcacgtgca gctggaagag     360

aggggactgc agaggggcga cttcagcctg tggctgaggc ctgccctgag aacagatgcc     420

ggcgagtacc acgctaccgt gcggctgcct aacagagccc tgagctgctc cctgagactg     480

agagtgggcc aggccagcat gatcgcctct ccatctggcg tgctgaagct gagcgactgg     540

gtgctgctga actgcagctt ctccagaccc gacagacccg tgtccgtgca ctggttccag     600

ggacagaaca gagtgcccgt gtacaacagc cccagacact tcctggccga gacattcctg     660

ctgctgcccc aggtgtcccc tctggactct ggcacatggg gctgcgtgct gacatacagg     720

gacggcttca acgtgtccat cacctacaac ctgaaggtgc tgggcctgga acccgtggct     780

cctctgacag tgtacgccgc cgagggcagc agagtggaac tgccttgtca tctgccaccc     840

ggcgtgggca caccttctct gctgatcgcc aagtggaccc ctccaggcgg aggacctgaa     900

ctgccagtgg ctggcaagag cggcaacttc accctgcacc tggaagcagt gggcctggct     960
```

```
caggccggca cctacacctg tagcatccat ctgcagggcc agcagctgaa cgccaccgtg   1020

acactggccg tgatcaccgt gacccccaag agctttggcc tgcctggctc cagaggcaag   1080

ctgctgtgtg aagtgacccc cgccagcggc aaagaaagat tcgtgtggcg gcctctgaac   1140

aacctgagca gatcctgccc aggccccgtg ctggaaatcc aggaagccag actgctggcc   1200

gagcggtggc agtgccagct gtatgaggga cagcgactgc tgggcgccac tgtgtacgct   1260

gctgagtcta gctctggcgc ccacagcgcc agaagaatca gcggcgatct gaagggcggc   1320

cacctgtgcc acacccagag cagccccaag ctgttctggg ccctggtggt ggtggccggc   1380

gtgctgtttt gttacggcct gctcgtgacc gtggccctgt gcgtgatctg gaccaacagc   1440

agaagaaaca gaggcggcca gagcgactac atgaacatga cccccagaag gcctggcctg   1500

accagaaagc cctaccagcc ttacgcccct gccagagact tcgccgccta cagacct      1557
```

```
<210> SEQ ID NO 140
<211> LENGTH: 519
<212> TYPE: PRT
<213> ORGANISM: Artificial Sequence
<220> FEATURE:
<223> OTHER INFORMATION: muLag3-CD28Cys

<400> SEQUENCE: 140

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255
```

```
Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Cys His Thr Gln Ser Ser
        435                 440                 445

Pro Lys Leu Phe Trp Ala Leu Val Val Val Ala Gly Val Leu Phe Cys
    450                 455                 460

Tyr Gly Leu Leu Val Thr Val Ala Leu Cys Val Ile Trp Thr Asn Ser
465                 470                 475                 480

Arg Arg Asn Arg Gly Gly Gln Ser Asp Tyr Met Asn Met Thr Pro Arg
                485                 490                 495

Arg Pro Gly Leu Thr Arg Lys Pro Tyr Gln Pro Tyr Ala Pro Ala Arg
            500                 505                 510

Asp Phe Ala Ala Tyr Arg Pro
        515
```

<210> SEQ ID NO 141
<211> LENGTH: 1530
<212> TYPE: DNA
<213> ORGANISM: Artificial Sequence
<220> FEATURE:
<223> OTHER INFORMATION: muLag3-9aas-CD28Cys

<400> SEQUENCE: 141

```
atgagagagg acctgctgct gggctttctg ctgctgggac tgctgtggga ggcccctgtg      60

gtgtcatctg gccctggcaa agaactgccc gtcgtgtggg ctcaggaagg cgctcctgtg     120

catctgccct gcagcctgaa gtcccccaac ctggacccca acttcctgag aagaggcggc     180

gtgatctggc agcaccagcc tgattctggc cagcccacac ctatccctgc cctggatctg     240

caccagggca tgcctagccc tagacagcct gcccctggca gatacaccgt gctgtctgtg     300

gctcctggcg gcctgagaag tggcagacag cctctgcacc ctcacgtgca gctggaagag     360

aggggactgc agaggggcga cttcagcctg tggctgaggc ctgccctgag aacagatgcc     420

ggcgagtacc acgctaccgt gcggctgcct aacagagccc tgagctgctc cctgagactg     480

agagtgggcc aggccagcat gatcgcctct ccatctggcg tgctgaagct gagcgactgg     540
```

```
gtgctgctga actgcagctt ctccagaccc gacagacccg tgtccgtgca ctggttccag    600

ggacagaaca gagtgcccgt gtacaacagc cccagacact tcctggccga gacattcctg    660

ctgctgcccc aggtgtcccc tctggactct ggcacatggg gctgcgtgct gacatacagg    720

gacggcttca acgtgtccat cacctacaac ctgaaggtgc tgggcctgga acccgtggct    780

cctctgacag tgtacgccgc cgagggcagc agagtggaac tgccttgtca tctgccaccc    840

ggcgtgggca caccttctct gctgatcgcc aagtggaccc ctccaggcgg aggacctgaa    900

ctgccagtgg ctggcaagag cggcaacttc accctgcacc tggaagcagt gggcctggct    960

caggccggca cctacacctg tagcatccat ctgcagggcc agcagctgaa cgccaccgtg   1020

acactggccg tgatcaccgt gacccccaag agctttggcc tgcctggctc cagaggcaag   1080

ctgctgtgtg aagtgacccc cgccagcggc aaagaaagat tcgtgtggcg gcctctgaac   1140

aacctgagca gatcctgccc aggccccgtg ctggaaatcc aggaagccag actgctggcc   1200

gagcggtggc agtgccagct gtatgaggga cagcgactgc tgggcgccac tgtgtacgct   1260

gctgagtcta gctctggcgc ccacagcgcc agaagaatct gccacaccca gagcagcccc   1320

aagctgttct gggccctggt ggtggtggcc ggcgtgctgt tttgttacgg cctgctcgtg   1380

accgtggccc tgtgcgtgat ctggaccaac agcagaagaa acagaggcgg ccagagcgac   1440

tacatgaaca tgacccccag aaggcctggc ctgaccagaa agccctacca gccttacgcc   1500

cctgccagag acttcgccgc ctacagacct                                    1530
```

<210> SEQ ID NO 142
<211> LENGTH: 510
<212> TYPE: PRT
<213> ORGANISM: Artificial Sequence
<220> FEATURE:
<223> OTHER INFORMATION: muLag3-9aas-CD28Cys

<400> SEQUENCE: 142

```
Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190
```

```
Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Cys His Thr Gln Ser Ser Pro Lys Leu Phe Trp Ala Leu Val Val
        435                 440                 445

Val Ala Gly Val Leu Phe Cys Tyr Gly Leu Leu Val Thr Val Ala Leu
    450                 455                 460

Cys Val Ile Trp Thr Asn Ser Arg Arg Asn Arg Gly Gly Gln Ser Asp
465                 470                 475                 480

Tyr Met Asn Met Thr Pro Arg Arg Pro Gly Leu Thr Arg Lys Pro Tyr
                485                 490                 495

Gln Pro Tyr Ala Pro Ala Arg Asp Phe Ala Ala Tyr Arg Pro
            500                 505                 510
```

<210> SEQ ID NO 143
<211> LENGTH: 765
<212> TYPE: DNA
<213> ORGANISM: Artificial Sequence
<220> FEATURE:
<223> OTHER INFORMATION: muTim3tm-CD28

<400> SEQUENCE: 143

```
atgttcagcg gcctgaccct gaactgcgtg ctcctgctgc tgcagctgct gctggccaga     60

agcctggaaa acgcctacgt gttcgaagtg ggcaagaacg cctacctgcc ctgcagctac    120

accctgtcta cacctggcgc cctggtgcct atgtgttggg gcaagggctt ctgcccttgg    180

agccagtgca ccaacgagct gctgagaacc gacgagagaa acgtgaccta ccagaagtcc    240
```

```
agcagatacc agctgaaggg cgacctgaac aagggcgacg tgtccctgat catcaagaac    300

gtgaccctgg acgaccacgg cacctactgc tgcagaatcc agttccccgg cctgatgaac    360

gacaagaagc tggaactgaa gctggacatc aaggccgcca aagtgacccc tgcccagaca    420

gcccacggcg actctacaac agccagcccc agaaccctga ccaccgagag gaacggcagc    480

gagacacaga ccctcgtgac actgcacaac aacaacggca ccaagatcag cacctgggcc    540

gacgagatca aggacagcgg cgagacaatc agaaccgcca tccacatcgg cgtgggcgtg    600

tccgctggac tgacactggc tctgatcatc ggagtgctga tcaacagcag aagaaacaga    660

ggcggccaga gcgactacat gaacatgacc cccagaaggc ctggcctgac cagaaagccc    720

taccagcctt acgcccctgc cagagacttc gccgcctaca gacct                    765
```

<210> SEQ ID NO 144
<211> LENGTH: 255
<212> TYPE: PRT
<213> ORGANISM: Artificial Sequence
<220> FEATURE:
<223> OTHER INFORMATION: muTim3tm-CD28

<400> SEQUENCE: 144

```
Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Asn Ser Arg Arg Asn Arg Gly Gly Gln Ser
    210                 215                 220

Asp Tyr Met Asn Met Thr Pro Arg Arg Pro Gly Leu Thr Arg Lys Pro
225                 230                 235                 240

Tyr Gln Pro Tyr Ala Pro Ala Arg Asp Phe Ala Ala Tyr Arg Pro
                245                 250                 255
```

<210> SEQ ID NO 145
<211> LENGTH: 783

<212> TYPE: DNA
<213> ORGANISM: Artificial Sequence
<220> FEATURE:
<223> OTHER INFORMATION: muTim3-CD28tm

<400> SEQUENCE: 145

```
atgttcagcg gcctgaccct gaactgcgtg ctcctgctgc tgcagctgct gctggccaga     60

agcctggaaa acgcctacgt gttcgaagtg ggcaagaacg cctacctgcc ctgcagctac    120

accctgtcta cacctggcgc cctggtgcct atgtgttggg gcaagggctt ctgcccttgg    180

agccagtgca ccaacgagct gctgagaacc gacgagagaa acgtgaccta ccagaagtcc    240

agcagatacc agctgaaggg cgacctgaac aagggcgacg tgtccctgat catcaagaac    300

gtgaccctgg acgaccacgg cacctactgc tgcagaatcc agttccccgg cctgatgaac    360

gacaagaagc tggaactgaa gctggacatc aaggccgcca aagtgacccc tgcccagaca    420

gcccacggcg actctacaac agccagcccc agaaccctga ccaccgagag gaacggcagc    480

gagacacaga ccctcgtgac actgcacaac aacaacggca ccaagatcag cacctgggcc    540

gacgagatca aggacagcgg cgagacaatc agaaccgcct tctgggccct ggtggtggtg    600

gccggcgtgc tgttttgtta cggcctgctc gtgaccgtgg ccctgtgcgt gatctggacc    660

aacagcagaa gaaacagagg cggccagagc gactacatga acatgacccc cagaaggcct    720

ggcctgacca gaaagcccta ccagccttac gcccctgcca gagacttcgc cgcctacaga    780

cct                                                                  783
```

<210> SEQ ID NO 146
<211> LENGTH: 261
<212> TYPE: PRT
<213> ORGANISM: Artificial Sequence
<220> FEATURE:
<223> OTHER INFORMATION: muTim3-CD28tm

<400> SEQUENCE: 146

```
Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
```

```
            180                 185                 190

Ala Phe Trp Ala Leu Val Val Val Ala Gly Val Leu Phe Cys Tyr Gly
        195                 200                 205

Leu Leu Val Thr Val Ala Leu Cys Val Ile Trp Thr Asn Ser Arg Arg
    210                 215                 220

Asn Arg Gly Gly Gln Ser Asp Tyr Met Asn Met Thr Pro Arg Arg Pro
225                 230                 235                 240

Gly Leu Thr Arg Lys Pro Tyr Gln Pro Tyr Ala Pro Ala Arg Asp Phe
                245                 250                 255

Ala Ala Tyr Arg Pro
            260


<210> SEQ ID NO 147
<211> LENGTH: 810
<212> TYPE: DNA
<213> ORGANISM: Artificial Sequence
<220> FEATURE:
<223> OTHER INFORMATION: muTim3-CD28Cys

<400> SEQUENCE: 147

atgttcagcg gcctgaccct gaactgcgtg ctcctgctgc tgcagctgct gctggccaga      60

agcctggaaa acgcctacgt gttcgaagtg ggcaagaacg cctacctgcc ctgcagctac     120

accctgtcta cacctggcgc cctggtgcct atgtgttggg gcaagggctt ctgcccttgg     180

agccagtgca ccaacgagct gctgagaacc gacgagagaa acgtgaccta ccagaagtcc     240

agcagatacc agctgaaggg cgacctgaac aagggcgacg tgtccctgat catcaagaac     300

gtgaccctgg acgaccacgg cacctactgc tgcagaatcc agttccccgg cctgatgaac     360

gacaagaagc tggaactgaa gctggacatc aaggccgcca aagtgacccc tgcccagaca     420

gcccacggcg actctacaac agccagcccc agaaccctga ccaccgagag gaacggcagc     480

gagacacaga ccctcgtgac actgcacaac aacaacggca ccaagatcag cacctgggcc     540

gacgagatca aggacagcgg cgagacaatc agaaccgcct gccacaccca gagcagcccc     600

aagctgttct gggccctggt ggtggtggcc ggcgtgctgt tttgttacgg cctgctcgtg     660

accgtggccc tgtgcgtgat ctggaccaac agcagaagaa acagaggcgg ccagagcgac     720

tacatgaaca tgacccccag aaggcctggc ctgaccagaa agccctacca gccttacgcc     780

cctgccagag acttcgccgc ctacagacct                                      810


<210> SEQ ID NO 148
<211> LENGTH: 270
<212> TYPE: PRT
<213> ORGANISM: Artificial Sequence
<220> FEATURE:
<223> OTHER INFORMATION: muTim3-CD28Cys

<400> SEQUENCE: 148

Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80
```

```
Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Cys His Thr Gln Ser Ser Pro Lys Leu Phe Trp Ala Leu Val Val
        195                 200                 205

Val Ala Gly Val Leu Phe Cys Tyr Gly Leu Leu Val Thr Val Ala Leu
    210                 215                 220

Cys Val Ile Trp Thr Asn Ser Arg Arg Asn Arg Gly Gly Gln Ser Asp
225                 230                 235                 240

Tyr Met Asn Met Thr Pro Arg Arg Pro Gly Leu Thr Arg Lys Pro Tyr
                245                 250                 255

Gln Pro Tyr Ala Pro Ala Arg Asp Phe Ala Ala Tyr Arg Pro
            260                 265                 270
```

<210> SEQ ID NO 149
<211> LENGTH: 783
<212> TYPE: DNA
<213> ORGANISM: Artificial Sequence
<220> FEATURE:
<223> OTHER INFORMATION: muTim3-9aas-CD28Cys

<400> SEQUENCE: 149

```
atgttcagcg gcctgaccct gaactgcgtg ctcctgctgc tgcagctgct gctggccaga     60

agcctggaaa acgcctacgt gttcgaagtg ggcaagaacg cctacctgcc ctgcagctac    120

accctgtcta cacctggcgc cctggtgcct atgtgttggg gcaagggctt ctgccccttgg    180

agccagtgca ccaacgagct gctgagaacc gacgagagaa acgtgaccta ccagaagtcc    240

agcagatacc agctgaaggg cgacctgaac aagggcgacg tgtccctgat catcaagaac    300

gtgaccctgg acgaccacgg cacctactgc tgcagaatcc agttccccgg cctgatgaac    360

gacaagaagc tggaactgaa gctggacatc aaggccgcca aagtgacccc tgcccagaca    420

gcccacggcg actctacaac agccagcccc agaaccctga ccaccgagag gaacggcagc    480

gagacacaga ccctcgtgac actgcacaac aacaacggca ccaagatcag cacctgggcc    540

gacgagatca agtgccacac ccagagcagc cccaagctgt tctgggccct ggtggtggtg    600

gccggcgtgc tgttttgtta cggcctgctc gtgaccgtgg ccctgtgcgt gatctggacc    660

aacagcagaa gaaacagagg cggccagagc gactacatga acatgacccc cagaaggcct    720

ggcctgacca gaaagcccta ccagccttac gcccctgcca gagacttcgc cgcctacaga    780

cct                                                                  783
```

<210> SEQ ID NO 150
<211> LENGTH: 261
<212> TYPE: PRT

```
<213> ORGANISM: Artificial Sequence
<220> FEATURE:
<223> OTHER INFORMATION: muTim3-9aas-CD28Cys

<400> SEQUENCE: 150

Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Cys His Thr Gln Ser Ser Pro Lys
            180                 185                 190

Leu Phe Trp Ala Leu Val Val Val Ala Gly Val Leu Phe Cys Tyr Gly
        195                 200                 205

Leu Leu Val Thr Val Ala Leu Cys Val Ile Trp Thr Asn Ser Arg Arg
    210                 215                 220

Asn Arg Gly Gly Gln Ser Asp Tyr Met Asn Met Thr Pro Arg Arg Pro
225                 230                 235                 240

Gly Leu Thr Arg Lys Pro Tyr Gln Pro Tyr Ala Pro Ala Arg Asp Phe
                245                 250                 255

Ala Ala Tyr Arg Pro
            260


<210> SEQ ID NO 151
<211> LENGTH: 1536
<212> TYPE: DNA
<213> ORGANISM: Artificial Sequence
<220> FEATURE:
<223> OTHER INFORMATION: huLag3tm-CD28

<400> SEQUENCE: 151

atgtgggaag cgcagtttct tggacttctt tttctccagc cgctgtgggt tgcgccagta      60

aagccgctcc aacccggtgc agaggttccg gtagtgtggg cgcaagaggg tgcaccagcg     120

cagctcccct gcagtccgac gattccgctg caagatttgt cactgcttag aagggcgggc     180

gtaacgtggc agcaccaacc ggatagtggc cctccggctg cagcaccagg gcacccactc     240

gcccccggcc ctcatcccgc agcaccgagc agctggggtc ctagaccacg cagatataca     300

gtactctcag taggtcccgg cggcctgcgg tccggtcgct tgccccttca acctagagta     360
```

```
cagctggatg aaagaggtcg acaacggggt gatttctccc tctggttgag gcctgcacga    420

cgagcagatg ctggggagta tagggctgcc gtacacctgc gagaccgcgc acttagttgt    480

agactccggc tccggctggg acaggcctct atgacagcgt ccccccctgg gtccctgcga    540

gcctctgatt gggtaatact caactgctca ttttctcggc cagatcgccc cgctagtgtt    600

cattggttcc gaaatcgcgg ccaaggtcgc gtgcctgttc gagaatctcc acaccaccat    660

ttggcggagt cttttctttt tctgcctcag gtctccccta tggactctgg accgtggggc    720

tgtattttga catatcggga tgggtttaac gtgagtataa tgtataatct cactgtcttg    780

ggtcttgagc cacctacgcc gctgacggtg tacgcgggag ccggcagccg ggttggtctg    840

ccctgcaggc tgcctgcagg agtcgggaca aggtcattcc ttacagcaaa gtggaccccg    900

ccaggtgggg ggcccgacct ccttgtaacg ggagataatg gagatttcac tctgagactt    960

gaggatgtct ctcaagctca ggctgggact tatacatgtc acattcactt gcaagaacag   1020

cagttgaatg cgacggttac cctggctatc ataacagtaa cacctaaatc tttcggtagt   1080

ccgggtagcc tgggcaaact gttgtgtgag gtaacccccg tgtcaggtca agagcggttc   1140

gtctggagct cattggacac tccctcacag cgatccttta gcggaccctg gctcgaagcc   1200

caagaagccc agctgctttc ccaaccatgg cagtgtcaac tctatcaggg tgagcgcctt   1260

ctcggtgcgg ctgtctactt caccgaattg tcctctccgg gagcgcaaag aagtggacgc   1320

gccccagggg ccctcccggc aggacacctt ctgctgtttt tgattttggg ggtacttagt   1380

ttgctgctgc ttgtcacagg cgctttcggt ttccgcagca agcggagcag aggcggccac   1440

agcgactaca tgaacatgac ccctagacgg cctggcccca ccagaaagca ctaccagccc   1500

tacgcccctc cccgggactt tgccgcctac agaagc                              1536
```

<210> SEQ ID NO 152
<211> LENGTH: 512
<212> TYPE: PRT
<213> ORGANISM: Artificial Sequence
<220> FEATURE:
<223> OTHER INFORMATION: huLag3tm-CD28

<400> SEQUENCE: 152

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160
```

```
Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe Arg Ser Lys Arg Ser Arg Gly Gly His
465                 470                 475                 480

Ser Asp Tyr Met Asn Met Thr Pro Arg Arg Pro Gly Pro Thr Arg Lys
                485                 490                 495

His Tyr Gln Pro Tyr Ala Pro Pro Arg Asp Phe Ala Ala Tyr Arg Ser
            500                 505                 510
```

<210> SEQ ID NO 153
<211> LENGTH: 1350
<212> TYPE: DNA
<213> ORGANISM: Artificial Sequence
<220> FEATURE:
<223> OTHER INFORMATION: huLag3 ectodomain

<400> SEQUENCE: 153

```
atgtgggaag cgcagtttct tggacttctt tttctccagc cgctgtgggt tgcgccagta     60
```

```
aagccgctcc aacccggtgc agaggttccg gtagtgtggg cgcaagaggg tgcaccagcg    120

cagctcccct gcagtccgac gattccgctg caagatttgt cactgcttag aagggcgggc    180

gtaacgtggc agcaccaacc ggatagtggc cctccggctg cagcaccagg gcacccactc    240

gcccccggcc ctcatcccgc agcaccgagc agctggggtc ctagaccacg cagatataca    300

gtactctcag taggtcccgg cggcctgcgg tccggtcgct tgccccttca acctagagta    360

cagctggatg aaagaggtcg acaacggggt gatttctccc tctggttgag gcctgcacga    420

cgagcagatg ctggggagta tagggctgcc gtacacctgc gagaccgcgc acttagttgt    480

agactccggc tccggctggg acaggcctct atgacagcgt cccccctgg gtccctgcga    540

gcctctgatt gggtaatact caactgctca ttttctcggc cagatcgccc cgctagtgtt    600

cattggttcc gaaatcgcgg ccaaggtcgc gtgcctgttc gagaatctcc acaccaccat    660

ttggcggagt cttttctttt tctgcctcag gtctccccta tggactctgg accgtggggc    720

tgtattttga catatcggga tgggtttaac gtgagtataa tgtataatct cactgtcttg    780

ggtcttgagc cacctacgcc gctgacggtg tacgcgggag ccggcagccg ggttggtctg    840

ccctgcaggc tgcctgcagg agtcgggaca aggtcattcc ttacagcaaa gtggaccccg    900

ccaggtgggg ggcccgacct ccttgtaacg ggagataatg gagatttcac tctgagactt    960

gaggatgtct ctcaagctca ggctgggact tatacatgtc acattcactt gcaagaacag   1020

cagttgaatg cgacggttac cctggctatc ataacagtaa cacctaaatc tttcggtagt   1080

ccgggtagcc tgggcaaact gttgtgtgag gtaacccccg tgtcaggtca agagcggttc   1140

gtctggagct cattggacac tccctcacag cgatccttta gcggaccctg gctcgaagcc   1200

caagaagccc agctgctttc ccaaccatgg cagtgtcaac tctatcaggg tgagcgcctt   1260

ctcggtgcgg ctgtctactt caccgaattg tcctctccgg gagcgcaaag aagtggacgc   1320

gccccagggg ccctcccggc aggacacctt                                    1350
```

<210> SEQ ID NO 154
<211> LENGTH: 450
<212> TYPE: PRT
<213> ORGANISM: Artificial Sequence
<220> FEATURE:
<223> OTHER INFORMATION: huLag3 ectodomain

<400> SEQUENCE: 154

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
```

```
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu
    450


<210> SEQ ID NO 155
<211> LENGTH: 63
<212> TYPE: DNA
<213> ORGANISM: Artificial Sequence
<220> FEATURE:
<223> OTHER INFORMATION: huLag3 transmembrane domain

<400> SEQUENCE: 155

ctgctgtttt tgattttggg ggtacttagt ttgctgctgc ttgtcacagg cgctttcggt      60

ttc                                                                     63


<210> SEQ ID NO 156
<211> LENGTH: 21
```

<212> TYPE: PRT
<213> ORGANISM: Artificial Sequence
<220> FEATURE:
<223> OTHER INFORMATION: huLag3 transmembrane domain

<400> SEQUENCE: 156

```
Leu Leu Phe Leu Ile Leu Gly Val Leu Ser Leu Leu Leu Leu Val Thr
1               5                   10                  15

Gly Ala Phe Gly Phe
            20
```

<210> SEQ ID NO 157
<211> LENGTH: 1554
<212> TYPE: DNA
<213> ORGANISM: Artificial Sequence
<220> FEATURE:
<223> OTHER INFORMATION: huLag3-CD28tm

<400> SEQUENCE: 157

```
atgtgggaag cgcagtttct tggacttctt tttctccagc cgctgtgggt tgcgccagta     60

aagccgctcc aacccggtgc agaggttccg gtagtgtggg cgcaagaggg tgcaccagcg    120

cagctcccct gcagtccgac gattccgctg caagatttgt cactgcttag aagggcgggc    180

gtaacgtggc agcaccaacc ggatagtggc cctccggctg cagcaccagg gcacccactc    240

gcccccggcc ctcatcccgc agcaccgagc agctggggtc ctagaccacg cagatataca    300

gtactctcag taggtcccgg cggcctgcgg tccggtcgct tgccccttca acctagagta    360

cagctggatg aaagaggtcg acaacggggt gatttctccc tctggttgag gcctgcacga    420

cgagcagatg ctggggagta tagggctgcc gtacacctgc gagaccgcgc acttagttgt    480

agactccggc tccggctggg acaggcctct atgacagcgt cccccccctgg gtccctgcga    540

gcctctgatt gggtaatact caactgctca ttttctcggc cagatcgccc cgctagtgtt    600

cattggttcc gaaatcgcgg ccaaggtcgc gtgcctgttc gagaatctcc acaccaccat    660

ttggcggagt cttttctttt tctgcctcag gtctccccta tggactctgg accgtggggc    720

tgtattttga catatcggga tgggtttaac gtgagtataa tgtataatct cactgtcttg    780

ggtcttgagc cacctacgcc gctgacggtg tacgcgggag ccggcagccg ggttggtctg    840

ccctgcaggc tgcctgcagg agtcgggaca aggtcattcc ttacagcaaa gtggaccccg    900

ccaggtgggg ggcccgacct ccttgtaacg ggagataatg gagatttcac tctgagactt    960

gaggatgtct ctcaagctca ggctgggact tatacatgtc acattcactt gcaagaacag   1020

cagttgaatg cgacggttac cctggctatc ataacagtaa cacctaaatc tttcggtagt   1080

ccgggtagcc tgggcaaact gttgtgtgag gtaacccccg tgtcaggtca agagcggttc   1140

gtctggagct cattggacac tccctcacag cgatccttta gcggaccctg gctcgaagcc   1200

caagaagccc agctgctttc ccaaccatgg cagtgtcaac tctatcaggg tgagcgcctt   1260

ctcggtgcgg ctgtctactt caccgaattg tcctctccgg gagcgcaaag aagtggacgc   1320

gccccagggg ccctcccggc aggacacctt ttctgggtgc tggtggtggt cggaggcgtg   1380

ctggcctgct acagcctgct ggtcaccgtg gccttcatca tcttttgggt ccgcagcaag   1440

cggagcagag gcggccacag cgactacatg aacatgaccc ctagacggcc tggccccacc   1500

agaaagcact accagcccta cgcccctccc cgggactttg ccgcctacag aagc          1554
```

<210> SEQ ID NO 158
<211> LENGTH: 518
<212> TYPE: PRT

<213> ORGANISM: Artificial Sequence
<220> FEATURE:
<223> OTHER INFORMATION: huLag3-CD28tm

<400> SEQUENCE: 158

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
```

```
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Phe Trp Val Leu Val Val Val Gly Gly Val Leu Ala Cys Tyr
    450                 455                 460

Ser Leu Leu Val Thr Val Ala Phe Ile Ile Phe Trp Val Arg Ser Lys
465                 470                 475                 480

Arg Ser Arg Gly Gly His Ser Asp Tyr Met Asn Met Thr Pro Arg Arg
                485                 490                 495

Pro Gly Pro Thr Arg Lys His Tyr Gln Pro Tyr Ala Pro Pro Arg Asp
            500                 505                 510

Phe Ala Ala Tyr Arg Ser
        515


<210> SEQ ID NO 159
<211> LENGTH: 1554
<212> TYPE: DNA
<213> ORGANISM: Artificial Sequence
<220> FEATURE:
<223> OTHER INFORMATION: huLag3-12aas-CD28Cys

<400> SEQUENCE: 159

atgtgggaag cgcagtttct tggacttctt tttctccagc cgctgtgggt tgcgccagta     60

aagccgctcc aacccggtgc agaggttccg gtagtgtggg cgcaagaggg tgcaccagcg    120

cagctcccct gcagtccgac gattccgctg caagatttgt cactgcttag aagggcgggc    180

gtaacgtggc agcaccaacc ggatagtggc cctccggctg cagcaccagg gcacccactc    240

gcccccggcc ctcatcccgc agcaccgagc agctggggtc ctagaccacg cagatataca    300

gtactctcag taggtcccgg cggcctgcgg tccggtcgct tgccccttca acctagagta    360

cagctggatg aaagaggtcg acaacggggt gatttctccc tctggttgag gcctgcacga    420

cgagcagatg ctggggagta tagggctgcc gtacacctgc gagaccgcgc acttagttgt    480

agactccggc tccggctggg acaggcctct atgacagcgt cccccctgg gtccctgcga    540

gcctctgatt gggtaatact caactgctca ttttctcggc cagatcgccc cgctagtgtt    600

cattggttcc gaaatcgcgg ccaaggtcgc gtgcctgttc gagaatctcc acaccaccat    660

ttggcggagt cttttctttt tctgcctcag gtctccccta tggactctgg accgtggggc    720

tgtattttga catatcggga tgggtttaac gtgagtataa tgtataatct cactgtcttg    780

ggtcttgagc cacctacgcc gctgacggtg tacgcgggag ccggcagccg ggttggtctg    840

ccctgcaggc tgcctgcagg agtcgggaca aggtcattcc ttacagcaaa gtggaccccg    900

ccaggtgggg ggcccgacct ccttgtaacg ggagataatg gagatttcac tctgagactt    960

gaggatgtct ctcaagctca ggctgggact tatacatgtc acattcactt gcaagaacag   1020

cagttgaatg cgacggttac cctggctatc ataacagtaa cacctaaatc tttcggtagt   1080

ccgggtagcc tgggcaaact gttgtgtgag gtaacccccg tgtcaggtca agagcggttc   1140

gtctggagct cattggacac tccctcacag cgatccttta gcggaccctg gctcgaagcc   1200

caagaagccc agctgctttc ccaaccatgg cagtgtcaac tctatcaggg tgagcgcctt   1260

ctcggtgcgg ctgtctactt caccgaattg tcctctccgg gagcgcaaag aagttgtccc   1320
```

```
agccctctgt ttcccggccc tagcaagcct ttctgggtgc tggtggtggt cggaggcgtg   1380

ctggcctgct acagcctgct ggtcaccgtg gccttcatca tcttttgggt ccgcagcaag   1440

cggagcagag gcggccacag cgactacatg aacatgaccc ctagacggcc tggccccacc   1500

agaaagcact accagcccta cgcccctccc cgggactttg ccgcctacag aagc         1554


<210> SEQ ID NO 160
<211> LENGTH: 518
<212> TYPE: PRT
<213> ORGANISM: Artificial Sequence
<220> FEATURE:
<223> OTHER INFORMATION: huLag3-12aas-CD28Cys

<400> SEQUENCE: 160

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320
```

```
Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Cys Pro Ser Pro Leu Phe Pro Gly Pro Ser
        435                 440                 445

Lys Pro Phe Trp Val Leu Val Val Val Gly Gly Val Leu Ala Cys Tyr
    450                 455                 460

Ser Leu Leu Val Thr Val Ala Phe Ile Ile Phe Trp Val Arg Ser Lys
465                 470                 475                 480

Arg Ser Arg Gly Gly His Ser Asp Tyr Met Asn Met Thr Pro Arg Arg
                485                 490                 495

Pro Gly Pro Thr Arg Lys His Tyr Gln Pro Tyr Ala Pro Pro Arg Asp
            500                 505                 510

Phe Ala Ala Tyr Arg Ser
        515
```

<210> SEQ ID NO 161
<211> LENGTH: 1314
<212> TYPE: DNA
<213> ORGANISM: Artificial Sequence
<220> FEATURE:
<223> OTHER INFORMATION: huLag3-12aas

<400> SEQUENCE: 161

```
atgtgggaag cgcagtttct tggacttctt tttctccagc cgctgtgggt tgcgccagta     60

aagccgctcc aacccggtgc agaggttccg gtagtgtggg cgcaagaggg tgcaccagcg    120

cagctcccct gcagtccgac gattccgctg caagatttgt cactgcttag aagggcgggc    180

gtaacgtggc agcaccaacc ggatagtggc cctccggctg cagcaccagg gcacccactc    240

gcccccggcc ctcatcccgc agcaccgagc agctggggtc ctagaccacg cagatataca    300

gtactctcag taggtcccgg cggcctgcgg tccggtcgct tgccccttca acctagagta    360

cagctggatg aaagaggtcg acaacggggt gatttctccc tctggttgag gcctgcacga    420

cgagcagatg ctggggagta tagggctgcc gtacacctgc gagaccgcgc acttagttgt    480

agactccggc tccggctggg acaggcctct atgacagcgt cccccccctgg gtccctgcga    540

gcctctgatt gggtaatact caactgctca ttttctcggc cagatcgccc cgctagtgtt    600

cattggttcc gaaatcgcgg ccaaggtcgc gtgcctgttc gagaatctcc acaccaccat    660

ttggcggagt cttttctttt tctgcctcag gtctccccta tggactctgg accgtggggc    720

tgtattttga catatcggga tgggtttaac gtgagtataa tgtataatct cactgtcttg    780

ggtcttgagc cacctacgcc gctgacggtg tacgcgggag ccggcagccg ggttggtctg    840

ccctgcaggc tgcctgcagg agtcgggaca aggtcattcc ttacagcaaa gtggaccccg    900
```

```
ccaggtgggg ggcccgacct ccttgtaacg ggagataatg gagatttcac tctgagactt    960

gaggatgtct ctcaagctca ggctgggact tatacatgtc acattcactt gcaagaacag   1020

cagttgaatg cgacggttac cctggctatc ataacagtaa cacctaaatc tttcggtagt   1080

ccgggtagcc tgggcaaact gttgtgtgag gtaacccccg tgtcaggtca agagcggttc   1140

gtctggagct cattggacac tccctcacag cgatccttta gcggaccctg gctcgaagcc   1200

caagaagccc agctgctttc ccaaccatgg cagtgtcaac tctatcaggg tgagcgcctt   1260

ctcggtgcgg ctgtctactt caccgaattg tcctctccgg gagcgcaaag aagt         1314
```

```
<210> SEQ ID NO 162
<211> LENGTH: 438
<212> TYPE: PRT
<213> ORGANISM: Artificial Sequence
<220> FEATURE:
<223> OTHER INFORMATION: huLag3-12aas

<400> SEQUENCE: 162

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
```

```
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser
        435
```

<210> SEQ ID NO 163
<211> LENGTH: 1590
<212> TYPE: DNA
<213> ORGANISM: Artificial Sequence
<220> FEATURE:
<223> OTHER INFORMATION: huLag3-CD28Cys

<400> SEQUENCE: 163

```
atgtgggaag cgcagtttct tggacttctt tttctccagc cgctgtgggt tgcgccagta     60

aagccgctcc aacccggtgc agaggttccg gtagtgtggg cgcaagaggg tgcaccagcg    120

cagctcccct gcagtccgac gattccgctg caagatttgt cactgcttag aagggcgggc    180

gtaacgtggc agcaccaacc ggatagtggc cctccggctg cagcaccagg gcacccactc    240

gcccccggcc ctcatcccgc agcaccgagc agctggggtc ctagaccacg cagatataca    300

gtactctcag taggtcccgg cggcctgcgg tccggtcgct tgccccttca acctagagta    360

cagctggatg aaagaggtcg acaacggggt gatttctccc tctggttgag gcctgcacga    420

cgagcagatg ctggggagta tagggctgcc gtacacctgc gagaccgcgc acttagttgt    480

agactccggc tccggctggg acaggcctct atgacagcgt cccccctgg gtccctgcga    540

gcctctgatt gggtaatact caactgctca ttttctcggc cagatcgccc cgctagtgtt    600

cattggttcc gaaatcgcgg ccaaggtcgc gtgcctgttc gagaatctcc acaccaccat    660

ttggcggagt cttttctttt tctgcctcag gtctccccta tggactctgg accgtggggc    720

tgtattttga catatcggga tgggtttaac gtgagtataa tgtataatct cactgtcttg    780

ggtcttgagc cacctacgcc gctgacggtg tacgcgggag ccggcagccg ggttggtctg    840

ccctgcaggc tgcctgcagg agtcgggaca aggtcattcc ttacagcaaa gtggaccccg    900

ccaggtgggg ggcccgacct ccttgtaacg ggagataatg gagatttcac tctgagactt    960

gaggatgtct ctcaagctca ggctgggact tatacatgtc acattcactt gcaagaacag   1020

cagttgaatg cgacggttac cctggctatc ataacagtaa cacctaaatc tttcggtagt   1080

ccgggtagcc tgggcaaact gttgtgtgag gtaacccccg tgtcaggtca agagcggttc   1140

gtctggagct cattggacac tccctcacag cgatccttta gcggaccctg gctcgaagcc   1200
```

```
caagaagccc agctgctttc ccaaccatgg cagtgtcaac tctatcaggg tgagcgcctt   1260

ctcggtgcgg ctgtctactt caccgaattg tcctctccgg gagcgcaaag aagtggacgc   1320

gccccagggg ccctcccggc aggacacctt tgtcccagcc ctctgtttcc cggccctagc   1380

aagcctttct gggtgctggt ggtggtcgga ggcgtgctgg cctgctacag cctgctggtc   1440

accgtggcct tcatcatctt ttgggtccgc agcaagcgga gcagaggcgg ccacagcgac   1500

tacatgaaca tgacccctag acggcctggc ccaccagaa agcactacca gccctacgcc   1560

cctccccggg actttgccgc ctacagaagc                                    1590
```

```
<210> SEQ ID NO 164
<211> LENGTH: 530
<212> TYPE: PRT
<213> ORGANISM: Artificial Sequence
<220> FEATURE:
<223> OTHER INFORMATION: huLag3-CD28Cys

<400> SEQUENCE: 164

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
```

```
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Cys Pro Ser Pro Leu Phe Pro Gly Pro Ser Lys Pro Phe Trp
    450                 455                 460

Val Leu Val Val Val Gly Gly Val Leu Ala Cys Tyr Ser Leu Leu Val
465                 470                 475                 480

Thr Val Ala Phe Ile Ile Phe Trp Val Arg Ser Lys Arg Ser Arg Gly
                485                 490                 495

Gly His Ser Asp Tyr Met Asn Met Thr Pro Arg Arg Pro Gly Pro Thr
            500                 505                 510

Arg Lys His Tyr Gln Pro Tyr Ala Pro Pro Arg Asp Phe Ala Ala Tyr
        515                 520                 525

Arg Ser
    530


<210> SEQ ID NO 165
<211> LENGTH: 792
<212> TYPE: DNA
<213> ORGANISM: Artificial Sequence
<220> FEATURE:
<223> OTHER INFORMATION: huTim3tm-CD28

<400> SEQUENCE: 165

atgttctccc atcttccctt cgactgtgtg ttgctccttc tcctcctgct tctcacccgg     60

tcaagcgaag tagagtaccg ggcggaagta ggtcagaacg catatctccc ctgtttttac    120

acacccgctg cgccgggaaa cctggttccc gtgtgttggg gaaagggggc atgccctgtt    180

ttcgagtgtg gcaacgtggt cctccggacg gatgagcgag acgtgaatta ttggacgagc    240

agatattggt tgaatggcga ttttagaaag ggtgatgtga gcttgaccat tgagaatgta    300

acgcttgctg atagcgggat atattgctgt agaattcaaa tccctggtat aatgaacgac    360

gaaaaattca atctgaagct ggtaattaag ccggccaagg tgacacccgc cccgacacga    420

cagcgcgact tcacggctgc ctttccacgc atgttgacca caaggggaca tggtccagcg    480

gagacccaga cacttggtag cctcccggac ataaacctca cacaaatatc cacgttggcg    540

aacgagctcc gagattccag gcttgcgaat gacctgaggg attctggagc taccatcaga    600

atcggtatct acataggtgc cgggatatgc gccggtctcg cacttgcctt gattttcggg    660
```

```
gcactgattc gcagcaagcg gagcagaggc ggccacagcg actacatgaa catgacccct    720

agacggcctg gccccaccag aaagcactac cagccctacg cccctccccg ggactttgcc    780

gcctacagaa gc                                                        792


<210> SEQ ID NO 166
<211> LENGTH: 264
<212> TYPE: PRT
<213> ORGANISM: Artificial Sequence
<220> FEATURE:
<223> OTHER INFORMATION: huTim3tm-CD28

<400> SEQUENCE: 166

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Arg
    210                 215                 220

Ser Lys Arg Ser Arg Gly Gly His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser
            260


<210> SEQ ID NO 167
<211> LENGTH: 606
<212> TYPE: DNA
<213> ORGANISM: Artificial Sequence
<220> FEATURE:
<223> OTHER INFORMATION: huTim3 ectodomain

<400> SEQUENCE: 167

atgttctccc atcttccctt cgactgtgtg ttgctccttc tcctcctgct tctcacccgg     60
```

```
tcaagcgaag tagagtaccg ggcggaagta ggtcagaacg catatctccc ctgtttttac    120

acacccgctg cgccgggaaa cctggttccc gtgtgttggg gaaagggggc atgccctgtt    180

ttcgagtgtg gcaacgtggt cctccggacg gatgagcgag acgtgaatta ttggacgagc    240

agatattggt tgaatggcga ttttagaaag ggtgatgtga gcttgaccat tgagaatgta    300

acgcttgctg atagcgggat atattgctgt agaattcaaa tccctggtat aatgaacgac    360

gaaaaattca atctgaagct ggtaattaag ccggccaagg tgacacccgc cccgacacga    420

cagcgcgact tcacggctgc ctttccacgc atgttgacca caaggggaca tggtccagcg    480

gagacccaga cacttggtag cctcccggac ataaacctca cacaaatatc cacgttggcg    540

aacgagctcc gagattccag gcttgcgaat gacctgaggg attctggagc taccatcaga    600

atcggt                                                                606
```

<210> SEQ ID NO 168
<211> LENGTH: 202
<212> TYPE: PRT
<213> ORGANISM: Artificial Sequence
<220> FEATURE:
<223> OTHER INFORMATION: huTim3 ectodomain

<400> SEQUENCE: 168

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly
        195                 200
```

<210> SEQ ID NO 169
<211> LENGTH: 63
<212> TYPE: DNA
<213> ORGANISM: Artificial Sequence
<220> FEATURE:
<223> OTHER INFORMATION: huTim3 transmembrane

<400> SEQUENCE: 169

```
atctacatag gtgccgggat atgcgccggt ctcgcacttg ccttgatttt cggggcactg     60

att                                                                   63


<210> SEQ ID NO 170
<211> LENGTH: 21
<212> TYPE: PRT
<213> ORGANISM: Artificial Sequence
<220> FEATURE:
<223> OTHER INFORMATION: huTim3 transmembrane

<400> SEQUENCE: 170

Ile Tyr Ile Gly Ala Gly Ile Cys Ala Gly Leu Ala Leu Ala Leu Ile
1               5                   10                  15

Phe Gly Ala Leu Ile
            20


<210> SEQ ID NO 171
<211> LENGTH: 810
<212> TYPE: DNA
<213> ORGANISM: Artificial Sequence
<220> FEATURE:
<223> OTHER INFORMATION: huTim3-CD28tm

<400> SEQUENCE: 171

atgttctccc atcttccctt cgactgtgtg ttgctccttc tcctcctgct tctcacccgg     60

tcaagcgaag tagagtaccg ggcggaagta ggtcagaacg catatctccc ctgtttttac    120

acacccgctg cgccgggaaa cctggttccc gtgtgttggg gaaagggggc atgccctgtt    180

ttcgagtgtg gcaacgtggt cctccggacg gatgagcgag acgtgaatta ttggacgagc    240

agatattggt tgaatggcga ttttagaaag ggtgatgtga gcttgaccat tgagaatgta    300

acgcttgctg atagcgggat atattgctgt agaattcaaa tccctggtat aatgaacgac    360

gaaaaattca atctgaagct ggtaattaag ccggccaagg tgacacccgc cccgacacga    420

cagcgcgact tcacggctgc ctttccacgc atgttgacca caaggggaca tggtccagcg    480

gagacccaga cacttggtag cctcccggac ataaacctca cacaaatatc cacgttggcg    540

aacgagctcc gagattccag gcttgcgaat gacctgaggg attctggagc taccatcaga    600

atcggtttct gggtgctggt ggtggtcgga ggcgtgctgg cctgctacag cctgctggtc    660

accgtggcct tcatcatctt ttgggtccgc agcaagcgga gcagaggcgg ccacagcgac    720

tacatgaaca tgacccctag acggcctggc cccaccagaa agcactacca gccctacgcc    780

cctccccggg actttgccgc ctacagaagc                                     810


<210> SEQ ID NO 172
<211> LENGTH: 270
<212> TYPE: PRT
<213> ORGANISM: Artificial Sequence
<220> FEATURE:
<223> OTHER INFORMATION: huTim3-CD28tm

<400> SEQUENCE: 172

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60
```

```
Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Phe Trp Val Leu Val Val
        195                 200                 205

Val Gly Gly Val Leu Ala Cys Tyr Ser Leu Leu Val Thr Val Ala Phe
    210                 215                 220

Ile Ile Phe Trp Val Arg Ser Lys Arg Ser Arg Gly Gly His Ser Asp
225                 230                 235                 240

Tyr Met Asn Met Thr Pro Arg Arg Pro Gly Pro Thr Arg Lys His Tyr
                245                 250                 255

Gln Pro Tyr Ala Pro Pro Arg Asp Phe Ala Ala Tyr Arg Ser
            260                 265                 270
```

<210> SEQ ID NO 173
<211> LENGTH: 846
<212> TYPE: DNA
<213> ORGANISM: Artificial Sequence
<220> FEATURE:
<223> OTHER INFORMATION: huTim3-CD28Cys

<400> SEQUENCE: 173

```
atgttctccc atcttccctt cgactgtgtg ttgctccttc tcctcctgct tctcacccgg     60

tcaagcgaag tagagtaccg ggcggaagta ggtcagaacg catatctccc ctgtttttac    120

acacccgctg cgccgggaaa cctggttccc gtgtgttggg gaaagggggc atgccctgtt    180

ttcgagtgtg gcaacgtggt cctccggacg gatgagcgag acgtgaatta ttggacgagc    240

agatattggt tgaatggcga ttttagaaag ggtgatgtga gcttgaccat tgagaatgta    300

acgcttgctg atagcgggat atattgctgt agaattcaaa tccctggtat aatgaacgac    360

gaaaaattca atctgaagct ggtaattaag ccggccaagg tgacacccgc cccgacacga    420

cagcgcgact tcacggctgc ctttccacgc atgttgacca caaggggaca tggtccagcg    480

gagacccaga cacttggtag cctcccggac ataaacctca cacaaatatc cacgttggcg    540

aacgagctcc gagattccag gcttgcgaat gacctgaggg attctggagc taccatcaga    600

atcggttgtc ccagccctct gtttcccggc cctagcaagc ctttctgggt gctggtggtg    660

gtcggaggcg tgctggcctg ctacagcctg ctggtcaccg tggccttcat catcttttgg    720

gtccgcagca agcggagcag aggcggccac agcgactaca tgaacatgac ccctagacgg    780

cctggcccca ccagaaagca ctaccagccc tacgcccctc cccgggactt tgccgcctac    840

agaagc                                                                846
```

<210> SEQ ID NO 174
<211> LENGTH: 282
<212> TYPE: PRT
<213> ORGANISM: Artificial Sequence
<220> FEATURE:
<223> OTHER INFORMATION: huTim3-CD28Cys

<400> SEQUENCE: 174

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Cys Pro Ser Pro Leu Phe
        195                 200                 205

Pro Gly Pro Ser Lys Pro Phe Trp Val Leu Val Val Val Gly Gly Val
    210                 215                 220

Leu Ala Cys Tyr Ser Leu Leu Val Thr Val Ala Phe Ile Ile Phe Trp
225                 230                 235                 240

Val Arg Ser Lys Arg Ser Arg Gly Gly His Ser Asp Tyr Met Asn Met
                245                 250                 255

Thr Pro Arg Arg Pro Gly Pro Thr Arg Lys His Tyr Gln Pro Tyr Ala
            260                 265                 270

Pro Pro Arg Asp Phe Ala Ala Tyr Arg Ser
        275                 280
```

<210> SEQ ID NO 175
<211> LENGTH: 810
<212> TYPE: DNA
<213> ORGANISM: Artificial Sequence
<220> FEATURE:
<223> OTHER INFORMATION: huTim3-12aas-CD28Cys

<400> SEQUENCE: 175

```
atgttctccc atcttccctt cgactgtgtg ttgctccttc tcctcctgct tctcacccgg     60

tcaagcgaag tagagtaccg ggcggaagta ggtcagaacg catatctccc ctgtttttac    120
```

```
acacccgctg cgccgggaaa cctggttccc gtgtgttggg gaaagggggc atgccctgtt    180

ttcgagtgtg gcaacgtggt cctccggacg gatgagcgag acgtgaatta ttggacgagc    240

agatattggt tgaatggcga ttttagaaag ggtgatgtga gcttgaccat tgagaatgta    300

acgcttgctg atagcgggat atattgctgt agaattcaaa tccctggtat aatgaacgac    360

gaaaaattca atctgaagct ggtaattaag ccggccaagg tgacacccgc cccgacacga    420

cagcgcgact tcacggctgc ctttccacgc atgttgacca caaggggaca tggtccagcg    480

gagacccaga cacttggtag cctcccggac ataaacctca cacaaatatc cacgttggcg    540

aacgagctcc gagattccag gcttgcgaat tgtcccagcc ctctgtttcc cggccctagc    600

aagcctttct gggtgctggt ggtggtcgga ggcgtgctgg cctgctacag cctgctggtc    660

accgtggcct tcatcatctt ttgggtccgc agcaagcgga gcagaggcgg ccacagcgac    720

tacatgaaca tgacccctag acggcctggc ccccaccagaa agcactacca gccctacgcc   780

cctccccggg actttgccgc ctacagaagc                                     810
```

<210> SEQ ID NO 176
<211> LENGTH: 270
<212> TYPE: PRT
<213> ORGANISM: Artificial Sequence
<220> FEATURE:
<223> OTHER INFORMATION: huTim3-12aas-CD28Cys

<400> SEQUENCE: 176

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Cys Pro
            180                 185                 190

Ser Pro Leu Phe Pro Gly Pro Ser Lys Pro Phe Trp Val Leu Val Val
        195                 200                 205

Val Gly Gly Val Leu Ala Cys Tyr Ser Leu Leu Val Thr Val Ala Phe
    210                 215                 220

Ile Ile Phe Trp Val Arg Ser Lys Arg Ser Arg Gly Gly His Ser Asp
225                 230                 235                 240
```

```
Tyr Met Asn Met Thr Pro Arg Arg Pro Gly Pro Thr Arg Lys His Tyr
                245                 250                 255

Gln Pro Tyr Ala Pro Pro Arg Asp Phe Ala Ala Tyr Arg Ser
            260                 265                 270


<210> SEQ ID NO 177
<211> LENGTH: 570
<212> TYPE: DNA
<213> ORGANISM: Artificial Sequence
<220> FEATURE:
<223> OTHER INFORMATION: huTim3-12aas

<400> SEQUENCE: 177

atgttctccc atcttccctt cgactgtgtg ttgctccttc tcctcctgct tctcacccgg      60

tcaagcgaag tagagtaccg ggcggaagta ggtcagaacg catatctccc ctgtttttac     120

acacccgctg cgccgggaaa cctggttccc gtgtgttggg gaaagggggc atgccctgtt     180

ttcgagtgtg gcaacgtggt cctccggacg gatgagcgag acgtgaatta ttggacgagc     240

agatattggt tgaatggcga ttttagaaag ggtgatgtga gcttgaccat tgagaatgta     300

acgcttgctg atagcgggat atattgctgt agaattcaaa tccctggtat aatgaacgac     360

gaaaaattca atctgaagct ggtaattaag ccggccaagg tgacacccgc cccgacacga     420

cagcgcgact tcacggctgc ctttccacgc atgttgacca caaggggaca tggtccagcg     480

gagacccaga cacttggtag cctcccggac ataaacctca cacaaatatc cacgttggcg     540

aacgagctcc gagattccag gcttgcgaat                                      570


<210> SEQ ID NO 178
<211> LENGTH: 190
<212> TYPE: PRT
<213> ORGANISM: Artificial Sequence
<220> FEATURE:
<223> OTHER INFORMATION: huTim3-12aas

<400> SEQUENCE: 178

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175
```

```
Ser Thr Leu Ala Asn Glu Leu Arg Asp Ser Arg Leu Ala Asn
            180                 185                 190


<210> SEQ ID NO 179
<211> LENGTH: 9
<212> TYPE: PRT
<213> ORGANISM: Artificial Sequence
<220> FEATURE:
<223> OTHER INFORMATION: F-MuLV encoded gag epitope

<400> SEQUENCE: 179

Cys Cys Leu Cys Leu Thr Val Phe Leu
1               5
```

IMMUNOMODULATORY FUSION PROTEINS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_360056_433C1. The text file is 311 KB, was created on Aug. 23, 2023, and is being submitted electronically.

BACKGROUND

T cell-based immunotherapies began to be developed when tumor-reactive T cells were found among a population of tumor-infiltrating lymphocytes (TILs) (Clark et al., *Cancer Res.* 29:705, 1969). One strategy, known as adoptive T cell transfer, in some contexts involves the isolation of tumor infiltrating lymphocytes pre-selected for tumor-reactivity, clonal expansion of the tumor-reactive T cells induced by anti-CD3 and anti-CD28 antibodies in the presence of IL-2, and finally infusing the expanded cell population back to the tumor-bearing patient (together with chemotherapy and repetitive administration of IL-2) (Dudley et al., *Science* 298:850, 2002). This form of adoptive T cell therapy with tumor infiltrating lymphocytes can be technically cumbersome and leads to complete remission in only a minor fraction of patients with melanoma and is rarely effective in other cancers (Besser et al., *Clin. Cancer Res.* 16:2646, 2010).

Isolation of tumor-reactive T cell clones led to the development of another immunotherapeutic approach—the generation of recombinant T cell receptors (TCRs) specific for particular antigens, which may be introduced into T cells, e.g., using a vector delivery system, to confer specificity for a desired target such as a tumor-associated peptide presented by a major histocompatibility complex (MEW) molecule expressed on a tumor cell (known as human leukocyte antigen (HLA) molecule in humans). Another approach introduces a synthetic receptor, termed a chimeric antigen receptor (CAR), which generally contains an antigen-binding domain, which, e.g., in the context of anti-tumor therapy can bind to a tumor-specific or associated antigen, linked to one or more intracellular component comprising an effector domains, such as a primary signaling domain such as a TCR signaling domain or in some contexts costimulatory signaling domains. Unlike administration of TILs, the basic procedure for engineered TCR or CAR T cell immunotherapy is generally to genetically modify human T cells with a transgene encoding a tumor targeting moiety, ex vivo expansion of the recombinant T cells, and transfusing the expanded recombinant T cells back into patients.

Adoptive T cell therapy using T cells expressing recombinant TCRs has been shown to have a promising clinical benefit, especially in certain B cell cancers. However, effective T cell activation often requires or is enhanced by a concurrent co-stimulatory signal (Chen and Flies, *Nat. Rev. Immunol.* 13: 227-242, 2013). In the tumor microenvironment, co-stimulatory molecules are generally downregulated. As a result, exogenous stimulus via IL-2 is typically needed for T cells that express recombinant TCRs specific for cancer antigens.

Activation of T cells is initiated when the TCR engages a specific peptide presented in MHC on an antigen-presenting cell (APC) (Rossy et al., *Frontiers in Immunol.* 3: 1-12, 2012). The point of interaction of the T cell and the APC becomes the immunological synapse, which is comprised of three concentric supramolecular activation clusters (SMACs), including the central cSMAC, peripheral pSMAC, and the distal dSMAC (Rossy et al., *Frontiers in Immunol.* 3: 1-12, 2012). Within the cSMAC, co-stimulatory receptors can recruit signaling molecules to amplify the TCR signal. Such co-stimulatory receptors can include CD28, and in some contexts form microclusters with the TCR to lower the threshold of activation (Chen and Flies, *Nat. Rev. Immunol.* 13: 227-242, 2013). Access to the cSMAC by transmembrane proteins expressed by T cells may be restricted by the size of the extracellular domain. For example, CD45 has a large ectodomain and is generally excluded from the immunological synapse, thereby preventing its ability to inhibit TCR signaling (James and Vale, *Nature* 487:64-69, 2012).

There remains a need in the immunotherapy field for alternative compositions and methods that provide immunomodulatory signals to host cells for treating various diseases, such as cancer or infections. Presently disclosed embodiments address these needs and provide other related advantages.

BRIEF SUMMARY

In certain aspects, the present disclosure is directed to a fusion protein, comprising an extracellular component that contains a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse.

In some embodiments, a length or spatial distance of a complex formed between the fusion protein and the target or a portion of such fusion protein::target complex (generally the extracellular portion of such complex) is or spans a particular distance, e.g., in some embodiments, is a distance that is less than or less than about a certain distance. In some aspects, a distance of the fusion protein::target complex (or, typically, the extracellular portion thereof) is less than at or about 50 nm, less than at or about 40 nm, less than at or about 30 nm, or less than at or about 20 nm or equal to or less than at or about 15 nm. In some embodiments, it is at or about 10, 11, 12, 13, 14, 15, 16, 17, 18, 19, or 20 nm, such as at or about 14 or 15 nm. In some aspects, the distance is one that is similar to a distance between membranes in an immunological synapse or is a distance that is the same, about the same, or substantially the same, as a distance between the membrane proximal-most portion, e.g., residue, of the extracellular domain of a TCR and the membrane proximal-most portion, e.g., residue, of an MHC (e.g., HLA, such as an MHCI or MHCII) molecule, with respect to a TCR-peptide/MHC complex or the distance spanned by the extracellular portions of such a complex (or spatial distance spanned by the extracellular portion known to be contained within a synapse, such as a complex containing CD8, CD4, CD28, and the respective binding partner or ligand thereof). In some embodiments, spatial distances of complexes refer to a distance between membranes of two different cells, wherein a first cell and a second cell each express on their surface a binding partner that can form a complex between the membranes when the cells are in proximity to each other. In some aspects, the distance is a distance that is the same, about the same, or substantially the same, as a distance spanned by the extracellular portions of a complex formed between a TCR and cognate interaction with an MHC molecule. In some aspects, such as where a fusion protein comprises a binding domain from a molecule ordinarily capable of entering an immunological synapse or co-localizing with an antigen receptor, the distance is similar to or the same as that spanned by a complex formed between the molecule (having the binding domain used in the fusion protein), and a natural binding partner thereof. In some aspects, such as where the fusion protein comprises a binding domain from a molecule ordinarily not capable of entering an immunological synapse or ordinarily not capable of co-localizing with an antigen receptor, the distance is different than, e.g., less than or substantially less than, that spanned by a complex formed between the molecule (having the binding domain or functional portion thereof used in the fusion protein), and a natural binding partner thereof.

In some embodiments, a binding domain within the extracellular component of a fusion protein of this disclosure contains a target-binding portion of a molecule capable of delivering an inhibitory signal, such as of an inhibitory molecule, e.g., an immunoinhibitory molecule, such as an immunoinhibitory receptor or immune checkpoint molecule. In some aspects, such a molecule is a glycoprotein, checkpoint family member. In certain embodiments, the fusion protein comprising a binding domain from a glycoprotein, checkpoint family member or is not a B7 or B7-binding molecule or is not a CD28-B7-superfamily member (e.g., is not a CD28, CTLA4, ICOS, or other B7 family binding molecule) Exemplary glycoprotein, checkpoint family members include CD200R, SIRPα, CD279 (PD-1), CD2, CD95 (Fas), CTLA4 (CD152), CD223 (LAG3), CD272 (BTLA), A2aR, KIR, TIM3, CD300, or LPA5, or a binding variant of any such molecule. In some embodiments, a binding domain within the extracellular component of a fusion protein of this disclosure comprises a binding partner of any of the foregoing, or a binding variant of any such molecule. In some aspects of such embodiments, the intracellular portion of a fusion protein includes a signaling domain capable of delivering a stimulatory, such as a costimulatory, signal to a lymphocyte, such as a T cell, such as a costimulatory region of CD28, 41BB, ICOS, or other costimulatory molecule. In some aspects, the intracellular portion of the fusion protein does not include an intracellular signaling domain of the inhibitory molecule, such as of a checkpoint or immunoinhibitory molecule, when the extracellular binding portion is from a checkpoint or immunoinhibitory molecule. In some aspects, a fusion protein does not include a primary signaling domain such as a CD3 signaling domain or other domain capable of delivering a primary signal to a T cell.

In certain aspects, the extracellular component or the binding portion thereof contains or is a binding domain of a molecule or ectodomain capable of specifically binding to CD200, such as a binding portion of a CD200R or variant thereof. In some embodiments, the binding domain is or includes a binding region of a molecule or of an ectodomain that is capable of specifically binding to a CD47, such as a SIRP ectodomain or CD47-binding region thereof, such as a SIRPα ectodomain or CD47-binding region thereof. In some embodiments, the binding domain is capable of binding to a PD-L1 or a PD-L2 or a LAG3 molecule. Exemplary targets may be one or more proteins whose expression is increased or upregulated in certain cells or tissues associated with or of a disease or condition to be treated or ameliorated with the fusion proteins and compositions provided herein, such as a tumor cell or tumor microenvironment, or is bound by a receptor generally upregulated on immune cells such as lymphocytes infiltrating a diseased tissue, such as a tumor.

In some embodiments, the extracellular component further includes one or more additional regions or domains, for example, from a molecule other than that from which the binding domain is derived or other than the molecule with which the binding domain shares identity. The one or more additional extracellular domain(s) may include a spacer region, such as one from an immunoglobulin molecule, which may contain all or a portion of a hinge, or constant region domain such as CH2 or CH3 domain, or from another cell surface molecule such as a costimulatory receptor, such as CD28. The additional extracellular domain(s) may include, in some aspects, a multimerization domain, e.g., a dimerization domain or sequence that may promote homo- or heterodimerization with another molecule, such as multimerization of two or more of the fusion proteins. In some embodiments, such a domain includes a portion of an extracellular domain of a CD28 molecule including at least the transmembrane-proximal-most cysteine, and generally an extracellular portion between such cysteine and the membrane, or modified variant thereof. In some aspects, such a domain includes an amino acid sequence as set forth in SEQ ID NO: 32, or portion thereof, or variant thereof such as having at least 90%, 95%, or 99% identity thereto. In some aspects, such a domain may be included in order to facilitate or promote multimerization. In some embodiments, a fusion protein contains an extracellular component including a CD200-binding domain, such as an extracellular portion (or portion thereof, such as a binding domain thereof) of a CD200R, such as an extracellular portion of CD200R having an amino acid sequence as set forth in SEQ ID NO: 25 or encoded by a nucleic acid molecule as set forth in SEQ ID NO: 2, or a CD200-binding portion thereof or variant thereof or binding portion thereof. In some aspects of such embodiments, the extracellular portion of the fusion protein further includes a portion of an extracellular region of CD28, such as up to about 9 to about 12 amino acids thereof (e.g., 9 amino acids or 12 amino acids), and in some aspects including a membrane-proximal-most cysteine residue of a CD28 extracellular region. In some such embodiments, the length of the CD200R portion of the extracellular region is reduced in length corresponding to the number of additional residues in the CD28-derived portion, such as by about 9 to about 12 amino acids (e,g, 9 amino acids or 12 amino acids), or by a sufficient number of amino acids that the distance spanned by the extracellular portion of a complex between the fusion protein and a CD200 molecule is similar to, substantially similar to, or the same as that spanned by the extracellular portion of a complex between a human CD200R, e.g., a CD200R, and CD200; or that spanned by the extracellular portion of a complex between a TCR in cognate interaction with an MHC molecule (e.g., MHC I or MHCII) in binding to a cognate peptide-MHC complex; or that of an immunological synapse. In some aspects, the fusion protein further includes a transmembrane domain, such as a CD28 transmembrane, such as a transmembrane domain encoded by the sequence set forth as SEQ ID NO: 4 or portion thereof, or a modified version thereof, such as a variant modified to contain additional charged regions or residues or hydrophilic residues to facilitate intermolecular interactions. In some embodiments, the protein further includes a CD28 intracellular signaling domain, such as a costimulatory domain of CD28, such as one that is capable of recruiting one or more adapter molecules to a CD28 in response to ligation. In some aspects, the CD28 intracellular domain includes or is a sequence encoded by the nucleotide sequence of SEQ ID NO: 5 or a portion or functional variant thereof.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD28 and an intracellular signaling domain of a CD137 (4-1BB).

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD137 (4-1BB).

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a SIRPα, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD279 (PD-1), (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD95 (Fas), (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a TIM3, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a LAG3, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD2, (b) the hydrophobic component comprises a transmembrane domain of a CD28, and (c) the intracellular component comprises an intracellular signaling domain of a CD28.

In certain aspects, the present disclosure is directed to a nucleic acid molecule encoding a fusion protein as described herein.

In certain aspects, the present disclosure is directed to a vector comprising a nucleic molecule that encodes a fusion protein as described herein.

In certain other aspects, the present disclosure is directed to a host cell comprising a fusion protein, nucleic acid, or vector as described herein.

In certain other aspects, a method of increasing the activity of an immune cell is provided, comprising administering to a subject in need of increased immune cell activity an effective amount of a host cell as described herein.

In other aspects, the present disclosure is directed to a method of enhancing or prolonging an immune response, comprising administering to a subject in need of enhanced or prolonged immune cell activity an effective amount of a host cell as described herein.

In still other aspects, the present disclosure provides a method of stimulating an antigen-specific T cell response, comprising administering to a subject in need of increased immune cell activity an effective amount of a host cell as described herein.

In other aspects, the present disclosure is directed to a method of inhibiting an immunosuppressive signaling pathway, comprising administering to a subject in need thereof an effective amount of a host cell as described herein.

In other aspects, the present disclosure is directed to a method of treating cancer, comprising administering to a subject having cancer a therapeutically effective amount of a host cell as described herein.

In other aspects, the present disclosure is directed to a method of inhibiting immune resistance of cancer cells, comprising administering to a subject in need thereof an effective amount of a host cell as described herein.

In still other aspects, the present disclosure provides a method for treating a tumor, comprising administering to a subject having a tumor a therapeutically effective amount of a host cell as described herein, wherein the administered host cell is capable of proliferating in an immunosuppressive tumor microenvironment.

A method of treating an infection, comprising administering to a subject having the infection a therapeutically effective amount of a host cell as described herein, is also provided by the present disclosure.

These and other aspects of the present invention will become apparent upon reference to the following detailed description and attached drawings.

9aas-CD28Cys (Thy1.1 homozygous) and eGFP control (Thy1.1 heterozygous) $TCR_{gag}$ T cells were co-injected into Cytoxan®-treated FBL-bearing B6 mice at $4\times10^6$ cells/mouse. IL-2 was administered every 2 days ($2\times10^4$ U/dose). On day 8 post-T cell transfer, mice were euthanized and spleens and inguinal lymph nodes harvested. (B) CD200R-9aas-CD28Cys $TCR_{gag}$ T cells accumulate in the spleen in response to FBL. (LN=lymph node; Spl=spleen). (C) Comparison of surface proteins 3 days post-transfer for T cells transduced to express CD200R-9aas-CD28Cys, T cells transduced with an empty vector, and endogenous T cells. CD200R-9aas-CD28Cys $TCR_{gag}$ T cells expressed reduced CD62L compared to control $TCR_{gag}$ T cells, suggesting an effector T cell phenotype. (D) Comparison of surface proteins 15 days post-transfer for cells transduced to express CD200R-9aas-CD28Cys$^+$ T cells, T cells transduced with an empty vector, and endogenous T cells. CD200R-9aas-CD28Cys $TCR_{gag}$ T cells express similar levels of cell surface proteins compared to control $TCR_{gag}$ T cells.

FIGS. 4A to 4D show that adoptive immunotherapy with CD200R-CD28-transduced T cells can eradicate disseminated leukemia. (A) Experiment schematic. C57BL/6 mice were injected with $4\times10^6$ CD200$^+$ FBL cells. Five days later, CD200R-CD28tm, CD200R-CD28Cys, CD200R-9aas-CD28Cys, or eGFP $TCR_{gag}$ T cells were injected i.p. into Cy-treated FBL-bearing mice at $10^5$ cells/mouse. IL-2 was administered every 2 days ($2\times10^4$ U/dose) in a cohort of mice as indicated. (B) Representative example of expression of cell surface proteins in CD200R-CD28tm transduced T cells and non-transduced T cells on day of injection with IL-2, as determined by flow cytometry. (C) Survival of mice treated in the presence of IL-2 injections. (D) Survival of mice treated in the absence of IL-2 injections. Transfer of CD200R-9aas-CD28Cys $TCR_{gag}$ T cells significantly improved survival in the absence of IL-2 injections ($p<0.05$, log-rank Mantel-Cox test).

Figure 5A:
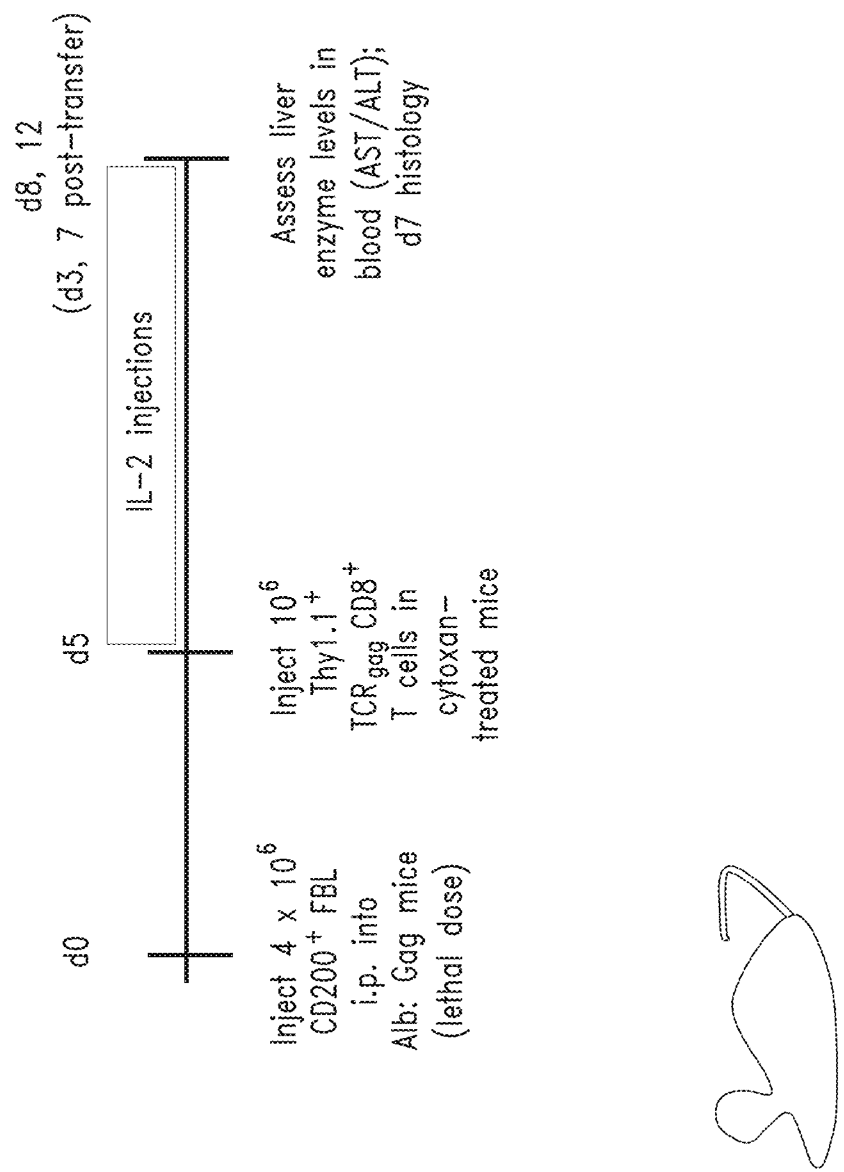
Figure 5B:
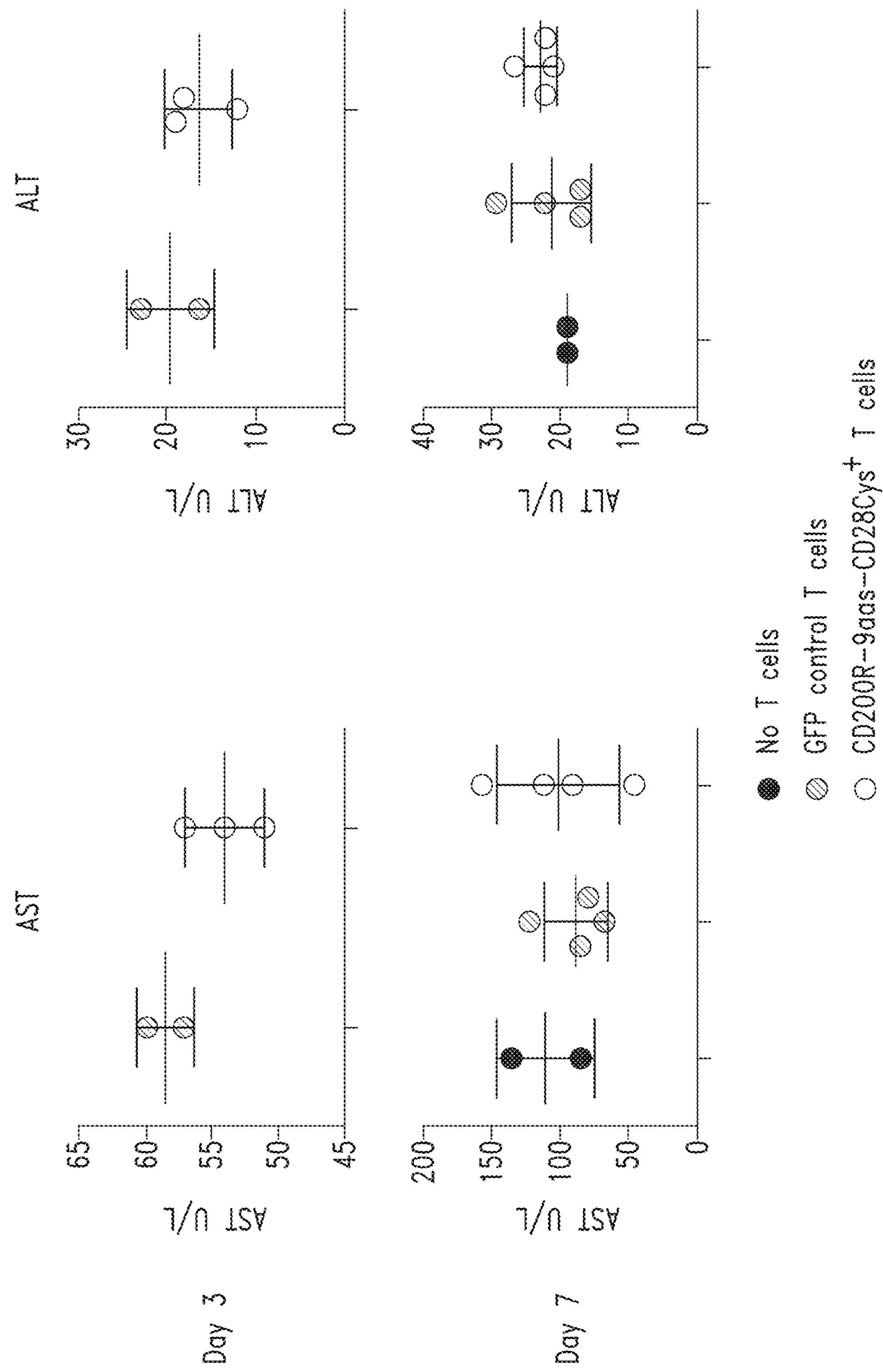
Figure 5C:
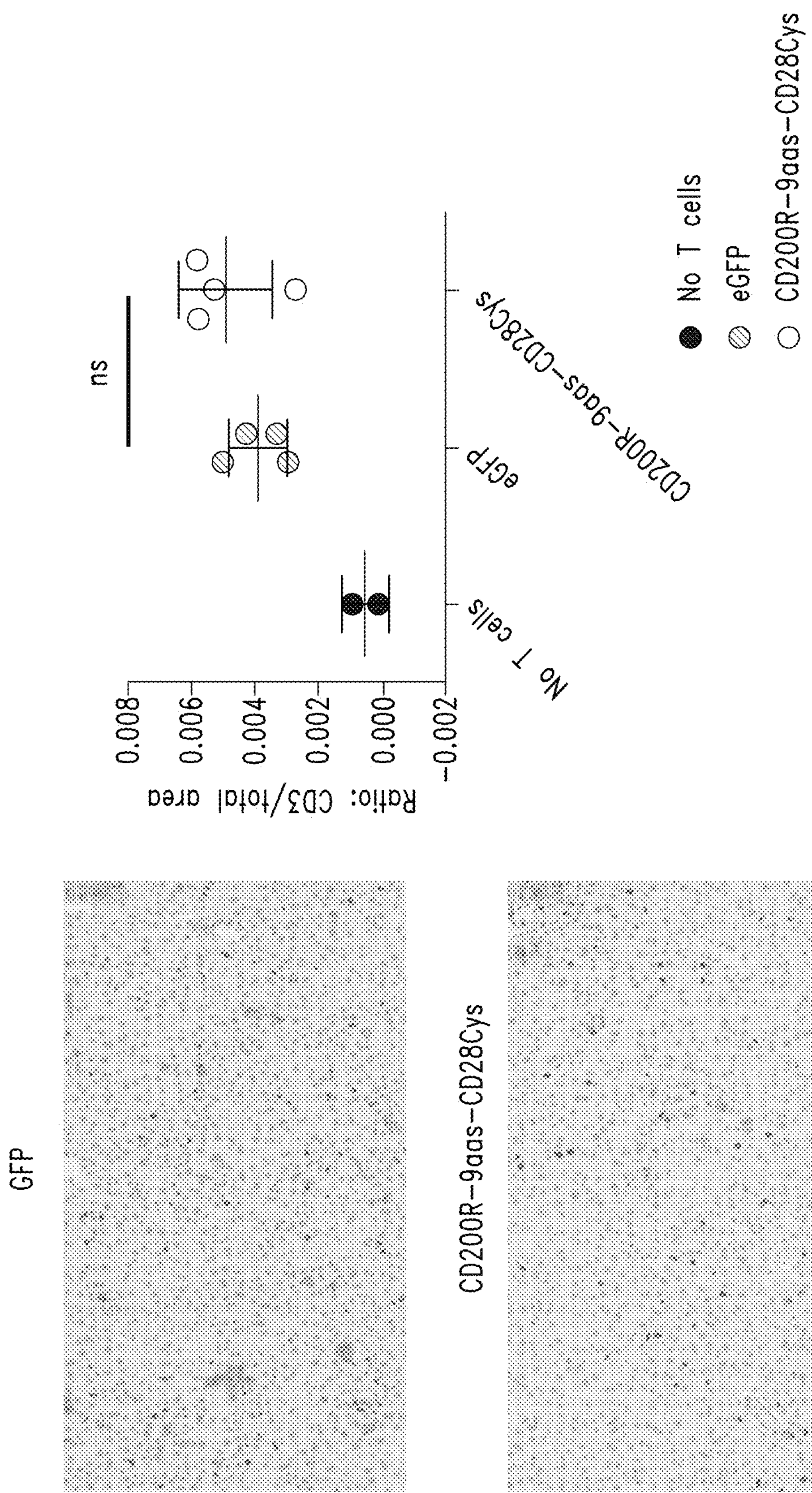

FIGS. 5A to 5C show that T cells expressing CD200R-9aas-CD28Cys do not induce detectable autoimmune liver damage or infiltrate normal tissues. (A) Experiment schematic. Cytoxan®-treated Alb/Gag mice were injected with $4\times10^6$ CD200$^+$ FBL cells. Five days later, CD200R-9aas-CD28Cys, and eGFP $TCR_{gag}$ T cells were injected i.p. into the Cytoxan®-treated FBL-bearing mice at $10^5$ cells/mouse. IL-2 was administered every 2 days ($2\times10^4$ U/dose) in a cohort of mice as indicated. Three and 7 days post-transfer, liver damage was assessed by quantification of serum levels of liver enzymes aspartate aminotransferase (AST) and alanine aminotransferase (ALT). (B) AST and ALT levels measured at 3 and 7 days post-transfer for mice receiving no T cells, control T cells expressing GFP, or T cells expressing CD200R-9aas-CD28Cys did not vary by treatment. (C) Assessment of T cell infiltration of normal tissue. Limited presence of T cells in liver tissue was observed using antibodies specific to the T cell marker CD3 (left panel), with no significant difference between recipients of CD200R-9aas-CD28Cys $TCR_{gag}$ or control $TCR_{gag}$ T cells (right panel).

FIGS. 6A to 6D show that 4-1BB co-stimulatory signaling domains promote accumulation and effector function of transduced T cells in vitro and promote survival of tumor-bearing recipients of transduced T cell in response to CD200$^+$ tumor target cells. (A) Schematic representation of CD200R-CD28 ("V"), -4-1BB ("VI"), and —CD28-4-1BB ("VII") constructs. (B) Expansion of transduced $TCR_{gag}$ T cells relative to non-transduced $TCR_{gag}$ T cells after weekly stimulation with irradiated CD200$^+$ FBL and splenocytes. CD200R-4-1BB and CD200R-CD28-4-1BB also promote accumulation of transduced T cells in vitro. (C) CD200R-9aas-4-1BB$^+$ CD8$^+$ T cells displayed an enhanced ability to lyse CD200$^+$ FBL cells in vitro relative to controls, using a standard CFSE-based cytotoxicity assay. The percentage of FBL of the sum of FBL and control tumor cells was determined by flow cytometry. The percentage lysis was determined by dividing the percent of FBL incubated with T cells by the percent of FBL incubated without T cells. (D) CD200R-41BB-transduced T cells also promote survival relative to controls. C57BL/6 mice were injected with $4\times10^6$ CD200$^+$ FBL cells. Five days later, CD200R-9aas-CD28, CD200R-9aas-4-1BB, CD200R-9aas-CD28-4-1BB, or eGFP $TCR_{gag}$ T cells were injected i.p. into Cytoxan®-treated FBL-bearing mice at $10^5$ cells/mouse.

FIGS. 7A to 7D show that human primary T cells transduced to express a WT1-specific TCR and a CD200Rtm-CD28 fusion protein exhibit enhanced proliferation to target cells that express CD200 and increased cytokine production in response to tumor cells that express CD200. (A) Expression of the $WT1_{126}$—specific TCR, C4, and CD200Rtm-CD28. (B) Expression of CD200 in T2 and K562 cells. T2 cells exhibit low-level endogenous CD200 expression. (C) Proliferation of T cells as indicated by CFSE. Cells that proliferate in response to antigen show reduced CFSE fluorescence intensity. T cells transduced with both C4 and the IFP show enhanced proliferation to target cells expressing low levels of CD200 relative to T cells transduced with C4 only. (D) Cytokine production in response to exposure to CD200dim tumor cells, as measured by flow cytometry. Relative to control T cells transduced with the TCR C4 alone, T cells transduced with both C4 and the IFP CD200Rtm-CD28 show increased cytokine production.

FIGS. 8A to 8E show that fusion proteins comprising SIRPα extracellular components and CD28 co-stimulatory signaling domains promote accumulation and proliferation of transduced T cells in vitro. (A) Schematic representation of exemplary SIRPα-CD28 constructs. Construct "I" contains SIRPα extracellular ("EC") and transmembrane ("TM") domains and a CD28 intracellular ("IC") signaling domain (SIRPαtm-CD28). Construct "II" contains the extracellular domain of SIRPα and the transmembrane and intracellular domains of CD28 (SIRPα-CD28tm). Constructs "III-VI" also incorporate a portion of the extracellular domain of CD28 to the transmembrane-proximal cysteine to promote multimerization and enhance CD28 signaling. To account for the extra extracellular amino acids (e.g., extra nine (9) amino acids for murine constructs, or twelve (12) amino acids for human constructs), some constructs have a truncated portion of an extracellular or intracellular domain (e.g., a SIRPα that preserves an N linked glycosylation site). Construct IV has a truncated portion of SIRPα that is truncated 6 amino acids to preserve an N linked glycosylation site. Construct V has a truncated portion of SIRPα that is truncated 9 amino acids. Construct VI has a truncated portion of SIRPα that is truncated 23 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) Expansion of transduced $TCR_{gag}$ T cells relative to non-transduced $TCR_{gag}$ T cells after weekly stimulation with irradiated SIRPα$^+$ FBL and splenocytes. SIRPα-CD28 constructs promote accumulation of transduced T cells in vitro, with SIRPα-9aas-CD28Cys exhibiting enhanced accumulation. (C) Proliferation of T cells transduced with SIRPα-CD28 constructs in a CellTrace™ Violet (CTV) dilution proliferation assay. T cells expressing SIRPα-CD28 constructs engineered to maintain T cell-tumor cell distance exhibited enhanced proliferation relative to nontransduced T cells. (D) $CD47^+$ tumor cells were killed after co-culture with SIRPα-$CD28^+$ T cells transduced to express SIRPαtm-CD28 or SIRPα-9aas-CD28Cys constructs. In contrast, tumor cells were not eradicated when cultured with T cells receiving empty vector, or a truncated SIRPα lacking its intracellular domain. (E) Results of an IncuCyte® assay used to quantify killing of $CD47^+$ tumor cells. $CD47^+$ FBL tumor cells were transduced with mCherry. Loss of red signal indicates killing of tumor cells. Killing of tumor cells was tested at the effector:target ratios of 10:1, 2:1, and 0.4:1. SIRPα-$CD28^+$ T cells killed $CD47^+$ tumor cells, even at the lowest effector-to-target ratio tested.

Figure 9A:
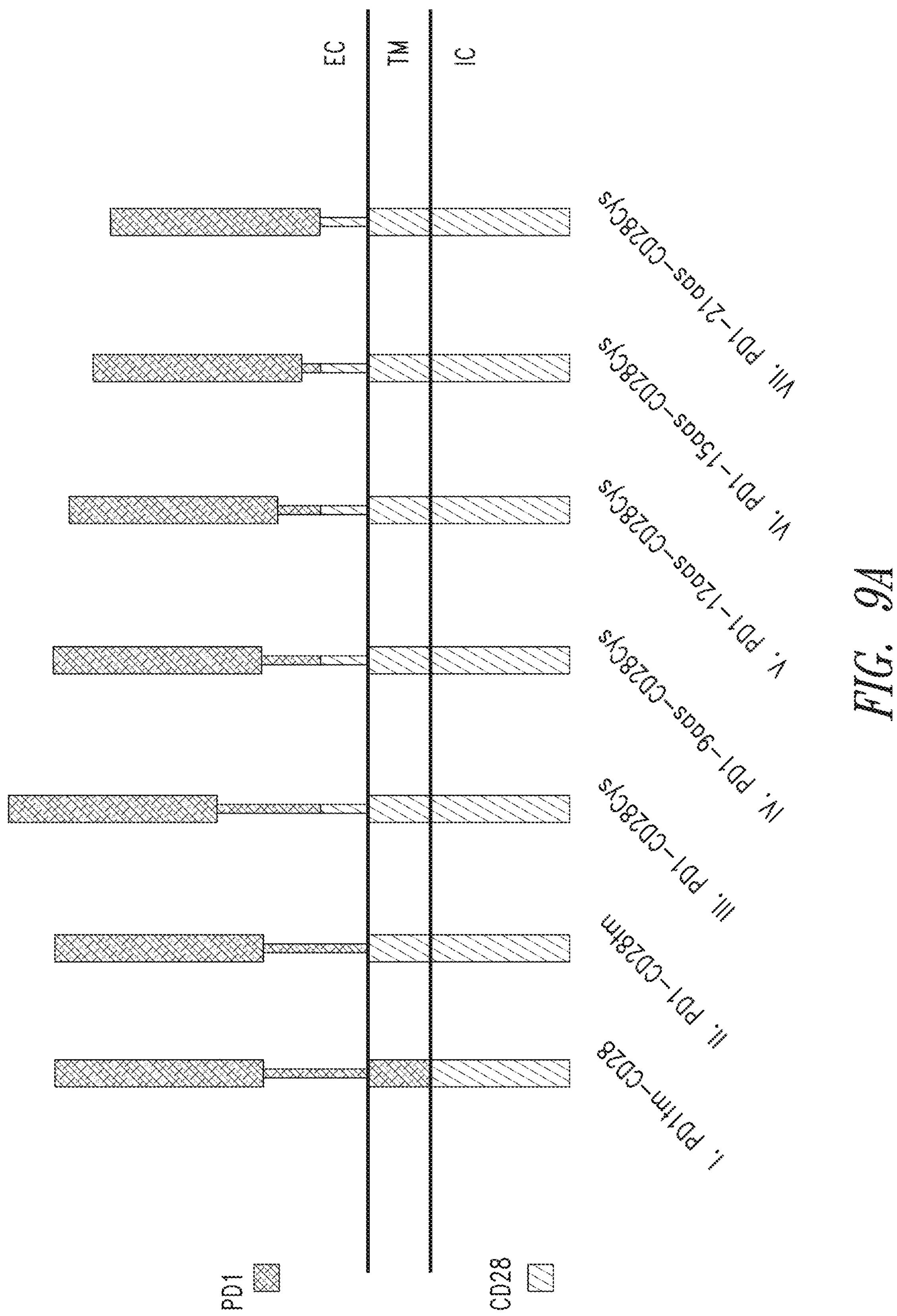
Figure 9B:
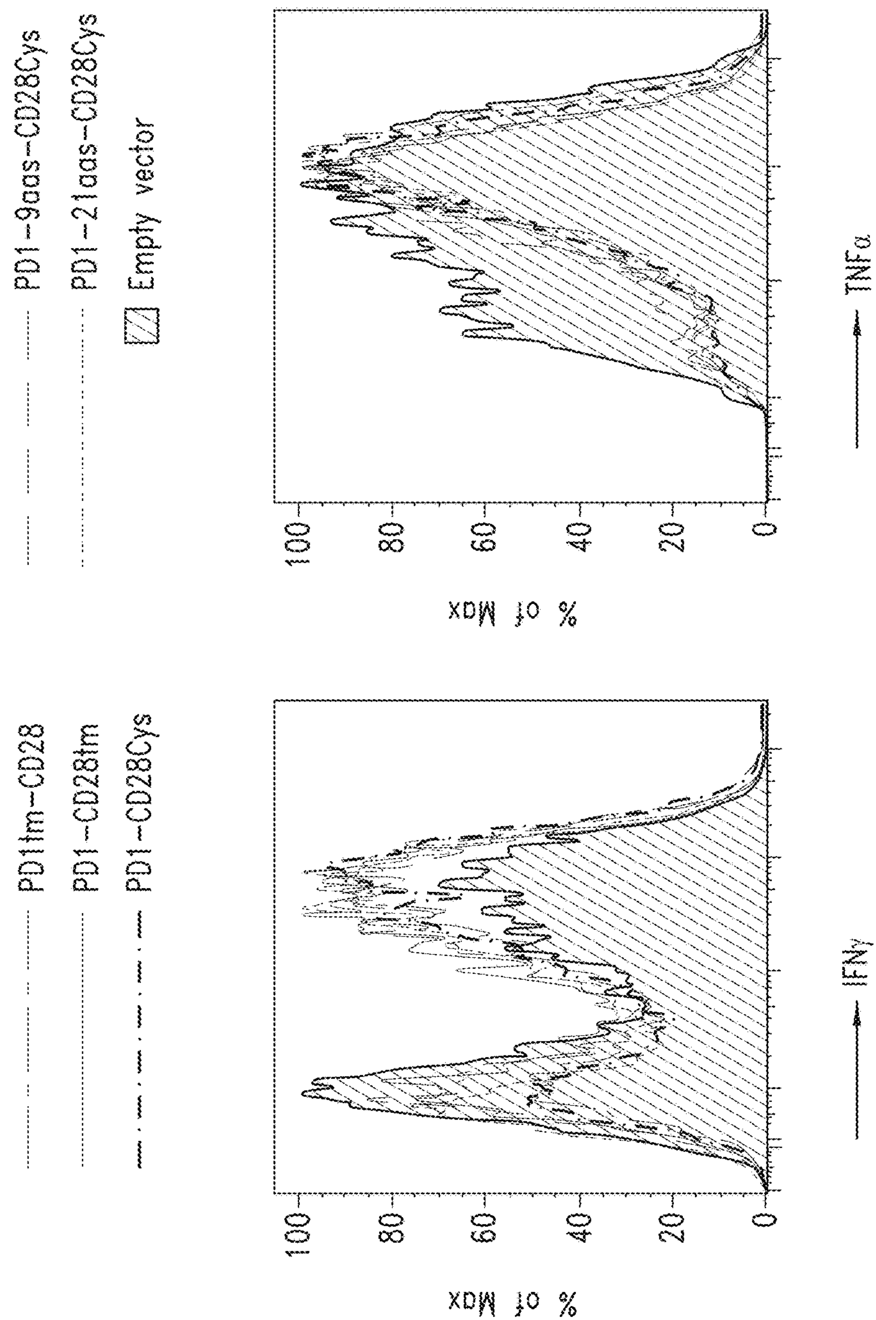

FIGS. 9A and 9B show that fusion proteins comprising PD-1 extracellular components and CD28 co-stimulatory signaling domains promote cytokine production in vitro. (A) Schematic representation of exemplary PD-1-CD28 constructs. Construct "I" contains PD-1 extracellular ("EC") and transmembrane ("TM") domains and a CD28 intracellular ("IC") signaling domain (PD1tm-CD28). Construct "II" contains the extracellular domain of PD-1 and the transmembrane and intracellular domains of CD28 (PD1-CD28tm). Constructs "III-VII" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), constructs IV-VII have a truncated portion of PD-1. Construct IV has a truncated portion of PD-1 that is truncated 9 amino acids. Construct V has a truncated portion of PD-1 that is truncated 12 amino acids. Construct VI has a truncated portion of PD-1 that is truncated 15 amino acids. Construct VII has a truncated portion of PD-1 that is truncated 21 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) PD1-$CD28^+$ T cells exhibited increased cytokine production in response to stimulation for 5 hours in the presence of Brefeldin A with FBL cells that endogenously express the PD-1 ligands, PD-L1 and PD-L2. Stimulated T cells were assessed for intracellular expression of the effector cytokines, IFNγ and TNFα, by flow cytometry.

Figure 10:
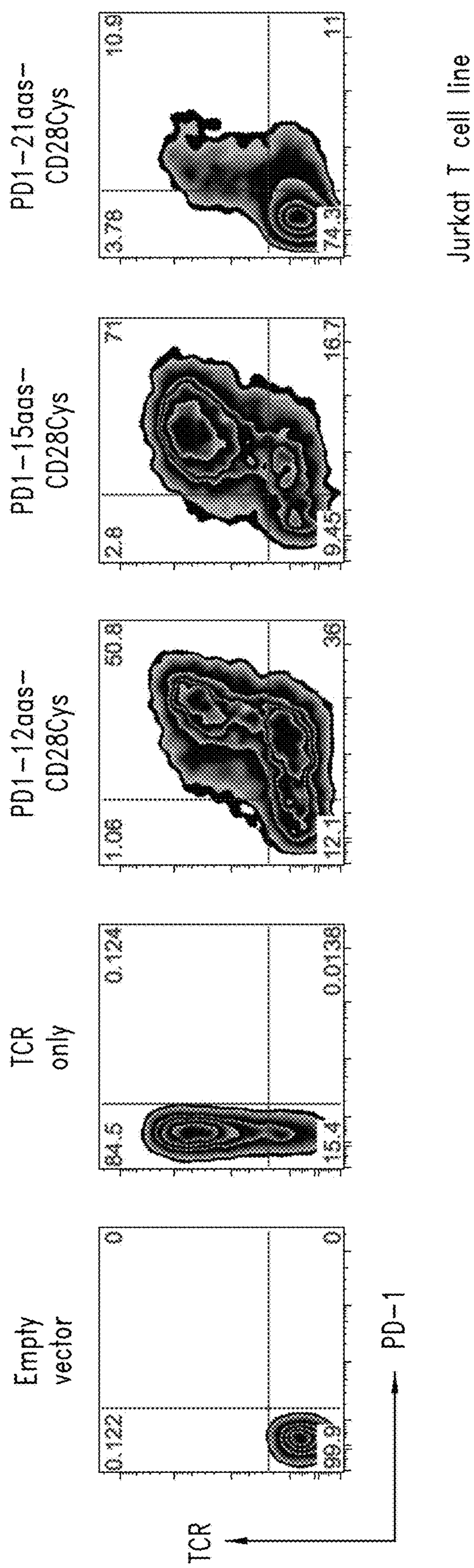

FIG. 10 shows co-expression of the TCR C4 and a PD-1 IFP (PD1-12aas-CD28Cys, PD1-15aas-CD28Cys, or PD1-21aas-CD28Cys). T cells transduced with C4 and PD1-12aas-CD28Cys or PD1-15aas-CD28Cys exhibited high transduction efficiencies and expression of both proteins.

Figure 11A:
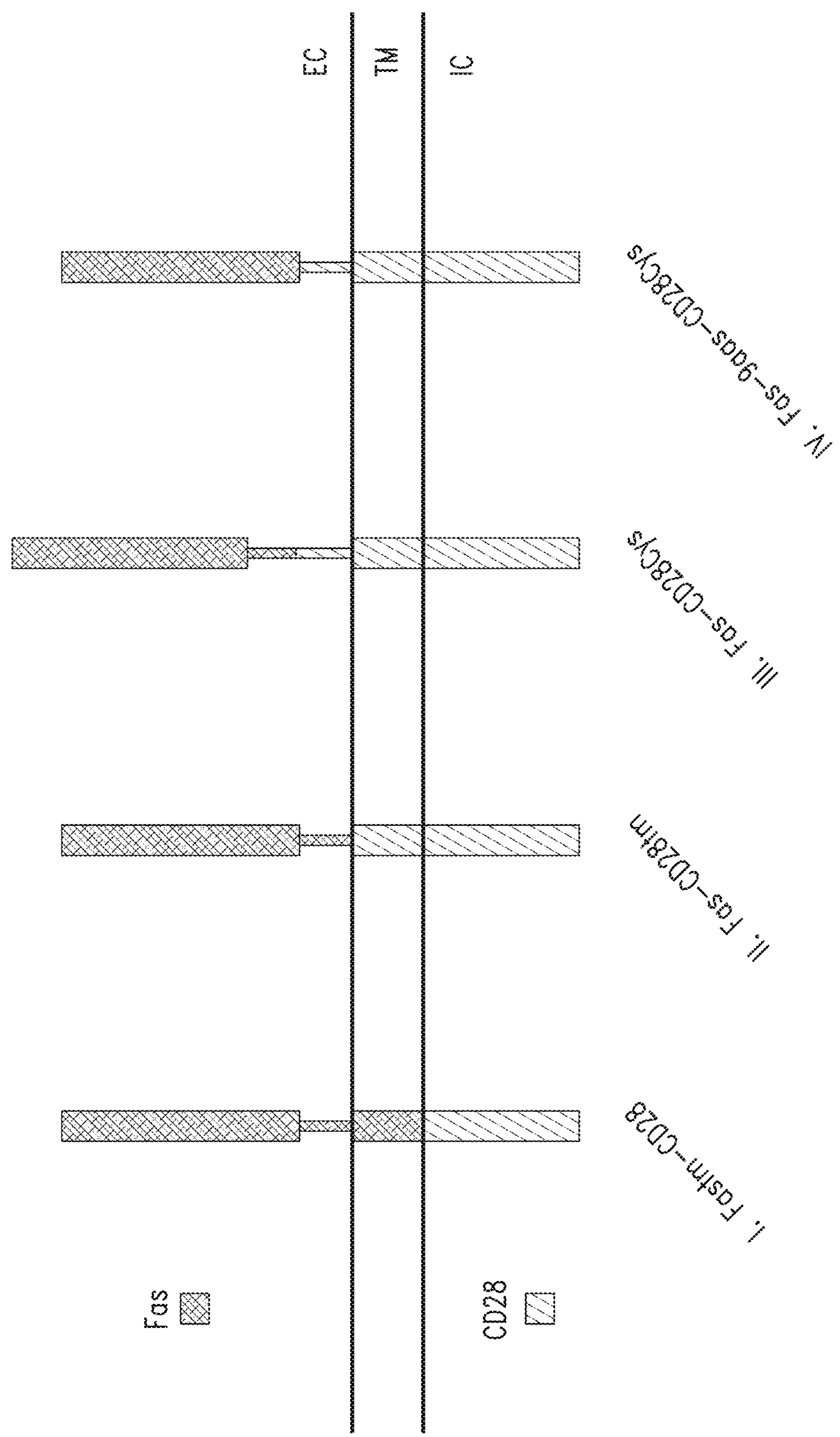
Figure 11B:
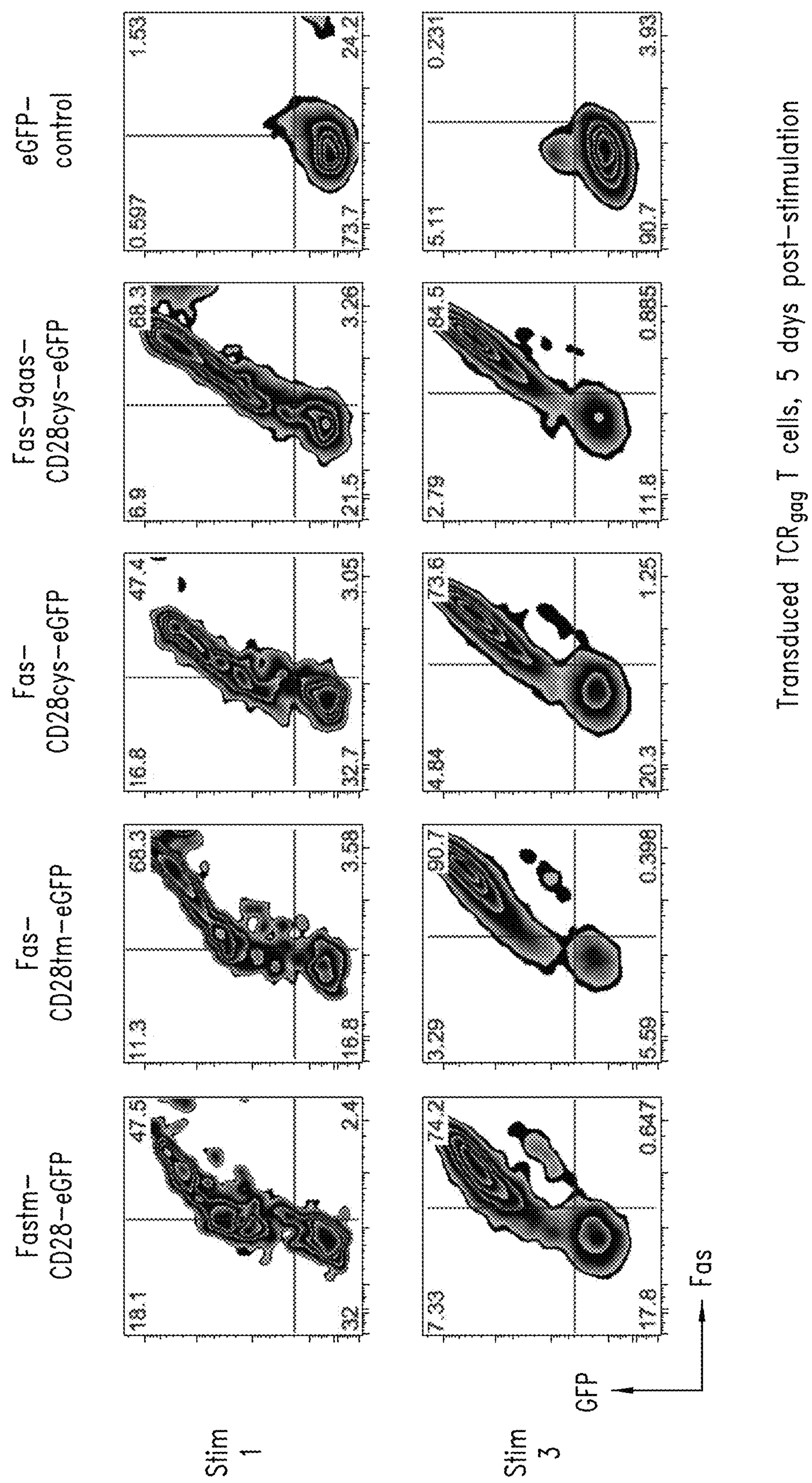
Figure 11C:
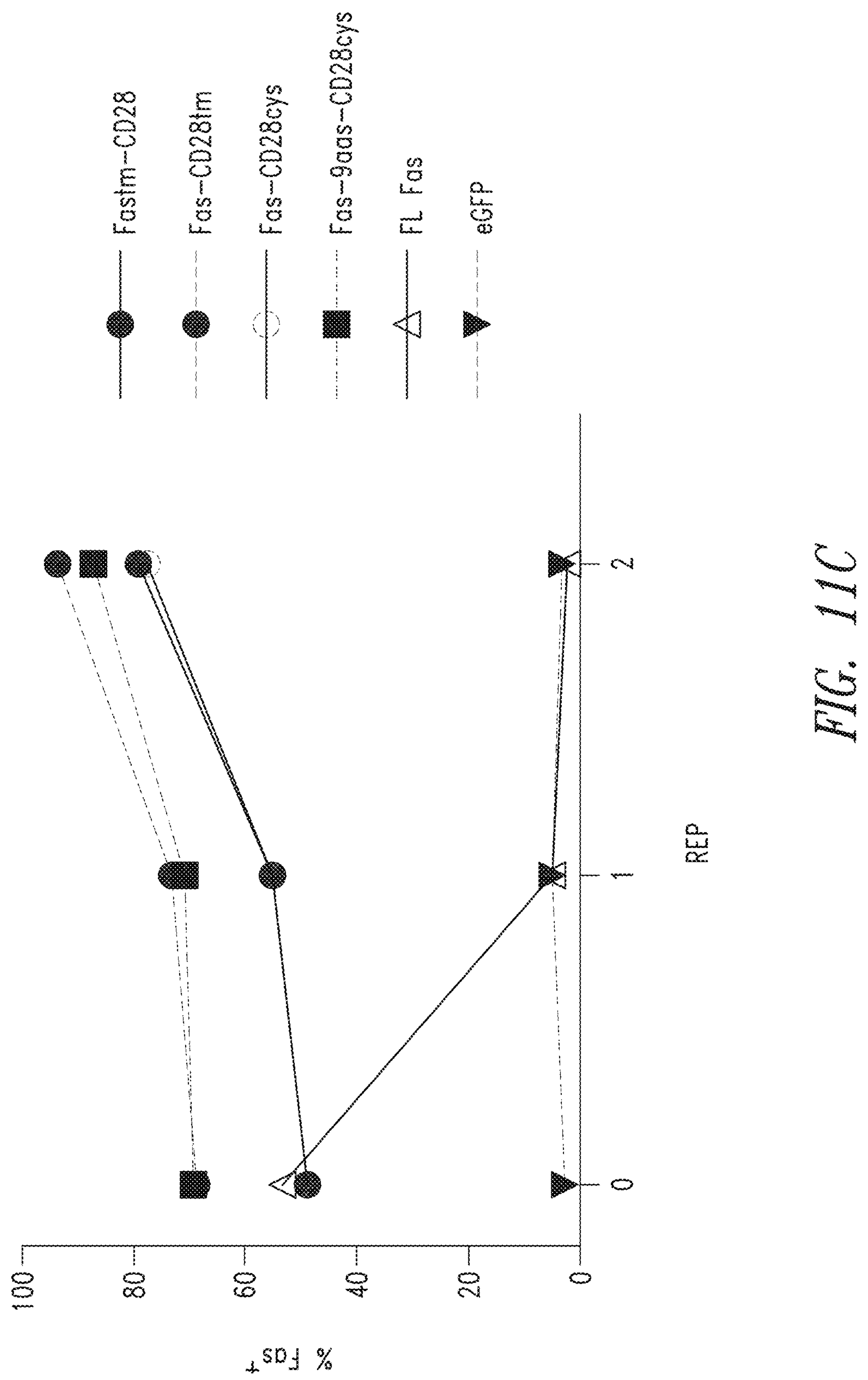

FIGS. 11A to 11C show that fusion proteins comprising Fas extracellular components and CD28 co-stimulatory signaling domains accumulate in vitro upon stimulation with irradiated FBL cells. (A) Schematic representation of exemplary Fas-CD28 constructs. Construct "I" contains Fas extracellular ("EC") and transmembrane ("TM") domains and a CD28 intracellular ("IC") signaling domain (Fastm-CD28). Construct "II" contains the extracellular domain of Fas and the transmembrane and intracellular domains of CD28 (Fas-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of Fas, wherein the Fas extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Accumulation of $TCR_{gag}$ T cells transduced with Fas constructs over multiple stimulations with irradiated FBL cells. All of the constructs promoted accumulation of T cells relative to control T cells. (C) Expression of Fas-CD28 constructs but not full-length (FL) Fas promoted survival or expansion of T cells upon multiple stimulations in vitro.

Figure 12A:
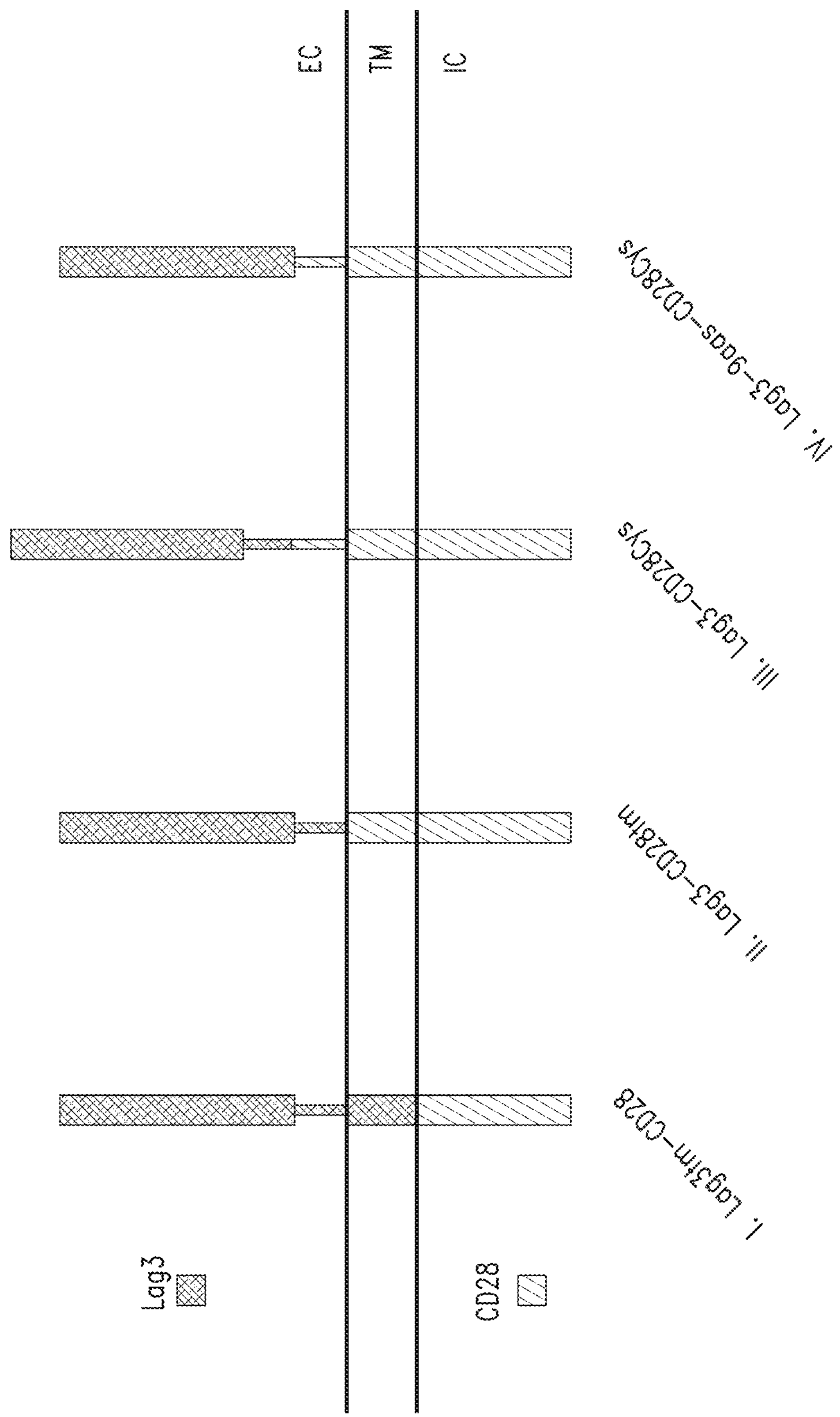
Figure 12B:
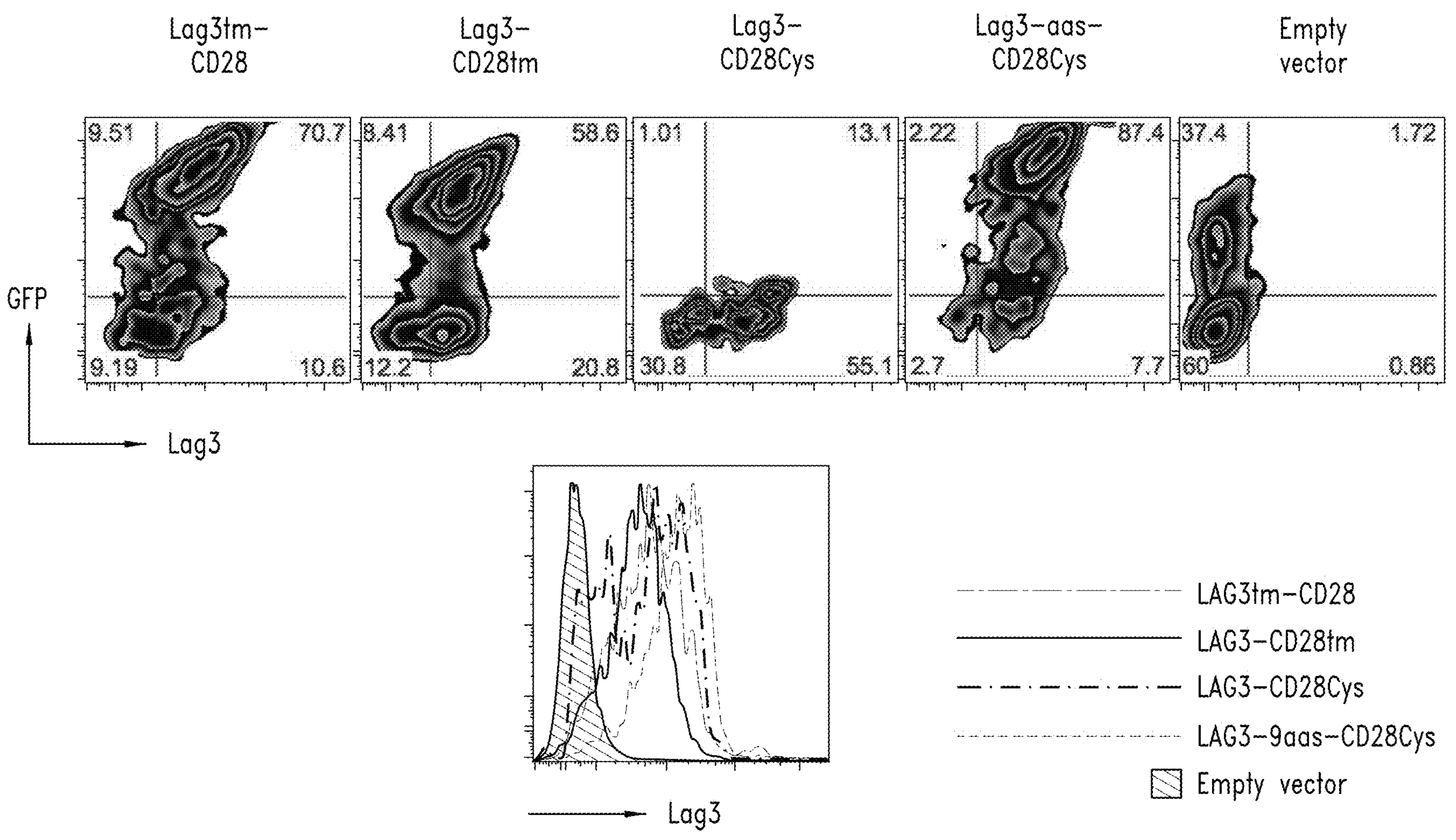

FIGS. 12A and 12B show the structure and expression of fusion proteins comprising LAG3 extracellular components and CD28 co-stimulatory signaling domains. (A) Schematic representation of exemplary LAG3-CD28 constructs. Construct "I" contains LAG3 extracellular ("EC") and transmembrane ("TM") domains and a CD28 intracellular ("IC") signaling domain (LAG3tm-CD28). Construct "II" contains the extracellular domain of LAG3 and the transmembrane and intracellular domains of CD28 (LAG3-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of LAG3, wherein the LAG3 extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Expression of LAG3-CD28 constructs by murine $CD8^+$ T cells, as determined by anti-LAG3 antibody staining and flow cytometry. T cells transduced to express LAG3-CD28 constructs (LAG3tm-CD28; LAG3-CD28tm; LAG3-CD28Cys; LAG3-9aas-CD28Cys) exhibited expression of the constructs, in contrast with control T cells that received empty vector.

Figure 13A:
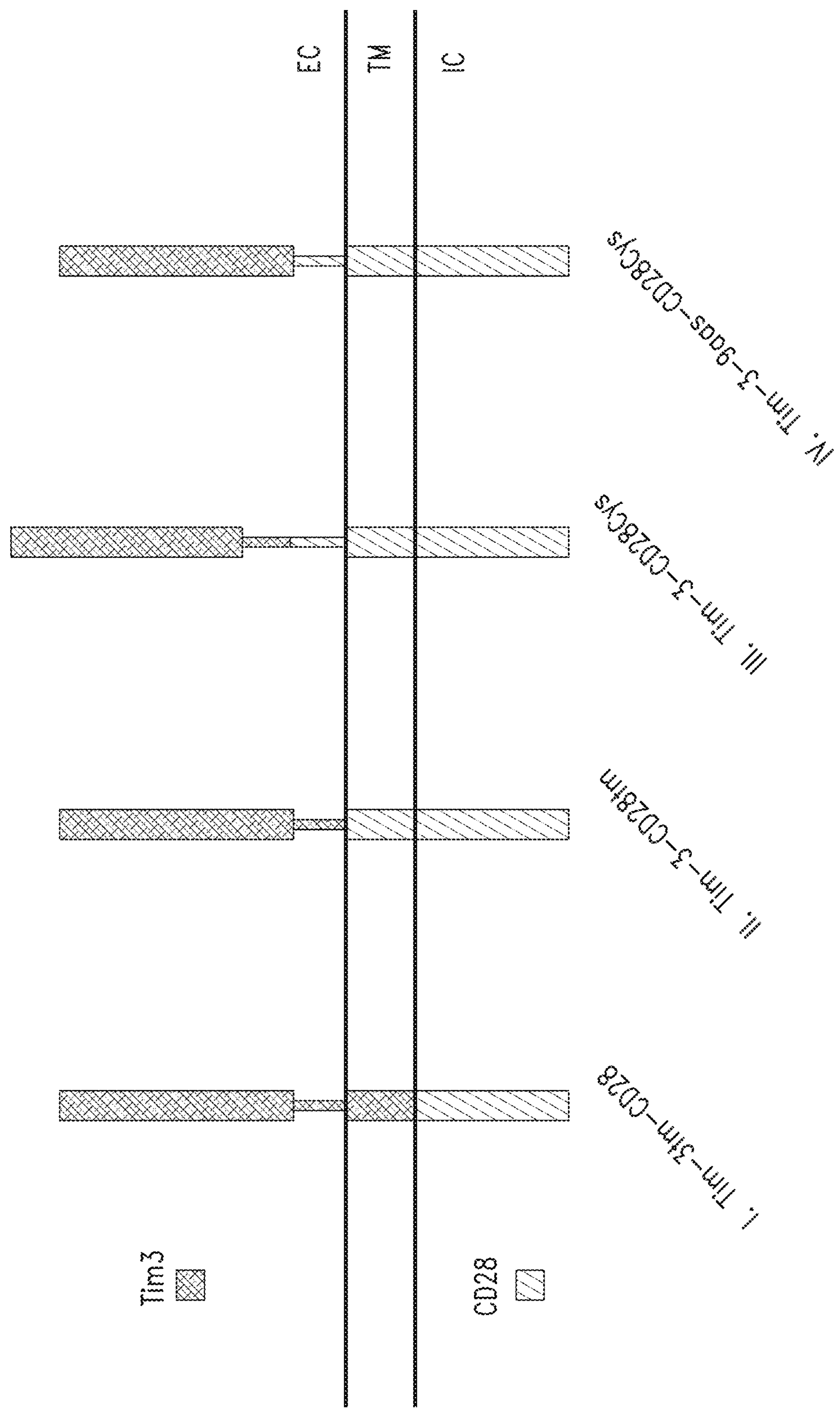
Figure 13B:
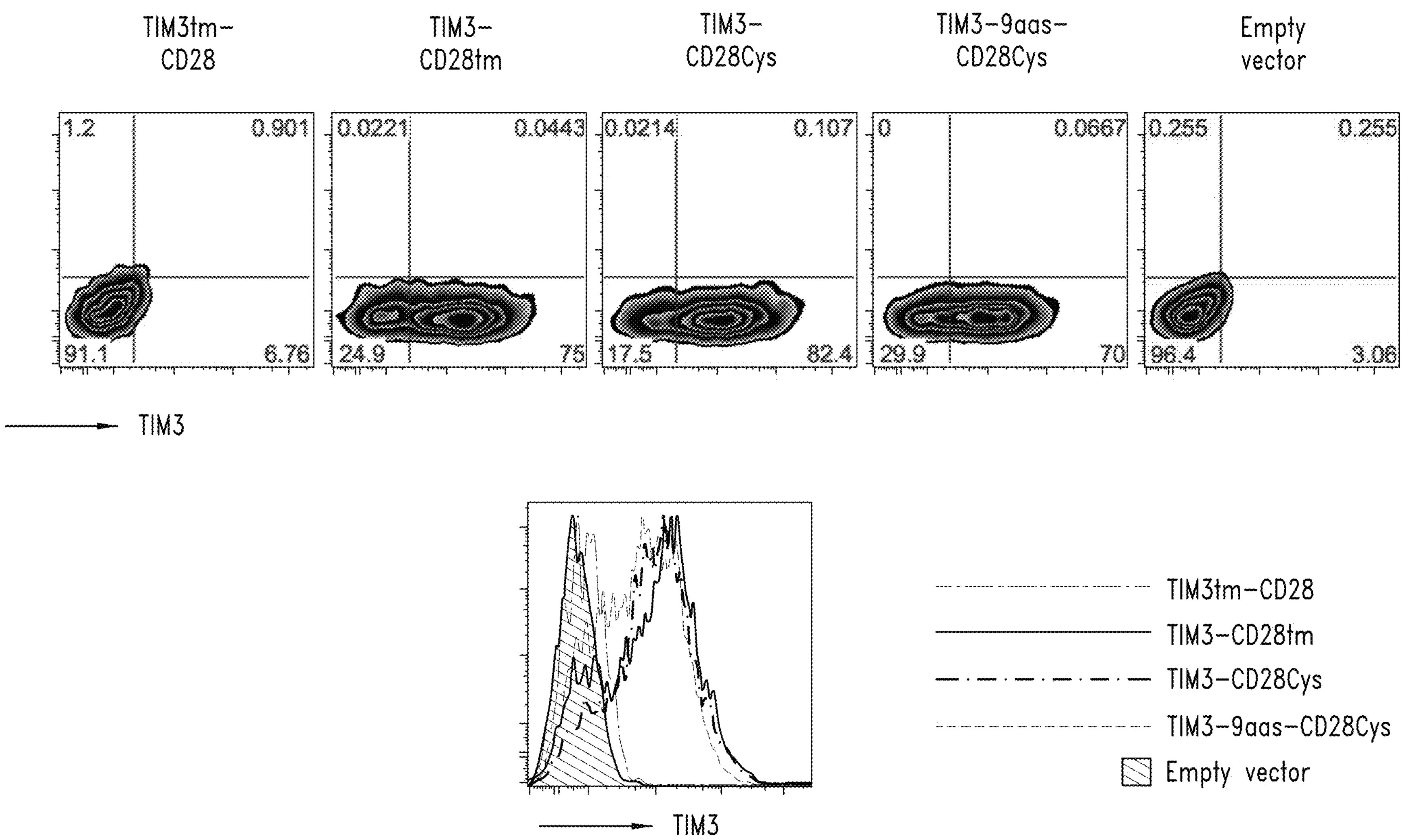

FIGS. 13A and 13B show the structure and expression of fusion proteins comprising TIM3 extracellular components and CD28 co-stimulatory signaling domains. (A) Schematic representation of exemplary TIM3-CD28 constructs. Construct "I" contains TIM3 extracellular ("EC") and transmembrane ("TM") domains and a CD28 intracellular ("IC") signaling domain (TIM3tm-CD28). Construct "II" contains the extracellular domain of TIM3 and the transmembrane and intracellular domains of CD28 (TIM3-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of TIM3, wherein the TIM3 extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Expression of TIM3-CD28 constructs by murine $CD8^+$ T cells, as determined by anti-TIM3 antibody staining and flow cytometry. T cells transduced to express TIM3-CD28 constructs (TIM3tm-CD28; TIM3-CD28tm; TIM3-

CD28Cys; TIM3-9aas-CD28Cys) typically exhibited expression of the constructs, in contrast with control T cells that received empty vector.

DETAILED DESCRIPTION

The instant disclosure provides fusion proteins that modulate signaling in a host cell, such as an immune cell. For example, fusion proteins of this disclosure can provide an activation or co-stimulatory signal in a human T cell, wherein the T cell may optionally be engineered to have a preferred antigen-specific TCR. These immunomodulatory fusion proteins (IFPs) can interact with ubiquitously expressed targets or with targets that are commonly upregulated or overexpressed in non-normal cells (e.g., a cancer cell). Such IFPs have an extracellular binding domain and an intracellular signaling domain. By transducing T cells with engineered TCRs (e.g., high affinity TCRs) and fusion proteins of this disclosure that generate activation signals, certain embodiments of T cells may no longer require exogenous co-stimulation upon interaction with, for example, a tumor cell.

In certain aspects, the present disclosure provides host cells (e.g., immune cells such as T cells, dendritic cells, NK cells or the like) comprising an IFP, vectors encoding IFPs, and methods of activating T cells comprising an IFP for various therapeutic applications, including the treatment of a disease in subject (e.g., cancer, infectious disease).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, or module or protein includes extensions, deletions, mutations, or any combination thereof (e.g., amino acids at the amino- or carboxy-terminus or between domains) that, in combination, contribute to at most 20% (e.g., at most 15%, 10%, 8%, 6%, 5%, 4%, 3%, 2%, or 1%) of the length of a domain, region, or module or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "heterologous" or "non-endogenous" or "exogenous" refers to any gene, protein, compound, molecule, or activity that is not native to a host cell or a subject, or is any gene, protein, compound, molecule, or activity native to a host or host cell that has been altered or mutated such that the structure, activity or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a molecule or activity found in or derived from a host cell, species, or strain. For example, a heterologous or exogenous molecule or gene encoding the molecule may be homologous to a native host or host cell molecule or gene that encodes the molecule, respectively, but may have an altered structure, sequence, expression level or combinations thereof. A non-endogenous molecule may be from the same species, a different species, or a combination thereof.

As used herein, the term "endogenous" or "native" refers to a gene, protein, compound, molecule, or activity that is normally present in a host or host cell and has no engineered alterations.

A "binding domain" (also referred to as a "binding region" or "binding moiety"), as used herein, refers to a molecule, such as a peptide, oligopeptide, polypeptide or protein, that possesses the ability to specifically and non-covalently associate, unite, or combine with a target molecule (e.g., CD200, CD47, CD19, CD20, CD22, ROR1, mesothelin, PD-L1, PD-L2, PSMA, WT-1, cyclin-A1). A binding domain includes any naturally occurring, synthetic, semi-synthetic, or recombinantly produced binding partner for a biological molecule or other target of interest or binding protein thereof. In some embodiments, the binding domain is an antigen-binding domain, such as an antibody or T cell receptor (TCR) or functional binding domain or antigen-binding fragment thereof. Exemplary binding domains include receptor ectodomains (e.g., those of CD200R, PD-1, CTLA4, BTLA, CD2, Fas) or binding portions thereof, ligands (e.g., cytokines such as IL35, chemokines) or binding portions thereof, single chain antibody variable regions (e.g., domain antibodies, sFv, scFv, Fab) or binding portions thereof, antigen-binding regions of T cell receptors (TCRs), such as single chain TCRs (scTCRs), or synthetic polypeptides selected for the specific ability to bind to a biological molecule.

In some embodiments, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, or binds to such target molecule while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains refer to those binding domains with a $K_a$ of at least $10^7$ $M^{-1}$, at least $10^8$ $M^{-1}$, at least $10^9$ $M^1$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a Ka (equilibrium association constant) for the target antigen that is higher than the wild type binding domain, or due to a $K_d$ (dissociation constant) for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., *Ann. N.Y. Acad. Sci.* 51:660, 1949; and U.S. Pat. Nos. 5,283,173, 5,468,614, or the equivalent).

As used herein, a "fusion protein" refers to a polypeptide that, in a single chain, has at least two distinct domains, wherein the domains are not naturally found together in a protein. A nucleic acid molecule encoding a fusion protein may be constructed using PCR, recombinantly engineered, or the like, or such fusion proteins can be made using methods of protein synthesis. A fusion protein may further contain other components (e.g., covalently bound), such as a tag or bioactive molecule. In certain embodiments, a fusion protein expressed or produced by a host cell (e.g., T cell) locates to the cell surface, where the fusion protein is anchored to the cell membrane with a portion of the fusion protein located extracellularly (e.g., containing a binding domain) and a portion of the fusion protein located intracellularly (e.g., containing a signaling domain).

A "hydrophobic component," as used herein, means any amino acid sequence having a three-dimensional structure that is thermodynamically stable in a cell membrane, and generally ranges in length from about 15 amino acids to about 30 amino acids. The structure of a hydrophobic component may comprise an alpha helix, a beta barrel, a beta sheet, a beta helix, or any combination thereof. In certain embodiments, a hydrophobic component is comprised of a "transmembrane domain" from a known transmembrane protein, which is a portion of a transmembrane protein that can insert into or span a cell membrane. In further embodiments, a hydrophobic component or transmembrane domain can be disposed between and connect the extracellular and intracellular portions of a fusion protein. Additionally, the hydrophobic component may be modified to contain charged regions or hydrophilic residues to facilitate intermolecular interactions.

As used herein, an "intracellular signaling domain" is an intracellular portion of molecule, such as one used in a fusion protein of this disclosure, that can directly or indirectly promote a response such as a co-stimulatory, positive, or activating biological or physiological response in a cell when receiving the appropriate signal. In certain embodiments, an intracellular signaling domain is part of a protein or protein complex that receives a signal when bound, or itself can bind directly to a target molecule to transmit a signal to other components in the cell. An intracellular signaling domain may directly promote a cellular response when it contains one or more signaling domains or motifs, such as an immunoreceptor tyrosine-based activation motif (ITAM), a kinase domain, a co-stimulatory domain, or the like. In other embodiments, an intracellular signaling domain will indirectly promote a cellular response by associating with one or more other proteins that in turn directly promote a cellular response. In some embodiments, an intracellular signaling domain or functional fragment thereof may be from a CD3ε, CD3δ, CD3ζ, CD25, CD27, CD28, CD40, CD47, CD79A, CD79B, CD134 (OX40), CD137 (41BB), CD150 (SLAMF1), CD278 (ICOS), CD357 (GITR), CARD11, DAP10, DAP12, FcRα, FcRβ, FcRγ, Fyn, Lck, LAT, LRP, NKG2D, NOTCH1, NOTCH2, NOTCH3, NOTCH4, ROR2, Ryk, Slp76, pTα, TCRα, TCRβ, TRIM, Zap70, PTCH2, or any combination thereof. In some embodiments, an intracellular signaling domain or functional fragment thereof does not comprise a CD3.

A "multimerization domain," as used herein, refers to a polypeptide molecule or region that preferentially interacts or associates with another polypeptide molecule or region, directly or indirectly, wherein the interaction of multimerization domains substantially contribute to or efficiently promote multimerization (i.e., the formation of a dimer, trimer, tetramer, or higher order multimers, which may be a homodimer, heterodimer, homotrimer, heterotrimer, homomultimer, heteromultimer, or the like). For example, multimerization may be due to one or more types of molecular forces, including covalent bonds (e.g., disulfide bonds or bridges), ionic bonds, metallic bonds, electrostatic interactions, salt bridges, dipole-dipole forces, hydrogen bonding, Van der Waals forces, hydrophobic interactions, or any combination thereof. A multimer is stable under appropriate conditions (e.g., physiological conditions, in an aqueous solution suitable for expressing, purifying, or storing recombinant or engineered proteins, or under conditions for non-denaturing or non-reducing electrophoresis). Exemplary multimerization domains may comprise one or more disulfide bonds, zinc finger motif, a leucine zipper motif, helix-turn-helix, helix-loop-helix, or the like.

In certain embodiments, a fusion protein may contain a "linker," which can provide a spacer function to facilitate the interaction of two single chain fusion proteins, or positioning of one or more binding domains, so that the resulting polypeptide structure maintains a specific binding affinity to a target molecule or maintains signaling activity (e.g., effector domain activity) or both. Exemplary linkers include from one to about ten repeats of $Gly_xSer_y$, wherein x and y are independently an integer from 1 to 5.

"Junction amino acids" or "junction amino acid residues" refer to one or more (e.g., about 2-20) amino acid residues between two adjacent motifs, regions, or domains of a fusion protein, such as between a binding domain and an adjacent hydrophobic component, or on one or both ends of a hydrophobic component. Junction amino acids may result from the construct design of a fusion protein (e.g., amino acid residues resulting from the use of a restriction enzyme site during the construction of a nucleic acid molecule encoding a fusion protein). In certain embodiments, junction amino acids form a linker, such as those having from one to about ten repeats of $Gly_xSer_y$, wherein x and y are independently an integer from 1 to 5.

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MEW) receptor on the surface of the APC complexed with a peptide interacts with a TCR on the surface of a T cell.

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). TM can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced CD8+ cytotoxic T lymphocytes that have decreased expression of CD62L,CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+CD28−, and Qa-1 restricted T cells.

"T cell receptor" (TCR) refers to a molecule found on the surface of T cells (or T lymphocytes) that, in association with CD3, is generally responsible for recognizing antigens bound to major histocompatibility complex (MEW) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease,* 3rd Ed., Current Biology Publications, p. 4:33, 1997). TCR, as used in the present disclosure, may be from various animal species, including human, mouse, rat, cat, dog, goat, horse, or other mammals. TCRs may be cell-bound (i.e., have a transmembrane region or domain) or in soluble form.

"Major histocompatibility complex molecules" (MHC molecules), which is used interchangeably and is understood to also refer to the human counterpart human leukocyte antigen (HLA molecules), refer to glycoproteins that deliver peptide antigens to a cell surface. MEW class I molecules are heterodimers consisting of a membrane spanning α chain (with three a domains) and a non-covalently associated β2 microglobulin. MHC class II molecules are composed of two transmembrane glycoproteins, α and β, both of which span the membrane. Each chain has two domains. MEW (HLA) class I molecules deliver peptides originating in the cytosol to the cell surface, where peptide:MHC (or peptide: HLA in humans) complex is recognized by $CD8^+$ T cells. MEW (HLA) class II molecules deliver peptides originating in the vesicular system to the cell surface, where they are recognized by $CD4^+$ T cells. An MHC molecule may be from various animal species, including human, mouse, rat, or other mammals.

"Nucleic acid molecule", or polynucleotide, may be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

Variants of the nucleic acid molecules or polynucleotides of this disclosure are also contemplated. Variant polynucleotides are at least 90%, and preferably 95%, 99%, or 99.9% identical to one of the polynucleotides of defined sequence as described herein, or that hybridizes to one of those polynucleotides of defined sequence under stringent hybridization conditions of 0.015M sodium chloride, 0.0015M sodium citrate at about 65-68° C. or 0.015M sodium chloride, 0.0015M sodium citrate, and 50% formamide at about 42° C. The polynucleotide variants retain the capacity to encode a binding domain or fusion protein thereof having the functionality described herein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015M sodium chloride, 0.0015M sodium citrate at about 65-68° C. or 0.015M sodium chloride, 0.0015M sodium citrate, and 50% formamide at about 42° C. (see Sambrook et al., *Molecular Cloning: A Laboratory Manual,* 2nd Ed., Cold Spring Harbor Laboratory, Cold Spring Harbor, N.Y., 1989).

More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (Hy); bovine immune deficiency virus (BIV); and simian immunodeficiency virus (SIV).

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, preferred algorithms suitable for determining percent sequence identity and sequence similarity are the BLAST and BLAST 2.0 algorithms, which are described in Altschul et al. (1977) Nucleic Acids Res. 25:3389 and Altschul et al. (1990) J. Mol. Biol. 215:403, respectively.

"Treat" or "treatment" or "ameliorate" refers to medical management of a disease, disorder, or condition of a subject (e.g., a human or non-human mammal, such as a primate, horse, dog, mouse, or rat). In general, an appropriate dose or treatment regimen comprising a host cell expressing a fusion protein of this disclosure, and optionally an adjuvant or adjunctive therapy, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of a fusion protein or cell expressing a fusion protein of this disclosure (e.g., CD200R-CD28, SIRPα-CD28, CD200R-41BB, SIRPα-41BB, CD200R-CD28-41BB, SIRPα-CD28-4-1BB or other such fusion proteins), in the context of a disease or condition being treated, refers to that amount of fusion protein or number of cells sufficient to result in amelioration of one or more symptoms of the disease being treated in a statistically significant manner (e.g., reducing infection, reducing tumor size, inhibiting cancer growth or the like).

Immunomodulatory Fusion Proteins (IFPs)

In certain aspects, the present disclosure provides a fusion protein, comprising an extracellular component, a hydrophobic component, and an intracellular component. In some embodiments, the extracellular component includes a binding domain such as one that specifically binds to a target. In some embodiments, the binding domain is from a molecule that ordinarily, e.g., in its natural setting, is capable of delivering a negative or inhibitory signal when bound to its binding partner or ligand or receptor, such as an immunoinhibitory receptor or checkpoint molecule, or the target is an inhibitory receptor or ligand or checkpoint molecule or other inhibitory ligand. In some embodiments, the intracellular component includes a signaling domain, such as a costimulatory signaling domain or signaling region of a molecule generally capable of delivering a costimulatory or positive signal, e.g., to an immune cell. Thus, in some aspects, the fusion proteins are capable of delivering a positive or costimulatory signal in response to a binding event that in a natural setting would result in an inhibitory signal.

In some embodiments, the fusion protein is such that a particular distance is achieved. For example, in some embodiments, a fusion protein::target complex (such as one comprised of an extracellular portion of a complex formed between the fusion protein and the target by specific binding thereto) is of a particular length or spans a particular distance, such as a distance of up to a distance between membranes in an immunological synapse, or that spanned by the extracellular portion of a cognate complex between a TCR and WIC molecule, e.g., following specific recognition thereof by a TCR, or the distance spanned by the extracellular portion of a complex formed between the natural molecule and its natural binding partner. In some embodiments, the distance or length is sufficient to promote the colocalization of a fusion protein with antigen receptor or other signaling molecule when expressed in an immune cell, such as a T cell, or entry into an immunologic synapse.

By way of background, an immunological synapse is an interface between cells, which can form between a variety of cells, such as between immune cells (Rossy et al., *Frontiers in Immunol.* 3: 1-12, 2012; Hatherley et al., *Structure* 21:820, 2013). For example, in the case of a T cell contacting an antigen-presenting cell (APC), an immunological synapse can be formed by the binding of a TCR (found on the surface of a T cell) with an HLA-peptide (MHC-peptide for non-human) complex (found on the surface of, for example, APCs; HLA class I molecules can be found on the surface of all nucleated cells, while HLA class II can conditionally be expressed on all cell types but are regularly found on APCs). In addition, an immunological synapse may be organized into supramolecular activation clusters (SMACs), which can affect lymphocyte activation, direct antigen-HLA (or antigen-MHC) complex presentation to lymphocytes, and direct secretion of cytokines or lytic granules between cells. A SMAC can be comprised of three structures arranged in concentric circles: a central region (cSMAC) containing a high number of TCRs as well as co-stimulatory and inhibitory molecules, a peripheral region (pSMAC) where LFA-1 and talins are clustered, and a distal region (dSMAC) that is enriched for CD43 and CD45 molecules. In certain embodiments, an immunological synapse will span from about 10 nm to about 15 nm. For example, protein interactions found within the immunological synapse, such as the TCR::HLA-peptide interaction or a fusion protein-target interaction, generally span about 14 nm between membranes. In certain embodiments, the width of a SMAC in an immunological synapse does not exceed 15 nm.

In some embodiments, the extracellular span of a fusion protein::target complex is such that it can localize to a particular compartment of an immunological synapse. Some complexes thought to localize to various compartments of the immunological synapse are well-characterized with regard to the length of their extracellular span. For example, the MHC-TCR complex is thought to have an extracellular span of approximately 10-15 nm and more integrin-based complexes are thought to have extracellular spans on the order of approximately 40 nm (Alakoskela et al., *Biophys J* 100:2865, 2011). Additional exemplary complexes include the CD2-CD48 complex, which is thought to have an extracellular span of approximately 12.8 nm (Milstein et al., *J Blol Chem* 283:34414, 2008). Additionally, exemplary ligand-binding molecules thought to localize to the cSMAC include the TCR and MHC complexes, CD2, CD4, CD8, CD28, and ligands thereof (Dustin et al., *CSH Perspectives in Biology* 2:a002311, 2010); thus, it is contemplated that these molecules complexed with their natural ligands are of an appropriate size to localize to the cSMAC.

In some aspects, the length or distance or approximate length or distance of a particular construct or engineered extracellular portion thereof such as an extracellular portion of a fusion protein, or complex of any of the foregoing such as with a binding partner thereof, may be determined or modeled by known methods. In some exemplary models, a protein's tertiary structure, binding domains, and other characteristics may be approximated using an input amino acid or nucleic acid sequence. The tertiary structure of a protein may be used to approximate extracellular portion size, flexibility, and other characteristics useful for determining the approximate length of the extracellular portion of the protein or complex thereof. In general, methods for modeling or approximating the length of the extracellular portion of a protein are known. For example, molbiol-tools.ca and Swiss-Model contain multiple tools useful for predicting protein structure (see also Schwede, T., *Structure* 21:1531, 2013).

In certain embodiments, a fusion protein of this disclosure complexed, associated or interacting with a target is capable of residing within an immunological synapse. In some embodiments, the extracellular portion of a fusion protein::target complex spans an immunological synapse. In other embodiments, a fusion protein::target complex is localized in a supramolecular activation cluster (SMAC), such as a cSMAC. In further embodiments, the extracellular portion of a fusion protein::target complex spans an immunological synapse defined by the extracellular portion of a TCR::HLA-peptide interaction. In still further embodiments, the length of the extracellular portion of a fusion protein::target complex is about 12 nm to about 15 nm, or is about 14 nm.

The distance between the cell membranes of cells interacting in an immunological synapse may be measured by any method known in the art. For example, in particular embodiments, the distance may be measured by a subdiffraction-resolution method or electron microscopy (James and Vale, *Nature* 487:64-69, 2012).

In particular embodiments, a fusion protein as disclosed herein comprises an extracellular portion that extends less than 40 nm from the cell membrane. In some embodiments, a fusion protein as disclosed herein comprises an extracellular portion that extends less than 30 nm from the cell membrane. In some embodiments, a fusion protein as disclosed herein comprises an extracellular portion that extends less than 20 nm from the cell membrane. In some embodiments, a fusion protein as disclosed herein comprises an extracellular portion that extends less than 15 nm from the cell membrane.

In some embodiments, the provided fusion proteins provide the advantage of having an extracellular length or spatial distance as compared to the distance between cell membrane(s) that allows for entry into a synapse or co-localization with antigen receptor, or that mimic a distance or length present in the natural proteins. In some embodiments, where the extracellular portion of the fusion protein includes domain(s) from an additional molecule, which is from a different molecule from which a binding domain is obtained, the length of the extracellular component containing the binding domain is reduced, e.g., truncated, as compared to the extracellular region of the natural molecule, to provide for such similar length or distance. In some embodiments, a fusion protein as described herein comprises an extracellular component comprising an extracellular domain of a cell-surface receptor and a second domain (e.g., a linker or an extracellular domain of a second cell-surface receptor). In some such embodiments, to maintain an extracellular component capable of residing within an immunological synapse or spanning an immunological synapse when complexed with a target molecule, one or more domains of the extracellular component may be truncated.

In some diseases (e.g., cancer), the amplitude and quality of a T cell response resulting from antigen recognition by a T cell receptor (TCR) can be dysregulated (e.g., reduced) due to an imbalance between co-stimulatory and inhibitory signals, which can result in immune resistance. One advantage of certain fusion proteins of the instant disclosure is that a first signal can be converted into a qualitatively different second signal. For example, in some embodiments, the fusion proteins are such that a negative or inhibitory signal can effectively be converted into a positive or co-stimulatory signal to thereby relieve or minimize immune resistance associated with a disease, such as cancer. For example, upon binding to a target that, if bound by its natural binding partner, would result in inhibition or delivery of a negative signal, a fusion protein as provided herein, in some embodiments, is capable of instead delivering a positive, e.g., costimulatory signal, to a cell in which it is expressed, such as in a T cell. In certain embodiments, a fusion protein of this disclosure comprises an extracellular component associated with a negative signal and an intracellular component associated with a positive signal. An exemplary receptor found on the surface of T cells, cytotoxic T-lymphocyte-associated antigen 4 (CTLA4 or CD152), can receive an inhibitory signal when bound by one of its ligands, CD80 or CD86, found on APCs. CTLA4 regulates the amplitude of early stage T cell activation by counteracting the T cell co-stimulatory receptor CD28 (see Rudd et al., *Immunol. Rev.* 229:12, 2009). Another exemplary receptor found on the surface of T cells, programmed cell death protein 1 (PD-1 or CD279), can receive an inhibitory signal when bound by one of its ligands, PD-L1 (B7-H1, CD274) or PD-L2 (B7-DC, CD73), found on APCs. PD-1 limits the activity of T cells in peripheral tissues during inflammation and to minimize autoimmunity (see Keir et al., *Annu. Rev. Immunol.* 26:677, 2008). Representative fusion proteins of this disclosure comprising an extracellular component associated with a negative signal (e.g., CTLA4 or PD-1) and an intracellular component associated with a positive signal (e.g., CD28, CD137) include a CTLA4-CD28 fusion protein, a CTLA4-CD137 fusion protein, a CTLA4-CD28-CD137 fusion protein, a PD1-CD28 fusion protein, a PD1-CD137 fusion protein, or a PD1-CD28-CD137 fusion protein.

Fusion proteins of the instant disclosure may block or reduce the number of inhibitory signals received by an immune cell. For example, in some embodiments, a fusion protein as disclosed herein converts an inhibitory signal into a positive signal, thereby reducing the total number of inhibitory signals received by an immune cell or converting an ordinarily negative or inhibitory signal to a positive one. In other embodiments, a fusion protein as disclosed herein blocks the signaling of a wild-type receptor. For example, dominant negative fusion proteins are included within the scope of the disclosure. In some embodiments, a fusion protein as disclosed herein binds to a wild-type receptor and blocks signaling of the wild-type receptor by forming an oligomer with the wild-type receptor.

Yet another advantage of certain fusion proteins of the instant disclosure is that more than one such fusion protein may be expressed by a cell, providing multiple stimulatory signals. It has been observed that recombinant TCRs possessing multiple co-stimulatory domains may not produce adequate co-stimulatory signaling. Co-expressing multiple immunomodulatory fusion proteins, especially those capable of residing within an immunological synapse, may provide the co-stimulatory signaling necessary for T cells to avoid anergy and proliferate.

In some embodiments, a fusion protein of the instant disclosure operates in trans relative to a TCR or chimeric antigen receptor (CAR) or other antigen receptor. In some embodiments, a fusion protein as disclosed herein operates outside of the immunological synapse.

In yet another aspect, a fusion protein of the instant disclosure allows for enrichment of transduced T cells by restimulation with tumor cells expressing a ligand that binds to the fusion protein, without the need for sorting.

In one exemplary embodiment, a fusion protein comprising (a) an extracellular portion of a CD200R, (b) a transmembrane domain of a CD28, and (c) an intracellular signaling domain of a CD28 is provided. In some embodiments, the extracellular portion further comprises an extracellular portion of a CD28 extending from the CD28 transmembrane domain. In further embodiments, the extracellular portion of the CD200R comprises at least about 231 amino acids from the N-terminus of CD200R. In still further embodiments, the fusion protein further comprises an intracellular signaling domain of a CD137 (4-1BB).

In another exemplary embodiment, the present disclosure provides a fusion protein comprising (a) an extracellular portion of a SIRPα, (b) a transmembrane domain of a CD28, and (c) an intracellular signaling domain of a CD28. In some embodiments, the fusion protein further comprises an extracellular portion of a CD28 extending from the CD28 transmembrane domain. In further embodiments, the extracellular portion of the SIRPα comprises at least about 361 amino acids from the N-terminus of SIRPα. In still further embodiments, the fusion protein further comprises an intracellular signaling domain of a CD137 (4-1BB).

Component parts of the fusion proteins of the present disclosure are further described in detail herein.

Extracellular Component

As described herein, a fusion protein of the present disclosure generally comprises an extracellular component comprising a binding domain that specifically binds a target. Binding of a target by the fusion protein binding domain may (1) block the interaction of target with another molecule (e.g., block or interfere with a receptor-ligand interaction), (2) interfere, reduce or eliminate certain functions of the target (e.g., inhibitory signal transduction), (3) induce certain biological pathways not normally induced when the target is bound (e.g., converting an inhibitory or negative signal into a stimulatory or positive signal), such as in a cell in which the fusion protein is expressed, or any combination thereof. In some embodiments, the fusion proteins as described herein comprise an extracellular portion, wherein the extracellular portion comprises an extracellular portion of protein associated with a negative signal.

Exemplary binding domains of this disclosure may be ectodomains of cell-surface receptors, or binding portions thereof, ectodomains of cell-surface ligands, cytokines (e.g., IL35), chemokines, antibody-based binding domains, TCR-based binding domains, non-conventional binding domains, or any combination thereof. For example, binding domains comprising an ectodomain of CD200R, SIRPα, CD279 (PD-1), CD2, CD95 (Fas), CTLA4 (CD152), CD223 (LAG3), CD272 (BTLA), A2aR, KIR, TIM3, CD300, or LPA5 are within the scope of this disclosure. As used herein, an "ectodomain" from a cell-surface receptor or ligand includes a complete extracellular domain or a functional (binding) fragment thereof. In certain embodiments, an ectodomain comprises a mutated extracellular domain or a functional (binding) fragment thereof that has a higher avidity for target as compared to a wild-type or reference protein. In certain embodiments, an ectodomain comprises a variable-like domain or a CDR of a variable-like domain.

In some embodiments, a fusion protein contains an extracellular component comprising a CD200-binding domain, such as a CD200R ectodomain or CD200-binding portion thereof. By way of background, CD200R is a receptor that binds to CD200, a type-1 membrane protein of the immunoglobulin superfamily (Tonks et al., *Leukemia* 21:566-568, 2007). CD200 has been reported to be upregulated on various malignancies, including leukemias, multiple myeloma, and various solid tumors (e.g., melanoma, breast, and squamous cell carcinoma). In fact, high levels of CD200 expression have been linked with poor prognosis for acute myeloid leukemia (AML), and CD200R signaling has been shown to have an inhibitory effect on T cells (Coles et al., *Leukemia* 26: 2148-2151, 2012). In certain embodiments, a CD200R ectodomain includes a full length extracellular portion of a CD200R protein, a full length mature extracellular portion of a CD200R protein, a binding fragment of an extracellular portion of a CD200R protein, or a binding fragment of an extracellular portion of a CD200R protein along with a portion of the transmembrane domain of CD200R, or any combination thereof.

In further embodiments, a CD200R is encoded by a nucleic acid molecule as set forth in SEQ ID NO.:2. In certain other embodiments, a CD200R ectodomain comprises at least 200 amino acids from the N-terminus of CD200R. In some other embodiments, a CD200R is encoded by a nucleic acid molecule as set forth in SEQ ID NO.:11. In yet other embodiments, an extracellular portion of the CD200R comprises at least 180, 190, 200, 210, 220, 230, 231, 234, or 243 amino acids from the N-terminus of CD200R. For example, in certain embodiments, a CD200R is encoded by the nucleic acid molecule as set forth in SEQ ID NO.:8. In any of the aforementioned embodiments, a CD200R, a CD200R ectodomain, or any CD200R fragment thereof used in a fusion protein of this disclosure is a human CD200R. In further embodiments, there are provided CD200R ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:2.

In some embodiments, a CD200R comprises an amino acid sequence as set forth in SEQ ID NO.:25. In some embodiments, a CD200R comprises an amino acid sequence as set forth in SEQ ID NO.:34. In certain embodiments, a CD200R comprises an amino acid sequence as set forth in SEQ ID NO.:31. In any of the aforementioned embodiments, a CD200R, a CD200R ectodomain, or any CD200R fragment thereof used in a fusion protein of this disclosure is a human CD200R. In further embodiments, there are provided CD200R ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:25.

In some embodiments, a fusion protein contains an extracellular component comprising a CD47-binding domain such as a SIRPα ectodomain or binding portion thereof. By way of background, CD47 is a widely expressed transmembrane protein that plays a role in protecting cells from phagocytosis (Willingham et al., *PNAS* 109: 6662-6667, 2012). Binding of CD47 to SIRPα initiates SIRPα signaling, which inhibits phagocytosis by macrophages. Accordingly, downregulation of SIRPα will result in increased phagocytosis by macrophages. SIRPα is expressed on multiple human tumor types including AML, chronic myelogenous leukemia (CML), acute lymphoblastic leukemia (ALL), Non-Hodgkin lymphoma (NHL), multiple myeloma (MM), lung, bladder, and other solid tumors. In certain embodiments, a SIRPα ectodomain includes a full length extracellular portion of a SIRPα protein, a full length mature extracellular portion of a SIRPα protein, a binding fragment of an extracellular portion of a SIRPα protein, and a binding fragment of an extracellular portion of a SIRPα protein along with a portion of the transmembrane domain of SIRPα, or any combination thereof.

In further embodiments, a SIRPα ectodomain or binding portion thereof is encoded by a nucleic acid molecule as set forth in SEQ ID NO.:17. In certain embodiments, a SIRPα ectodomain comprises at least 300, 310, 320, 330, 340, 350, 360, 361, 370, 373, or more amino acids from the N-terminus of SIRPα. In some other embodiments, a SIRPα is encoded by a nucleic acid molecule as set forth in SEQ ID NO.:21. In any of the aforementioned embodiments, a SIRPα, a SIRPα ectodomain, or any SIRPα fragment thereof used in a fusion protein of this disclosure is a human SIRPα. In further embodiments, there are provided SIRPα ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:17.

In further embodiments, a SIRPα ectodomain comprises an amino acid sequence as set forth in SEQ ID NO.:40. In some embodiments, a SIRPα comprises an amino acid sequence as set forth in SEQ ID NO.:44. In any of the aforementioned embodiments, a SIRPα, a SIRPα ectodomain, or any SIRPα fragment thereof used in a fusion protein of this disclosure is a human SIRPα. In further embodiments, there are provided SIRPα ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:40.

In some embodiments, a fusion protein contains an extracellular component comprising a binding domain that binds to PD-L1, PD-L2, or both. In some embodiments, a fusion protein contains an extracellular component comprising a PD-1 ectodomain or ligand-binding portion thereof. In certain embodiments, a PD-1 ectodomain includes a full length extracellular portion of a PD-1 protein, a full length mature extracellular portion of a PD-1 protein, a binding fragment of an extracellular portion of a PD-1 protein, or a binding fragment of an extracellular portion of a PD-1 protein along with a portion of the transmembrane domain of PD-1, or any combination thereof. In certain embodiments, a PD-1 ectodomain comprises at least 80, 90, 100, 110, 120, 125, 130, 132, 135, 137, 140, 149, 150, 155, 158, 160, or 170 amino acids from the N-terminus of PD-1. For example, in certain embodiments, a PD-1 ectodomain is encoded by the nucleic acid molecule as set forth in SEQ ID NO.:91, 93, or 95. In further embodiments, a PD-1 ectodomain comprises at least from about 90 amino acids to at least about 130 amino acids from a PD-1 as set forth in SEQ ID NO.:60. In still further embodiments, a PD-1 ectodomain comprises 170 amino acids from the N-terminus of a PD-1 ectodomain, as set forth in SEQ ID NO.:90. In some embodiments, a PD-1 is encoded by a nucleic acid molecule as set forth in SEQ ID NO.:89. In any of the aforementioned embodiments, a PD-1, a PD-1 ectodomain, or any PD-1 fragment thereof used in a fusion protein of this disclosure is a human PD-1. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:60. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:90. In still further embodiments, there are provided PD-1 binding domains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:89.

In certain embodiments, a PD-1 ectodomain comprises the amino acid sequence as set forth in SEQ ID NO.:92, 94, or 96. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.: 92, 94, or 96. In any of the aforementioned embodiments, a PD-1, a PD-1 ectodomain, or any PD-1 fragment thereof used in a fusion protein of this disclosure is a human PD-1.

In some embodiments, a fusion protein contains an extracellular component comprising a CD2 ectodomain. In certain embodiments, a CD2 ectodomain is encoded by a nucleic acid molecule as set forth in SEQ ID NO.:61. In certain embodiments, a CD2 ectodomain includes a full length extracellular portion of a CD2 protein, a full length mature extracellular portion of a CD2 protein, a binding fragment of an extracellular portion of a CD2 protein, or a binding fragment of an extracellular portion of a CD2 protein along with a portion of the transmembrane domain of CD2, or any combination thereof. In any of the aforementioned embodiments, a CD2, a CD2 ectodomain, or any CD2 fragment thereof used in a fusion protein of this disclosure is a human CD2. In further embodiments, there are provided CD2 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_001767.3. In further embodiments, there are provided CD2 ectodomains s that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:61.

In some embodiments, a CD2 ectodomain comprises an amino acid sequence as set forth in SEQ ID NO.:62. In further embodiments, there are provided CD2 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:62. In any of the aforementioned embodiments, a CD2, a CD2 ectodomain, or any CD2 fragment thereof used in a fusion protein of this disclosure is a human CD2.

In some embodiments, a fusion protein contains an extracellular component comprising a binding domain that binds to FasL. In some embodiments, a fusion protein contains an extracellular component comprising a Fas (CD95) ectodomain. Fas is expressed on tumor-associated vasculature and prevents CD8 cell infiltration by inducing cell death. In certain embodiments, a Fas ectodomain includes a full length extracellular portion of a Fas protein, a full length mature extracellular portion of a Fas protein, a binding fragment of an extracellular portion of a Fas protein, and a binding fragment of an extracellular portion of a Fas protein along with a portion of the transmembrane domain of Fas, or any combination thereof. In some embodiments, a Fas ectodomain is encoded by a nucleic acid molecule as set forth in SEQ ID NO.:71. In yet other embodiments, a Fas ectodomain comprises at least 150, 160, 161, 166, 170, or 173 amino acids from the N-terminus of Fas. For example, in certain embodiments, a Fas is encoded by the nucleic acid molecule as set forth in SEQ ID NO.:73. In certain other embodiments, a Fas is encoded by the nucleic acid molecule as set forth in SEQ ID NO.:75. In any of the aforementioned embodiments, a Fas, a Fas ectodomain, or any Fas fragment thereof used in a fusion protein of this disclosure is a human Fas. In further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_000043.4. In still further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:71.

In some embodiments, a Fas ectodomain comprises an amino acid sequence as set forth in SEQ ID NO.:72. In certain embodiments, a Fas ectodomain comprises the amino acid sequence as set forth in SEQ ID NO.:74. In certain other embodiments, a Fas ectodomain comprises the amino acid sequence as set forth in SEQ ID NO.:76. In any of the aforementioned embodiments, a Fas, a Fas ectodomain, or any Fas fragment thereof used in a fusion protein of this disclosure is a human Fas. In further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:72.

In some embodiments, a fusion protein contains an extracellular component comprising a LAG3 (CD223) ectodomain. In certain embodiments, a LAG3 ectodomain includes a full length extracellular portion of a LAG3 protein, a full length mature extracellular portion of a LAG3 protein, a binding fragment of an extracellular portion of a LAG3 protein, and a binding fragment of an extracellular portion of a LAG3 protein along with a portion of the transmembrane domain of LAG3, or any combination thereof. For example, in some embodiments, a LAG3 ectodomain comprises about 420, 416, 415, 413, or 410 amino acids from the N terminus of LAG3. In any of the aforementioned embodiments, a LAG3, a LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_002286.5.

In further embodiments, a LAG3 is encoded by a nucleic acid molecule as set forth in SEQ ID NO.:153. In certain other embodiments, a LAG3 ectodomain comprises at least 430, 435, 438, 440, 445, or 450 amino acids from the N-terminus of LAG3. For example, in certain embodiments, a LAG3 is encoded by the nucleic acid molecule as set forth in SEQ ID NO.:161. In any of the aforementioned embodiments, a LAG3, LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:153.

In some embodiments, a LAG3 comprises an amino acid sequence as set forth in SEQ ID NO.:154. In some embodiments, a LAG3 comprises an amino acid sequence as set forth in SEQ ID NO.:162. In any of the aforementioned embodiments, a LAG3, a LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:154.

In some embodiments, a fusion protein contains an extracellular component comprising a TIM3 ectodomain. In certain embodiments, a TIM3 ectodomain includes a full length extracellular portion of a TIM3 protein, a full length mature extracellular portion of a TIM3 protein, a binding fragment of an extracellular portion of a TIM3 protein, and a binding fragment of an extracellular portion of a TIM3 protein along with a portion of the transmembrane domain of TIM3, or any combination thereof. In any of the aforementioned embodiments, a TIM3, a TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_032782.4.

In further embodiments, a TIM3 is encoded by a nucleic acid molecule as set forth in SEQ ID NO.:167. In certain other embodiments, a TIM3 ectodomain comprises at least 180, 185, 190, 195, or 200 amino acids from the N-terminus of TIM3. For example, in certain embodiments, a TIM3 is encoded by the nucleic acid molecule as set forth in SEQ ID NO.:177. In any of the aforementioned embodiments, a TIM3, TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:167.

In some embodiments, a TIM3 comprises an amino acid sequence as set forth in SEQ ID NO.:168. In some embodiments, a TIM3 comprises an amino acid sequence as set forth in SEQ ID NO.:178. In any of the aforementioned embodiments, a TIM3, a TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:168.

A binding domain may be any peptide that specifically binds a target of interest. Sources of binding domains include antibody variable regions from various species (which can be in the form of antibodies, sFvs, scFvs, Fabs, scFv-based grababody, or soluble VH domain or domain antibodies), including human, rodent, avian, or ovine. Additional sources of binding domains include variable regions of antibodies from other species, such as camelid (from camels, dromedaries, or llamas; Ghahroudi et al., *FEBS Lett.* 414:521, 1997; Vincke et al., *J. Biol. Chem.* 284:3273, 2009; Hamers-Casterman et al., *Nature* 363:446, 1993 and Nguyen et al., *J. Mol. Biol.* 275:413, 1998), nurse sharks (Roux et al., *Proc. Nat'l. Acad. Sci.* (*USA*) 95:11804, 1998), spotted ratfish (Nguyen et al., *Immunogen.* 54:39, 2002), or lamprey (Herrin et al., *Proc. Nat'l. Acad. Sci.* (*USA*) 105:2040, 2008 and Alder et al. *Nat. Immunol.* 9:319, 2008). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

An alternative source of non-conventional binding domains of this disclosure includes sequences that encode random peptide libraries or sequences that encode an engineered diversity of amino acids in loop regions of alternative non-antibody scaffolds, such as scTCR (see, e.g., Lake et al., *Int. Immunol.* 11:745, 1999; Maynard et al., *J. Immunol. Methods* 306:51, 2005; U.S. Pat. No. 8,361,794), fibrinogen domains (see, e.g., Weisel et al., *Science* 230:1388, 1985), Kunitz domains (see, e.g., U.S. Pat. No. 6,423,498), designed ankyrin repeat proteins (DARPins) (Binz et al., *J. Mol. Biol.* 332:489, 2003 and Binz et al., *Nat. Biotechnol.* 22:575, 2004), fibronectin binding domains (adnectins or monobodies) (Richards et al., *J. Mol. Biol.* 326:1475, 2003; Parker et al., *Protein Eng. Des. Selec.* 18:435, 2005 and Hackel et al. (2008) *J. Mol. Biol.* 381:1238-1252), cysteine-knot miniproteins (Vita et al. (1995) *Proc. Nat'l. Acad. Sci.* (*USA*) 92:6404-6408; Martin et al. (2002) *Nat. Biotechnol.* 21:71, 2002 and Huang et al. (2005) *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), lipocalin domains (see, e.g., WO 2006/095164, Beste et al., *Proc. Nat'l. Acad. Sci.* (*USA*) 96:1898, 1999 and Schönfeld et al., *Proc. Nat'l. Acad. Sci.* (*USA*) 106:8198, 2009), V-like domains (see, e.g., US Patent Application Publication No. 2007/0065431), C-type lectin domains (Zelensky and Gready, *FEBS J.* 272:6179, 2005; Beavil et al., *Proc. Nat'l. Acad. Sci.* (*USA*) 89:753, 1992 and Sato et al., *Proc. Nat'l. Acad. Sci.* (*USA*) 100:7779, 2003), $mAb^2$ or Fcab™ (see, e.g., PCT Patent Application Publication Nos. WO 2007/098934; WO 2006/072620), armadillo repeat proteins (see, e.g., Madhurantakam et al., *Protein Sci.* 21: 1015, 2012; PCT Patent Application Publication No. WO 2009/040338), affilin (Ebersbach et al., *J. Mol. Biol.* 372: 172, 2007), affibody, avimers, knottins, fynomers, atrimers, cytotoxic T-lymphocyte associated protein-4 (Weidle et al., *Cancer Gen. Proteo.* 10:155, 2013) or the like (Nord et al., *Protein Eng.* 8:601, 1995; Nord et al., *Nat. Biotechnol.* 15:772, 1997; Nord et al., *Euro. J. Biochem.* 268:4269, 2001; Binz et al., *Nat. Biotechnol.* 23:1257, 2005; Boersma and Pluckthun, *Curr. Opin. Biotechnol.* 22:849, 2011).

In some embodiments, a binding domain is a single chain T cell receptor (scTCR) comprising $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or comprising $V_\alpha$-$C_\alpha$, $V_\beta$-$C_\beta$, $V_\alpha$-$V_\beta$ pair specific for a target of interest (e.g., peptide-MHC complex or peptide-HLA complex).

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an ectodomain of a molecule having an amino acid sequence of a TCR $V_\alpha$, $V_\beta$, $C_\alpha$, or $C_\beta$, wherein each CDR comprises zero changes or at most one, two, or three changes, from a TCR or fragment or derivative thereof that specifically binds to a target of interest.

In certain embodiments, a binding domain $V_\alpha$, $V_\beta$, $C_\alpha$, or $C_\beta$ region of the present disclosure can be derived from or based on a $V_\alpha$, $V_\beta$, $C_\alpha$, or $C_\beta$ of a known TCR (e.g., a high-affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR comprises zero changes or at most one, two, or three changes and provided a binding domain containing a modified $V_\alpha$, $V_\beta$, $C_\alpha$, or $C_\beta$ region can still specifically bind its target with an affinity similar to wild type. In certain embodiments, a TCR has an affinity for a peptide-HLA complex ranging from about 10 μM to about 500 μM. In further embodiments, a TCR has a high affinity for a peptide-HLA complex ranging from about 10 nM to about 200 pM.

In certain aspects, a fusion protein according to the present disclosure has an extracellular component comprised of a binding domain that specifically binds a target (e.g., a ligand or receptor), wherein the extracellular component optionally includes one or more other functional subcomponents or domains, such as a multimerization domain, a linker, junction amino acids, or any combination thereof.

In certain embodiments, a fusion protein disclosed herein further comprises an additional extracellular region in addition to the binding domain or in addition to the portion derived from the molecule from which the binding domain is derived, such as a spacer or a multimerization domain. For example, in some aspects a multimerization domain is contained in or is a part of the extracellular component of the fusion protein. For example, a multimerization domain may be created by altering (e.g., mutating) the extracellular component, or a multimerization domain may be created by adding 1 to about 50 amino acid residues to the extracellular component. A multimerization domain may be located between the binding domain of the extracellular component and hydrophobic component of a fusion protein of this disclosure. In certain embodiments, a fusion protein expressed on a cell surface comprises a multimerization domain within the extracellular component and is proximal to the cell membrane, within one to 50 amino acids from the hydrophobic component. For example, a fusion protein multimerization domain may comprise one or more cysteine residues located within 30, 25, 20, 15, 14, 13, 12, 11, 10, 9 8, 7, 6, 5, 4, 3, 2, 1 or 0 amino acids from the fusion protein hydrophobic component, wherein such one or more cysteine residues from one fusion protein can form one or more disulfide bridges with one or more other fusion proteins. In some embodiments, the additional extracellular portion is derived from the same molecule from which a transmembrane or stimulatory region of the fusion protein is derived.

In further embodiments, interaction(s) between multimerization domains of two or more fusion proteins substantially contribute to or efficiently promote signal transduction (e.g., immune cell stimulation or activation) as compared to a fusion protein monomer. In certain embodiments, multimerization of fusion proteins promote signal transduction in a host cell in a statistically significant manner over fusion protein monomers. In further embodiments, multimerization of fusion proteins that promotes or enhances signal transduction in a host cell is via a disulfide bridge.

An exemplary multimer is a “dimer,” which refers to a biological entity containing two molecules, such as two fusion proteins, associated with each other. Such a dimer is considered a “homodimer” when the two associated fusion proteins have substantially similar or identical amino acid sequences. Similarly, multimerization of three substantially or fully identical fusion proteins is referred to as a “homotrimer.” In some embodiments, a multimerization domain comprises at least one cysteine residue, wherein a multimerization domain cysteine residue from a first fusion protein can form a disulfide bridge with a multimerization domain cysteine residue from a second fusion protein. In certain embodiments, a fusion protein dimer forms via a disulfide bridge. In other embodiments, a fusion protein trimer forms via two or more disulfide bridges. Alternatively, a dimer, homodimer, trimer or homotrimer may multimerize via a zinc finger motif or a leucine zipper motif. In still further embodiments, a fusion protein comprises a plurality of multimerization domains, which can be located extracellularly, intracellularly or both.

In some embodiments, a multimerization domain contained in the extracellular component of a fusion protein comprises an extracellular portion extending from the hydrophobic component. For example, in some embodiments, a multimerization domain contained in the extracellular component of a fusion protein comprises an extracellular portion of a CD28 extending from a CD28 transmembrane domain. In some embodiments, an extracellular portion of the CD28 comprises about 5, 6, 7, 8, 9, 10, 11, 12, 13, 14, 15, or up to about 25 amino acids adjacent to the transmembrane domain. In some embodiments, the extracellular portion of the CD28 comprises 9 amino acids or 12 amino acids adjacent to the transmembrane domain. In some embodiments, the extracellular portion of a CD28 comprises the amino acid sequence encoded by a nucleic acid molecule as set forth in SEQ ID NO.:9. In some embodiments, the extracellular portion of a CD28 comprises the amino acid sequence as set forth in SEQ ID NO.:32. In yet another exemplary embodiment, a multimerization domain contained in the extracellular component of a fusion protein comprises an extracellular portion of a CD137 (4-1BB) (e.g., ranging from one to about 50 amino acids) extending from a CD137 (4-1BB) transmembrane domain. In certain embodiments, the multimerization domain and the hydrophobic component are from different proteins. For example, a multimerization domain contained in the extracellular component of a fusion protein comprises an extracellular portion of a CD28 extending from a CD137 transmembrane domain, or comprises an extracellular portion of a CD137 extending from a CD28 transmembrane domain. In any of the aforementioned embodiments, a multimerization domain may further comprise a glycosylation site.

In some embodiments, a fusion protein may contain a linker or junction amino acids connecting, for example, an extracellular component with a multimerization domain or connecting an extracellular component with a hydrophobic component or connecting a hydrophobic component with an intracellular component. In some embodiments, the linker is a $Gly_xSer_y$, wherein x and y are independently an integer from 1 to 5.

A target molecule, which is specifically bound by a binding domain contained in a fusion protein of the present disclosure, may be found on or in association with a cell of interest (“target cell”). Exemplary target cells include an immune cell, a cancer cell, a cell associated with an autoimmune disease or disorder or with an inflammatory disease or disorder, and an infectious organism or cell (e.g., bacteria, virus, virus-infected cell), or any cell presenting antigen complexed with a MEW or human leukocyte antigen (HLA). A cell of an infectious organism, such as a mammalian parasite, is also contemplated as a target cell. In some embodiments, the target is an immunosuppressive ligand. In some embodiments, the target is selected from a CD47, CD58, CD80, CD86, CD95L (FasL), CD200, CD270 (HVEM), CD274 (PD-L1), or GALS.

Intracellular Component

An intracellular component contained in a fusion protein of the present disclosure will have an intracellular signaling domain, such as an activating domain or a co-stimulatory domain, capable of transmitting functional signals to a cell. In certain embodiments, an intracellular signaling domain will indirectly promote a cellular response by associating with one or more other proteins that directly promote a cellular response. An intracellular signaling domain may include one, two, three or more receptor signaling domains, costimulatory domains, or combinations thereof. Any intracellular component comprising an activating domain, co-stimulatory domain, or both from any of a variety of signaling molecules (e.g., signal transduction receptors) may be used in the fusion proteins of this disclosure.

As used herein, an "intracellular signaling domain" from a cell-surface receptor or ligand includes a complete intracellular domain, a portion comprising an intracellular signaling domain, or a functional (signaling) fragment thereof. In certain embodiments, an intracellular signaling domain comprises a mutated intracellular domain or a functional (signaling) fragment thereof that has increased signaling activity as compared to a wild-type or reference intracellular signaling domain.

A "co-stimulatory molecule" as used herein refers to a receptor or cell-surface molecule that can transduce signals into T cells to positively modulate T cell activation (Chen and Flies, *Nat. Rev. Immunol.* 13: 227-242, 2013). By way of background, T cell activation and proliferation requires two signals mediated through engagement of the T cell antigen-specific receptor (TCR) and a co-stimulatory signal, most typically binding of CD28 by CD80 and CD86 (Ledbetter et al., *Blood* 75:1531, 1990).

An intracellular signaling domain or functional fragment thereof useful in the fusion proteins of this disclosure may be from a CD3ε, CD3δ, CD3ζ, CD25, CD27, CD28, CD40, CD47, CD79A, CD79B, CD134 (OX40), CD137 (4-1BB), CD150 (SLAMF1), CD278 (ICOS), CD357 (GITR), CARD11, DAP10, DAP12, FcRα, FcRβ, FcRγ, Fyn, Lck, LAT, LRP, NKG2D, NOTCH1, NOTCH2, NOTCH3, NOTCH4, ROR2, Ryk, Slp76, pTα, TCRα, TCRβ, TRIM, Zap70, PTCH2, or any combination thereof. In some embodiments, an intracellular signaling domain or functional fragment thereof does not comprise a primary signal. In some embodiments, an intracellular signaling domain does not comprise a CD3.

In some embodiments, an intracellular signaling domain of a fusion protein of this disclosure comprises a CD28. CD28 signaling promotes proliferation of T cells stimulated via the TCR (Chen and Flies, *Nat. Rev. Immunol.* 13: 227-242, 2013). CD28 forms disulfide-linked homodimers, as a result of the cysteine residue proximal to the transmembrane domain (Lazar-Molnar et al., *Cell Immunol.* 244: 125-129, 2006). In certain embodiments, a CD28 signaling domain includes a full length intracellular portion of a CD28 protein, a full length mature intracellular portion of a CD28 protein, a signaling fragment of an intracellular portion of a CD28 protein, and a signaling fragment of an intracellular portion of a CD28 protein along with a transmembrane domain or fragment thereof of CD28, or any combination thereof.

In some embodiments, an intracellular signaling domain of a fusion protein contains an intracellular signaling domain of a CD137 (4-1BB). CD137 is a co-stimulatory molecule, wherein binding of CD137 to its ligand (4-1BBL or CD137L) is associated with T cell activation and proliferation (Cheuk et al., *Cancer Gene Therapy* 11: 215-226, 2004). In certain embodiments, a CD137 signaling domain includes a full length intracellular portion of a CD137 protein, a full length mature intracellular portion of a CD137 protein, a signaling fragment of an intracellular portion of a CD137 protein, and a signaling fragment of an intracellular portion of a CD137 protein along with a transmembrane domain or fragment thereof of CD137, or any combination thereof.

In certain embodiments, an intracellular signaling domain comprises a lymphocyte receptor signaling domain or comprises an amino acid sequences having one or a plurality of immunoreceptor tyrosine-based activation motifs (ITAMs). In still further embodiments, an intracellular signaling domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

In some exemplary embodiments, the present disclosure provides a fusion protein having an extracellular component comprising an extracellular portion of a CD200R that specifically binds CD200, an intracellular component comprising an intracellular portion of CD28, and a hydrophobic component connecting the extracellular and intracellular components, provided that a fusion protein::target complex spans a distance similar to a distance between membranes in an immunological synapse.

In particular embodiments, an intracellular component of a fusion protein of the instant disclosure comprises a CD28, a CD137 (4-1BB) or both. For example, in some embodiments, an intracellular component comprises the amino acid sequence encoded by a nucleic acid molecule as set forth in in SEQ ID NO.:5. In some other embodiments, an intracellular component comprises an amino acid sequence encoded by a nucleic acid molecule as set forth in SEQ ID NO.:13. In some embodiments, an intracellular component comprises two intracellular signaling domains, for example, a CD28 and a CD137 (4-1BB). In some embodiments, an intracellular component comprises an amino acid sequence encoded by a nucleic acid molecule as set forth in SEQ ID NO.:5 and the amino acid sequence encoded by the nucleotide sequence as set SEQ ID NO.:13.

Hydrophobic Component

A hydrophobic portion contained in a single chain fusion protein of the present disclosure will allow a fusion protein of this disclosure to associate with a cellular membrane such that a portion of the fusion protein will be located extracellularly and a portion will be located intracellularly (e.g., intracellular signaling domain). A hydrophobic component will generally be disposed within the cellular membrane phospholipid bilayer. In certain embodiments, one or more junction amino acids may be disposed between and connecting a hydrophobic portion with an intracellular signaling domain.

In certain embodiments, a hydrophobic domain is a transmembrane domain, such as one derived from an integral membrane protein (e.g., receptor, cluster of differentiation (CD) molecule, enzyme, transporter, cell adhesion molecule, or the like). In some embodiments, the hydrophobic domain comprises a transmembrane domain found in or derived from an integral membrane protein, wherein the transmembrane domain has been modified by the addition, removal, or replacement of one or more amino acids with at least one different amino acid, or any combination thereof, such as charged or hydrophilic residues that facilitate intermolecular interactions. Thus, the term "hydrophobic domain" includes transmembrane domains having, for example, modifications that may reduce hydrophobicity.

In some embodiments, the hydrophobic component comprises a transmembrane domain of a CD2, CD3ε, CD3δ, CD3ζ, CD25, CD27, CD28, CD40, CD47, CD79A, CD79B, CD80, CD86, CD95 (Fas), CD134 (OX40), CD137

(4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), TIM3, CD300, CD357 (GITR), A2aR, DAP10, FcRα, FcRβ, FcRγ, Fyn, GALS, KIR, Lck, LAT, LPA5, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, or Zap70. In particular embodiments, a hydrophobic portion is a transmembrane domain from CD28, CD4, CD8, CD27, or CD137 (4-1BB). In certain embodiments, a transmembrane domain is a CD28 transmembrane domain having an amino acid sequence encoded by a nucleic acid molecule as set forth in SEQ ID NO.:4. In certain other embodiments, a transmembrane domain is a CD200R transmembrane domain having an amino acid sequence encoded by a nucleic acid molecule as set forth in SEQ ID NO.:3. In still other embodiments, a transmembrane domain is a SIRPα transmembrane domain having an amino acid sequence encoded by a nucleic acid molecule as set forth in SEQ ID NO.:18. In further embodiments, a transmembrane domain is a CD2 transmembrane domain having an amino acid sequence encoded by a nucleic acid molecule as set forth in SEQ ID NO.:63. In still further embodiments, a transmembrane domain is a Fas transmembrane domain having an amino acid sequence encoded by a nucleic acid molecule as set forth in SEQ ID NO.:77. In still further embodiments, a transmembrane domain is a TIM3 transmembrane domain. In still further embodiments, a transmembrane domain is a TIM3 transmembrane domain having an amino acid sequence encoded by a nucleic acid molecule as set forth in SEQ ID NO.:169. In still further embodiments, a transmembrane domain is a LAG3 transmembrane domain. In some embodiments, a transmembrane domain is a LAG3 transmembrane domain having an amino acid sequence encoded by a nucleic acid molecule as set forth in SEQ ID NO.:155.

Nucleic Acids and Host Cells

In certain aspects, the present disclosure provides nucleic acid molecules that encode any one or more of the fusion proteins described herein, which may be immunomodulatory fusion proteins (IFPs). Such nucleic acid molecules can be inserted into an appropriate vector (e.g., viral vector or non-viral plasmid vector) for introduction in a host cell of interest (e.g., hematopoietic progenitor cell, T cell).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a gene or operon. In certain embodiments, a cell, such as a T cell, obtained from a subject may be converted into a non-natural or recombinant cell (e.g., a non-natural or recombinant T cell) by introducing a nucleic acid that encodes a fusion protein as described herein and whereby the cell expresses a fusion protein.

In certain embodiments, nucleic acid molecules encoding fusion proteins may be codon optimized to enhance or maximize expression in certain types of cells, such as T cells (Scholten et al., *Clin. Immunol.* 119: 135-145, 2006).

In one exemplary embodiment, the present disclosure provides a nucleic acid molecule that encodes a CD200R-CD28 construct (huCD200Rtm-CD28), wherein the extracellular component comprises a CD200R ectodomain, the hydrophobic component comprises the transmembrane domain of a CD200R, and the intracellular component comprises the intracellular signaling domain of a CD28. For example, in one embodiment, a nucleic acid molecule as set forth in SEQ ID NO.:1 is provided.

In another exemplary embodiment, the present disclosure provides a nucleic acid molecule that encodes a CD200R-CD28 construct (huCD200R-CD28tm), wherein the hydrophobic component comprises the transmembrane domain of a CD28. For example, in one embodiment, the disclosure provides a nucleic acid molecule as set forth in SEQ ID NO.:6.

In other exemplary embodiments, the present disclosure provides a nucleic acid molecule that encodes a CD200R-CD28 construct, wherein the extracellular comprises a truncated extracellular domain of CD200R and an extracellular portion of CD28. For example, the CD200R extracellular domain may be truncated by 9 amino acids (e.g., huCD200R-9aas-CD28Cys, SEQ ID NO.:7) or by 12 amino acids (e.g., huCD200R-12aas-CD28Cys, SEQ ID NO.:10).

In one exemplary embodiment, the present disclosure provides a nucleic acid molecule that encodes a CD200R-CD28-4-1BB construct (huCD200R-9aas-CD28Cystm-41BBic or huCD200R-12aas-CD28Cystm-41BBic), wherein the intracellular component comprises the intracellular signaling domain of CD137 (4-1BB). For example, in one embodiment, the nucleic acid molecule has the nucleotide sequence as set forth in SEQ ID NO.:12 or SEQ ID NO.:14.

In another exemplary embodiment, the present disclosure provides a nucleic acid molecule that encodes a CD200R-CD28-4-1BB construct (huCD200R-9aas-CD28Cys tm is 41BBic or huCD200R-12aas-CD28Cys tm ic-41BBic), wherein the intracellular component comprises the intracellular signaling domain of CD28 and of CD137 (4-1BB). In one embodiment, for example, the nucleic acid of the present disclosure has the nucleotide sequence as set forth in SEQ ID NO.:9 or SEQ ID NO.:15.

In other exemplary embodiments, the present disclosure provides a nucleic acid molecule that encodes a SIRPα-CD28 construct. For example, the present disclosure includes a nucleic acid molecule as set forth in SEQ ID NO.:16 (huSIRPαtm-CD28) or SEQ ID NO.:19 (huSIRPα-CD28tm).

In other exemplary embodiments, the present disclosure provides a nucleic acid molecule that encodes a SIRPα-CD28 construct, wherein the extracellular component comprises a truncated extracellular domain of SIRPα and an extracellular portion of CD28. For example, the SIRPα extracellular domain may be truncated by 12 amino acids (e.g., huSIRPα-12aas-CD28Cys, SEQ ID NO.:20).

In one exemplary embodiment, the present disclosure provides a nucleic acid molecule that encodes a SIRPα-CD28-4-1BB construct (huSIRPα-12aas-CD28Cystm-41BBic), wherein the intracellular component comprises the intracellular signaling domain of CD137 (4-1BB). For example, in one embodiment, the nucleic acid of the present disclosure has the nucleotide sequence as set forth in SEQ ID NO.:22.

In another exemplary embodiment, the present disclosure provides a nucleic acid molecule that encodes a SIRPα-CD28-4-1BB construct (huSIRPα-12aas-CD28Cys tm ic-41BBic), wherein the intracellular component comprises the intracellular signaling domain of CD28 and of CD137 (4-1BB). In one embodiment, for example, the nucleic acid of the present disclosure has the nucleotide sequence as set forth in SEQ ID NO.:23.

In other exemplary embodiments, the present disclosure provides a nucleic acid molecule that encodes a PD-1-CD28 construct. For example, the present disclosure includes a nucleic acid molecule as set forth in SEQ ID NO.:97 (huPD1-CD28Cys).

In other exemplary embodiments, the present disclosure provides a nucleic acid molecule that encodes a PD-1-CD28 construct, wherein the extracellular component comprises a truncated extracellular domain of PD-1 and an extracellular portion of CD28. For example, the PD-1 extracellular domain may be truncated by 12 amino acids (e.g., huPD1-12aas-CD28Cys, SEQ ID NO.:99), 15 amino acids (e.g., huPD1-15aas-CD28Cys, SEQ ID NO.:101), or 21 amino acids (e.g., huPD1-21aas-CD28Cys, SEQ ID NO.:103).

In other exemplary embodiments, the present disclosure provides a nucleic acid molecule that encodes a CD2-CD28 construct. For example, the present disclosure includes a nucleic acid molecule as set forth in SEQ ID NO.:69 (huCD2-CD28Cys).

In other exemplary embodiments, the present disclosure provides a nucleic acid molecule that encodes a Fas-CD28 construct. For example, the present disclosure includes a nucleic acid molecule as set forth in SEQ ID NO.:83 (huFas-CD28Cys).

In other exemplary embodiments, the present disclosure provides a nucleic acid molecule that encodes a Fas-CD28 construct, wherein the extracellular component comprises a truncated extracellular domain of Fas and an extracellular portion of CD28. For example, the Fas extracellular domain may be truncated by 7 amino acids (e.g., huFas-7aas-CD28Cys, SEQ ID NO.:85) or 12 amino acids (e.g., huFas-12aas-CD28Cys, SEQ ID NO.:87).

In other exemplary embodiments, the present disclosure provides a nucleic acid molecule that encodes a TIM3-CD28 construct. For example, the present disclosure includes a nucleic acid molecule as set forth in SEQ ID NO.:173 (huTIM3-CD28Cys). Also included within the scope of the disclosure is a TIM3-CD28 fusion protein, wherein the extracellular component comprises a truncated extracellular domain of TIM3 and an extracellular portion of CD28. For example, the TIM3 extracellular domain may be truncated by 12 amino acids (e.g., huTIM3-12aas-CD28Cys, SEQ ID NO.:175).

In other exemplary embodiments, the present disclosure provides a nucleic acid molecule that encodes a LAG3-CD28 construct. For example, the present disclosure includes a nucleic acid molecule as set forth in SEQ ID NO.:163 (huLAG3-CD28Cys). Also included within the scope of the disclosure is a LAG3-CD28 fusion protein, wherein the extracellular component comprises a truncated extracellular domain of LAG3 and an extracellular portion of CD28. For example, the LAG3 extracellular domain may be truncated by 12 amino acids (e.g., huLAG3-12aas-CD28Cys, SEQ ID NO.:159).

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous nucleic acid sequence encoding a fusion protein or a non-endogenous nucleic acid sequence encoding a fusion protein specific for a target. A viral vector may be a retroviral vector or a lentiviral vector. A viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising green fluorescent protein (GFP), an extracellular domain of human CD2, or a truncated human EGFR (huEGFRt; see Wang et al., *Blood* 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptide, or any combination thereof.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g., green fluorescent protein, huEGFRt).

In some embodiments, a vector encoding a fusion protein as disclosed herein may encode more than one fusion protein. For example, a vector may encode two different fusion proteins (e.g., a first fusion protein comprising a PD-1 ectodomain and a second fusion protein comprising a TIM3 ectodomain).

In some embodiments, a vector encoding a fusion protein as disclosed herein may further comprise an antigen-specific TCR. In some embodiments, the antigen-specific TCR is exogenous. In some embodiments, the antigen-specific TCR is specific to a HLA (MHC) class I restricted antigen. In some embodiments, the antigen is a cancer-specific antigen.

Embodiments wherein the cancer-specific antigen comprises WT-1, mesothelin, or cyclin-A1 are also within the scope of the disclosure. In still other embodiments, a vector that encodes a fusion protein as disclosed herein further encodes a ligand, which may be CD200, CD47, PD-L1, or CD58. In yet further embodiments, a vector that encodes a fusion protein as disclosed herein further encodes an siRNA for reducing the expression of an endogenous receptor. In some particular embodiments, the endogenous receptor is CD200R, SIRPα, CD279 (PD-1), CD95 (Fas) or CD2.

In some embodiments, host cells capable of expressing a fusion protein of this disclosure on the cell surface are immune cells. In some embodiments, host cells capable of expressing a fusion protein of this disclosure on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell may be enriched or purified. T cell lines are well known in the art, some of which are described in Sandberg et al., *Leukemia* 21:230, 2000. In certain embodiments, T cells that lack endogenous expression of TCRα and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In some embodiments, T cells may be engineered to express a TCR specific to a particular antigen.

In certain embodiments, a host cell transfected to express a fusion protein of this disclosure is a functional T cell, such as a virus-specific T cell, a tumor antigen specific cytotoxic T cell, a naïve T cell, a memory stem T cell, a central or effector memory T cell, γδ T cells, or a CD4+ CD25+ regulatory T cell. In further embodiments, a nucleic acid molecule encoding a fusion protein of this disclosure is introduced into bulk CD8+ T cells, naïve CD8+ T cells, CD8+ $T_{CM}$ cells, CD8+ $T_{EM}$ cells, or any combination thereof. In still further embodiments, a nucleic acid molecule encoding a fusion protein of this disclosure is introduced into bulk CD4+ T cells, naïve CD4+ T cells, CD4+ $T_{CM}$ cells, CD4+ $T_{EM}$ cells, or any combination thereof. In other embodiments, a nucleic acid molecule encoding a fusion protein of this disclosure is introduced into a population of T cells enriched for naïve CD8+ T cells and CD8+ $T_{CM}$ cells. In still other embodiments, a nucleic acid molecule encoding a fusion protein of this disclosure is introduced into a population of T cells enriched for naïve CD4+ T cells and CD4+ $T_{CM}$ cells. In any of the aforementioned embodiments, the T cells further contain a nucleic acid molecule encoding an engineered antigen-specific T cell receptor (TCR), an engineered antigen-specific high affinity TCR, an exogenous co-stimulatory molecule, a chimeric antigen receptor (CAR), or any combination thereof.

In certain embodiments, a host cell transfected to express a fusion protein of this disclosure is a functional natural killer cell.

One or more growth factor cytokines that promote proliferation of T cells expressing a fusion protein of this disclosure may be added to the culture used to expand T cells. The cytokines may be human or non-human. Exemplary growth factor cytokines that may be used promote T cell proliferation include IL2, IL15, or the like.

In certain embodiments, a host T cell transfected to express a fusion protein of this disclosure is a $CD4^+$ T cell that also expresses an antigen-specific high-affinity TCR specific to a HLA (MHC) class I restricted antigen (see Soto et al., *Cancer Immunol Immunother.* 62: 359-369, 2013).

In certain embodiments, a host T cell transfected to express a fusion protein of this disclosure also expresses a recombinant TCR specific to a cancer antigen. In some embodiments, the cancer antigen is a WT1. "WT1" refers to Wilm's tumor 1, a transcription factor that contains four zinc-finger motifs at the C-terminus and a proline/glutamine-rich DNA binding domain at the N-terminus. WT1 has an essential role in the normal development of the urogenital system and is mutated in a small subset of patients with Wilm's tumors. High expression of WT1 has been observed in various cancers, including, breast cancer, ovarian cancer, acute leukemias, vascular neoplasms, melanomas, colon cancer, lung cancer, thyroid cancer, bone and soft tissue sarcoma, and esophageal cancer. Alternative splicing has been noted for WT1.

In certain embodiments, a host T cell transfected to express a fusion protein of this disclosure also expresses a recombinant TCR specific to mesothelin. "Mesothelin" (MSLN) refers to a gene that encodes a precursor protein that is cleaved into two products, megakaryocyte potentiating factor and mesothelin. Megakaryocyte potentiation factor functions as a cytokine that can stimulate colony formation in bone marrow megakaryocytes. Mesothelin is a glycosylphosphatidylinositol-anchored cell-surface protein that may function as a cell adhesion protein. This protein is overexpressed in epithelial mesotheliomas, ovarian cancers and in specific squamous cell carcinomas. Alternative splicing results in multiple transcript variants.

In certain embodiments, a host T cell transfected to express a fusion protein of this disclosure also expresses a recombinant TCR specific to cyclin-A1.

In certain embodiments, a host T cell transfected to express a fusion protein of this disclosure also expresses a CAR.

In still other embodiments, a host cell that expresses a fusion protein as disclosed herein further comprises a ligand, which may be CD200, CD47, PD-L1, or CD58. In yet further embodiments, a host cell that expresses a fusion protein as disclosed herein further expresses an siRNA for reducing the expression of an endogenous receptor. In some particular embodiments, the endogenous receptor is CD200R, SIRPα, CD279 (PD-1), CD95 (Fas), or CD2.

In some embodiments, a host cell that expresses a fusion protein as disclosed herein may express more than one fusion protein. For example, the host cell may express two different fusion proteins (e.g., a first fusion protein comprising a PD-1 ectodomain and a second fusion protein comprising a TIM3 ectodomain).

Uses

Diseases that may be treated with cells expressing fusion proteins as described in the present disclosure include cancer, infectious diseases (viral, bacterial, protozoan infections), immune diseases (e.g., autoimmune), or aging-related diseases (e.g., senescence). Adoptive immune and gene therapy are promising treatments for various types of cancer (Morgan et al., *Science* 314:126, 2006; Schmitt et al., *Hum. Gene Ther.* 20:1240, 2009; June, *J. Clin. Invest.* 117:1466, 2007) and infectious disease (Kitchen et al., *PLoS One* 4:38208, 2009; Rossi et al., *Nat. Biotechnol.* 25:1444, 2007; Zhang et al., *PLoS Pathog.* 6:e1001018, 2010; Luo et al., *J. Mol. Med.* 89:903, 2011).

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to a fusion protein T cell therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-Barré Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In particular embodiments, a method of treating a subject with the fusion protein as disclosed herein include acute myelocytic leukemia, acute lymphocytic leukemia, and chronic myelocytic leukemia.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, infection with cytosolic pathogens whose antigens are processed and displayed with HLA (MHC) Class I molecules, are treated with fusion proteins of this disclosure.

A fusion protein of this disclosure may be administered to a subject in cell-bound form (e.g., gene therapy of target cell population (mature T cells (e.g., $CD8^+$ or $CD4^+$ T cells) or other cells of T cell lineage)). In a particular embodiment, cells of T cell lineage expressing fusion proteins administered to a subject are syngeneic, allogeneic, or autologous cells.

Pharmaceutical compositions including fusion proteins of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration. The present disclosure provides pharmaceutical compositions comprising cells expressing a fusion protein as disclosed herein and a pharmaceutically acceptable carrier, diluents, or excipient. Suitable excipients include water, saline, dextrose, glycerol, or the like and combinations thereof.

In some embodiments, the disclosure is directed to a method of increasing the activity of an immune cell, enhancing or prolonging an immune response, stimulating an antigen-specific T cell response, inhibiting an immunosuppressive signaling pathway, treating cancer or a tumor, inhibiting immune resistance of cancer cells, or treating an infection, comprising administering to a subject in need thereof an effective amount of a host cell expressing a fusion protein as described herein. In further embodiments, a host cell for use in any of the aforementioned methods further expresses an engineered antigen-specific TCR, an engineered antigen-specific high affinity TCR, a CAR, a co-stimulatory molecule, or any combination thereof. In particular embodiments, methods of treating leukemia are provided, comprising co-expressing a fusion protein as disclosed herein and a recombinant, antigen-specific TCR.

In some embodiments, there are provided methods of inducing or enhancing a Class I HLA response by a CD4+ T cell, comprising administering to a subject in need thereof an effective amount of a CD4+ T cell expressing a fusion protein as described herein. In further embodiments, a host cell for use in inducing or enhancing a Class I HLA response by a CD4+ T cell further expresses an engineered antigen-specific TCR, an engineered antigen-specific high affinity TCR, a CAR, a co-stimulatory molecule, or any combination thereof.

In any of the aforementioned embodiments, the methods are effective in the absence of administering exogenous IL-2.

In still other embodiments, a subject of any of the aforementioned methods is further treated with an adjunctive therapy, such as a chemotherapy. Exemplary chemotherapeutic agents include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSKTM; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL®, Bristol-Myers Squibb Oncology, Princeton, N.J.) and docetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above.

In some embodiments, the adjunctive therapy is a vaccine, an inhibitor of an immunosuppression signal, a B-Raf inhibitor, a MEK inhibitor, a tyrosine kinase inhibitor, a cytotoxic agent, a chemotherapeutic, or any combination thereof. In some embodiments, the inhibitor of an immunosuppression signal is an antibody or siRNA. In some embodiments, the antibody or siRNA is specific for PD-1, PD-L1, PD-L2, CTLA4, LAG3, KIR, CD244, B7-H3, B7-H4, BTLA, HVEM, GALS, TIM3, A2aR, or any combination thereof.

EXAMPLES

Example 1

CD200R-CD28 Fusion Protein Constructions

Figure 1A:
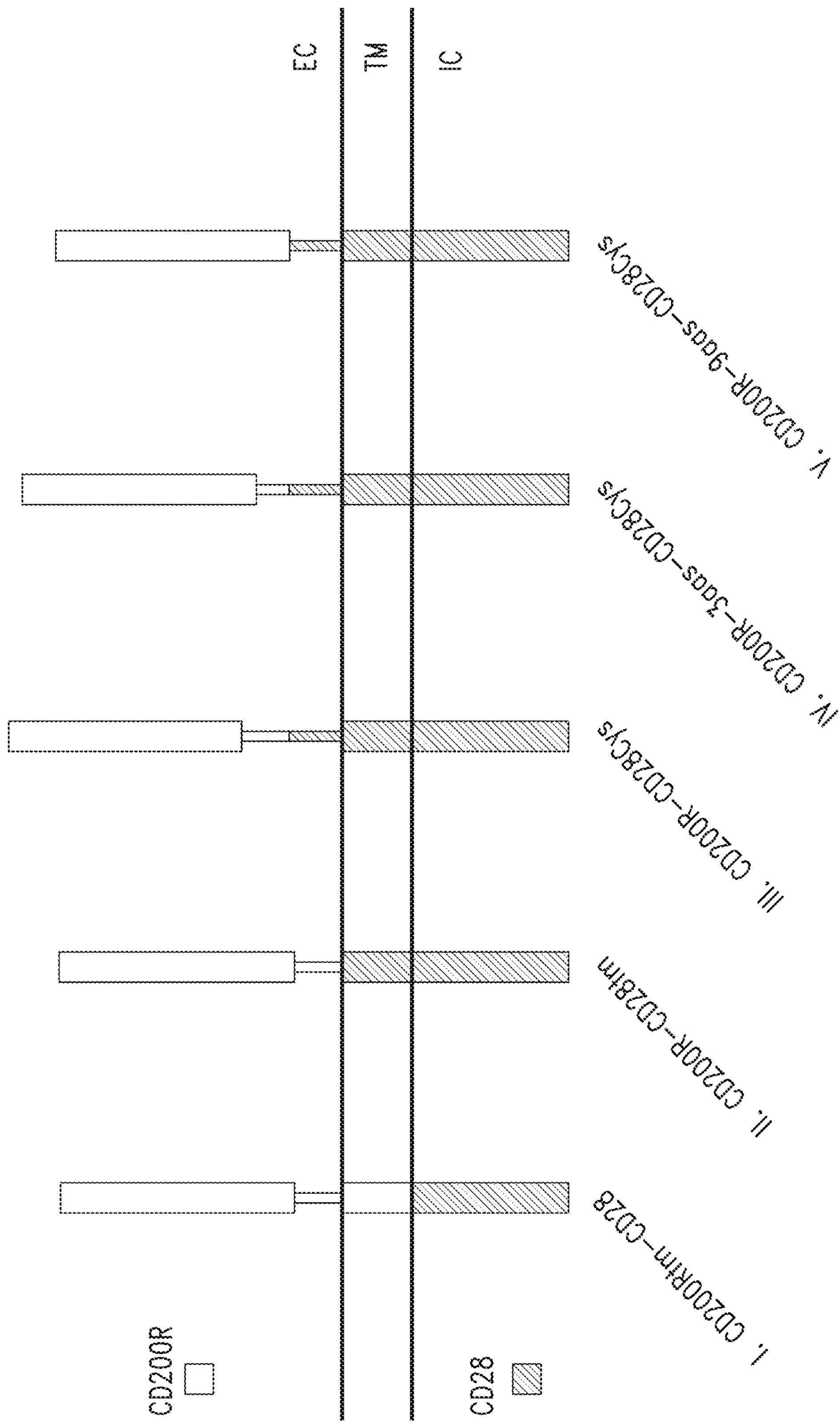
FIGS. 1A and 1B show CD200R-CD28 constructs expressed at high levels on primary murine $CD8^+$ T cells. (A) Schematic representation of exemplary CD200R-CD28 constructs. Construct “I” contains CD200R extracellular (“EC”) and transmembrane (“TM”) domains and a CD28 intracellular (“IC”) signaling domain (CD200Rtm-CD28). Construct “II” contains the extracellular domain of CD200R and the transmembrane and intracellular domains of CD28 (CD200R-CD28tm). Constructs “III-V” also incorporate a portion of the extracellular domain of CD28 to the transmembrane-proximal cysteine to promote multimerization and enhance CD28 signaling. To account for any extra extracellular amino acids (e.g., from one to about 50 amino acids; such as exemplary murine constructs disclosed here contain an extra nine (9) amino acids and exemplary human constructs disclosed here contain twelve (12) amino acids), some constructs have a truncated portion of an extracellular or intracellular domain (e.g., a CD200R that preserves an N linked glycosylation site). For example, construct IV has a truncated portion of CD200R that is truncated by 3 amino acids. Construct V has a truncated portion of CD200R that is truncated 9 amino acids. Constructs “I”, “II”, and “V” maintain the short spatial distance between the cells (e.g., between a T cell and an antigen presenting cell) and may co-localize with the TCR within the cSMAC and deliver a strong co-stimulatory signal. (B) Transgenic expression of murine CD200R-CD28 constructs on $TCR_{gag}$ T cells as detected by anti-CD200R antibody. The control vector contains green fluorescent protein (GFP).

Exemplary fusion proteins as described herein are illustrated using schematic representations in FIG. 1A. Exemplary fusion proteins include immunomodulatory fusion proteins (IFPs) comprised of the extracellular domain of CD200R or a portion thereof, and an intracellular signaling domain of CD28 or a portion thereof (FIG. 1A, constructs I-V). The hydrophobic component may be comprised of the transmembrane domain of either CD200R (FIG. 1A, construct I) or CD28 (FIG. 1A, constructs II-V), or portions thereof. In some exemplary CD200R-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., FIG. 1A construct III, CD200R-CD28Cys; construct IV, CD200R-3aas-CD28Cys; and construct V, CD200R-9aas-CD28Cys). The extracellular component may comprise all or a portion of the extracellular domain of CD200R. In some embodiments, the extracellular component comprises the entire extracellular domain of CD200R (FIG. 1A, constructs In other examples, the extracellular component comprises the first 235 amino acids (preserving an N-linked glycosylation site) (e.g., FIG. 1A, construct IV, CD200R-3aas-CD28Cys) or the first 229 amino acids (e.g., FIG. 1A, construct V, CD200R-9aas-CD28Cys) from the N-terminus of CD200R. The size of the extracellular component, which may be manipulated by adjusting the fusion protein construct, may affect the ability of the fusion protein to enter the immunological synapse and co-localize with the TCR within the cSMAC to deliver a strong co-stimulatory signal. Additionally, the CD200R-CD28 construct has the capacity to convert what would typically be an inhibitory signal from the binding of CD200R to its target into a positive signal generated by the CD28 intracellular signaling domain.

An exemplary nucleic acid molecule encoding a CD200R-CD28 fusion protein comprises the following elements (5' to 3'): Extracellular Component (CD200R)-Multimerization Domain (CD28 Cysteine)-Hydrophobic Component (CD28 transmembrane)-Intracellular Component (CD28 intracellular). In some embodiments, a nucleic acid molecule encoding a CD200R-CD28 fusion protein comprises a nucleic acid molecule as set forth in any one of SEQ ID NOS.:47-51 or 1, 6, 7, 10, 12, 14, or 15.

Nucleic acids encoding the constructs were ordered from Invitrogen or generated in-house by PCR then directionally TOPO-cloned into the pENTR™/D-TOPO® vector (Invitrogen), and transferred into the retroviral vector pMP71-attR using Gateway ° technology (Invitrogen). In certain embodiments, the nucleic acid molecules encoding IFPs of the instant disclosure were codon optimized before cloning into the pMP71-attR retroviral vector.

Example 2

Transgenic Expression of CD200R-CD28 Constructs

A preclinical mouse model for disseminated leukemia, based on the murine C57BL/6 Friend virus-induced erythroleukemia (FBL) and $TCR_{gag}$ transgenic mice, was used to determine if CD200R-CD28 chimeric receptors can improve T cell function.

TCR transgenic mice were generated to produce $CD8^+$ T cells specific for the gag epitope ($TCR_{gag}$). C57BL/6 (B6) mice were purchased from the Jackson Laboratory. $TCR_{gag}$ transgenic mice express a TCR transgene specific for the Friend virus gag epitope in $CD8^+$ T cell (Ohlen et al., *J. Immunol.* 166: 2863-2870, 2001). All animal studies performed were approved under the University of Washington Institutional Animal Care and Use Committee protocol (Protocol #2013-01). The murine B6 Friend virus induced erythroleukemia (FBL) expresses the F-MuLV encoded gag epitope (peptide CCLCLTVFL (SEQ ID NO.:179)).

CD200R-CD28 chimeric constructs based on murine genes were inserted into the pMP71 retroviral vector and used to transduce primary mouse splenocytes stimulated with anti-CD3 and anti-CD28 antibodies. Constructs were designed as described in Example 1, and ordered from Invitrogen or generated in-house by PCR. The constructs were then directionally TOPO-cloned into the pENTR™/D-TOPO® vector (Invitrogen), and transferred into the retroviral vector pMP71-attR using Gateway® technology (Invitrogen). The retroviral packaging cell line Plat-E (Morita et al., 2000, *Gene Therapy* 7:1063-1066, 2000; Cell Biolabs, Inc.) was transduced with the retroviral vector using Effectene® transduction reagent (Qiagen). Viral supernatant was collected on days 2 and 3 and then used to transduce $TCR_{gag}$ T cells.

One day prior to the transfection, $TCR_{gag}$ T cells were stimulated with anti-CD3/CD28 and 100 U/mL rhIL-2. Transduction of $TCR_{gag}$ T cells was performed in 12 well plates in the presence of IL-2 and polybrene by spinfection for 90 minutes at 1000 g. FBL cells were transduced with CD200 with polybrene spinfection, similar to T cell transduction, and subsequently sorted to generate a homogenous population.

Figure 1B:
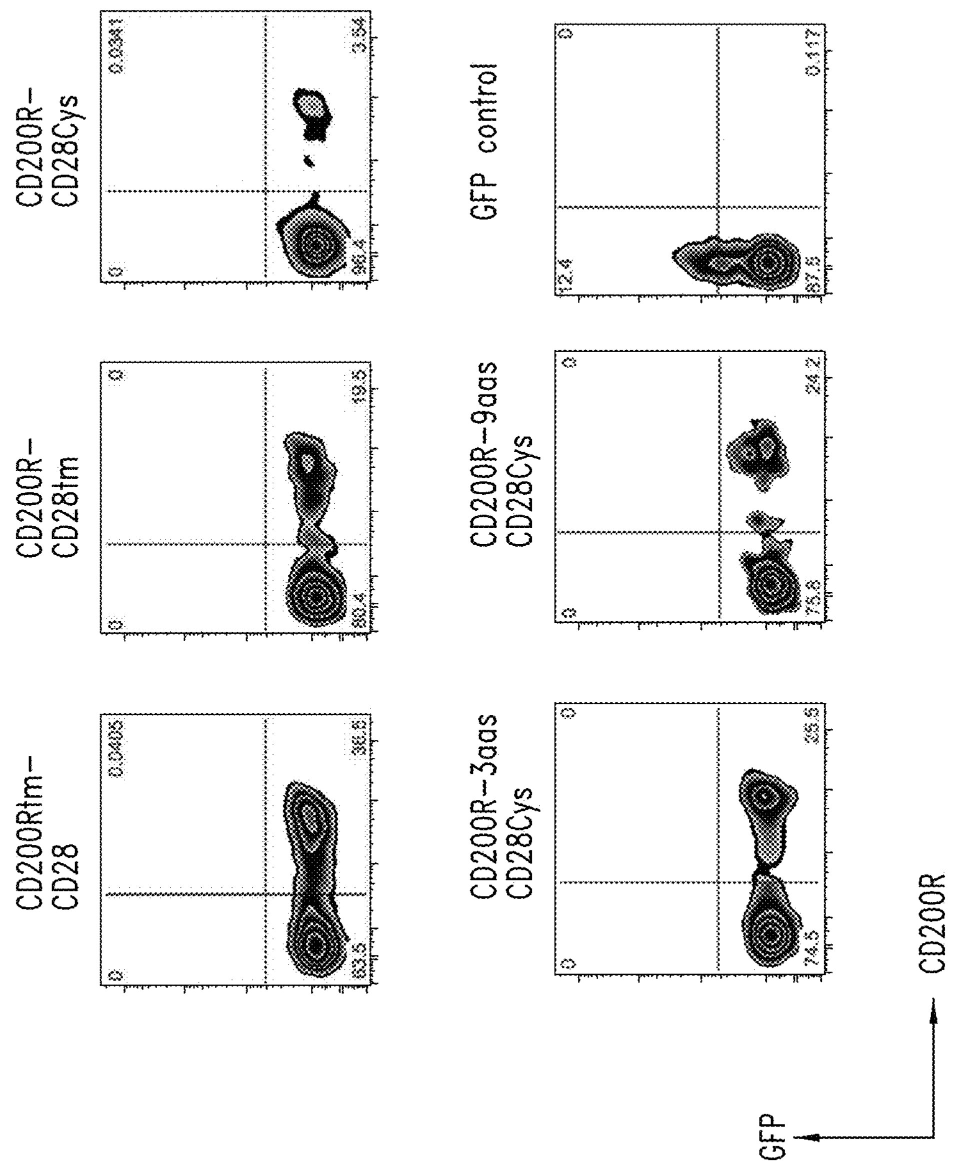

Five days after transduction, $CD8^+$ T cells were analyzed for construct expression by anti-CD200R antibody staining and flow cytometry (FIG. 1B). A vector encoding green fluorescent protein (GFP) was used as a control. Transduction efficiency ranged from 4-36% and the mean fluorescent intensity (MFI) of the transduced cells was similar between constructs.

Example 3

CD200R-CD28 Constructs Promote In Vitro Proliferation, Accumulation, and Effector Function of Transduced T Cells The CD200R-CD28 constructs described in Examples 1 and 2 were assessed for their abilities to promote proliferation, accumulation, and effector function of $TCR_{gag}$ T cells.

Expansion of Effector Cells In Vitro $TCR_{gag}$ effector cells were generated in vitro as previously described (Stromnes et al., *J. Clin. Invest.* 120: 3722-34, 2010). Irradiated antigen presenting splenocytes ($5\times10^6$), irradiated FBL ($3\times10^6$), and $TCR_{gag}$ tg cells ($10^6$) were cultured together with IL-2 (50 U/mL) in 10 mL of culture media (IMDM supplemented with non-essential amino acids, 2 glutamine, 100 U/mL penicillin/streptomycin, 10% FBS, and 50 μM 2-mercapatoethanol). T cells were restimulated weekly and assessed by flow cytometry 5-7 days after the last stimulation.

In Vitro T Cell Proliferation Assay $TCR_{gag}$ T cells were transduced as in Example 2. To assess T cell proliferation in vitro, $TCR_{gag}$ T cells were stained with CellTrace™ Violet (CTV, Life Technologies) according to the manufacturer's protocol. CTV-labeled Tg T cells ($10^5$) and GFP control T cells were stimulated with titrating numbers of CD200" FBL or $CD200^+$ FBL cells. After 3 days, CTV dilution of $TCR_{gag}$ T cells was assessed by flow cytometry.

Figure 2A:
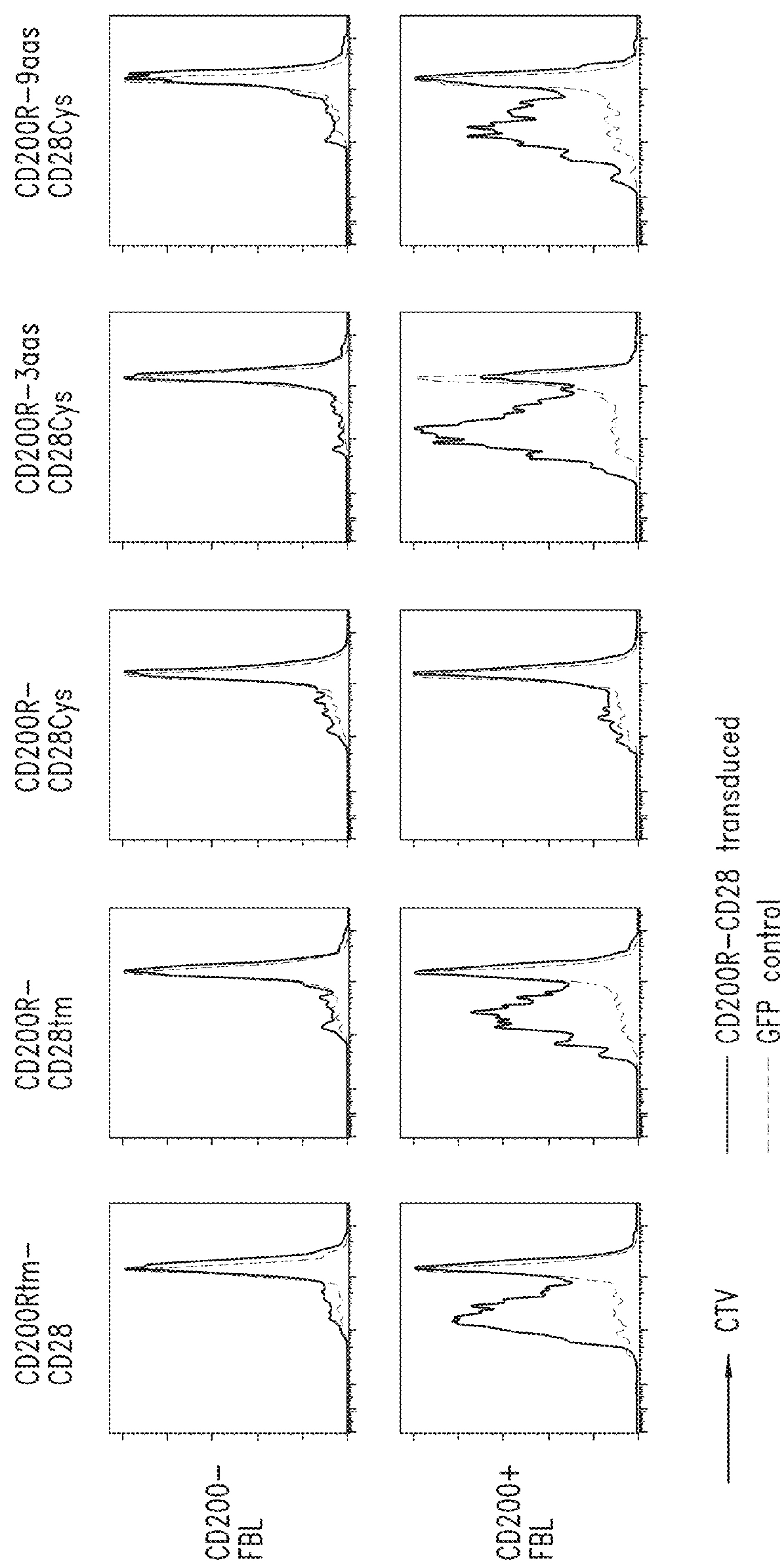
FIGS. 2A to 2G show that CD200R-CD28 constructs promote proliferation, accumulation, and effector function in response to $CD200^+$ tumor target cells in vitro, and accumulate in the immunological synapse. Splenocytes from naive $TCR_{gag}$ mice were stimulated in vitro with anti-CD3, anti-CD28, and recombinant human IL-2 (100 U/ml) and transduced with retroviral supernatant for 2 days. Cells were restimulated every 7 days with irradiated FBL and splenocytes and cultured with rhIL-2 (50 U/mL) for up to three stimulations. T cells were used for assays 5-7 days after the last stimulation. (A) Proliferation of CD200R-CD28 and GFP control $TCR_{gag}$ T cells as measured by CellTrace™ Violet dilution. T cells were stimulated with $CD200^-$ FBL (upper panels) or $CD200^+$ FBL (lower panels) for 3 days. (B) Preferential expansion/survival of transduced $TCR_{gag}$ T cells during co-culture with non-transduced $TCR_{gag}$ T cells during weekly cycles of stimulation with irradiated $CD200^+$ FBL and splenocytes. (C) Enrichment of transduced T cells. Repeated restimulation with irradiated $CD200^+$ tumor cells enriched the cells transduced with CD200R-9aas-CD28Cys compared to wild-type T cells transduced with an empty GFP control vector. (D) Increased CD200R and CD200 signal intensity at T cell:FBL synapse. Lipid rafts are increased at the immunological synapse (I). CD200R-9aas-CD28Cys fusion proteins co-localized with lipid rafts, indicating that the fusion proteins concentrate within the immunological synapse (III, IV). (E) $CD200R\text{-}CD28^+$ $CD8^+$ T cells display enhanced ability to lyse $CD200^+$ FBL cells in vitro. Target tumor cells were labeled with different dilutions of the fluorescent dye 5,6-carboxyfluorescein diacetate succinimidyl ester (CFSE), as indicated. Effector $TCR_{gag}$ T cells transduced with the indicated CD200R-CD28 fusion protein or an empty vector control were incubated at the indicated effector to target ratio with a 1:1 mix of $CD200^+$ FBL (CFSE") and non-specific EL4 ($CFSE^{lo}$) control targets for 5 hours. The percentage of FBL of the sum of FBL and control tumor cells was determined by flow cytometry. The percentage lysis was determined by dividing the percent of FBL incubated with T cells by the percent of FBL incubated without T cells. (F) Target tumor cells for CFSE assay in (G). Target tumor cells were labeled with different dilutions of the fluorescent dyes CellTrace™ Violet (CTV) or CFSE. A 1:1:1 mix of EL4 cells (CTV+), $CD200^+$ FBL (CFSE) and non-specific EL4 ($CFSE^{lo}$) control targets was generated. (G) CFSE cytotoxicity assay. $TCR_{gag}$ T cells were transduced with CD200R-CD28 receptor or GFP control vector. Effector $TCR_{gag}$ T cells were incubated at the indicated effector to target ratio with a 1:1 mix of $CD200^+$ FBL or $CD200^+$ FBL and non-specific EL4 control targets for 4 hours. The percentage of FBL of the sum of FBL and control tumor cells was determined by flow cytometry. The percentage lysis was determined by dividing the percent of FBL incubated with T cells by the percent of FBL incubated without T cells.

Flow cytometry results indicating the number of $TCR_{gag}$ T cells after stimulation with titrating numbers of CD200– FBL cells (upper) or $CD200^+$ FBL (lower) are shown in FIG. 2A. Four of the five CD200R-CD28 constructs tested dramatically improved proliferation of $TCR_{gag}$ T cells in response to $CD200^+$ FBL (blue lines) compared to GFP control-transduced T cells (red lines).

In Vitro T Cell Accumulation Assay

To determine if the enhanced proliferation also resulted in increased accumulation of transduced cells, the proportion of transduced cells in the total $TCR_{gag}$ population over multiple cycles of stimulation with irradiated $CD200^+$ FBL was measured.

Figure 2B:
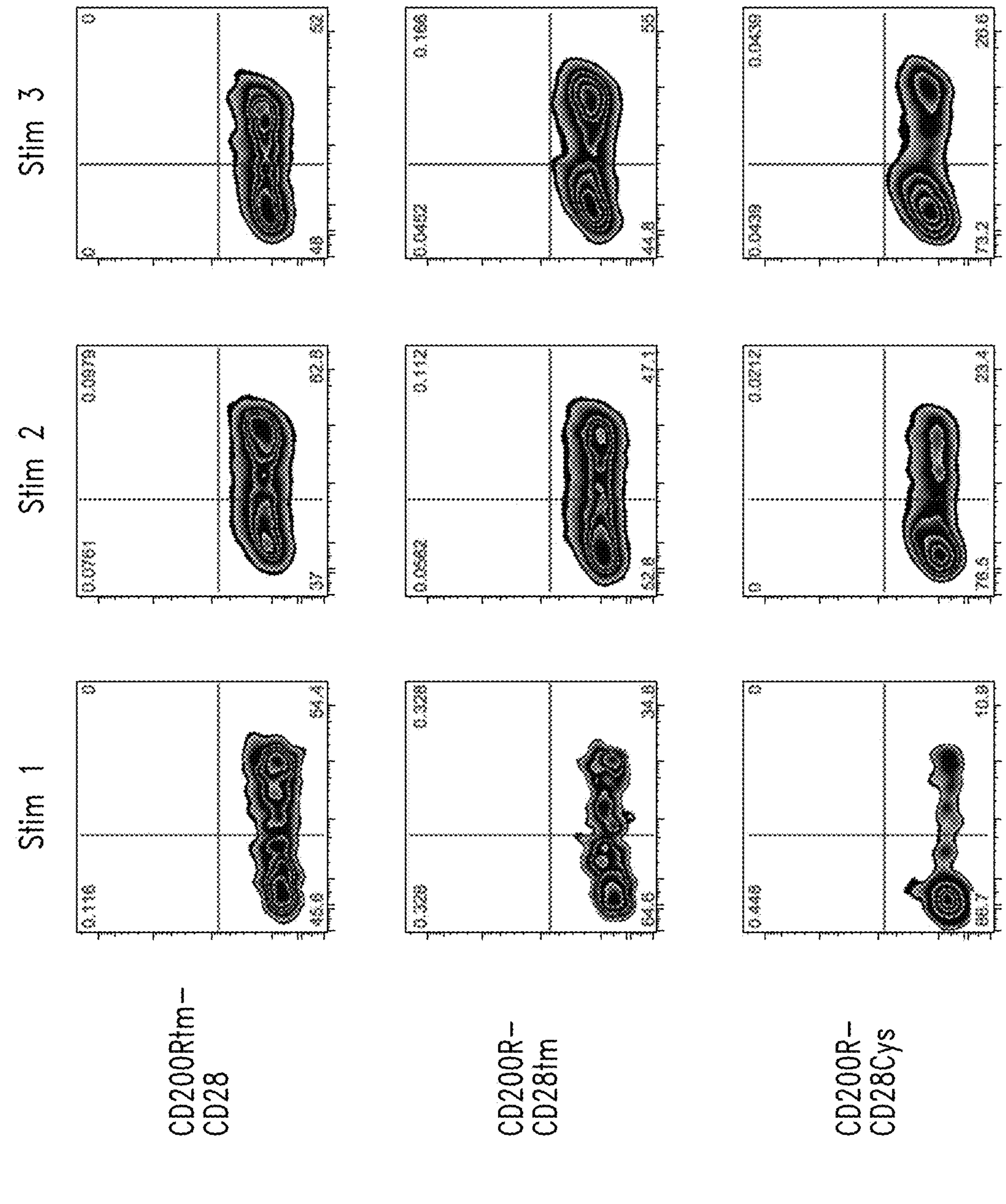
Figure 2B:
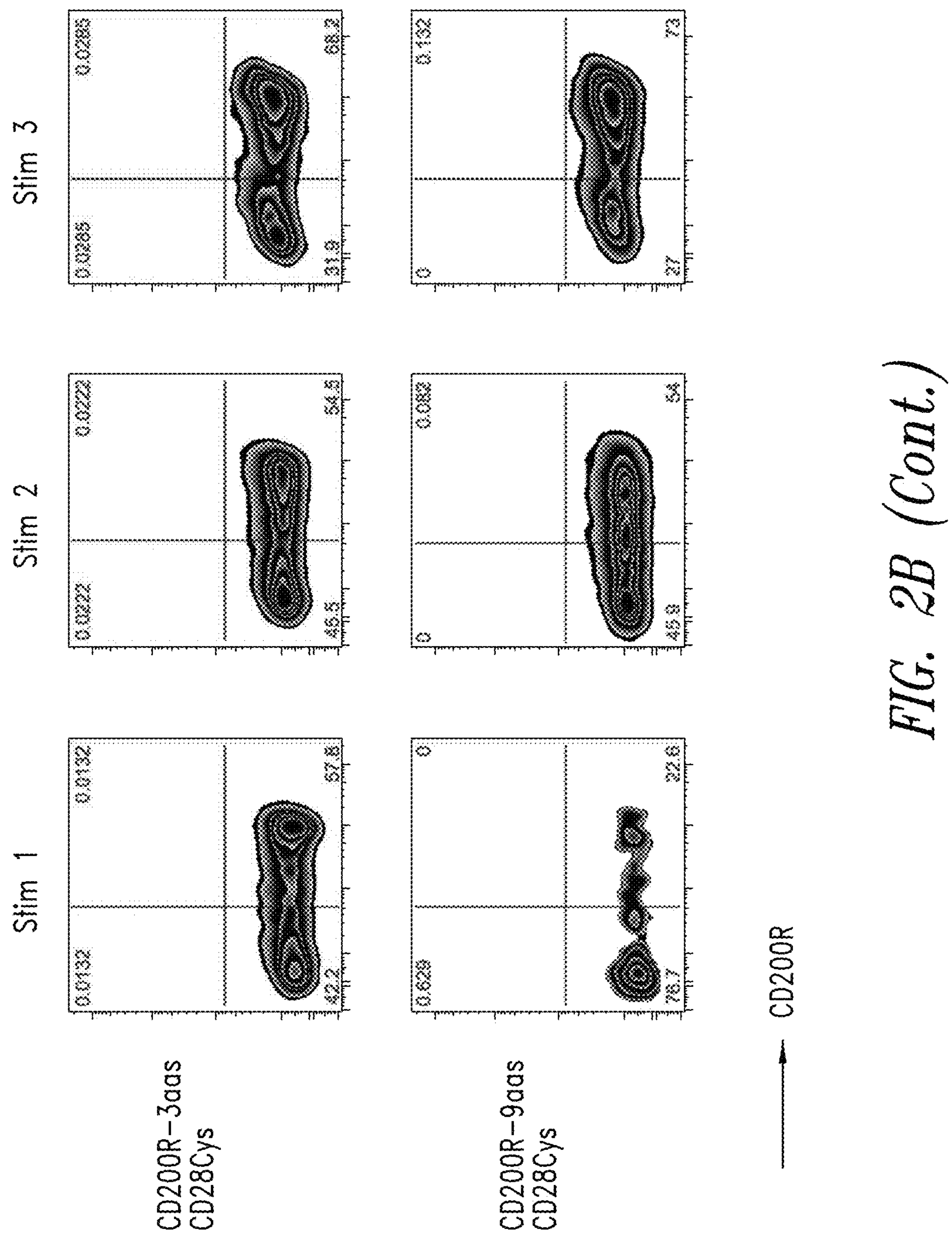

Several of the constructs promoted accumulation of transduced T cells, including CD200R-CD28tm, CD200R-CD28Cys, CD200R-3aas-CD28Cys, and CD200R-9aas-CD28Cys (FIG. 2B). Of these constructs, CD200R-9aas-CD28Cys exhibited the greatest increase in transduced T cells over multiple stimulations, resulting in more than a 3-fold expansion over 3 stimulations.

In Vitro T Cell Enrichment Assay

Figure 2C:
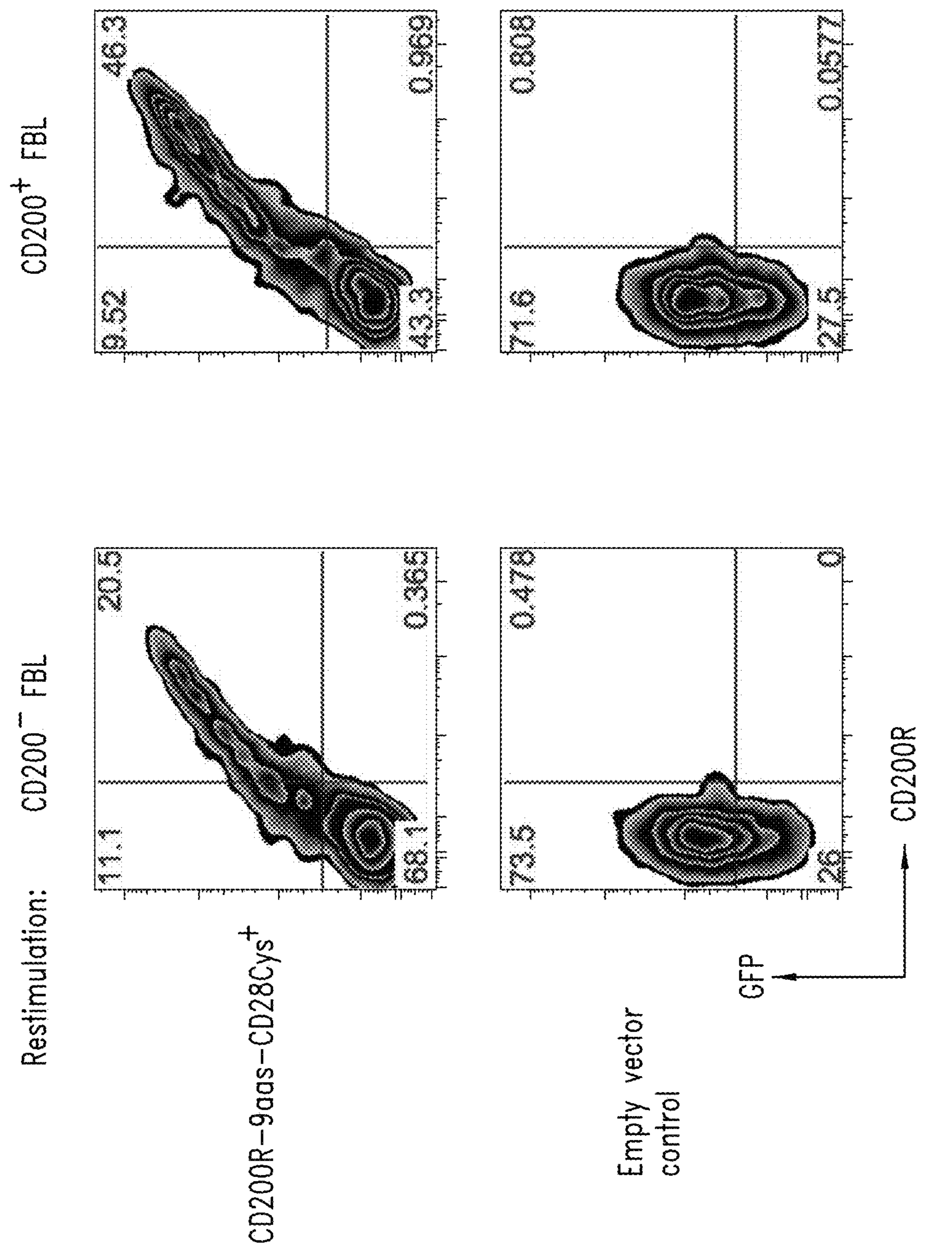

A mixed population of transduced and nontransduced $CD8^+$ T cells were restimulated with $CD200^+$ or $CD200^-$ irradiated FBL cells to determine if restimulation would enrich the population for the transduced CD200R-9aas-CD28Cys $IFP^+$ T cells. Repeated restimulation with irradiated $CD200^+$ tumor cells enriched the cells transduced with the IFP compared to wild type T cells, demonstrating that recognition of a target expressing the ligand for the CD200R-9aas-CD28Cys IRP enhances the response (FIG. 2C).

In Vitro Colocalization Assay

Figure 2D:
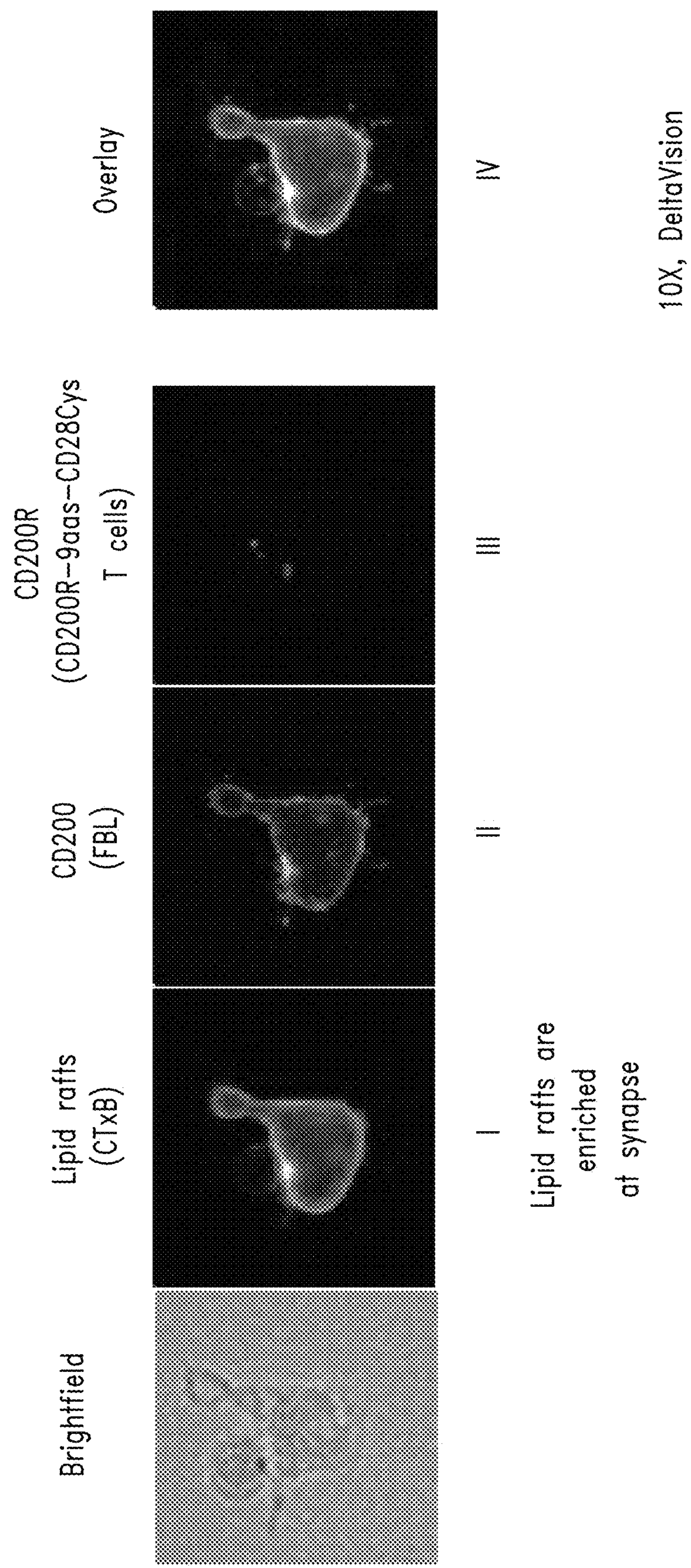

Transduced T cells were imaged by microscopy to determine if the CD200R-9aas-CD28Cys IFP colocalized with the cognate ligand in the immunological synapse (IS) during T cell activation. CTxB was used to stain lipids within the cell membrane, which are enriched at the synapse (FIG. 2D, panel I). Labeled antibodies that target CD200 expressed by the FBL cell (FIG. 2D, panel II) or CD200R expressed by the T cell (FIG. 2D, panel III) were used to visualize the location of the molecules in relation to the IS. CD200 ligand and CD200R colocalized within the IS (FIG. 2D, panel IV), demonstrating that the construct is sized appropriately to be accommodated by the immunologic synapse.

CFSE-Based Cytotoxicity Assay

Increased CD28 signaling also promotes effector function (Chen and Flies, *Nat. Rev. Immunol.* 13: 227-242, 2013). CD200R-CD28 fusion protein-transduced T cells were tested for increased killing of target tumor cells. FBL and control EL4 tumors were incubated for 10 minutes at room temperature with 2.5 μM ($CFSE_{hi}$) or 0.25 μM ($CFSE^{lo}$) CFSE in PBS, respectively. Excess dye was removed by washing tumor cells in serum-containing media. A 1:1 mixture of EL4 and FBL tumor cells was incubated with titrated numbers of CD200R-CD28 or GFP vector transduced $TCR_{gag}$ in vitro expanded effector T cells for 4 hours in 96-well, round-bottom plates at 37° C. and 5% $CO_2$. Specific FBL lysis was determined by flow cytometric analyses of the % $CFSE_{hi}$ (FBL) of total CFSE positive cells (FBL+EL4) remaining in the well.

Figure 2E:
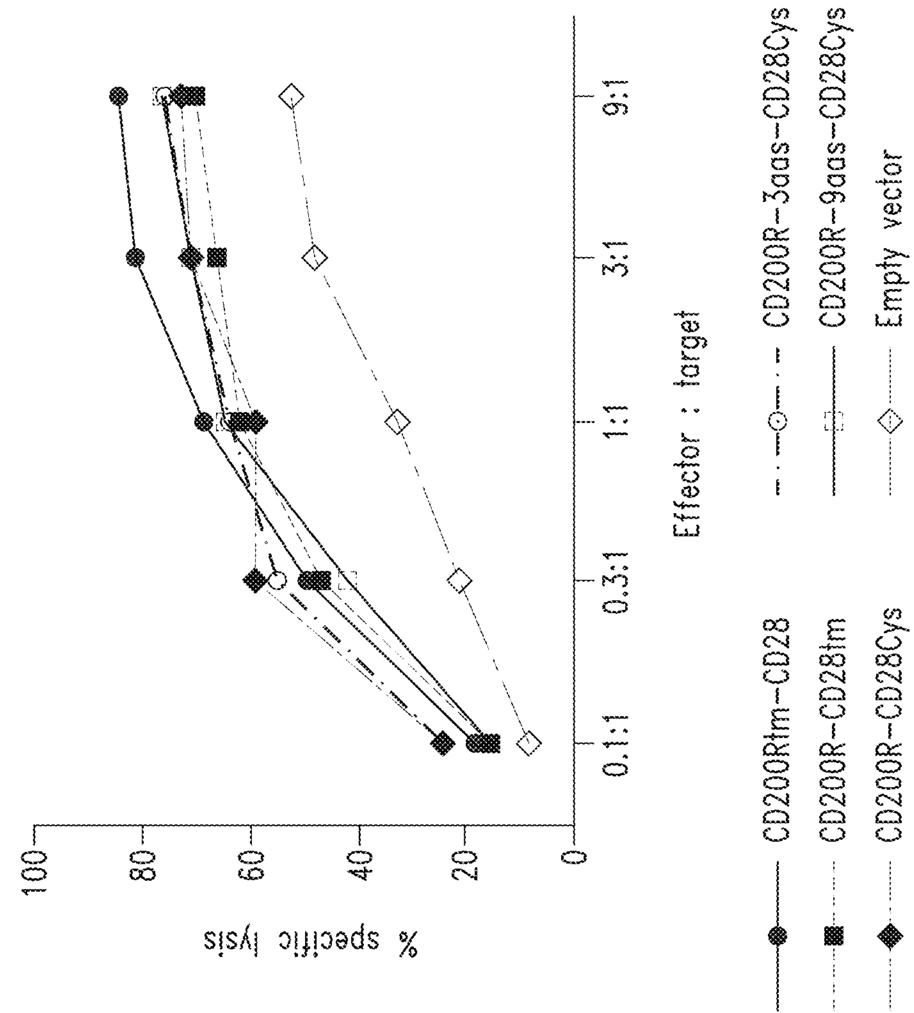
Figure 2E:
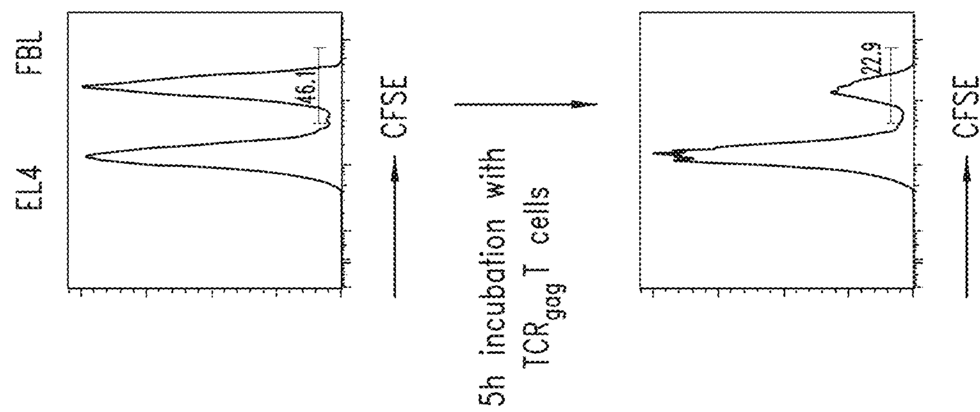
Figure 2F:
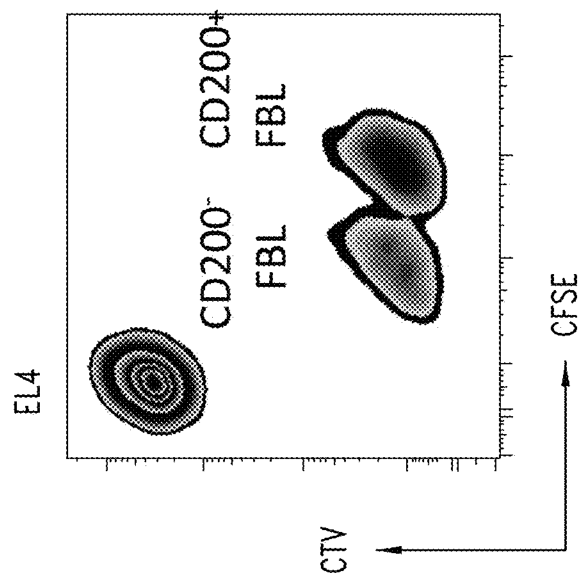
Figure 2G:
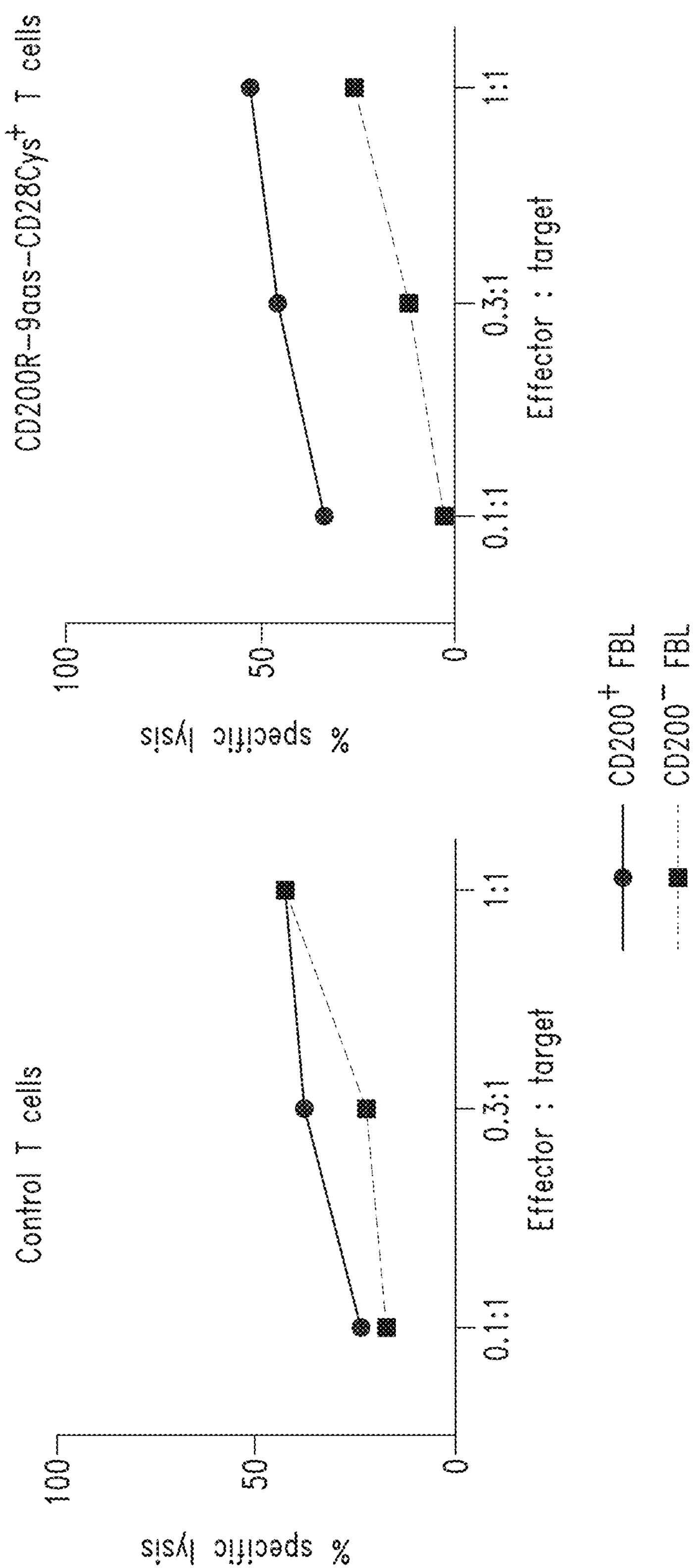

$TCR_{gag}$ T cells transduced with CD200R-CD28 constructs displayed an enhanced ability to lyse FBL tumor in vitro compared to $TCR_{gag}$ T cells transduced with an empty vector (FIGS. 2E, 2G). Target tumor cells were labeled with different dilutions of the fluorescent dyes CellTrace™ Violet (CTV) or CFSE to generate a 1:1:1 mix of EL4 cells (CTV+), $CD200^+$ FBL (CFSE) and non-specific EL4 ($CFSE^{lo}$) control targets (FIG. 2F). Additionally, control GFP-transduced $TCR_{gag}$ T cells lysed $CD200^-$ FBL and $CD200^+$ FBL at equal efficiencies (FIG. 2G). By contrast, $TCR_{gag}$ T cells transduced with CD200R-9aas-CD28Cys exhibited increased killing of $CD200^+$ FBL cells compared to control T cells, lysing over 40% of $CD200^+$ FBL at the lowest E:T ratio tested (FIG. 2G).

Taken together, these data show that CD200R-CD28 constructs function to increase accumulation and the lytic activity of transduced T cells in response to tumor cell stimulation.

Example 4

T Cells Transduced with CD200R-9Aas-CD28Cys Exhibit Enhanced Accumulation In Vivo in Response to Recognition of FBL B6 mice were injected with $4\times10^6$ live FBL leukemia intraperitoneal (i.p.) as previously described (Stromnes et al., *J. Clin. Invest.* 120: 3722-34, 2010). After allowing 5 days for the FBL to disseminate, mice received 180 mg/kg cyclophosphamide (Cy, "Cytoxan®") i.p. at least 6 hours before transfer of the effector T cells. For survival studies, $10^5$ $TCR_{gag}$ T cells which previously underwent 1-3 stimulations in vitro were transferred into tumor-bearing mice. To assess short-term proliferation and accumulation, $2\times10^6$ of each of fusion protein-transduced and a GFP-control-transduced T cells were co-injected into tumor-bearing mice and the mice euthanized for analysis 8 days later. Mice were regularly monitored for tumor burden and euthanized if evidence of tumor progression predicted mortality would occur within 24-48 hours.

Figure 3A:
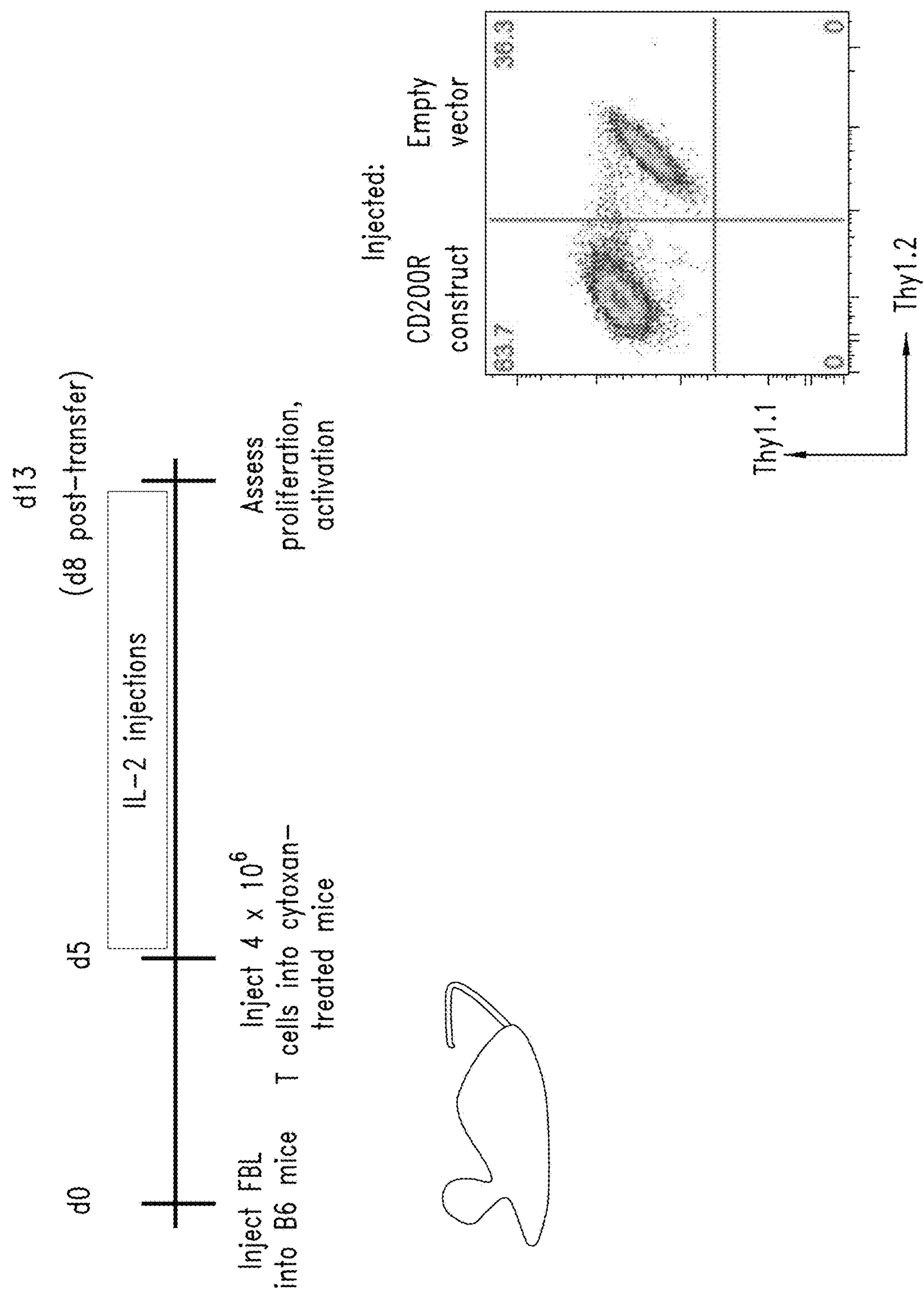
FIGS. 3A to 3D show that T cells transduced with CD200R-9aas-CD28Cys preferentially accumulate in response to tumor challenge in vivo and express surface proteins consistent with an effector phenotype after injection into Cytoxan®-treated, FBL-bearing mice. Transduced $TCR_{gag}$ T cells were generated as described in Example 2. (A) Experimental schematic. C57BL/6 mice were injected with $4\times10^6$ $CD200^+$ FBL cells. Five days later, CD200R-
Figure 3B:
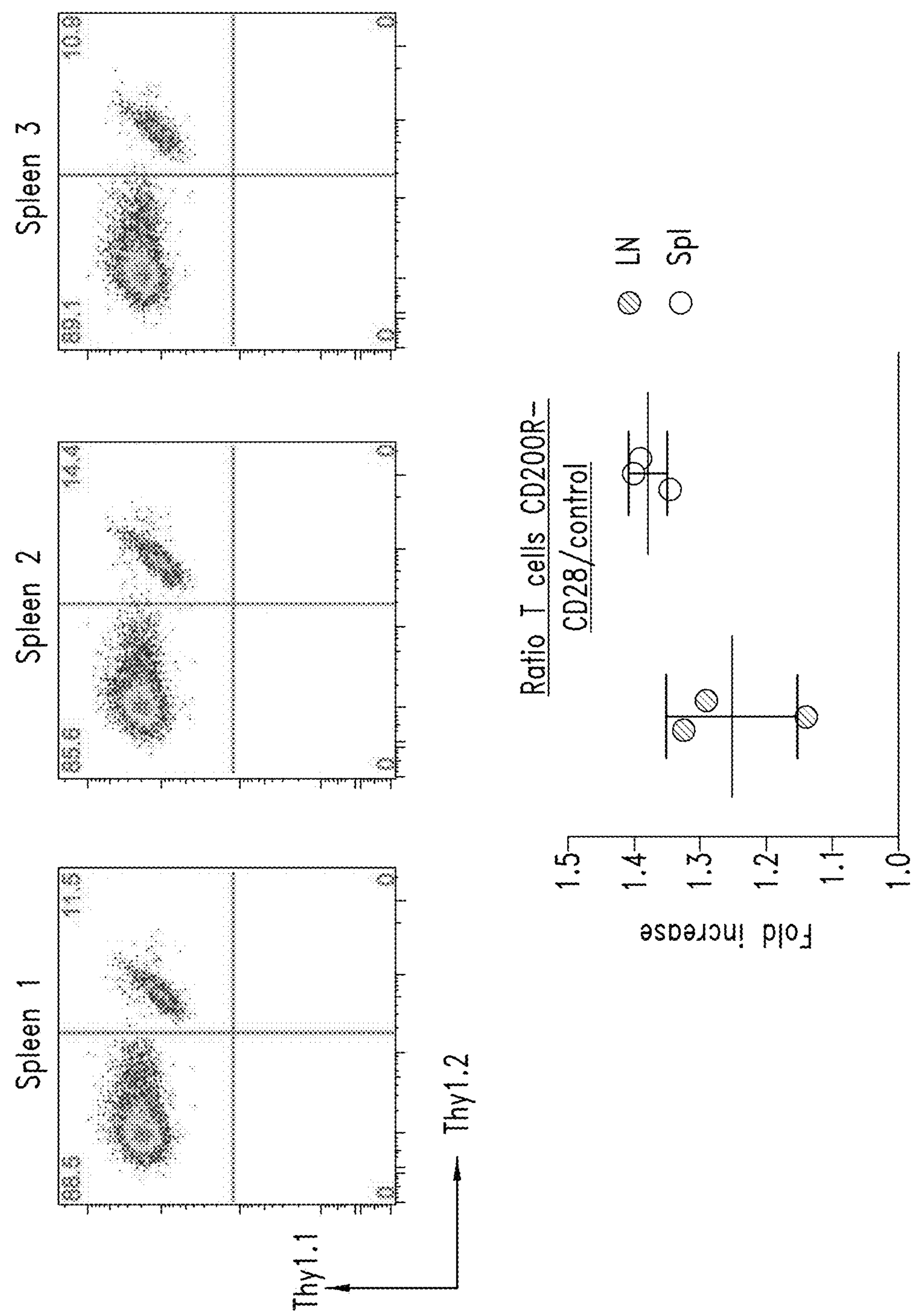
Figure 3C:
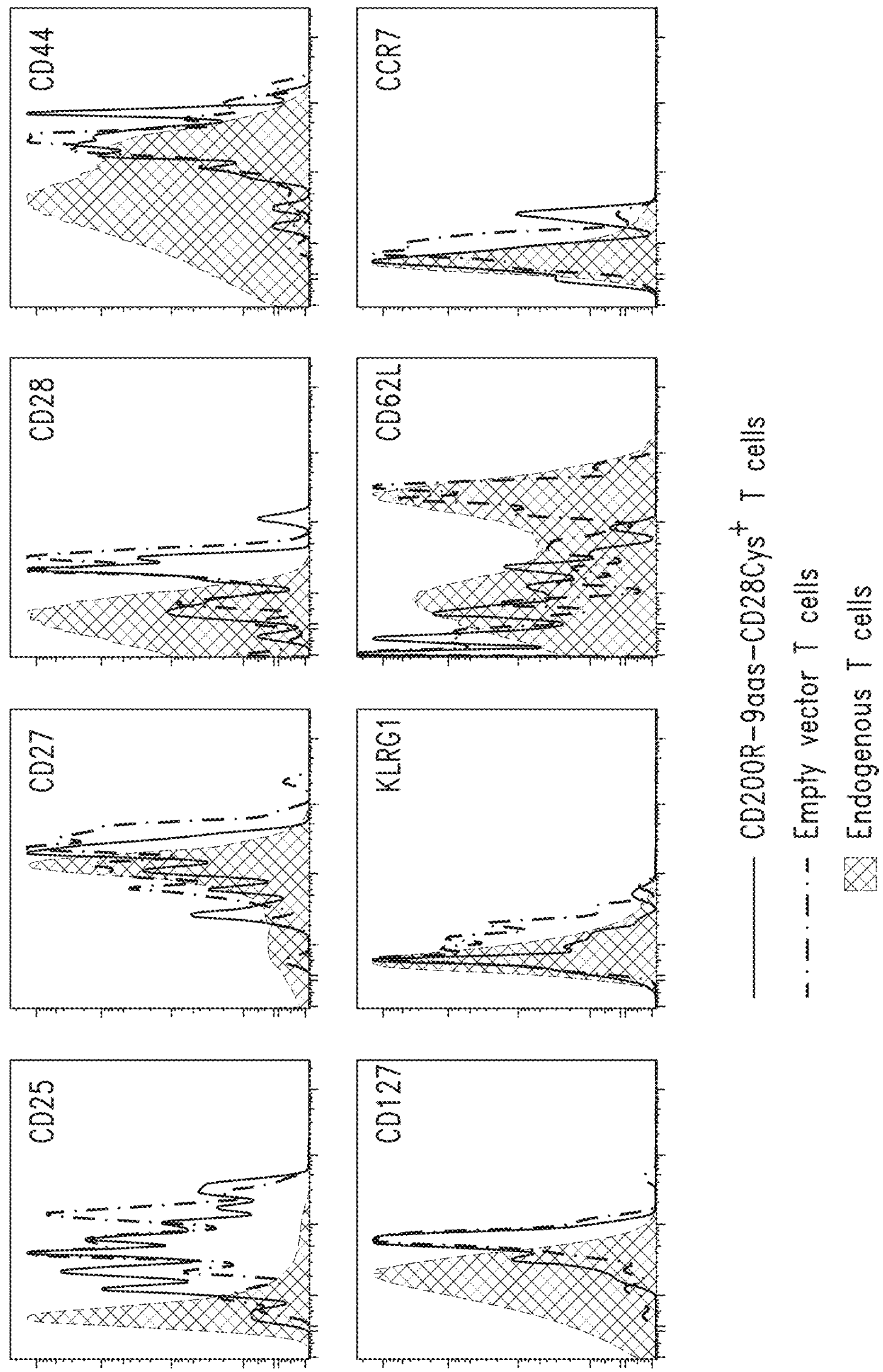
Figure 3D:
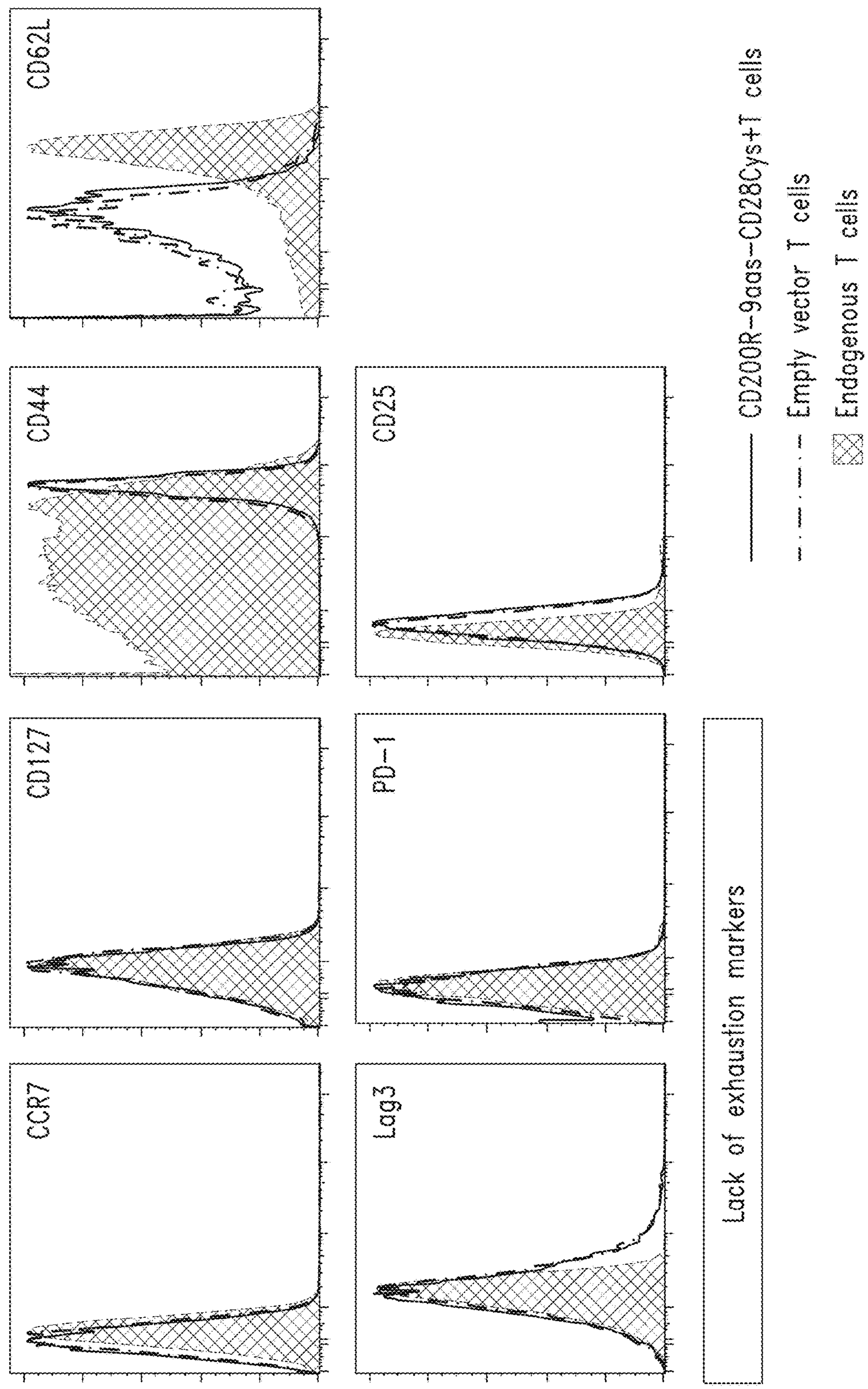

To assess whether CD200R-9aas-CD28Cys fusion protein-transduced T cells exhibited greater proliferation and accumulation in vivo in response to recognition of FBL, a mixed population of fusion protein-transduced and control cells were transferred into tumor-bearing mice and the ratio of cells by ex vivo analysis were compared 8 days after transfer (FIG. 3A). By use of congenic markers, transduced T cells were detected at a 1.2-1.4-fold greater ratio over control cells in both the spleen and lymph nodes relative to the ratio that was injected (FIG. 3B). Transduced CD200R-9aas-$CD28Cys^+$ $TCR_{gag}$ T cells exhibited reduced CD62L expression 3 days post-transfer to tumor-bearing mice, suggesting an effector T cell phenotype (FIG. 3C). By day 15, transduced and control T cells exhibited similar phenotypes, including a lack of exhaustion markers (FIG. 3D). Similar to the in vitro findings, T cells that expressed CD200R-9aas-CD28Cys displayed increased accumulation in response to tumor stimulation in vivo. Furthermore, they exhibited protein expression patterns consistent with an effector T cell phenotype for at least 3 days following transfer to tumor-bearing mice.

Example 5

Adoptive Immunotherapy with CD200R-CD28$^+$ T Cells Exhibits Greater Activity in Therapy of Disseminated Leukemia Adoptive immunotherapy with T cells transduced with CD200R-CD28 mediated increased therapeutic activity in the preclinical mouse model of disseminated leukemia.

Figure 4A:
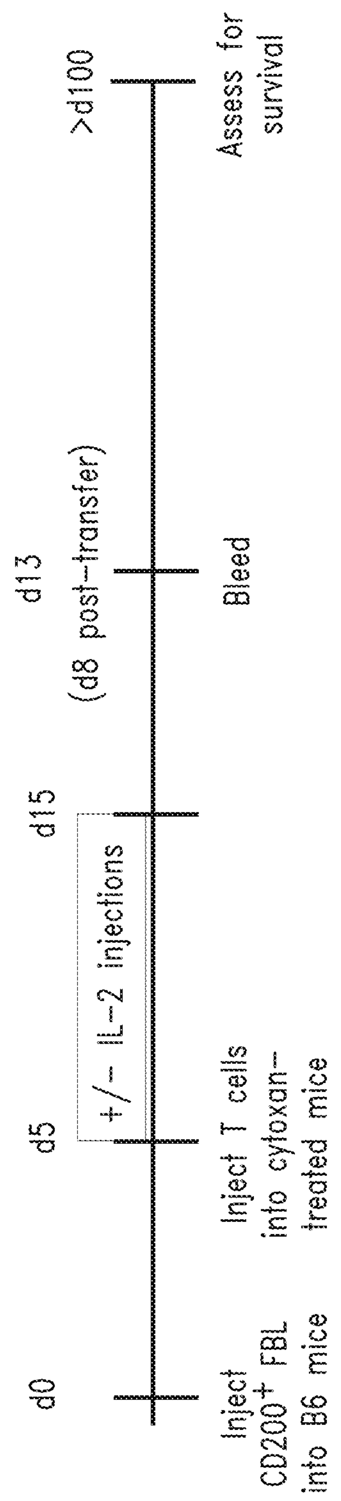
Figure 4B:
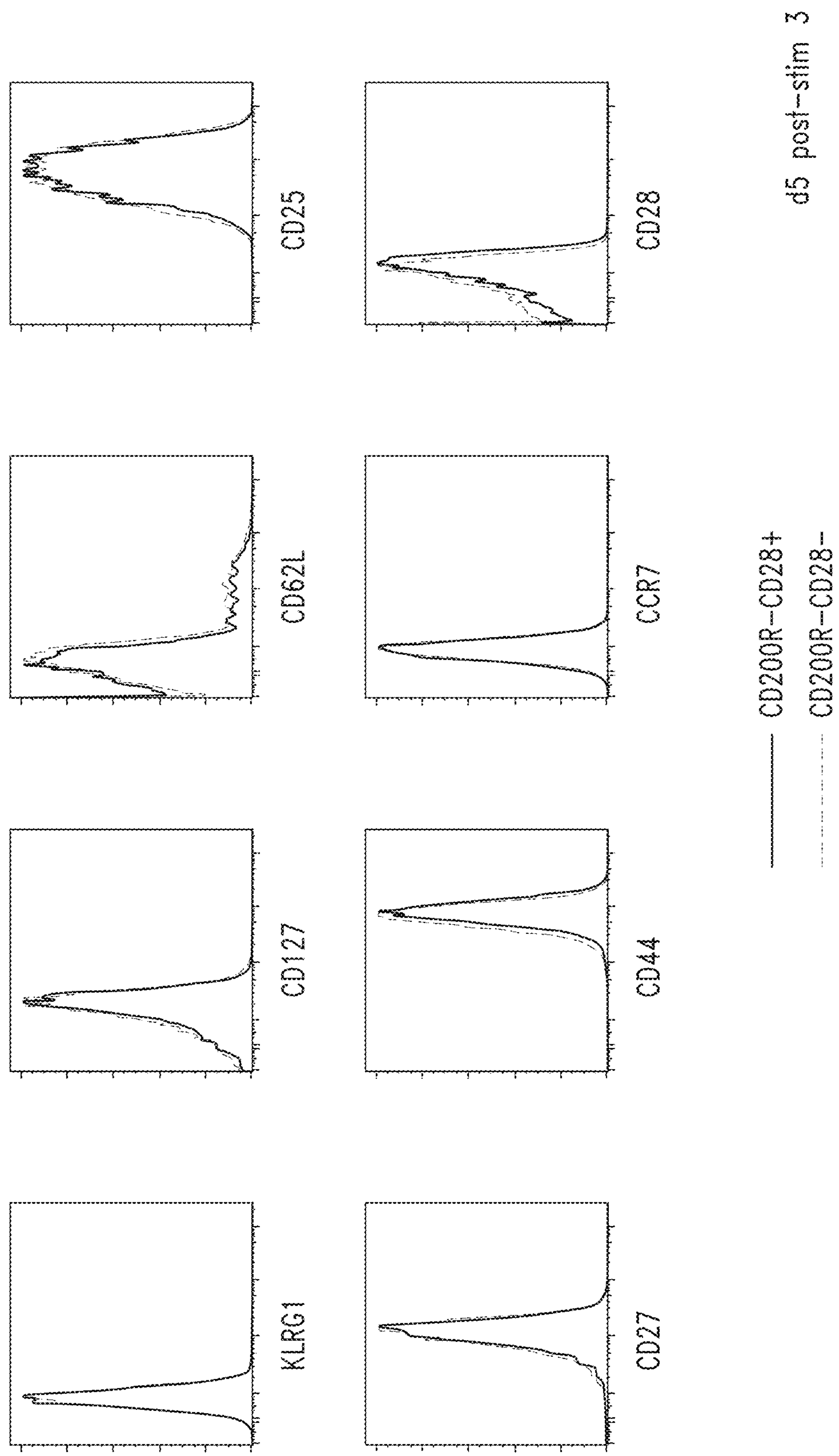

Mice were injected with a lethal dose of CD200$^+$ FBL leukemia and five days later, cohorts of Cy-treated mice received additional therapy with $10^5$ T cells (FIG. 4A). The contribution of the CD28 cysteine bond to efficacy mediated by the CD200R-CD28 construct was assessed by comparing T cells transduced with CD200R-CD28tm, CD200R-9aas-CD28Cys, and GFP control constructs as shown in FIG. 1A. IL-2 was administered for 10 days as an additional therapeutic reagent to a cohort of mice to promote the activity of the T cells (Stromnes et al., *J. Clin. Invest.* 120: 3722-34, 2010). Before injection, T cells were assessed for various surface proteins by flow cytometry. Transduced and control $TCR_{gag}$ T cells displayed similar phenotypes, indicating that transduction did not alter the phenotype of the cells prior to injection (FIG. 4B).

Figure 4C:
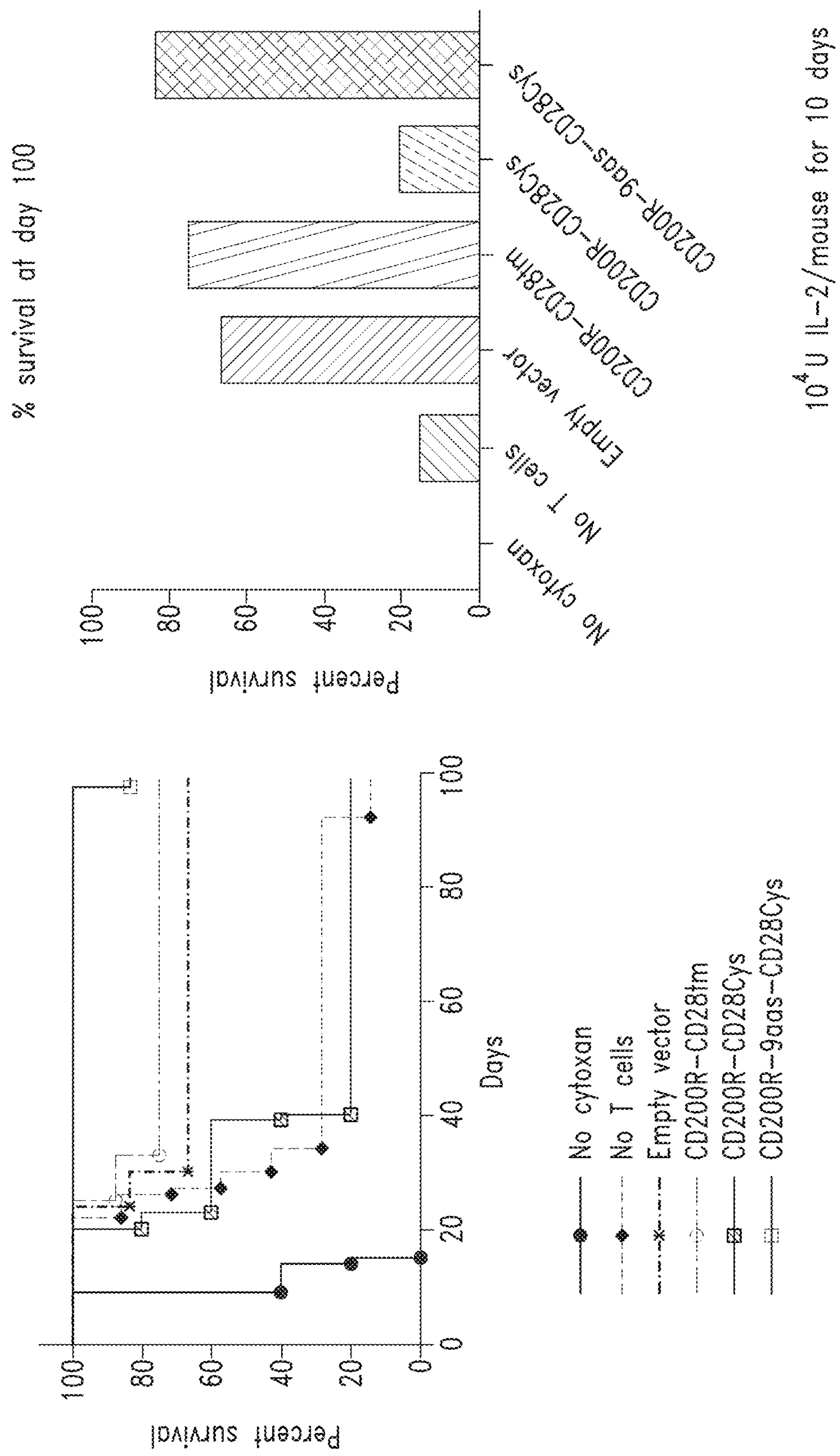
Figure 4D:
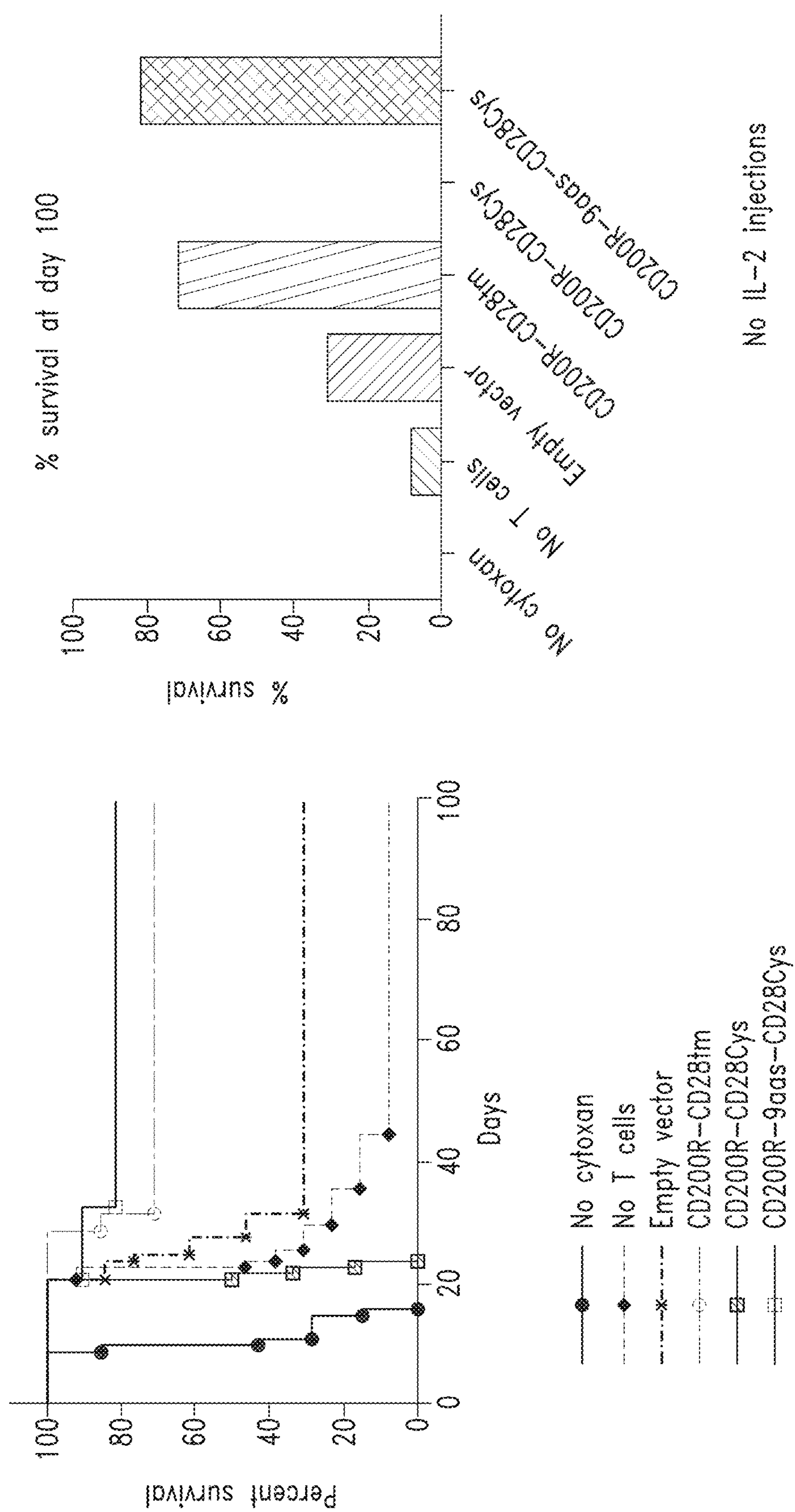

In the small cohort of mice that received IL-2 injections, T cells improved survival but a significant difference in the survival of mice that received the different groups of T cells could not be detected (FIG. 4C). However, in the cohort of mice that did not receive IL-2 injections, there was a significant improvement in the survival of mice that received T cells transduced with CD200R-CD28 constructs appropriately sized to fit within the immunological synapse (FIG. 4D). The majority of the mice not receiving T cells, receiving T cells transduced with the GFP control vector or T cells transduced with the largest ectodomain (CD200R-CD28Cys IFP) did not survive beyond day 30 (FIGS. 4C and 4D, black solid, dashed, and orange lines, respectively). In contrast, 71% of mice that received CD200R-CD28tm$^+$ T cells and 83% of mice that received CD200R-9aas-CD28Cys$^+$ T cells survived more than 100 days post-therapy (FIGS. 4C and 4D, green and red lines, respectively). These data suggest that transduction of T cells with CD200R-CD28 constructs that span a distance similar to a distance between membranes in an immunological synapse provides sufficient costimulation to overcome the dependence of T cell immunotherapy on injection of exogenous IL-2. Furthermore, although there were differences in proliferation and accumulation between the CD200Rtm-CD28 and CD200R-9aas-CD28Cys constructs tested in mice that did not receive injections of exogenous IL-2, both IFPs effectively enhanced T cell immunotherapy to significantly improve the clinical outcome from otherwise progressive leukemia.

Example 6

CD200R-9AAs-CD28Cys$^+$ T Cells do not Cause Autoreactivity with Endogenous Tissues and do not Exhibit Infiltration of Normal Tissues In Vivo To determine if transduction of $TCR_{gag}$ T cells lowered the threshold of activation sufficiently to result in autoreactivity with endogenous tissues, autoimmune toxicity was assessed in transgenic mice engineered to express the FBL gag tumor Ag as a self-antigen in hepatocytes, under control of the albumin promoter (FIG. 5A). $TCR_{gag}$ effectors were generated in vitro and $10^6$ were transferred into Cytoxan®-treated Alb:Gag mice with disseminated leukemia. At 3 and 7 days post-transfer, liver damage was assessed by quantification of serum levels of the liver enzymes aspartate aminotransferase (AST) and alanine aminotransferase (ALT). Adoptive therapy with control or CD200R-9aas-CD28Cys$^+$ $TCR_{gag}$ cells in mice did not affect serum levels of AST or ALT at days 3 or 7 post-transfer, indicating that CD200R-9aas-CD28Cys does not induce detectable autoimmune liver damage in Alb:Gag mice (FIG. 5B).

T cells transduced with IFP do not exhibit increased infiltration of normal tissues compared to control T cells. Mice were euthanized 7 days post-transfer and liver sections were stained with an antibody to the T cell marker CD3 to quantify T cell infiltration. Limited presence of T cells in liver tissue was observed, with no significant difference between recipients of CD200R-9aas-CD28Cys$^+$ or control $TCR_{gag}$, indicating no increased lymphocytic cellular infiltration as a result of IFP expression (FIG. 5C).

Example 7

4-1BB Co-Stimulatory Signaling Domain Promotes Accumulation of Transduced T Cells In Vitro Co-stimulatory receptor 4-1BB is upregulated on activated T cells, which promotes T cell survival and cytokine production (Chen and Flies, *Nat. Rev. Immunol.* 13: 227-242, 2013). To assess if the intracellular signaling domain of 4-1BB, with or without the intracellular signaling domain of CD28, could induce increased T cell proliferation and accumulation, IFPs using 4-1BB (CD200R-9aas-4-1BB) or combining 4-1BB with CD28 (CD200R-9aas-CD28-4-1BB) were generated (FIG. 6A) using the methods described in Example 2. $TCR_{gag}$ T cells were transduced as in Example 2, and $TCR_{gag}$ effector cells were generated in vitro as in Example 3.

Figure 6A:
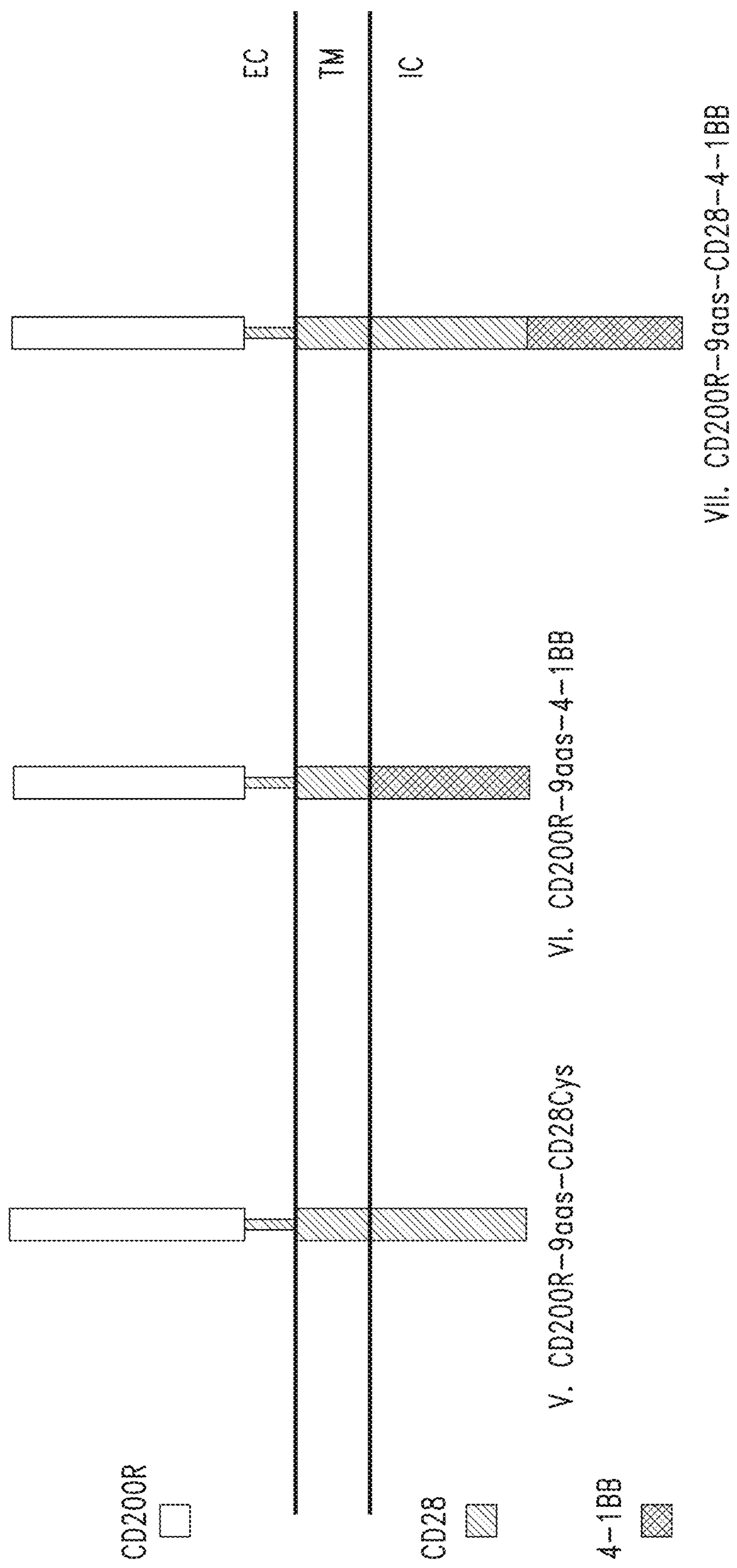
Figure 6B:
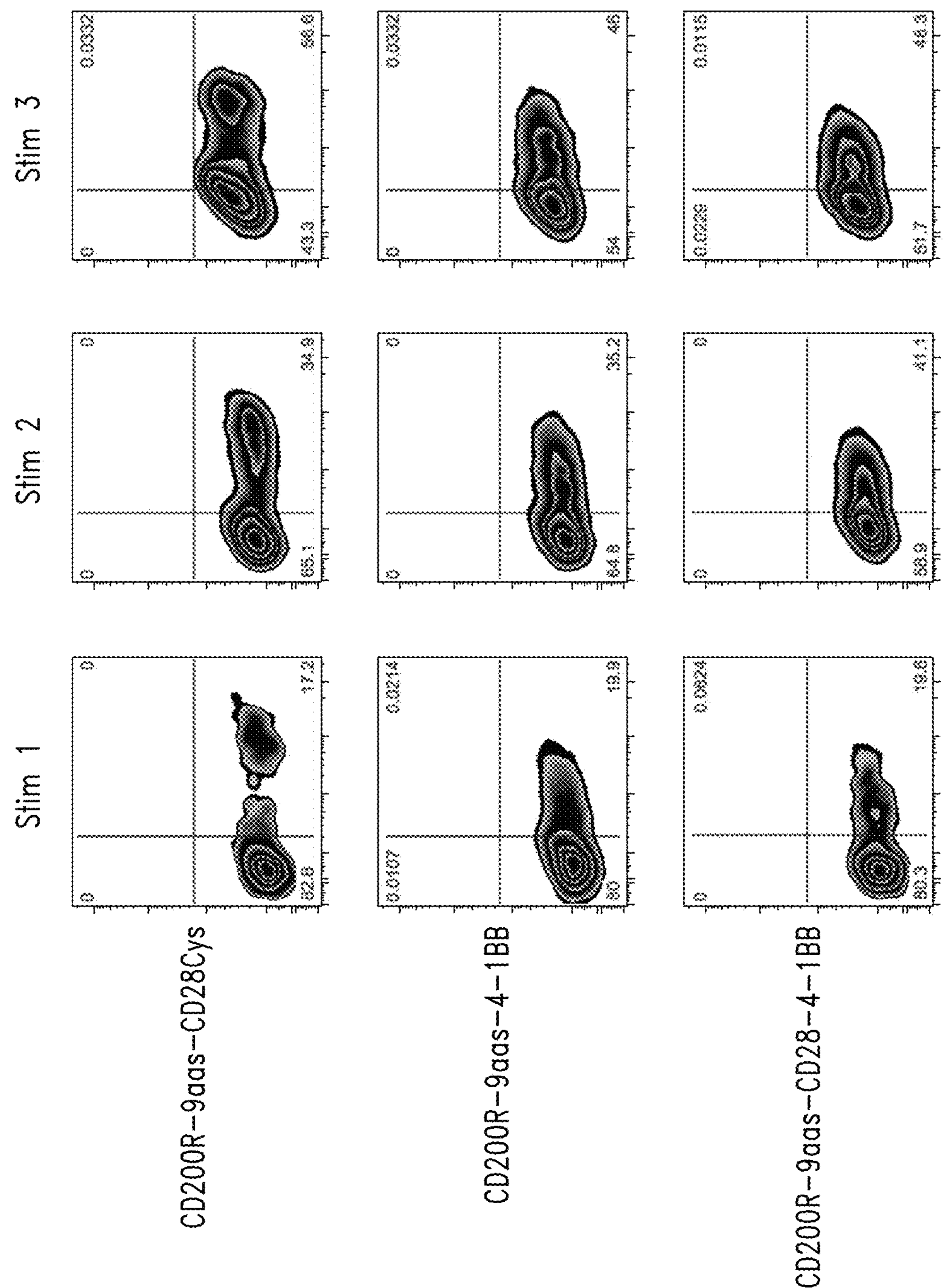

As was observed with CD200R-9aas-CD28Cys, T cells transduced with the 4-1BB constructs accumulated over multiple rounds of stimulation in vitro (FIG. 6B). These data indicate that 4-1BB IFPs also promote proliferation and survival of T cells.

Figure 6C:
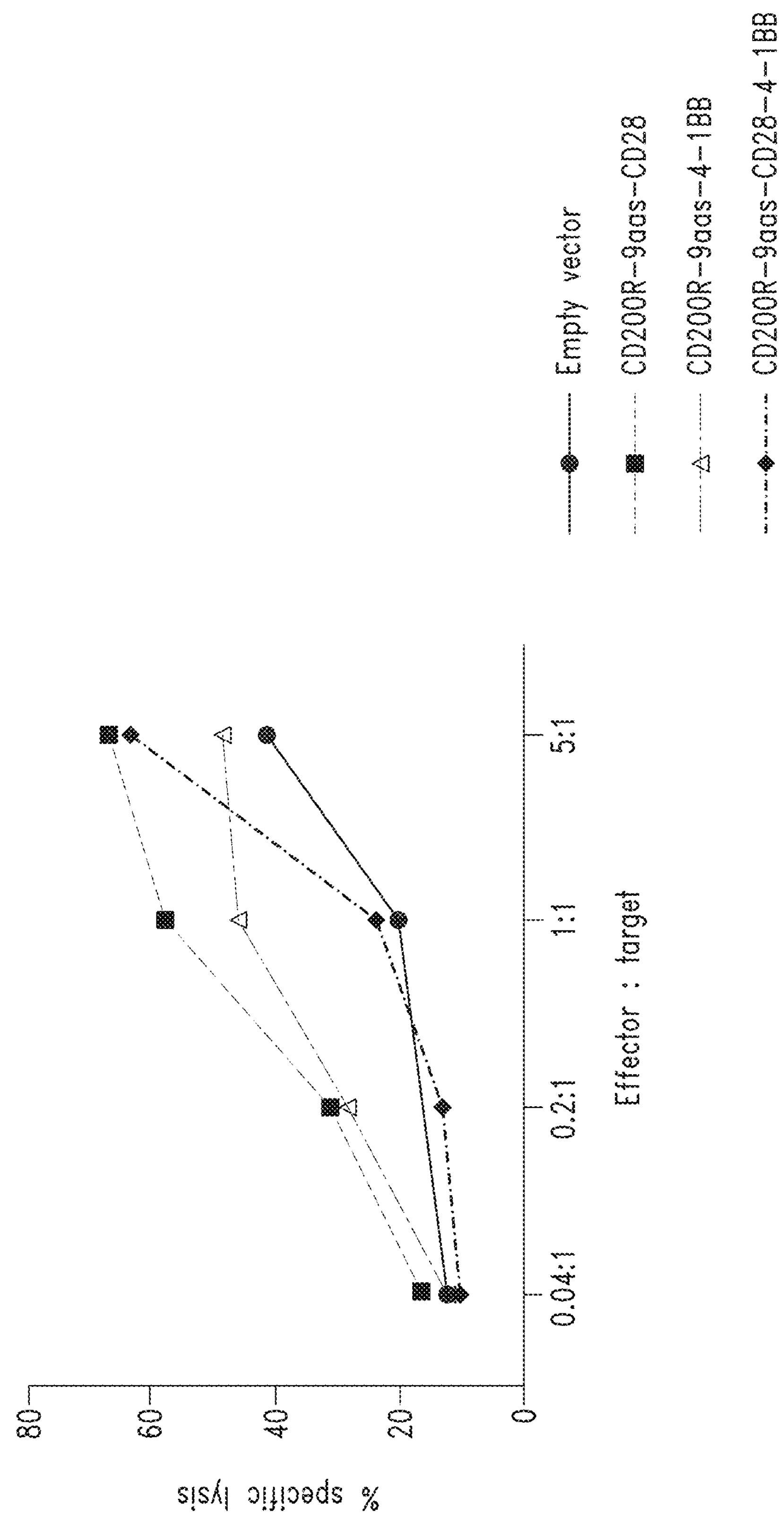
Figure 6D:
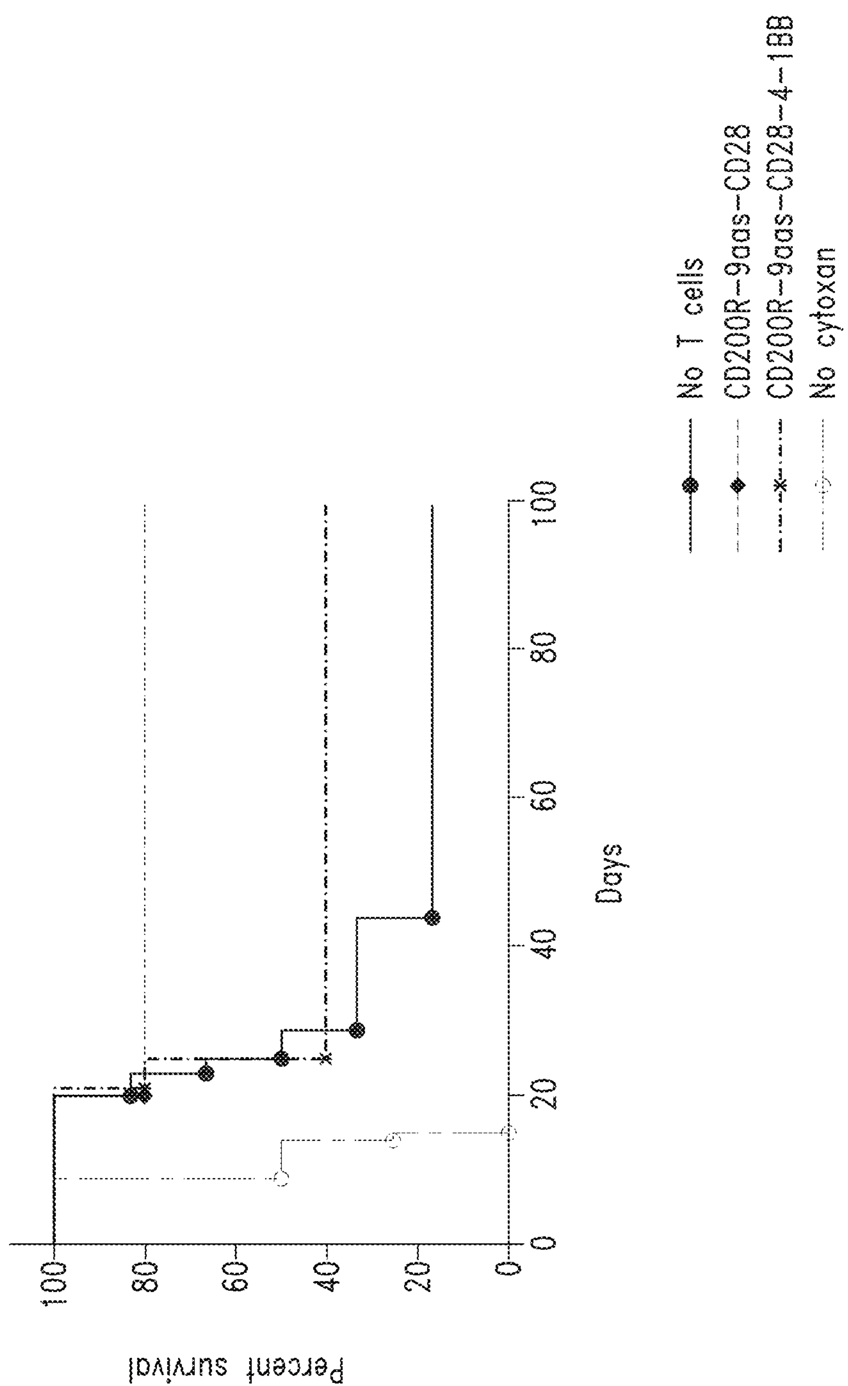

$TCR_{gag}$ T cells transduced with a CD200R-4-1BB displayed an enhanced ability to lyse FBL tumor in vitro using the CFSE-based cytotoxicity assay described in Example 3 (FIG. 6C). CD200R-41BB-transduced T cells also promote survival (FIG. 6D).

Example 8

Figure 7A:
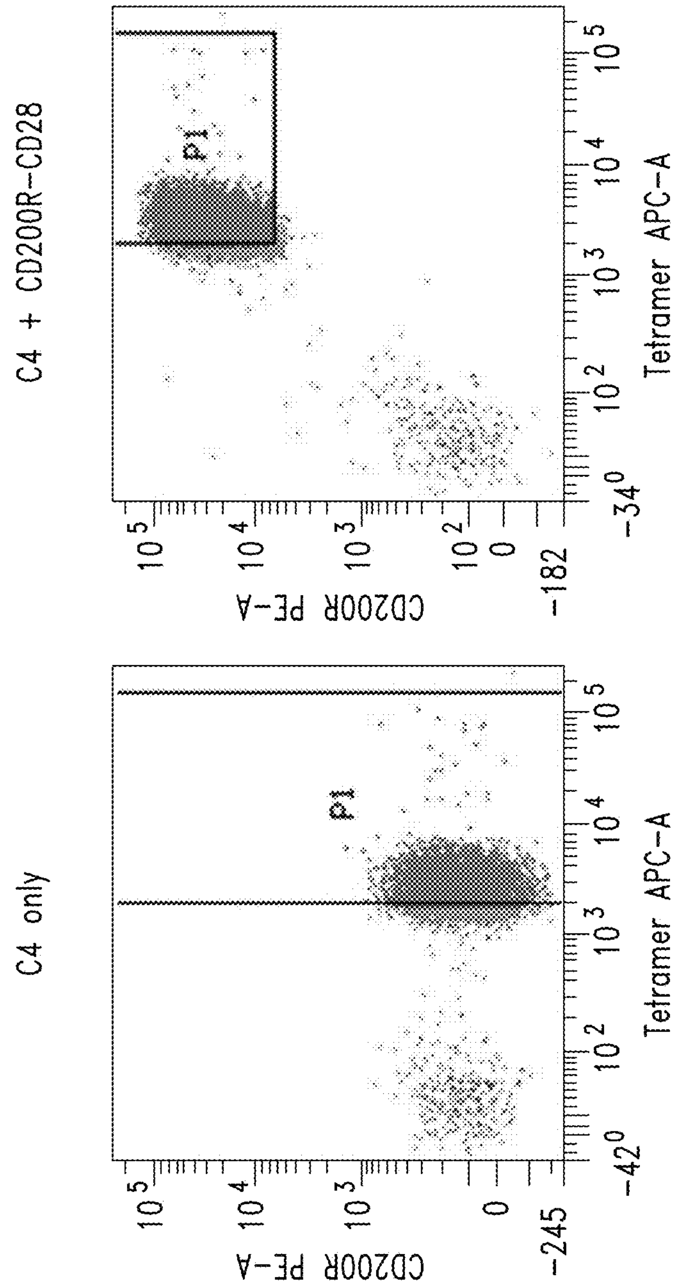

Co-Expression of Cd200RTM-CD28 Enhances Function in WT1-Specific TCR Primary T Cells A human CD200Rtm-CD28 construct (SEQ ID NO.:1) was generated to determine if IFP expression enhanced T cell function of human primary T cells. The construct was combined with the beta and alpha chains of the HLA-A2-restricted $WT1_{126}$-specific TCR "C4" by linking the genes with P2A elements (FIG. 7A). The first P2A sequence was codon optimized to prevent genetic recombination with the second P2A sequence. To generate lentiviruses, 293 T/17 cells ($3\times10^6$ cells/plate) were transduced with human constructs in the pRRLSIN and the packaging vectors pMDLg/pRRE, pMD2-G, and pRSV-REV using Effectene® (Qiagen). Culture media was changed on day 1 post-transfection and virus-containing supernatant collected on days 2 and 3, and aliquots frozen for future use.

The Jurkat human T cell subline, which lacks an endogenous TCR, was used to test expression of the IFP and TCRs. These Jurkat T cells were transduced by spinfection of $2\times10^6$ cells with 2 ml of retroviral supernatant at 1000 g for 90 min at 32° C. Transduction of the Jurkat human T cell line with the three-gene construct resulted in high expression of the IFP and expression of the TCR at a similar MFI as T cells transduced with the TCR only (FIG. 7A).

To transduce primary human T cells, peripheral blood mononuclear cells (PBMC) were harvested from HLA-A2+ donors. $CD8^+$ T cells were purified using Miltenyi magnetic beads and stimulated with Human T cell Expander CD3/CD28 Dynabeads™ (Life Technologies) and 50 IU/ml IL-2. Four hours following stimulation, T cells were transduced as described above for Jurkat T cells. T cells were restimulated every 10-14 days with a rapid expansion protocol (REP), as has been previously described (Ho et al., *J Immunol Methods* 310:40-52, 2006).

Figure 7B:
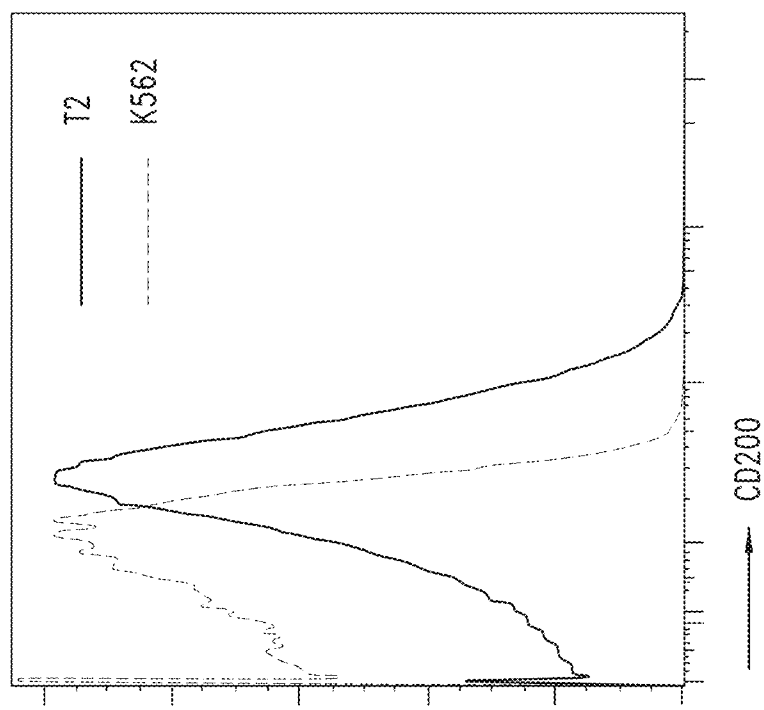

The human cell line T2 was used as an APC, because it is deficient in TAP and thus cannot present endogenous peptides, while low level MHCI expression allows presentation of exogenously loaded peptides. Expression of CD200 by the T2 cells was assessed by flow cytometry (FIG. 7B). T2 cells exhibited a low level of endogenous CD200 expression (FIG. 7B).

Figure 7C:
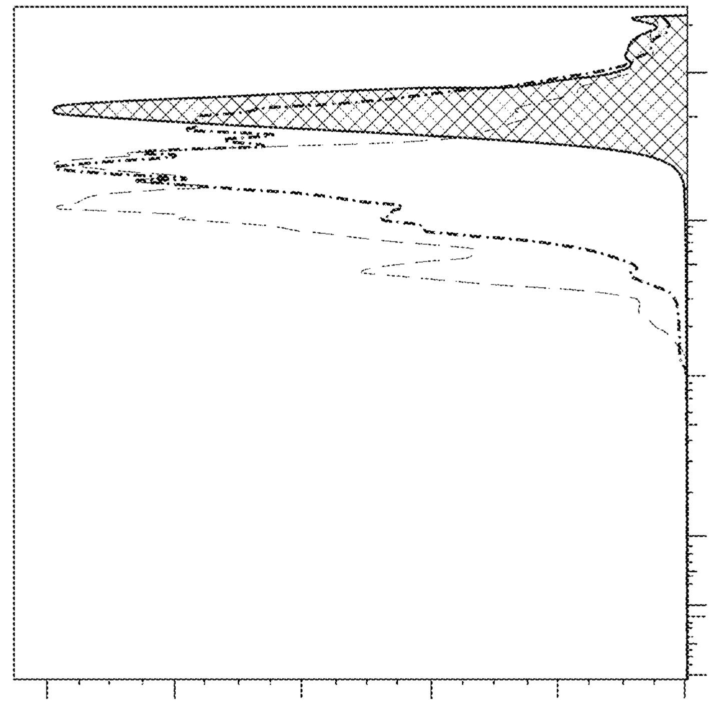
Figure 7C:
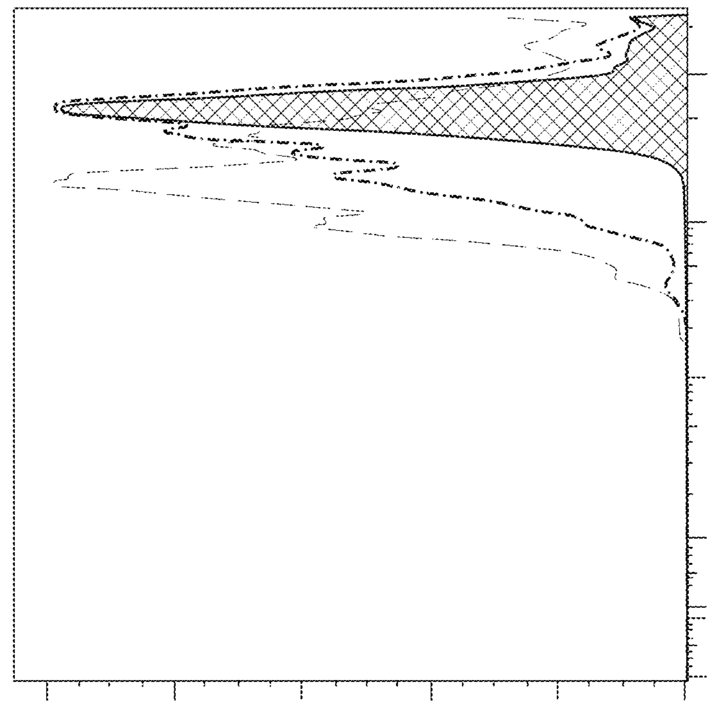
Figure 7D:
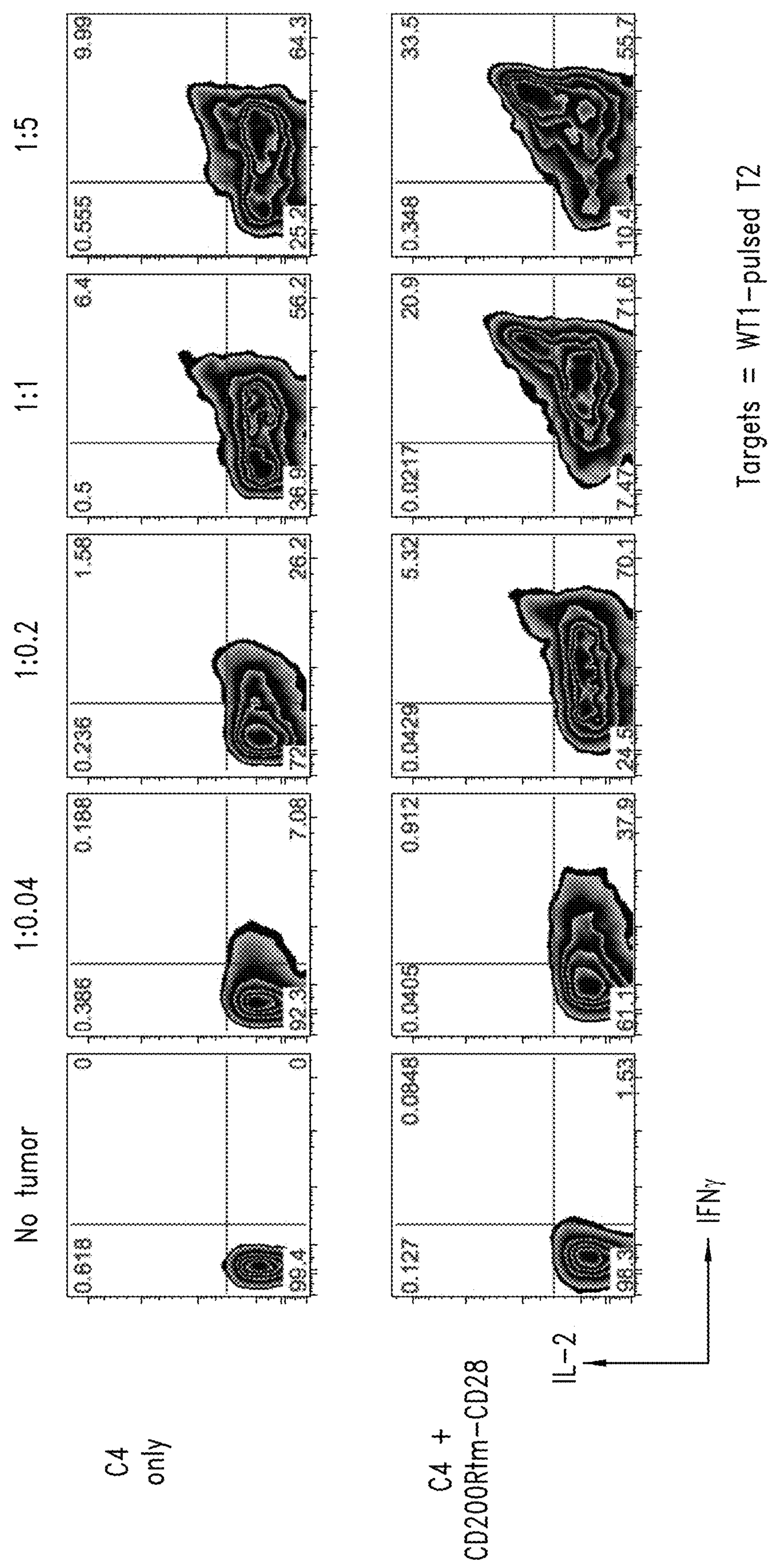

Transduced T cells were stimulated with $WT1_{126}$-pulsed T2 cells. Despite a low level of CD200 expression on the target cells, CD200Rtm-CD28-transduced T cells exhibited enhanced proliferation as compared to T cells transduced with the C4 TCR alone (FIG. 7C). In addition, stimulated CD200Rtm-CD28-transduced T cells (i.e., $IFP^+$ T cells) produced increased levels of IFNγ and IL-2 compared to control T cells when exposed to CD200dim tumor cells (FIG. 7D).

Overall, these results showed that primary T cells transduced to express a human CD200Rtm-CD28 construct and the beta and alpha chains of a $WT1_{126}$-specific TCR exhibited enhanced proliferation and increased cytokine production relative to T cells transduced with the TCR construct alone.

Example 9

Figure 8A:
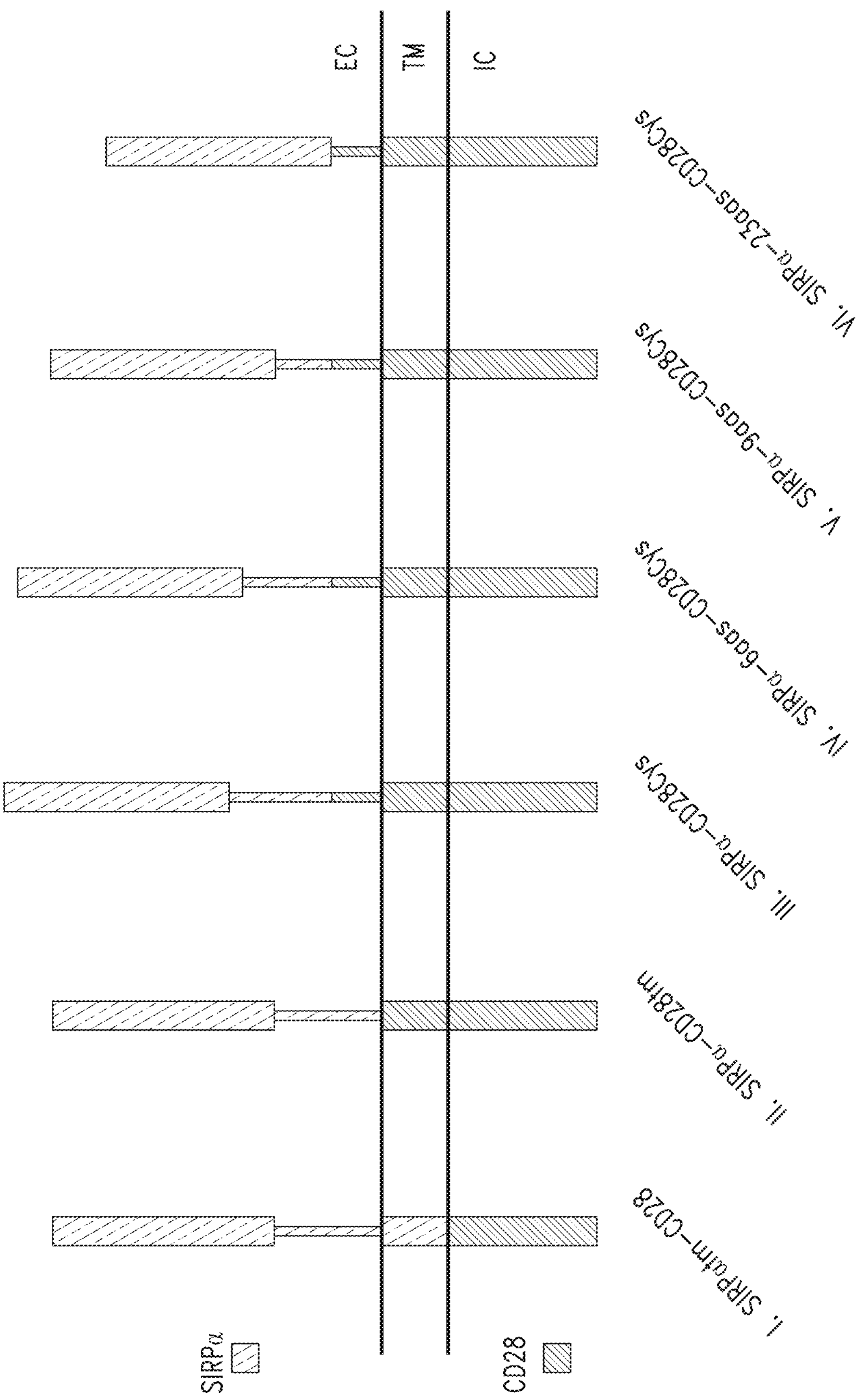

$SIRP_A$-CD28 Fusion Protein Constructs Promote Accumulation of Transduced T Cells In Vitro Exemplary fusion proteins as described herein also include IFPs comprised of the extracellular domain of SIRPα, or portions thereof, and an intracellular signaling domain of CD28 (FIG. 8A). The hydrophobic component may be comprised of the transmembrane domain of either SIRPα or CD28, or portions thereof. In some exemplary SIRPα-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., SIRPα-CD28Cys, SIRPα-6aas-CD28Cys, SIRPα-9aas-CD28Cys, and SIRPα-9aas-CD28Cys). The extracellular component may comprise all or a portion of the extracellular domain of SIRPα. In some embodiments, the extracellular component comprises the entire extracellular domain of SIRPα. In other examples, the extracellular component comprises the first 367 amino acids (e.g., SIRPα-6aas-CD28Cys), the first 364 amino acids (e.g., SIRPα-9aas-CD28Cys), or the first 350 (SIRPα-23aas-CD28Cys) amino acids from the N-terminus of SIRPα. The size of the extracellular component may affect the ability of the fusion protein to enter the immunological synapse and co-localize with the TCR within the cSMAC to deliver a strong co-stimulatory signal. In some examples, the extracellular component comprises a truncated SIRPα, which may alter the size of the extracellular component. For example, to account for the additional extracellular amino acids of the extracellular domain of the fusion protein (e.g., an additional 9 or 12 amino acids), SIRPα-6aas-CD28 has a truncated portion of SIRPα that preserves a natural N-linked glycosylation site. In another example, SIRPα-23aas-CD28 has a truncated portion of SIRPα that lacks the entire stem region of the SIRPα extracellular domain. Additionally, a SIRPα-CD28 construct has the capacity to convert a signal initiated by the binding of SIRPα to its target into a positive (e.g., costimulatory) signal generated by the CD28 intracellular signaling domain.

IFPs using SIRPα extracellular components were generated (FIG. 8A) using the methods described in Example 2. $TCR_{gag}$ T cells were transduced as in Example 2, and $TCR_{gag}$ effector cells were generated in vitro as in Example 3. FBL cells were transduced with CD47 or mCherry with polybrene spinfection, similar to T cell transduction, and subsequently sorted to generate a homogenous population.

Figure 8B:
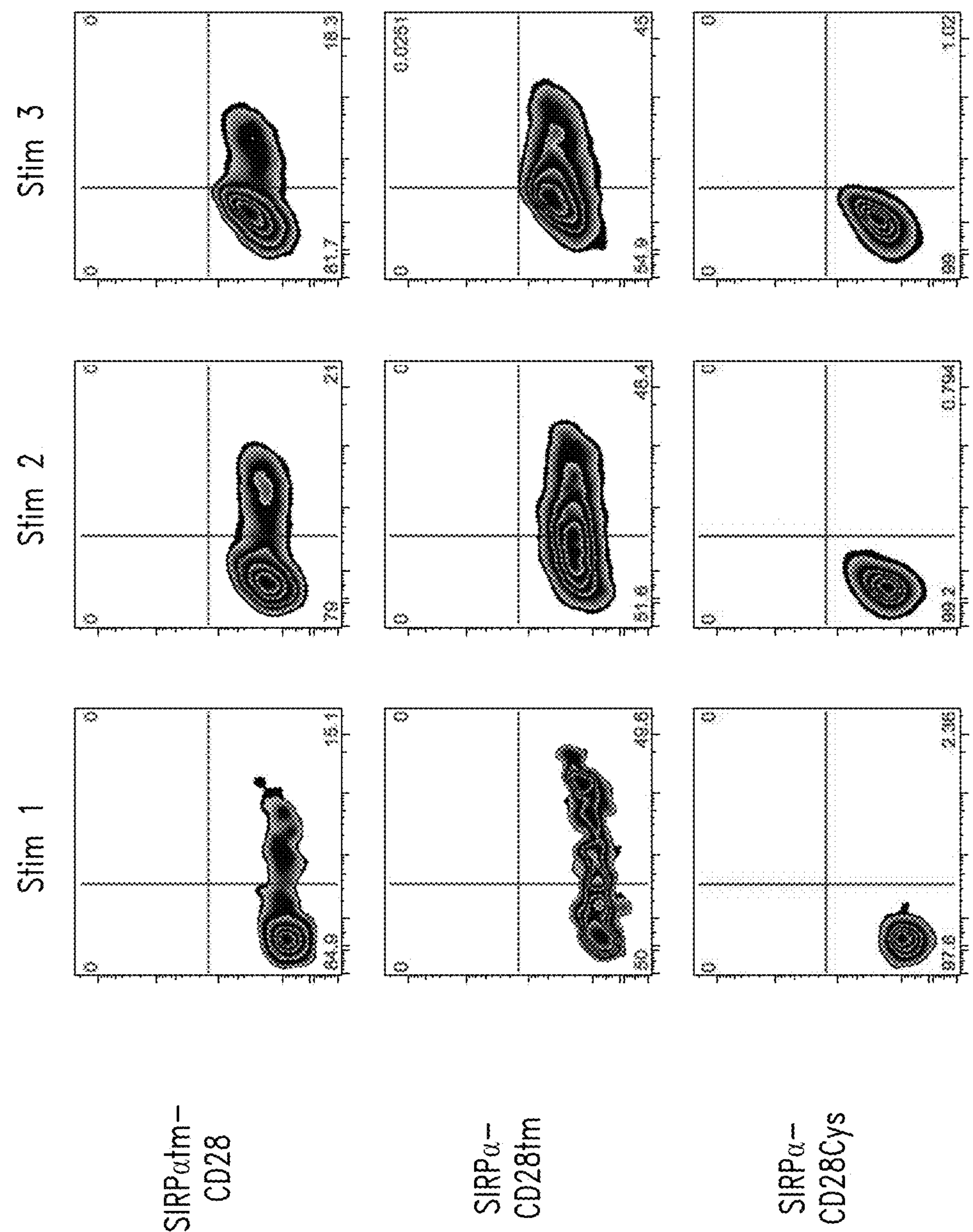
Figure 8B:
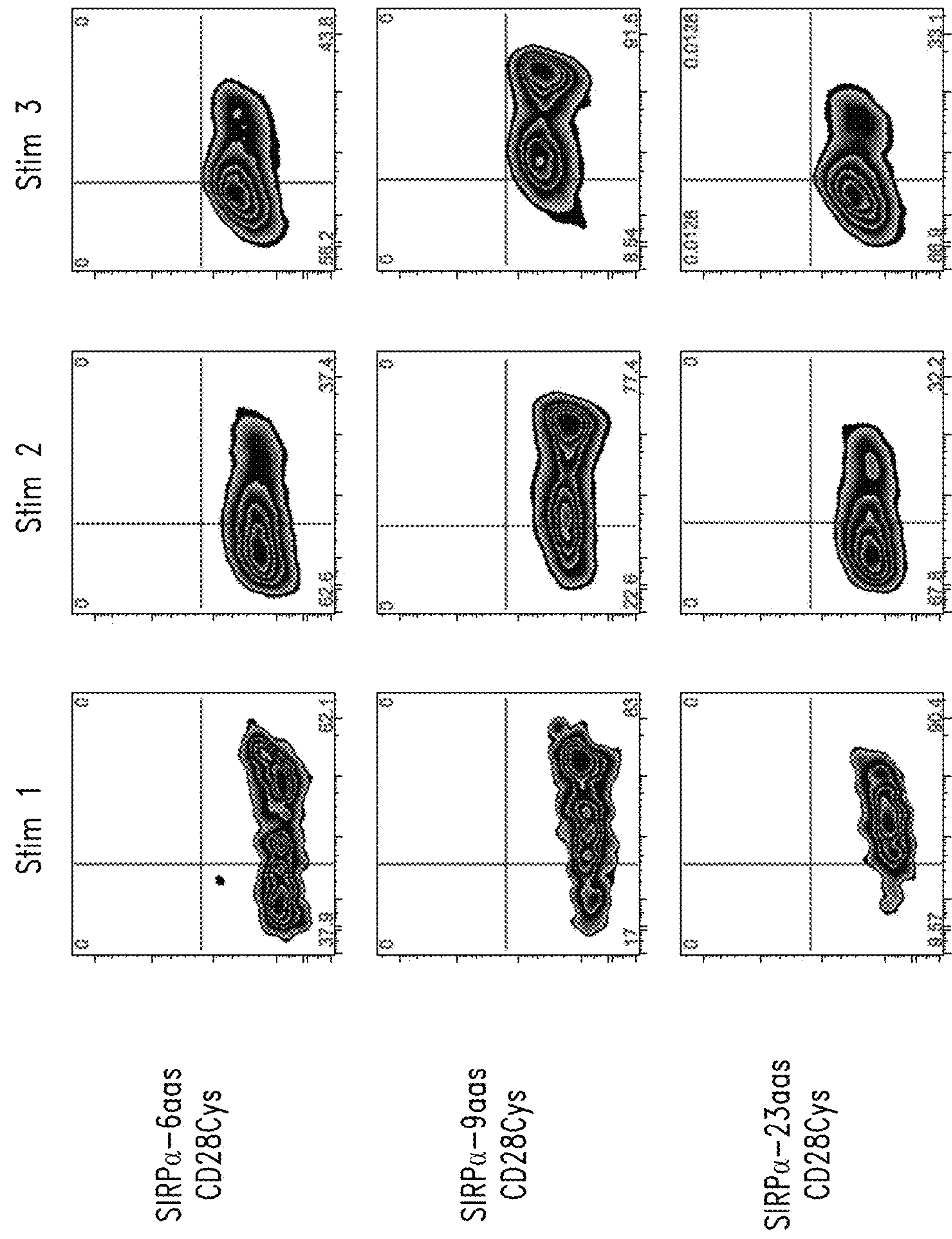

As was observed with CD200R-9aas-CD28Cys, T cells transduced with the SIRPα constructs accumulated over multiple rounds of stimulation in vitro (FIG. 8B). These data suggest that SIRPα-CD28 IFPs also promote proliferation and survival of T cells.

Figure 8C:
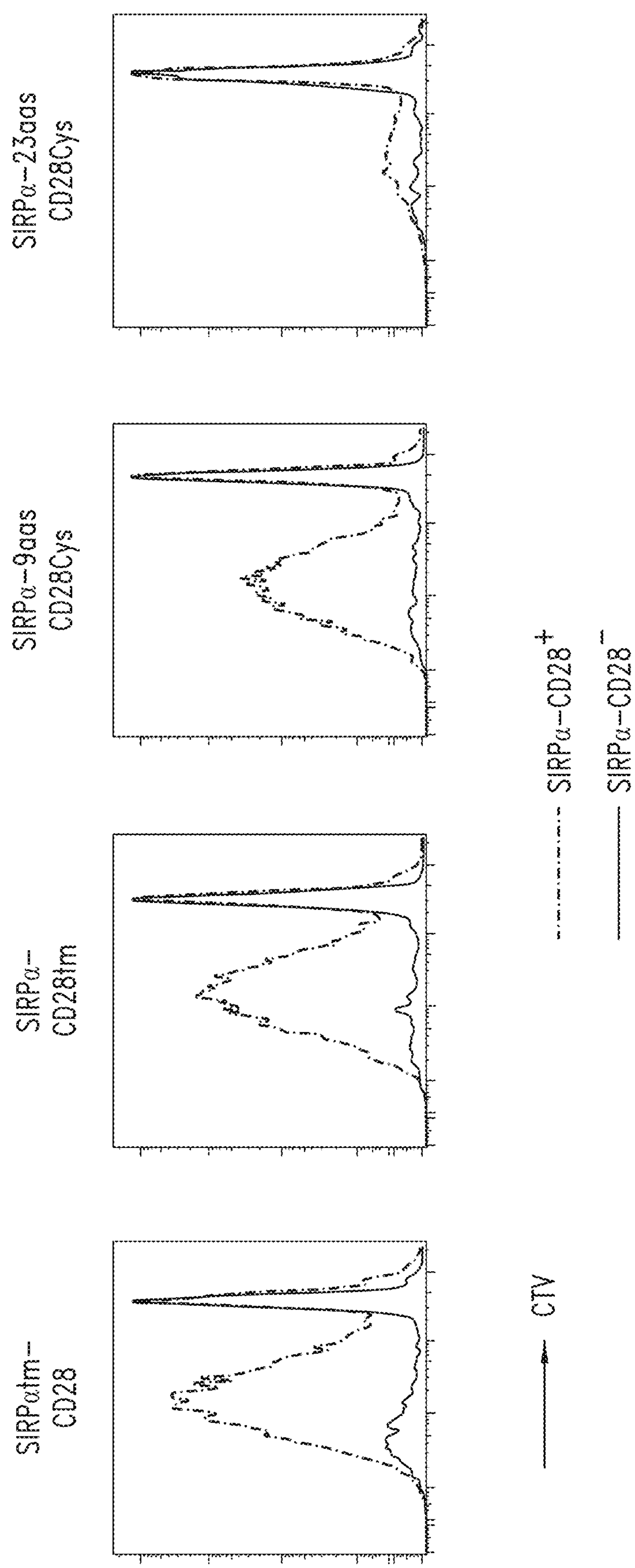
Figure 8D:
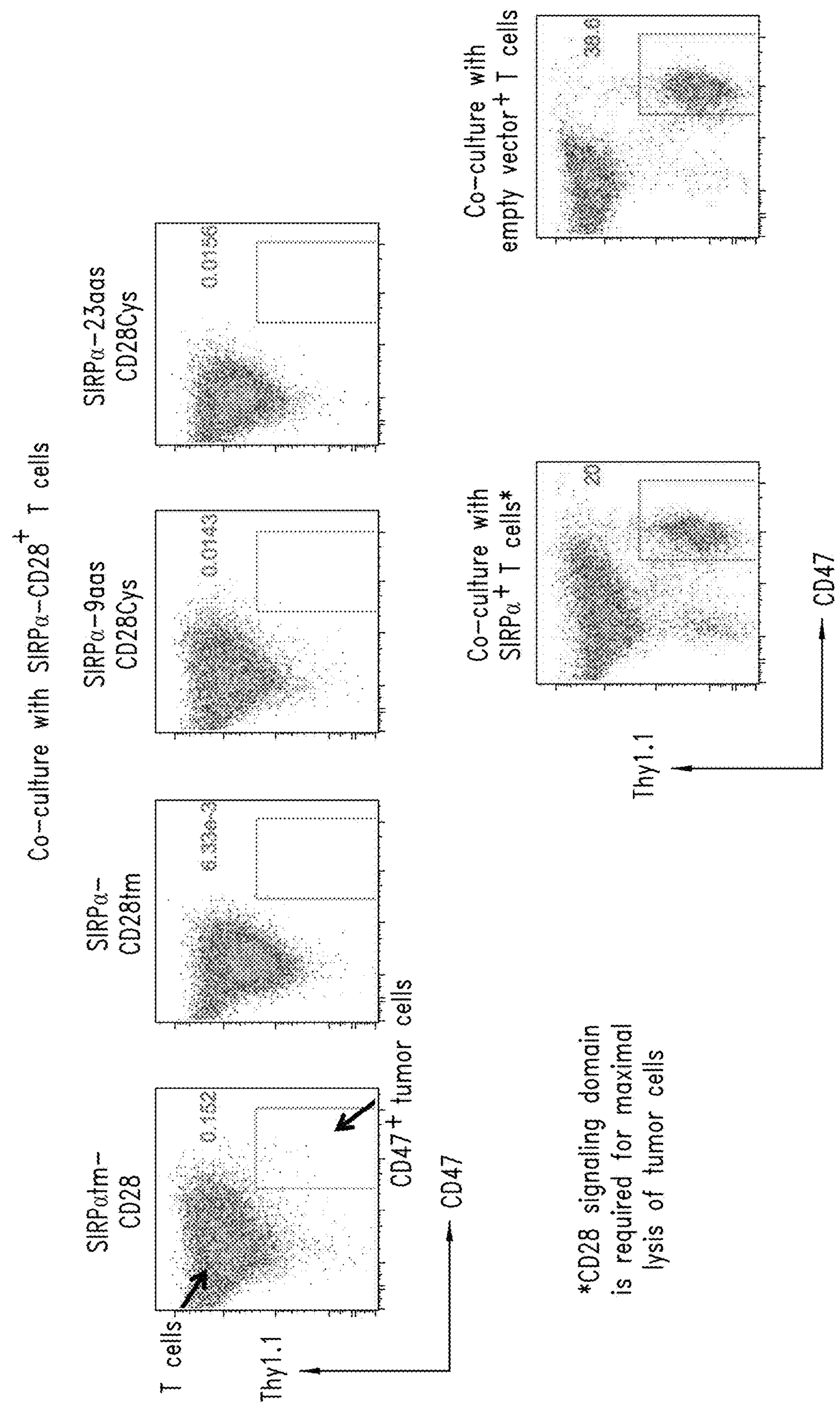
Figure 8E:
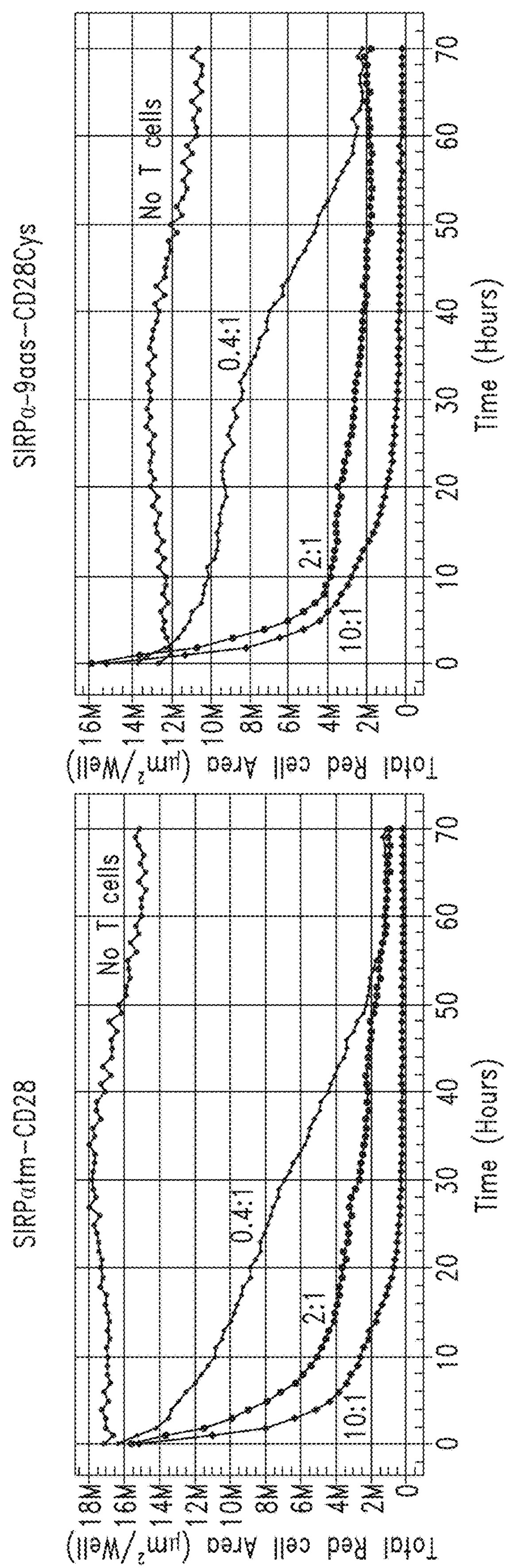

To assess T cell proliferation in vitro, a CTV Dilution Proliferation assay was performed as described in Example 2. As was observed with CD200R-9aas-CD28Cys, T cells transduced with the SIRPα constructs engineered to maintain the T cell-tumor cell synapse distance exhibited enhanced proliferation as compared to control T cells (FIG. 8C). In addition, $CD47^+$ tumor cells were efficiently killed after 3 days of co-culture with SIRPα-$CD28^+$ T cells but not control T cells or T cells transduced with a SIRPα construct that lacked an intracellular signaling domain (FIG. 8D). To further assess the lytic capacity of SIRPα-$CD28^+$ T cells, an IncuCyte® assay was used to quantify killing of $CD47^+$ FBL. A total of $10^5$ $mCherry^+$ $CD47^+$ FBL were co-cultured in 24-well plates with a titration of human T cells transduced with SIRPα-CD28 constructs. The plate was incubated in an IncuCyte® (Essen BioScience) inside a cell culture incubator for 70 hours. Images were captured every hour to monitor killing of tumor cells, as determined by loss of red signal. SIRPα-$CD28^+$ T cells killed $CD47^+$ tumor cells, even at the lowest effector-to-target ratio tested (0.4:1; FIG. 8E).

Example 10

PD-1-CD28 Fusion Protein Constructs Promote Cytokine Production in Transduced T Cells In Vitro Exemplary fusion proteins as described herein also include IFPs comprised of the extracellular domain of PD-1, or portions thereof, and an intracellular signaling domain of CD28 (FIG. 9A). The transmembrane component may be comprised of the transmembrane domain of either PD-1 or CD28, or portions thereof. In some exemplary PD1-CD28 fusion proteins, the transmembrane component comprises the transmembrane domain of CD28 and the extracellular component further comprises an extracellular portion of CD28, particularly an extracellular cysteine residue adjacent to the transmembrane component (e.g., PD1-CD28Cys, PD1-9aas-CD28Cys, and PD1-21aas-CD28Cys) to promote inter-chain dimerization. The extracellular component may comprise all or a portion of the extracellular domain of PD-1, or may be truncated (e.g., -9aas in murine constructs, -12aas or -15aas in human constructs; lacking the stem region of PD-1, -21aas) to maintain the short spatial distance between the cells to facilitate access of the liganded receptor to the immunologic synapse. Additionally, a PD1-CD28 construct has the capacity to convert what would typically be an inhibitory signal from the binding of PD1 to its target into a positive (e.g., costimulatory) signal generated by the CD28 intracellular signaling domain.

IFPs comprising PD-1 extracellular components were generated (FIG. 9A) using the methods described in Example 2. $TCR_{gag}$ T cells were transduced as in Example 2, and $TCR_{gag}$ effector cells were generated in vitro as in Example 3.

Murine PD1-CD28 IFPs were generated using constructs I-IV and VII (FIG. 9A). PD1-$CD28^+$ T cells were restimulated in the presence of Brefeldin A (to retain produced cytokines) with FBL cells endogenously expressing the PD-1 ligands, PD-L1 and PD-L2. After 5 hours, cells were fixed and treated with the BD Cytofix/Cytoperm™ kit, to allow intracellular staining of the effector cytokines, IFNγ and TNFα. Transduction with each of the five PD1-CD28 constructs enhanced production of intracellular cytokines compared to control T cells (FIG. 9B).

Human PD1-CD28 IFPs were generated using constructs I-III and V-VII (FIG. 9A). Vectors containing the PD1-CD28 IFP and C4 TCR were generated as described above. Jurkat T cells were transduced as described above. T cells transduced with the TCR and PD1-12aas-CD28Cys or PD1-15aas-CD28Cys exhibited high transduction efficiencies and expression of both proteins (FIG. 10).

Example 11

Fas-CD28 Fusion Protein Constructs Promote Accumulation and Enhanced Function in Transduced T Cells In Vitro Exemplary fusion proteins as described herein also include IFPs comprised of the extracellular domain of Fas, or portions thereof, and an intracellular signaling domain of CD28 (FIG. 11A). The transmembrane component may be comprised of the domain of either Fas or CD28, or portions thereof. In some exemplary Fas-CD28 fusion proteins, the transmembrane component comprises the transmembrane domain of CD28 and the extracellular component further comprises an extracellular portion of CD28, particularly an extracellular cysteine residue adjacent to the transmembrane component (e.g., Fas-CD28Cys and Fas-9aas-CD28Cys). The extracellular component may comprise all or a portion of the extracellular domain of Fas or may be truncated to preserve maintain a short spatial distance between the cells (-9aas) upon receptor-ligand interaction. Additionally, a Fas-CD28 construct has the capacity to convert a signal initiated by the binding of Fas to its target into a positive (e.g., costimulatory) signal generated by the CD28 intracellular signaling domain.

IFPs comprising Fas extracellular components were generated (FIG. 11A) using the methods described in Example 2. $TCR_{gag}$ T cells were transduced as in Example 2, and $TCR_{gag}$ effector cells were generated in vitro as in Example 3.

To determine if expression of the Fas-CD28 IFP results in increased accumulation of transduced cells, the proportion of transduced cells from the mixed population in the total $TCR_{gag}$ population was measured over multiple cycles of stimulation with irradiated FBL, as described in Example 3. All of the constructs promoted accumulation of transduced T cells compared to control T cells (FIG. 11B). In addition, expression of Fas-CD28 constructs but not full-length (FL) Fas promoted survival or expansion of T cells upon multiple stimulations in vitro FIG. 11C).

Example 12

LAG3-CD28 Fusion Protein Constructs

Exemplary fusion proteins as described herein also include IFPs comprised of the extracellular domain of LAG3, or portions thereof, and an intracellular signaling domain of CD28 (FIG. 12A). The transmembrane component may be comprised of the domain of either LAG3 or CD28, or portions thereof. In some exemplary LAG3-CD28 fusion proteins, the transmembrane component comprises the transmembrane domain of CD28 and the extracellular component further comprises an extracellular portion of CD28, particularly an extracellular cysteine residue adjacent to the transmembrane component (e.g., LAG3-CD28Cys and LAG3-9aas-CD28Cys). The extracellular component may comprise all or a portion of the extracellular domain of LAG3 or may be truncated to maintain a short spatial distance between the cells (e.g., -9aas) upon receptor-ligand interaction. Additionally, a LAG3-CD28 construct has the capacity to convert what would typically be an inhibitory signal from the binding of LAG3 to its target into a positive (e.g., costimulatory) signal generated by the CD28 intracellular signaling domain.

IFPs using LAG3 extracellular components were generated (FIG. 12A) using the methods described in Example 2. T cells were transduced with LAG3-eGFP constructs as described. Five days after transduction, $CD8^+$ T cells were analyzed for construct expression by anti-LAG3 antibody staining and flow cytometry (FIG. 12B). A vector encoding only green fluorescent protein (GFP) was used as a control. All constructs exhibited expression of LAG3 (FIG. 12B).

Example 13

TIM3-CD28 Fusion Protein Constructs

Exemplary fusion proteins as described herein also include IFPs comprised of the extracellular domain of TIM3, or portions thereof, and an intracellular signaling domain of CD28 (FIG. 13A). The transmembrane component may be comprised of the domain of either TIM3 or CD28, or portions thereof. In some exemplary TIM3-CD28 fusion proteins, the transmembrane component comprises the transmembrane domain of CD28 and the extracellular component further comprises an extracellular portion of CD28, particularly an extracellular cysteine residue adjacent to the transmembrane component (e.g., TIM3-CD28Cys and TIM3-9aas-CD28Cys). The extracellular component may comprise all or a portion of the extracellular domain of TIM3 or may be truncated to maintain the short spatial distance between the cells (e.g., -9aas). Additionally, a TIM3-CD28 construct has the capacity to convert what would typically be an inhibitory signal from the binding of TIM3 to its target into a positive signal generated by the CD28 intracellular signaling domain.

New IFPs using TIM3 extracellular components were generated (FIG. 13A) using the methods described in Example 2. T cells were transduced with GFP-TIM3 constructs as described. Five days after transduction, $CD8^+$ T cells were analyzed for construct expression by anti-TIM3 antibody staining and flow cytometry (FIG. 13B). A vector encoding only green fluorescent protein (GFP) was used as a control. Most constructs exhibited similar expression of TIM3 (FIG. 13B).

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications, and non-patent publications referred to in this specification or listed in the Application Data Sheet, including but not limited to U.S. Provisional Patent Application No. 62/128,979 filed Mar. 5, 2015, PCT Application No. PCT/US2016/021064 filed Mar. 4, 2016, and U.S. patent application Ser. No. 15/555,951 filed Sep. 5, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A fusion protein comprising the amino acid sequence encoded by a nucleic acid molecule as set forth in any one of SEQ ID NOs.:19, 20, 22, and 23.

2. A fusion protein comprising the amino acid sequence set forth in any one of SEQ ID NOs.:42, 43, 45, and 46.

3. The fusion protein of claim 2, comprising the amino acid sequence set forth in SEQ ID NO.:42.

4. The fusion protein of claim 2, comprising the amino acid sequence set forth in SEQ ID NO.:43.

5. The fusion protein of claim 2, comprising the amino acid sequence set forth in SEQ ID NO.:45.

6. The fusion protein of claim 2, comprising the amino acid sequence set forth in SEQ ID NO.:46.

7. The fusion protein of claim 2, consisting of the amino acid sequence set forth in SEQ ID NO.:42.

8. The fusion protein of claim 2, consisting of the amino acid sequence set forth in SEQ ID NO.:43.

9. The fusion protein of claim 2, consisting of the amino acid sequence set forth in SEQ ID NO.:45.

10. The fusion protein of claim 2, consisting of the amino acid sequence set forth in SEQ ID NO.:46.

11. A nucleic acid molecule encoding a fusion protein, wherein the fusion protein comprises the amino acid sequence set forth in any one of SEQ ID NOs.:42, 43, 45, and 46.

12. A vector comprising a nucleic acid molecule that encodes a fusion protein, wherein the fusion protein comprises the amino acid sequence set forth in any one of SEQ ID NOs.:42, 43, 45, and 46.

13. A host cell comprising a nucleic acid molecule that encodes a fusion protein, wherein the fusion protein comprises the amino acid sequence set forth in any one of SEQ ID NOs.:42, 43, 45, and 46.

14. The host cell of claim 13, wherein the host cell is a T cell.

15. The host cell of claim 13, wherein the host cell is a CD4+ cell or a CD8+ T cell.

16. The host cell of claim 13, wherein the host cell is an immune system cell.

* * * * *